US012735724B2

(12) United States Patent
Wang et al.

(10) Patent No.: US 12,735,724 B2
(45) Date of Patent: Sep. 15, 2026

(54) COMPOSITIONS AND METHODS FOR RECOMBINANT PARVOVIRUS PRODUCTION

(71) Applicant: AAVNERGENE INC., Rockville, MD (US)

(72) Inventors: Qizhao Wang, Rockville, MD (US); Daozhan Yu, Rockville, MD (US); Yu Liu, Rockville, MD (US); Cuiping Chen, Rockville, MD (US); Rongze Yang, Rockville, MD (US)

(73) Assignee: AAVNERGENE INC., Rockville, MD (US)

( * ) Notice: Subject to any disclaimer, the term of this patent is extended or adjusted under 35 U.S.C. 154(b) by 724 days.

(21) Appl. No.: 18/181,952

(22) Filed: Mar. 10, 2023

(65) Prior Publication Data

US 2023/0365991 A1 Nov. 16, 2023

Related U.S. Application Data

(60) Provisional application No. 63/341,201, filed on May 12, 2022.

(51) Int. Cl.
*C12N 15/86* (2006.01)
*C07K 14/005* (2006.01)
*C12N 7/00* (2006.01)

(52) U.S. Cl.
CPC .... *C12N 15/86* (2013.01); *C12N 2710/10043* (2013.01); *C12N 2750/00043* (2013.01); *C12N 2750/14143* (2013.01)

(58) Field of Classification Search
None
See application file for complete search history.

(56) References Cited

U.S. PATENT DOCUMENTS

| | | | | |
|---|---|---|---|---|
| 5,139,941 | A | 8/1992 | Muzyczka et al. | |
| 5,945,335 | A | 8/1999 | Colosi | |
| 6,114,148 | A | 9/2000 | Seed et al. | |
| 11,779,655 | B2 * | 10/2023 | Clark ................. | C07K 14/4702 424/93.2 |
| 2008/0194511 | A1 | 8/2008 | Graghia-Akli et al. | |
| 2013/0095558 | A1 * | 4/2013 | Huang ..................... | C12N 7/02 435/239 |

FOREIGN PATENT DOCUMENTS

| | | |
|---|---|---|
| EP | 3722434 | 10/2020 |
| WO | 2020086881 | 4/2020 |

OTHER PUBLICATIONS

Gattoni, Renata, et al. "Splicing of the E2A Premessenger RNA of Adenovirus Serotype 2: Multiple Pathways in Spite of Excision of the Entire Large Intron." Journal of Molecular Biology, vol. 187, No. 3, 1986, pp. 379-397, https://doi.org/10.1016/0022-2836(86)90440-7 (Year: 1986).*

Grimm, et al. "Novel Tools for Production and Purification of Recombinant Adenoassociated Virus Vectors", Human Gene Therapy, Mary Ann Liebert, vol. 9 No. 18, Dec. 10, 1998.

Xiao, et al. Production of High-Titer Recombinant Adeno-associated Virus Vectors in the Absence of Helper Adenovirus, Journal of Virology, The American Society For Microbiology, vol. 72, No. 3 Mar. 1, 1998.

Matsushita, et al. "Adeno-Associated Virus Vectors Can Be Efficiently Produced Without Helper Virus" Gene Therapy, Nature Publishing Group, vol. 5 No. 7 Jul. 1, 1998.

International Search Report and Written Opinion, Issued in International Patent Application No. PCT/US2023/064152 Mail date Jun. 27, 2023.

Douglas McCarty, et al.; "Sequences Required for Coordinate Induction of Adeno-Associated Virus p19 and p40 Promoters by Rep Protein"; Journal of Virology 1991 pp. 2936-2945 vol. 65 No. 6.

Richard Samulski, et al.; "Helper-Free Stocks of Recombinant Adeno-Associated Viruses: Normal Integration Does Not Require Viral Gene Expression"; Journal of Virology 1989 pp. 3822-3828; vol. 63 No. 9.

* cited by examiner

*Primary Examiner* — Anna Skibinsky
*Assistant Examiner* — Catherine L Mccormick
(74) *Attorney, Agent, or Firm* — Michael Ye; Kalos Athena Wang PLLC

(57) ABSTRACT

Expression constructs and methods for recombinant parvovirus production are disclosed. In some embodiments, the expression construct encodes (1) adenovirus E4 and E2a proteins, (2) parvovirus proteins necessary for the production of the recombinant parvovirus, and (3) a recombinant parvovirus genome, thus allowing production of the recombinant parvovirus by transfecting a host cell with a single expression construct.

20 Claims, 42 Drawing Sheets

Specification includes a Sequence Listing.

```
P5-AAV2  GGTCCTGTATTAGAGGTCA-CGTGAGTGTTTTGCGACATTTTGCGACACCATGTGGTCACGCTG-GGTAT
P5I      GGTCCTGTATTAGAGGTCAACGTGAGTGTTTTGCGACATTTTGCGACACCATGTGGTCACGCTGAGGTAT

P5-AAV2  TTAAGCCCGAGTGAGCACGCAGG--GT---CTCCATTTTGAAGCGGGAGGTTTGAACGCGCAGCCGCC 131 (SEQ ID NO:14)
P5I      ATATGGCCGAGTGAGCGAGCAGGATGCAACCTCCATTTTGAC  CGCGAAATTTGAACGAGCAGCCGCC 137 (SEQ ID NO:15)
```

| | Experiment1 | Experiment2 | Experiment3 | Experiment4 | Experiment5 | Experiment6 | AVERAGE Titers(VG/ml) | rcAAV(VG/ml) |
|---|---|---|---|---|---|---|---|---|
| P5-AAV2 | 5.60E+11 | 5.97E+11 | 7.69E+11 | 3.73E+11 | 3.79E+11 | 5.09E+11 | 5.31±0.15*E+11 | |
| P5I | 6.59E+11 | 6.44E+11 | 8.00E+11 | 6.65E+11 | 6.76E+11 | 8.60E+11 | 7.17±0.90*E+11 | |

SEQ ID NO:1
D2-1275 bp Ad2 sequence
CCCTGGCTTCGGGTTCTATGTAAACTCCTTCATGCGCCGCTGCCCTGATAACATCCACCACCGCAGAA
TAAGCCACACCCAGCCAACCTACACATTCGTTCTGCGAGTCACACACGGGAGGAGCGGGAAGAGCT
GGAAGAACCATGTTTTTTTTTTTTTATTCCAAAAGATTATCCAAAACCTCAAAATGAAGATCTATTAAG
TGAACGCGCTCCCCTCCGGTGGCGTGGTCAAACTCTACAGCCAAAGAACAGATAATGGCATTTGTAA
GATGTTGCACAATGGCTTCCAAAAGGCAAACTGCCCTCACGTCCAAGTGGACGTAAAGGCTAAACCC
TTCAGGGTGAATCTCCTCTATAAACATTCCAGCACCTTCAACCATGCCCAAATAATTTTCATCTCGCCA
CCTTATCAATATGTCTCTAAGCAAATCCCGAATATTAAGTCCGGCCATTGTAAAAATCTGCTCCAGAG
CGCCCTCCACCTTCAGCCTCAAGCAGCGAATCATGATTGCAAAAATTCAGGTTCCTCACAGACCTGTA
TAAGATTCAAAAGCGGAACATTAACAAAAATACCGCGATCCCGTAGGTCCCTTCGCAGGGCCAGCT
GAACATAATCGTGCAGGTCTGCACGGACCAGCGCGGCCACTTCCCCGCCAGGAACCATGACAAAAG
AACCCACACTGATTATGACACGCATACTCGGAGCTATGCTAACCAGCGTAGCCCCTATGTAAGCTTG
TTGCATGGGCGGCGATATAAAATGCAAGGTGCTGCTCAAAAAATCAGGCAAAGCCTCGCGCAAAAA
AGCAAGCACATCGTAGTCATGCTCATGCAGATAAAGGCAGGTAAGTTCCGGAACCACCACAGAAAA
AGACACCATTTTTCTCTCAAACATGTCTGCGGGTTCCTGCATTAAACACAAAATAAAATAACAAAAAA
AAAAACATTTAAACATTAGAAGCCTGTCTTACAACAGGAAAAACAACCCTTATAAGCATAAGACGGA
CTACGGCCATGCCGGCGTGACCGTAAAAAAACTGGTCACCGTGATTAAAAAGCACCACCGACAGTT
CCTCGGTCATGTCCGGAGTCATAATGTAAGACTCGGTAAACACATCAGGTTGGTTAACATCGGTCAG
TGCTAAAAAGCGACCGAAATAGCCCGGGGGAATACATACCCGCAGGCGTAGAGACAACATTACAGC
CCCCATAGGAGGTATAACAAAATTAATAGGAGAGAAAAACACATAAACACCTGAAAAACCCTCCTG
CC

SEQ ID NO:2
D1-711 bp Ad2 sequence
CTACATGGGGGTAGAGTCATAATCGTGCATCAGGATAGGGCGGTGGTGCTGCAGCAGCGCGCGAA
TAAACTGCTGCCGCCGCCGCTCCGTCCTGCAGGAATACAACATGGCAGTGGTCTCCTCAGCGATGAT
TCGCACCGCCCGCAGCATGAGACGCCTTGTCCTCCGGGCACAGCAGCGCACCCTGATCTCACTTAAA
TCAGCACAGTAACTGCAGCACAGCACCACAATATTGTTCAAAATCCCACAGTGCAAGGCGCTGTATC
CAAAGCTCATGGCGGGGACCACAGAACCCACGTGGCCATCATACCACAAGCGCAGGTAGATTAAGT
GGCGACCCCTCATAAACACGCTGGACATAAACATTACCTCTTTTGGCATGTTGTAATTCACCACCTCC
CGGTACCATATAAACCTCTGATTAAACATGGCGCCATCCACCACCATCCTAAACCAGCTGGCCAAAA
CCTGCCCGCCGGCTATGCACTGCAGGGAACCGGGACTGGAACAATGACAGTGGAGAGCCCAGGAC
TCGTAACCATGGATCATCATGCTCGTCATGATATCAATGTTGGCACAACACAGGCACACGTGCATAC
ACTTCCTCAGGATTACAAGCTCCTCCCGCGTCAGAACCATATCCCAGGGAACAACCCATTCCTGAATC
AGCGTAAATCCCACACTGCAGGGAAGACCTCGCACGTAACTCAC

FIG. 14 (CONT.)

SEQ ID NO:3
D3-1897 bp Ad2 sequence
TACAAATTTGCGAAGGTAAGCCGACGTCCACAGCCCCGGAGTGAGTTTCAACCCCGGAGCCGCGGA
CTTTTCGTCAGGCGAGGGACCCTGCAGCTCAAAGGTACCGATAATTTGACTTTCGCTAAGCAGTTGC
GAATTGCAGACCAGGGAGCGGTGCGGGGTGCATAGGTTGCAGCGACAGTGACACTCCAGTAGGCC
GTCACCG
CTCACGTCTTCCATGATGTCGGAGTGGTAGGCAAGGTAGTTGGCTAGCTGCAGAAGGTAGCAGTGA
CCCCAAAGCGGCGGAGGGCATTCACGGTACTTAATGGGCACAAAGTCGCTAGGAAGCGCACAGCA
GGTGGCGGGCAGAATTCCTGAACGCTCTAGGATAAAGTTCCTAAAGTTTTGCAACATGCTTTGACTG
GTGAAGTCTGGCAGACCCTGTTGCAGGGTTTTAAGCAGGCGTTCGGGGAAGATAATGTCCGCCAGG
TGCGCGGCCACGGAGCGCTCGTTGAAGGCCGTCCATAGGTCCTTCAAGTTTTGCTTTAGCAGCTTCT
GCAGCTCCTTTAGGTTGCGCTCCTCCAGGCATTGCTGCCACACGCCCATGGCCGTTTGCCAGGTGTA
GCACAGAAATAAGTAAACGCAGTCGCGGACGTAGTCGCGGCGCGCCTCGCCCTTGAGCGTGGAATG
AAGCACGTTTTGCCCGAGGCGGTTTTCGTGCAAAATTCCAAGGTAGGAGACCAGGTTGCAGAGCTC
CACGTTGGAAATTTTGCAGGCCTGGCGCACGTAGCCCTGGCGAAAGGTGTAGTGCAACGTTTCCTCT
AGCTTGCGCTGCATCTCCGGGTCAGCAAAGAACCGCTGCATGCACTCAAGCTCCACGGTAACAAGCA
CTGCGGCCATCATTAGCTTGCGTCGCTCCTCCAAGTCGGCAGGCTCGCGCGTCTCAAGCCAGCGCGC
CAGCTGCTCATCGCCAACTGCGGGTAGGCCCTCCTCGGTTTGTTCTTGCAAGTTTGCATCCCTCTCCA
GGGGTCGTGCACGGCGCACGATCAGCTCGCTCATGACTGTGCTCATAACCTTGGGGGGTAGGTTAA
GTGCCGGGTAGGCAAAGTGGGTGACCTCGATGCTGCGTTTCAGCACGGCTAGGCGCGCGTTGTCAC
CCTCAAGTTCCACCAGCACTCCACAGTGACTTTCATTTTCGCTGTTTTCTTGTTGCAG

SEQ ID NO:4
Codon optimized Ad2 E2a coding sequence
ATGGCCAGTCGGGAAGAGGAGCAGCGCGAAACCACCCCCGAGCGCGGACGCGGTGCGGCGCGAC
GTCCACCAACCATGGAGGACGTGTCGTCCCCGTCGCCGTCGCCGCCGCCTCCCCGCGCGCCCCCAAA
AAAGAGACTGCGGAGACGCCTGGAGTCCGAGGACGAGGAAGACAGTTCCCAGGACGCTCTGGTGC
CTAGGACACCATCTCCAAGACCCTCCACTTCCACCGCCGACCTGGCCATTGCCAGCAAAAAAAAGAA
GAAGAGGCCCTCCCCTAAACCTGAACGACCACCCAGCCCAGAAGTGATCGTGGACTCAGAGGAAGA
GCGCGAGGACGTCGCTCTGCAGATGGTGGGATTCAGCAATCCACCTGTGCTCATCAAGCACGGCAA
AGGGGGAAAACGGACCGTGCGCAGGCTGAACGAGGATGATCCTGTGGCAAGGGGCATGAGGACA
CAGGAGGAGAAGGAAGAATCCTCCGAGGCCGAGAGCGAGAGCACAGTGATTAATCCACTGTCCCT
GCCAATTGTGAGCGCTTGGGAGAAGGGAATGGAGGCCGCCCGGGCCCTGATGGACAAGTACCACG
TGGACAACGACCTGAAGGCTAATTTCAAACTGCTGCCTGACCAGGTGGAGGCCCTGGCTGCCGTGT
GCAAGACATGGCTGAATGAGGAGCATAGAGGGCTGCAGCTGACCTTTACATCAAACAAGACCTTTG
TGACCATGATGGGCAGGTTTCTGCAGGCCTACCTGCAATCTTTCGCCGAAGTGACTTACAAGCACCA
CGAGCCCACCGGCTGCGCCCTGTGGCTGCACAGATGCGCCGAGATTGAGGGCGAGCTGAAATGCCT
GCACGGCTCTATCATGATTAACAAGGAGCACGTGATCGAGATGGATGTGACTTCCGAAAACGGCCA
GCGCGCCCTGAAGGAGCAGTCCAGCAAGGCCAAGATCGTGAAGAACAGGTGGGGCAGGAACGTG
GTGCAGATTTCTAACACAGACGCCAGATGTTGCGTGCATGACGCCGCCTGCCCTGCCAATCAGTTTA
GCGGCAAGAGCTGCGGAATGTTCTTCAGCGAGGGAGCCAAGGCGCAAGTGGCCTTCAAGCAGATC
AAGGCCTTCATGCAAGCCCTGTATCCAAATGCCCAGACCGGCC

FIG. 14 (CONT.)

ACGGCCACCTCCTGATGCCCCTGCGCTGCGAATGTAACTCCAAGCCCGGCCACGCCCCTTTCCTGGG
CAGGCAGCTGCCAAAACTGACCCCTTTTGCCCTGAGCAACGCCGAAGATCTGGATGCCGATCTGATC
AGCGACAAGTCCGTGCTGGCCTCCGTTCACCACCCCGCCCTGATCGTGTTCCAGTGCTGCAATCCCGT
GTACAGGAATAGCAGAGCTCAGGGTGGAGGCCCCAACTGCGACTTCAAGATCTCCGCCCCAGATCT
GCTGAACGCTCTCGTGATGGTGCGGAGCCTGTGGTCTGAGAACTTCACAGAGCTGCCCCGCATGGT
GGTGCCCGAGTTCAAGTGGAGCACTAAGCATCAGTACCGGAATGTGTCTCTGCCCGTGGCCCACTCT
GACGCCAGACAGAATCCTTTTGACTTCTGA

SEQ ID NO:5

Wild-type Ad2 E2a amino acid sequence

MASREEEQRETTPERGRGAARRPPTMEDVSSPSPSPPPPRAPPKKRLRRRLESEDEEDSSQDALVPRTPS
PRPSTSTADLAIASKKKKKRPSPKPERPPSPEVIVDSEEEREDVALQMVGFSNPPVLIKHGKGGKRTVRRL
NEDDPVARGMRTQEEKEESSEAESESTVINPLSLPIVSAWEKGMEAARALMDKYHVDNDLKANFKLLPD
QVEALAAVCKTWLNEEHRGLQLTFTSNKTFVTMMGRFLQAYLQSFAEVTYKHHEPTGCALWLHRCAEI
EGELKCLHGSIMINKEHVIEMDVTSENGQRALKEQSSKAKIVKNRWGRNVVQISNTDARCCVHDAACP
ANQFSGKSCGMFFSEGAKAQVAFKQIKAFMQALYPNAQTGHGHLLMPLRCECNSKPGHAPFLGRQLP
KLTPFALSNAEDLDADLISDKSVLASVHHPALIVFQCCNPVYRNSRAQGGGPNCDFKISAPDLLNALVMV
RSLWSENFTELPRMVVPEFKWSTKHQYRNVSLPVAHSDARQNPFDF*

SEQ ID NO:6 mini-pHelper plasmid sequence

GGATCCATCGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTT
CGCCCTTTGACGTTGGAGTCCACGTTCTTTAATAGTGGACTCTTGTTCCAAACTGGAACAACACTCAA
CCCTATCTCGGTCTATTCTTTTGATTTATAAGGGATTTTGCCGATTTCGGCCTATTGGTTAAAAAATGA
GCTGATTTAACAAAAATTTAACGCGAATTTTAACAAAATATTAACGCTTACAATTTAGGTGGCACTTT
TCGGGGAAATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGATTGAACAAGATG
GATTGCACGCAGGTTCTCCGGCCGCTTGGGTGGAGAGGCTATTCGGCTATGACTGGGCACAACAGA
CAATCGGCTGCTCTGATGCCGCCGTGTTCCGGCTGTCAGCGCAGGGGCGCCCGGTTCTTTTTGTCAA
GACCGACCTGTCCGGTGCCCTGAATGAACTGCAAGACGAGGCAGCGCGGCTATCGTGGCTGGCCAC
GACGGGCGTTCCTTGCGCAGCTGTACTCGACGTTGTCACTGAAGCGGGAAGGGACTGGCTGCTATT
GGGCGAAGTGCCGGGGCAGGATCTCCTGTCATCTCACCTTGCTCCTGCCGAGAAAGTATCCATCATG
GCTGATGCAATGCGGCGGCTGCATACGCTTGATCCGGCTACCTGCCCATTCGACCACCAAGCGAAAC
ATCGCATCGAGCGAGCACGTACTCGGATGGAAGCCGGTCTTGTCGATCAGGATGATCTGGACGAAG
AGCATCAGGGGCTCGCGCCAGCCGAACTGTTCGCCAGGCTCAAGGCGAGCATGCCCGACGGCGAG
GATCTCGTCGTGACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTTGGCTACCCGTG
ATATTGCTGAAGAGCTTGGCGGCGAATGGGCTGACCGCTTCCTCGTG

FIG. 14 (CONT.)

CTTTACGGTATCGCCGCTCCCGATTCGCAGCGCATCGCCTTCTATCGCCTTCTTGACGAGTTCTTCTGA
CTGTCAGACCAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTCCACTGAGC
GTCAGACCCCGTAGAAAAGATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTTCTTCTAGTGTAGCCGTAGTTA
GGCCACCACTTCAAGAACTCTGTAGCACCGCCTACATACCTCGCTCTGCTAATCCTGTTACCAGTGGC
TGCTGCCAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTATTACCGCCTTTG
AGTGAGCTGATCATATGGTTTAAACGTCGACGTAATCCGTAGATGTACCTGGACATCCAGGTGATGC
CGGCGGCGGTGGTGGAGGCGCGCGGAAAGTCGCGGACGCGGTTCCAGATGTTGCGCAGCGGCAA
AAAGTGCTCCATGGTCGGGACGCTCTGGCCGGTGAGGCGTGCGCAGTCGTTGACGCTCTAGACCGT
GCAAAAGGAGAGCCTGTAAGCGGGCACTCTTCCGTGGTCTGGTGGATAAATTCGCAAGGGTATCAT
GGCGGACGACCGGGGTTCGAACCCCGGATCCGGCCGTCCGCCGTGATCCATGCGGTTACCGCCCGC
GTGTCGAACCCAGGTGTGCGACGTCAGACAACGGGGGAGCGCTCCTTTTGGCTTCCTTCCAGGCGC
GGCGGCTGCTGCGCTAGCTTTTTTGGCCACTGGCCGCGCGCGGCGTAAGCGGTTAGGCTGGAAAGC
GAAAGCATTAAGTGGCTCGCTCCCTGTAGCCGGAGGGTTATTTTCCAAGGGTTGAGTCGCAGGACC
CCCGGTTCGAGTCTCGGGCCGGCCGGACTGCGGCGAACGGGGGTTTGCCTCCCCGTCATGCAAGAC
CCCGCTTGCAAATTCCTCCGGAAACAGGGACGAGCCCCTTTTTTGCTTTTCCCAGATGCATCCGGTGC
TGCGGCAGATGCGCCCCCCTCCTCAGCAGCGGCAAGAGCAAGAGCAGCGGCAGACATGCAGGGCA
CCCTCCCCTTCTCCTACCGCGTCAGGAGGGGCAACATCCTACATCGATTCTAGTGAATCCACAGAAAC
TAGCGAGGTAAGCACTTACTCTATGTCTTTTACATGGTCCTGGGAAAGTGGAAAATACACCACTGAA
ACTTTTGCTACCAACTCTTACACCTTCTCCTACATTGCCCAGGAATAAAGAATCGTGAACCTGTTGCAT
GTTATGTTTCAACGTGTTTATTTTTCAATTGCAGAAAATTTCAAGTCATTTTTCATTCAGTAGTATAGC
CCCACCACCACATAGCTTATATTGATCACCGTACCTTAATCAAACTCACAGAACCCTAGTATTCAACCT
GCCACCTCCCTCCCAACACACAGAGTACACAGTCCTTTCTCCCCGGCTGGCCTTAAAAAGCATCATAT
CATGGGTAACAGACATATTCTTAGGTGTTATATTCCACACGGTTTCCTGTCGAGCCAAACGCTCATCA
GTGATATTAATAAACTCCCCGGGCAGCTCGCTTAAGTTCATGTCGCTGTCCAGCTGCTGAGCCACAG
GCTGCTGTCCAACTTGCGGTTGCTCAACGGGCGGCGAAGGGGAAGTCCACGCGTTGTGCATTGTCA
AAGTGTTACATTCGGGCAGCAGCGGATGATCCTCCAGTATGGTAGCGCGGGTCTCTGTCTCAAAAG
GAGGTAGGCGATCCCTACTGTACGGAGTGCGCCGAGACAACCGAGATCGTGTTGGTCGTAGTGTCA
TGCCAAATGGAACGCCGGACGTAGTCATATTTCCTGAAGCAAAACCAGGTGCGGGCGTGACAAACA
GATCTGCGTCTCCGGTCTGGTCGCTTAGCTCGCTCTGTGTAGTAGTTGTAGTATATCCACTCTCTCAA
AGCATCCAGGCGCCTAGGCAAAATAGCACCCTCCCGCTCCAGAACAACATACAGCGCTTCCACAGCG
GCAGCCATAACAGTCAGCCTTACCAGTAAAAAAACCTATTAAAAAACACCACTCGACACGGCACCAG
CTCAATCAGTCACAGTGTAAAAAGGGCCAAGTACAGAGCGAGTATATATAGGACTAAAAAATGACG
TAACGGTTAAAGTCCACAAAAAACACCCAGAAAACCGCACGCGAACCTACGCCCAGAAACGAAAGC
CAAAAAACCCACAACTTCCTCAAATCTTCACTTCCG

FIG. 14 (CONT.)

TTTTCCCACGATACGTCACTTCCCATTTTAAAAAAACTACAATTCCCAATACATGCAAGTTACTCCGCC
CTAAAACGCCCGGGCGACCGCACCCTGTGACGAAAGCCGCCCGCAAGCTGCGCCCCTGAGTTAGTC
ATCTGAACTTCGGCCTGGGCGTCTCTGGGAAGTACCACAGTGGTGGGAGCGGGACTTTCCTGGTAC
ACCAGGGCAGCGGGCCAACTACGGGGATTAAGGTTATTACGAGGTGTGGTGGTAATAGCCGCCTGT
TCGAGGAGAATTCGGTTTCGGTGGGCGCGGATTCCGTTGACCCGGGATATCATGTGGGGTCCCGCG
CTCATGTAGTTTATTCGGGTTGAGTAGTCTTGGGCAGCTCCAGCCGCAAGTCCCATTTGTGGCTGGT
AACTCCACATGTAGGGCGTGGGAATTTCCTTGCTCATAATGGCGCTGACGACAGGTGCTGGCGCCG
GGTGTGGCCGCTGGAGATGACGTAGTTTTCGCGCTTAAATTTGAGAAAGGGCGCGAAACTAGTCCT
TAAGAGTCAGCGCGCAGTATTTGCTGAAGAGAGCCTCCGCGTCTTCCAGCGTGCGCCGAAGCTGAT
CTTCGCTTTTGTGATACAGGCAGCTGCGGGTGAGGGAGCGCAGAGACCTGTTTTTTATTTTCAGCTC
TTGTTCTTGGCCCCTGCTTTGTTGAAATATAGCATACAGAGTGGGAAAAATCCTATTTCTAAGCTCGC
GGGTCGATACGGGTTCGTTGGGCGCCAGACGCAGCGCTCCTCCTCCTGCTGCTGCCGCCGCTGTGG
ATTTCTTGGGCTTTGTCAGAGTCTTGCTATCCGGTCGCCTTTGCTTCTGTGTGACCGCTGCTGTTGCTG
CCGCTGCCGCTGCCGCCGGTGCAGTAGGGGCTGTAGAGATGACGGTAGTAATGCAGGATGTTACG
GGGGAAGGCCACGCCGTGATGGTAGAGAAGAAAGCGGCGGGCGAAGGAGATGTTGCCCCCACAG
TCTTGCAAGCAAGCAACTATGGCGTTCTTGTGCCCGCGCCACGAGCGGTAGCCTTGGCGCTGTTGTT
GCTCTTGGGCTAACGGCGGCGGCTGCTTAGACTTACCGGCCCTGGTTCCAGTGGTGTCCCATCTACG
GTTGGGTCGGCGAACAGGCAGTGCCGGCGGCGCCTGAGGAGCGGAGGTTGTAGCGATGCTGGGA
ACGGTTGCCAATTTCTGGGGCGCCGGCGAGGGGAATGCGACCGAGGGTGACGGTGTTTCGTCTGA
CACCTCTTCGGCCTCGGAAGCTTCGTCTAGGCTGTCCCAGTCTTCCATCATCTCCTCCTCCTCGTCCAA
AACCTCCTCTGCCTGACTGTCCCAGTATTCCTCCTCGTCCGTGGGTGGCGGCGGCGGCAGCTGCAGC
TTCTTTTTGGGTGCCATCCTGGGAAGCAAGGGCCCGCGGCTGCTGATAGGGCTGCGGCGGCGGGG
GGATTGGGTTGAGCTCCTCGCCGGACTGGGGGTCCAGGTAAACCCCCCGTCCCTTTCGTAGCAGAA
ACTCTTGGCGGGCTTTGTTGATGGCTTGCAATTGGCCAAGGATGTGGCCCTGGGTAATGACGCAGG
CGGTAAGCTCCGCATTTGGCGGGCGGGATTGGTCTTCGTAGAACCTAATCTCGTGGGCGTGGTAGT
CCTCAGGGAGAAGGAAATGGCCAGTCGGGAAGAGGAGCAGCGCGAAACCACCCCCGAGCGCGGA
CGCGGTGCGGCGCGACGTCCACCAACCATGGAGGACGTGTCGTCCCCGTCGCCGTCGCCGCCGCCT
CCCCGCGCGCCCCCAAAAAAGAGACTGCGGAGACGCCTGGAGTCCGAGGACGAGGAAGACAGTTC
CCAGGACGCTCTGGTGCCTAGGACACCATCTCCAAGACCCTCCACTTCCACCGCCGACCTGGCCATT
GCCAGCAAAAAAAAGAAGAAGAGGCCCTCCCCTAAACCTGAACGACCACCCAGCCCAGAAGTGATC
GTGGACTCAGAGGAAGAGCGCGAGGACGTCGCTCTGCAGATGGTGGGATTCAGCAATCCACCTGT
GCTCATCAAGCACGGCAAAGGGGGAAAACGGACCGTGCGCAGGCTGAACGAGGATGATCCTGTGG
CAAGGGGCATGAGGACACAGGAGGAGAAGGAAGAATCCTCCGAGGCCGAGAGCGAGAGCACAGT
GATTAATCCACTGTCCCTGCCAATTGTGAGCGCTTGGGAGAAGGGAATGGAGGCCGCCCGGGCCCT
GATGGACAAGTACCACGTGGACAACGACCTGAAGGCTAATTTCAAACTGCTGCCTGACCAGGTGGA
GGCCCTGGCTGCCGTGTGCAAGACATGGCTGAATGAGGAGCATAGAGGGCTGCAGCTGACCTTTAC
ATCAAACAAGACCTTTGTGACCATGATGGGCAGGTTTCTGCAGGCCTACCTGCAATCTTTCGCCGAA
GTGACTTACAAGCACCACGAGCCCACCGGCTGCGCCCTGTGGCTGCACAGATGCGCCGAGATTGAG
GGCGAGCTGAAATGCCTGCACGGCTCTATCATGATTAACAAGGAGCACGTGATCGAGATGGATGTG
ACTTCCGAAAACGGCCAGCGCGCCCTGAAGGAGCAGTCCAGCAAGGCCAAGATCGTGAAGAACAG
GTGGGGCAGGAACGTGGTGCAGATTTCTAACACAGACGCCAGATGTTGCGTGCATGACGCCGCCTG
CCCTGCCAATCAGTTTAGCGGCAAGAGCTGCGGAATGT

FIG. 14 (CONT.)

TCTTCAGCGAGGGAGCCAAGGCGCAAGTGGCCTTCAAGCAGATCAAGGCCTTCATGCAAGCCCTGT
ATCCAAATGCCCAGACCGGCCACGGCCACCTCCTGATGCCCCTGCGCTGCGAATGTAACTCCAAGCC
CGGCCACGCCCCTTTCCTGGGCAGGCAGCTGCCAAAACTGACCCCTTTTGCCCTGAGCAACGCCGAA
GATCTGGATGCCGATCTGATCAGCGACAAGTCCGTGCTGGCCTCCGTTCACCACCCCGCCCTGATCG
TGTTCCAGTGCTGCAATCCCGTGTACAGGAATAGCAGAGCTCAGGGTGGAGGCCCCAACTGCGACT
TCAAGATCTCCGCCCCAGATCTGCTGAACGCTCTCGTGATGGTGCGGAGCCTGTGGTCTGAGAACTT
CACAGAGCTGCCCCGCATGGTGGTGCCCGAGTTCAAGTGGAGCACTAAGCATCAGTACCGGAATGT
GTCTCTGCCCGTGGCCCACTCTGACGCCAGACAGAATCCTTTTGACTTCTGAACGGCGCAGACGGCA
AGGGTGGGGGGTAAATAATCACCCGAGAGTGTACAAATAAAAACATTTGCCTTTATTGAAAGTGTCT
CCTAGTACATTATTTTTACATGTTTTTCAAGTGACAAAAAGAAGTGGCGCTCCTAATCTGCGCACTGT
GGCTGCGGAAGTAGGGCGAGTGGCGCTCCAGGAAGCTGTAGAGCTGTTCCTGGTTGCGACGCAGG
GTGGGCTGTACCTGGGGACTGTTAAGCATGGAGTTGGGTACC

SEQ ID NO:7

Codon optimized Ad2 E4orf6/7 coding sequence

ATGACCACAAGCGGCGTGCCCTTTGGCATGACCCTGAGGCCAACCAGGAGCAGGCTGTCCAGACGC
ACACCATACAGCAGGGACCGGCTGCCTCCTTTCGAGACAGAGACCAGAGCCACTATCCTCGAGGAT
CATCCTCTGCTGCCTGAGTGCAATACACTGACCATGCACAATGCCTGGACCTCCCCTTCCCCCCCCGT
GGAACAGCCACAGGTGGGACAGCAGCCTGTGGCCCAGCAGCTGGACAGCGACATGAACCTGAGCG
AACTGCCCGGCGAGTTCATCAATATCACCGACGAGAGACTGGCCAGACAGGAGACCGTGTGGAATA
TCACCCCCAAAAATATGAGCGTGACCCACGACATGATGCTGTTCAAAGCCAGCCGGGGCGAGAGAA
CCGTGTACAGCGTGTGCTGGGAGGGCGGCGGAAGACTGAATACTAGGGTGCTGTGA

SEQ ID NO:8

Wild-type Ad2 E4orf6/7 amino acid sequence

MTTSGVPFGMTLRPTRSRLSRRTPYSRDRLPPFETETRATILEDHPLLPECNTLTMHNAWTSPSPPVEQP
QVGQQPVAQQLDSDMNLSELPGEFINITDERLARQETVWNITPKNMSVTHDMMLFKASRGERTVYSV
CWEGGGRLNTRVL*

SEQ ID NO: 9

Mini pHelper 1.0

TTTGGCTTCCTTCCAGGCGCGGCGGCTGCTGCGCTAGCTTTTTTGGCCACTGGCCGCGCGCGGCGTA
AGCGGTTAGGCTGGAAAGCGAAAGCATTAAGTGGCTCGCTCCCTGTAGCCGGAGGGTTATTTTCCA
AGGGTTGAGTCGCAGGACCCCCGGTTCGAGTCTCGGGCCGGCCGGACTGCGGCGAACGGGGGTTT
GCCTCCCCGTCATGCAAGACCCCGCTTGCAAATTCCTCCGGAAACAGGGACGAGCCCCTTTTTTGCTT
TTCCCAGATGCATCCGGTGCTGCGGCAGATGCGCCCCCCTCCTCAGCAGCGGCAAGAGCAAGAGCA
GCGGCAGACATGCAGGGCACCCTCCCCTTCTCCTACCGCGTCAGGAGGGGCAACATCCTACATCGAT
TCTAGTGAATCCACAGAAACTAGCGAGGTAAGCACTTACTCTATGTCTTTTACATGGTCCTGGGAAA
GTGGAAAATACACCACTGAAACTTTTGCTACCAACTCTTACACCTTCTCCTACATTGCCCAGGAATAA
AGAATCGTGAACCTGTTGCATGTTATGTTTCAACGTGTTTATTTTTCAATTGCAGAAAATTTCAAGTC
ATTTTTCATTCAGTAGTATAGCCCCACCACCACATAGCTTATATTGATCACCGTACCTTAATCAAACTC
ACAGAACCCTAGTATTCAACCTGCCA

FIG. 14 (CONT.)

CCTCCCTCCCAACACACAGAGTACACAGTCCTTTCTCCCCGGCTGGCCTTAAAAAGCATCATATCATG
GGTAACAGACATATTCTTAGGTGTTATATTCCACACGGTTTCCTGTCGAGCCAAACGCTCATCAGTGA
TATTAATAAACTCCCCGGGCAGCTCGCTTAAGTTCATGTCGCTGTCCAGCTGCTGAGCCACAGGCTG
CTGTCCAACTTGCGGTTGCTCAACGGGCGGCGAAGGGGAAGTCCACGCCTACATGGGGGTAGAGTC
ATAATCGTGCATCAGGATAGGGCGGTGGTGCTGCAGCAGCGCGCGAATAAACTGCTGCCGCCGCCG
CTCCGTCCTGCAGGAATACAACATGGCAGTGGTCTCCTCAGCGATGATTCGCACCGCCCGCAGCATG
AGACGCCTTGTCCTCCGGGCACAGCAGCGCACCCTGATCTCACTTAAATCAGCACAGTAACTGCAGC
ACAGCACCACAATATTGTTCAAAATCCCACAGTGCAAGGCGCTGTATCCAAAGCTCATGGCGGGGAC
CACAGAACCCACGTGGCC
ATCATACCACAAGCGCAGGTAGATTAAGTGGCGACCCCTCATAAACACGCTGGACATAAACATTACC
TCTTTTGGCATGTTGTAATTCACCACCTCCCGGTACCATATAAACCTCTGATTAAACATGGCGCCATCC
ACCACCATCCTAAACCAGCTGGCCAAAACCTGCCCGCCGGCTATGCACTGCAGGGAACCGGGACTG
GAACAATGACAGTGGAGAGCCCAGGACTCGTAACCATGGATCATCATGCTCGTCATGATATCAATGT
TGGCACAACACAGGCACACGTGCATACACTTCCTCAGGATTACAAGCTCCTCCCGCGTCAGAACCAT
ATCCCAGGGAACAACCCATTCCTGAATCAGCGTAAATCCCACACTGCAGGGAAGACCTCGCACGTAA
CTCACGTTGTGCATTGTCAAAGTGTTACATTCGGGCAGCAGCGGATGATCCTCCAGTATGGTAGCGC
GGGTCTCTGTCTCAAAAGGAGGTAGGCGATCCCTACTGTACGGAGTGCGCCGAGACAACCGAGATC
GTGTTGGTCGTAGTGTCATGCCAAATGGAACGCCGGACGTAGTCATATTTCCTGAAGCAAAACCAG
GTGCGGGCGTGACAAACAGATCTGCGTCTCCGGTCTCGTCGCTTAGCTCGCTCTGTGTAGTAGTTGT
AGTATATCCACTCTCTCAAAGCATCCAGGCGCCTAGGCAAAATAGCACCCTCCCGCTCCAGAACAAC
ATACAGCGCTTCCACAGCGGCAGCCATAACAGTCAGCCTTACCAGTAAAAAAACCTATTAAAAAACA
CCACTCGACACGGCACCAGCTCAATCAGTCACAGTGTAAAAAGGGCCAAGTACAGAGCGAGTATAT
ATAGGACTAAAAAATGACGTAACGGTTAAAGTCCACAAAAAACACCCAGAAAACCGCACGCGAACC
TACGCCCAGAAACGAAAGCCAAAAAACCCACAACTTCCTCAAATCTTCACTTCCGTTTTCCCACGATA
CGTCACTTCCCATTTTAAAAAAACTACAATTCCCAATACATGCAAGTTACTCCGCCCTAAAACGCCCG
GGCGACCGCACCCTGTGACGAAAGCCGCCCGCAAGCTGCGCCCCTGAGTTAGTCATCTGAACTTCG
GCCTGGGCGTCTCTGGGAAGTACCACAGTGGTGGGAGCGGGACTTTCCTGGTACACCAGGGCAGC
GGGCCAACTACGGGGATTAAGGTTATTACGAGGTGTGGTGGTAATAGCCGCCTGTTCGAGGAGAAT
TCGGTTTCGGTGGGCGCGGATTCCGTTGACCCGGGATATCATGTGGGGTCCCGCGCTCATGTAGTTT
ATTCGGGTTGAGTAGTCTTGGGCAGCTCCAGCCGCAAGTCCCATTTGTGGCTGGTAACTCCACATGT
AGGGCGTGGGAATTTCCTTGCTCATAATGGCGCTGACGACAGGTGCTGGCGCCGGGTGTGGCCGCT
GGAGATGACGTAGTTTTCGCGCTTAAATTTGAGAAAGGGCGCGAAACTAGTCCTTAAGAGTCAGCG
CGCAGTATTTGCTGAAGAGAGCCTCCGCGTCTTCCAGCGTGCGCCGAAGCTGATCTTCGCTTTTGTG
ATACAGGCAGCTGCGGGTGAGGGAGCGCAGAGACCTGTTTTTTATTTTCAGCTCTTGTTCTTGGCCC
CTGCTTTGTTGAAATATAGCATACAGAGTGGGAAAAATCCTATTTCTAAGCTCGCGGGTCGATACGG
GTTCGTTGGGCGCCAGACGCAGCGCTCCTCCTCCTGCTGCTGCCGCCGCTGTGGATTTCTTGGGCTTT
GTCAGAGTCTTGCTATCCGGTCGCCTTTGCTTCTGTGTGACCGCTGCTGTTGCTGCCGCTGCCGCTGC
CGCCGGTGCAGTAGGGGCTGTAGAGATGACGGTAGTAATGCAGGATGTTACGGGGGAAGGCCACG
CCGTGATGGTAGAGAAGAAAGCGGCGGGCGAAGGAGATGTTGCCCCCACAGTCTTGCAAGCAAGC
AACTATGGCGTTCTTGTGCCCGCGCCACGAGCGGTAGCCTTGGCGCTGTTGTTGCTCTTGGGCTAAC
GGCGGCGGCTGCTTAGACTTACCGGCCCTGGTTCCAGTGGTGTCCCATCTACGGTTGGGTCGGCGA
ACAGGCAGTGCCGGCGGCGCCTGAGGAGCGGAGGTTGTAGCGATGCTGGGAACGGTTGCCAATTT
CTGGGGCGCCGGCGAGGGGAATGCGACCGAGGGTGACGGTGTTTCGTCTGACACCTCTTCGGCCTC
GGAAGCTTCGTCTAGGCTG

FIG. 14 (CONT.)

TCCCAGTCTTCCATCATCTCCTCCTCCTCGTCCAAAACCTCCTCTGCCTGACTGTCCCAGTATTCCTCCT
CGTCCGTGGGTGGCGGCGGCGGCAGCTGCAGCTTCTTTTTGGGTGCCATCCTGGGAAGCAAGGGCC
CGCGGCTGCTGATAGGGCTGCGGCGGCGGGGGGATTGGGTTGAGCTCCTCGCCGGACTGGGGGTC
CAGGTAAACCCCCCGTCCCTTTCGTAGCAGAAACTCTTGGCGGGCTTTGTTGATGGCTTGCAATTGG
CCAAGGATGTGGCCCTGGGTAATGACGCAGGCGGTAAGCTCCGCATTTGGCGGGCGGGATTGGTCT
TCGTAGAACCTAATCTCGTGGGCGTGGTAGTCCTCAGGGAGAAGGAAATGGCCAGTCGGGAAGAG
GAGCAGCGCGAAACCACCCCCGAGCGCGGACGCGGTGCGGCGCGACGTCCACCAACCATGGAGGA
CGTGTCGTCCCCGTCGCCGTCGCCGCCGCCTCCCCGCGCGCCCCCAAAAAAGAGACTGCGGAGACG
CCTGGAGTCCGAGGACGA
GGAAGACAGTTCCCAGGACGCTCTGGTGCCTAGGACACCATCTCCAAGACCCTCCACTTCCACCGCC
GACCTGGCCATTGCCAGCAAAAAAAAGAAGAAGAGGCCCTCCCCTAAACCTGAACGACCACCCAGC
CCAGAAGTGATCGTGGACTCAGAGGAAGAGCGCGAGGACGTCGCTCTGCAGATGGTGGGATTCAG
CAATCCACCTGTGCTCATCAAGCACGGCAAAGGGGGAAAACGGACCGTGCGCAGGCTGAACGAGG
ATGATCCTGTGGCAAGGGGCATGAGGACACAGGAGGAGAAGGAAGAATCCTCCGAGGCCGAGAG
CGAGAGCACAGTGATTAATCCACTGTCCCTGCCAATTGTGAGCGCTTGGGAGAAGGGAATGGAGGC
CGCCCGGGCCCTGATGGACAAGTACCACGTGGACAACGACCTGAAGGCTAATTTCAAACTGCTGCCT
GACCAGGTGGAGGCCCTGGCTGCCGTGTGCAAGACATGGCTGAATGAGGAGCATAGAGGGCTGCA
GCTGACCTTTACATCAAACAAGACCTTTGTGACCATGATGGGCAGGTTTCTGCAGGCCTACCTGCAA
TCTTTCGCCGAAGTGACTTACAAGCACCACGAGCCCACCGGCTGCGCCCTGTGGCTGCACAGATGCG
CCGAGATTGAGGGCGAGCTGAAATGCCTGCACGGCTCTATCATGATTAACAAGGAGCACGTGATCG
AGATGGATGTGACTTCCGAAAACGGCCAGCGCGCCCTGAAGGAGCAGTCCAGCAAGGCCAAGATC
GTGAAGAACAGGTGGGGCAGGAACGTGGTGCAGATTTCTAACACAGACGCCAGATGTTGCGTGCA
TGACGCCGCCTGCCCTGCCAATCAGTTTAGCGGCAAGAGCTGCGGAATGTTCTTCAGCGAGGGAGC
CAAGGCGCAAGTGGCCTTCAAGCAGATCAAGGCCTTCATGCAAGCCCTGTATCCAAATGCCCAGACC
GGCCACGGCCACCTCCTGATGCCCCTGCGCTGCGAATGTAACTCCAAGCCCGGCCACGCCCCTTTCC
TGGGCAGGCAGCTGCCAAAACTGACCCCTTTTGCCCTGAGCAACGCCGAAGATCTGGATGCCGATCT
GATCAGCGACAAGTCCGTGCTGGCCTCCGTTCACCACCCCGCCCTGATCGTGTTCCAGTGCTGCAAT
CCCGTGTACAGGAATAGCAGAGCTCAGGGTGGAGGCCCCAACTGCGACTTCAAGATCTCCGCCCCA
GATCTGCTGAACGCTCTCGTGATGGTGCGGAGCCTGTGGTCTGAGAACTTCACAGAGCTGCCCCGC
ATGGTGGTGCCCGAGTTCAAGTGGAGCACTAAGCATCAGTACCGGAATGTGTCTCTGCCCGTGGCC
CACTCTGACGCCAGACAGAATCCTTTTGACTTCTGAACGGCGCAGACGGCAAGGGTGGGGGTAAA
TAATCACCCGAGAGTGTACAAATAAAAACATTTGCCTTTATTGAAAGTGTCTCCTAGTACATTATTTTT
ACATGTTTTTCAAGTGACAAAAAGAAGTGGCGCTCCTAATCTGCGCACTGTGGCTGCGGAAGTAGG
GCGAGTGGCGCTCCAGGAAGCTGTAGAGCTGTTCCTGGTTGCGACGCAGGGTGGGCTGTACCTGG
GGACTGTTAAGCATGGAGTTGGGTACCGGATCCATCGCGCCCTGTAGCGGCGCATTAAGCGCGGCG
GGTGTGGTGGTTACGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTAGGGTGATGGTTCACGTAG
TGGGCCATCGCCCTGATAGACGGTTTTTCGCCCTTTGACGTTGGAGTCCACGTTCTTTAATAGTGGAC
TCTTGTTCCAAACTGGAACAACACTCAACCCTATCTCGGTCTATTCTTTTGATTTATAAGGGATTTTGC
CGATTTCGGCCTATTGGTTAAAAAATGAGCTGATTTAACAAAAATTTAACGCGAATTTTAACAAAATA
TTAACGCTTACAATTTAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAATATTGAAA
AAGGAAGAGTatgattga

FIG. 14 (CONT.)

cggtatcgccgctcccgattcgcagcgcatcgccttctatcgccttcttgacgagttcttctgaCTGTCAGACCAAGTTTACTC
ATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTTGCAAACAAAAAAACCACCG
CTACCAGCGGTGGTTTGTTTGCCGGATCAAGAGCTACCAACTCTTTTTCCGAAGGTAACTGGCTTCA
GCAGAGCGCAGATACCAAATACTGTTCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATCATATGGTTTAA
ACGTCGACGTAATCCGTAGATGTACCTGGACATCCAGGTGATGCCGGCGGCGGTGGTGGAGGCGC
GCGGAAAGTCGCGGACGCGGTTCCAGATGTTGCGCAGCGGCAAAAAGTGCTCCATGGTCGGGACG
CTCTGGCCGGTGAGGCGTGCGCAGTCGTTGACGCTCTAGACCGTGCAAAAGGAGAGCCTGTAAGCG
GGCACTCTTCCGTGGTCTGGTGGATAAATTCGCAAGGGTATCATGGCGGACGACCGGGGTTCGAAC
CCCGGATCCGGCCGTCCGCCGTGATCCATGCGGTTACCGCCCGCGTGTCGAACCCAGGTGTGCGAC
GTCAGACAACGGGGGAGCGCTCCT

SEQ ID. NO.:10
Mini-pHelper-AAV2
GGTACCCAACTCCATGCTTAACAGTCCCCAGGTACAGCCCACCCTGCGTCGCAACCAGGAACAGCTC
TACAGCTTCCTGGAGCGCCACTCGCCCTACTTCCGCAGCCACAGTGCGCAGATTAGGAGCGCCACTT
CTTTTTGTCACTTGAAAAACATGTAAAAATAATGTACTAGGAGACACTTTCAATAAAGGCAAATGTTT
TTATTTGTACACTCTCGGGTGATTATTTACCCCCCACCCTTGCCGTCTGCGCCGTTCAGAAGTCAAAA
GGATTCTGTCTGGCGTCAGAGTGGGCCACGGGCAGAGACACATTCCGGTACTGATGCTTAGTGCTC
CACTTGAACTCGGGCACCACCATGCGGGGCAGCTCTGTGAAGTTCTCAGACCACAGGCTCCGCACCA
TCACGAGAGCGTTCAGCAGATCTGGGGCGGAGATCTTGAAGTCGCAGTTGGGGCCTCCACCCTGAG
CTCTGCTATTCCTGTACACGGGATTGCAGCACTGGAACACGATCAGGGCGGGGTGGTGAACGGAGG
CCAGCACGGACTTGTCGCTGATCAGATCGGCATCCAGATCTTCGGCGTTGCTCAGGGCAAAAGGGG
TCAGTTTTGGCAGCTGCCTGCCCAGGAAAGGGGCGTGGCCGGGCTTGGAGTTACATTCGCAGCGCA
GGGGCATCAGGAGGTGGCCGTGGCCGGTCTGGGCATTTGGATACAGGGCTTGCATGAAGGCCTTG
ATCTGCTTGAAGGCCACTTGCGCCTTGGCTCCCTCGCTGAAGAACATTCCGCAGCTCTTGCCGCTAAA
CTGATTGGCAGGGCAGGCGGCGTCATGCACGCAACATCTGGCGTCTGTGTTAGAAATCTGCACCAC
GTTCCTGCCCCACCTGTTCTTCACGATCTTGGCCTTGCTGGACTGCTCCTTCAGGGCGCGCTGGCCGT
TTTCGGAAGTCACATCCATCTCGATCACGTGCTCCTTGTTAATCATGATAGAGCCGTGCAGGCATTTC
AGCTCGCCCTCAATCTCGGCGCATCTGTGCAGCCACAGGGCGCAGCCGGTGGGCTCGTGGTGCTTG
TAAGTCACTTCGGCGAAAGATTGCAGGTAGGCCTGCAGAAACCTGCCCATCATGGTCACAAAGGTCT
TGTTTGATGTAAAGGTCAGCTGCAGCCCTCTATGCTCCTCATTCAGCCATGTCTTGCACACGGCAGCC
AGGGCCTCCACCTGGTCAGGCAGCAGTTTGAAATTAGCCTTCAGGTCGTTGTCCACGTGGTACTTGT
CCATCAGGGCCCGGGCGGCCTCCATTCCCTTCTCCCAAGCGCTCACA

FIG. 14 (CONT.)

ATTGGCAGGGACAGTGGATTAATCACTGTGCTCTCGCTCTCGGCCTCGGAGGATTCTTCCTTCTCCTC
CTGTGTCCTCATGCCCCTTGCCACAGGATCATCCTCGTTCAGCCTGCGCACGGTCCGTTTTCCCCCTTT
GCCGTGCTTGATGAGCACAGGTGGATTGCTGAATCCCACCATCTGCAGAGCGACGTCCTCGCGCTCT
TCCTCTGAGTCCACGATCACTTCTGGGCTGGGTGGTCGTTCAGGTTTAGGGGAGGGCCTCTTCTTCTT
TTTTTTGCTGGCAATGGCCAGGTCGGCGGTGGAAGTGGAGGGTCTTGGAGATGGTGTCCTAGGCAC
CAGAGCGTCCTGGGAACTGTCTTCCTCGTCCTCGGACTCCAGGCGTCTCCGCAGTCTCTTTTTTGGGG
GCGCGCGGGGAGGCGGCGGCGACGGCGACGGGGACGACACGTCCTCCATGGTTGGTGGACGTCG
CGCCGCACCGCGTCCGCGCTCGGGGGTGGTTTCGCGCTGCTCCTCTTCCCGACTGGCCATTTCCTTCT
CCCTGAGGACTACCACGCCCACGAGATTAGGTTCTACGAAGACCAATCCCGCCCGCCAAATGCGGA
GCTTACCGCCTGCGTCATTACCCAGGGCCACATCCTTGGCCAATTGCAAGCCATCAACAAAGCCCGC
CAAGAGTTTCTGCTACGAAAGGGACGGGGGGTTTACCTGGACCCCCAGTCCGGCGAGGAGCTCAAC
CCAATCCCCCCGCCGCCGCAGCCCTATCAGCAGCCGCGGGCCCTTGCTTCCCAGGATGGCACCCAAA
AAGAAGCTGCAGCTGCCGCCGCCGCCACCCACGGACGAGGAGGAATACTGGGACAGTCAGGCAGA
GGAGGTTTTGGACGAGGAGGAGGAGATGATGGAAGACTGGGACAGCCTAGACGAAGCTTCCGAG
GCCGAAGAGGTGTCAGACGAAACACCGTCACCCTCGGTCGCATTCCCCTCGCCGGCGCCCCAGAAA
TTGGCAACCGTTCCCAGCATCGCTACAACCTCCGCTCCTCAGGCGCCGCCGGCACTGCCTGTTCGCC
GACCCAACCGTAGATGGGACACCACTGGAACCAGGGCCGGTAAGTCTAAGCAGCCGCCGCCGTTAG
CCCAAGAGCAACAACAGCGCCAAGGCTACCGCTCGTGGCGCGGGCACAAGAACGCCATAGTTGCTT
GCTTGCAAGACTGTGGGGGCAACATCTCCTTCGCCCGCCGCTTTCTTCTCTACCATCACGGCGTGGCC
TTCCCCCGTAACATCCTGCATTACTACCGTCATCTCTACAGCCCCTACTGCACCGGCGGCAGCGGCAG
CGGCAGCAACAGCAGCGGTCACACAGAAGCAAAGGCGACCGGATAGCAAGACTCTGACAAAGCCC
AAGAAATCCACAGCGGCGGCAGCAGCAGGAGGAGGAGCGCTGCGTCTGGCGCCCAACGAACCCGT
ATCGACCCGCGAGCTTAGAAATAGGATTTTTCCCACTCTGTATGCTATATTTCAACAAAGCAGGGGC
CAAGAACAAGAGCTGAAAATAAAAAACAGGTCTCTGCGCTCCCTCACCCGCAGCTGCCTGTATCACA
AAAGCGAAGATCAGCTTCGGCGCACGCTGGAAGACGCGGAGGCTCTCTTCAGCAAATACTGCGCGC
TGACTCTTAAGGACTAGTTTCGCGCCCTTTCTCAAATTTAAGCGCGAAAACTACGTCATCTCCAGCGG
CCACACCCGGCGCCAGCACCTGTCGTCAGCGCCATTATGAGCAAGGAAATTCCCACGCCCTACATGT
GGAGTTACCAGCCACAAATGGGACTTGCGGCTGGAGCTGCCCAAGACTACTCAACCCGAATAAACT
ACATGAGCGCGGGACCCCACATGATATCCCGGGTCAACGGAATCCGCGCCCACCGAAACCGAATTC
TCCTCGAACAGGCGGCTATTACCACCACACCTCGTAATAACCTTAATCCCCGTAGTTGGCCCGCTGCC
CTGGTGTACCAGGAAAGTCCCGCTCCCACCACTGTGGTACTTCCCAGAGACGCCCAGGCCGAAGTTC
AGATGACTAACTCAGGGGCGCAGCTTGCGGGCGGCTTTCGTCACAGGGTGCGGTCGCCCGGGCGTT
TTAGGGCGGAGTAACTTGCATGTATTGGGAATTGTAGTTTTTTTAAAATGGGAAGTGACGTATCGTG
GGAAAACGGAAGTGAAGATTTGAGGAAGTTGTGGGTTTTTTGGCTTTCGTTTCTGGGCGTAGGTTC
GCGTGCGGTTTTCTGGGTGTTTTTTGTGGACTTTAACCGTTACGTCATTTTTTAGTCCTATATATACTC
GCTCTGTACTTGGCCCTTTTTACACTGTGACTGATTGAGCTGGTGCCGTGTCGAGTGGTGTTTTTTAA
TAGGTTTTTTTACTGGTAAGGCTGACTGTTATGGCTGCCGCTGTGGAAGCGCTGTATGTTGTTCTGG
AGCGGGAGGGTGCTATTTTGCCTAGGCGCCTGGATGCTTTGAGAGAGTGGATATACTACAACTACT
ACACAGAGCGAGCTAAGCGACGAGACCGGAGACGCAGATCTGTTTGTCACGCCCGCACCTGGTTTT
GCTTCAGGAAATATGACTACGTCCGGCGTTCCATTTGGCATGACACTACGACCAACACGATCTCGGT
TGTCTCGGCGCACTCCGTACAGTAGGGATCGCCTACCTCCTTTTGAGACAGAGACCCGCGCTACCAT
ACTGGAGGATCATCCGCTGCTGCCCGAATGTAACACTTTGACAATGCACAACGTGAGTTACGTGCGA
GGTCTTCCCTGCAGTGTGGGATTTACGCTGATTCA

FIG. 14 (CONT.)

GGAATGGGTTGTTCCCTGGGATATGGTTCTGACGCGGGAGGAGCTTGTAATCCTGAGGAAGTGTAT
GCACGTGTGCCTGTGTTGTGCCAACATTGATATCATGACGAGCATGATGATCCATGGTTACGAGTCC
TGGGCTCTCCACTGTCATTGTTCCAGTCCCGGTTCCCTGCAGTGCATAGCCGGCGGGCAGGTTTTGG
CCAGCTGGTTTAGGATGGTGGTGGATGGCGCCATGTTTAATCAGAGGTTTATATGGTACCGGGAGG
TGGTGAATTACAACATGCCAAAAGAGGTAATGTTTATGTCCAGCGTGTTTATGAGGGGTCGCCACTT
AATCTACCTGCGCTTGTGGTATGATGGCCACGTGGGTTCTGTGGTCCCCGCCATGAGCTTTGGATAC
AGCGCCTTGCACTGTGGGATTTTGAACAATATTGTGGTGCTGTGCTGCAGTTACTGTGCTGATTTAA
GTGAGATCAGGGTGCGCTGCTGTGCCCGGAGGACAAGGCGTCTCATGCTGCGGGCGGTGCGAATC
ATCGCTGAGGAGACCACTGCCATGTTGTATTCCTGCAGGACGGAGCGGCGGCGGCAGCAGTTTATT
CGCGCGCTGCTGCAGCACCACCGCCCTATCCTGATGCACGATTATGACTCTACCCCCATGTAGGCGT
GGACTTCCCCTTCGCCGCCCGTTGAGCAACCGCAAGTTGGACAGCAGCCTGTGGCTCAGCAGCTGG
ACAGCGACATGAACTTAAGCGAGCTGCCCGGGGAGTTTATTAATATCACTGATGAGCGTTTGGCTCG
ACAGGAAACCGTGTGGAATATAACACCTAAGAATATGTCTGTTACCCATGATATGATGCTTTTTAAG
GCCAGCCGGGGAGAAAGGACTGTGTACTCTGTGTGTTGGGAGGGAGGTGGCAGGTTGAATACTAG
GGTTCTGTGAGTTTGATTAAGGTACGGTGATCAATATAAGCTATGTGGTGGTGGGGCTATACTACTG
AATGAAAAATGACTTGAAATTTTCTGCAATTGAAAAATAAACACGTTGAAACATAACATGCAACAGG
TTCACGATTCTTTATTCCTGGGCAATGTAGGAGAAGGTGTAAGAGTTGGTAGCAAAAGTTTCAGTGG
TGTATTTTCCACTTTCCCAGGACCATGTAAAAGACATAGAGTAAGTGCTTACCTCGCTAGTTTCTGTG
GATTCACTAGAgcggccgcggtcctgtattagAGGTCAACGTGAGTGTTTTGCGACATTTTGCGACACCATG
TGGTCACGCtgaggtatatatggccgagtgagcgagcaggatGCAACctccattttgAccgcgaaAtttgaacgagcagccg
ccaTgCcggggttttacgagattgtgattaaggtccccagcgaccttgacgAgcatctgcccggcatttctgacagctttgtgaactg
ggtggccgagaaggaatgggagttgccgccagattctgacatggatctgaatctgattgagcaggcacccctgaccgtggccgaga
agctgcagcgcgactttctgacggaatggcgccgtgtgagtaaggcAccggaggcccttttctttgtgcaatttgagaagggagag
agctacttccacatgcacgtgctcgtggaaaccaccggggtgaaatccatggttttgggacgtttcctgagtcagattcgcgaaaaa
ctgattcagagaatttaccgcgggatcgagccgactttgccaaactggttcgcggtcacaaagaccagaaatggcgccggaggcgg
gaacaaggtggtggatgagtgctacatccccaattacttgctccccaaaacccagcctgagctccagtgggcgtggactaatatgga
acagtatttaagcgcctgtttgaatctcacggagcgtaaacggttggtggcgcagcatctgacgcacgtgtcgcagacgcaggagc
agaacaaagagaatcagaatcccaattctgatgcgccggtgatcagatcaaaaacttcagccaggtacatggagctggtcgggtg
gctcgtggacaaggggattacctcggagaagcagtggatccaggaggaccaggcctcatacatctccttcaatgcggcctccaact
cgcggtcccaaatcaaggctgccttggacaatgcgggaaagattatgagcctgactaaaaccgcccccgactacctggtgggccag
cagcccgtggaggacatttccagcaatcggatttataaaattttggaactaaacgggtacgatccccaatatgcggcttccgtctttc
tgggatgggccacgaaaaagttcggcaagaggaacaccatctggctgtttgggcctgcaactaccgggaagaccaacatcgcgga
ggccatagcccacactgtgcccttctacgggtgcgtaaactggaccaatgagaactttcccttcaacgactgtgtcgacaagatggt
gatctggtgggaggaggggaagatgaccgccaaggtcgtggagtcggccaaagccattctcggaggaagcaaggtgcgcgtgga
ccagaaatgcaagtcctcggcccagatagacccgactcccgtgatcgtcacctccaacaccaacatgtgcgccgtgattgacggga
actcaacgaccttcgaacaccagcagccgttgcaagaccggatgttcaaatttgaactcacccgccgtctggatcatgactttggga
aggtcaccaagcaggaagtcaaagactttttccggtgggcaaaggatcacgtggttgaggtggagcatgaattctacgtcaaaaag
ggtggagccaagaaaagacccgcccccagtgacgcagatataagtgagcccaaacgggtgcgcgagtcagttgcgcagccatcg
acgtcagacgcggaagcttcgatcaactacgcagacaggtacGTaaacaaatgttctcgtcacgtgggcatgaatctgatgctgtt
tccctgcagacaatgcgagagaatgaatcagaattcaaatatctgcttcactcacggacagaaagactgtttagagtgctttcccgt
gtcagaatctcaacccgtttctgtcgtcaaaaaggcgtatcagaaactgtgctacattcatcatatcatgggaaaggtgccagacgc
ttgcactgcctgcgatctggtcaatgtggatttggatgactgcatctttgaacaataaatgatttaaatcaggtatggctgccgatggt
tatcttccagattggctcgaggacactctctctgaaggaataag

FIG. 14 (CONT.)

acagtggtggaagctcaaacctggcccaccaccaccaaagcccgcagagcggcataaggacgacagcaggggtcttgtgcttcct
gggtacaagtacctcggacccttcaacggactcgacaagggagagccggtcaacgaggcagacgccgcggccctcgagcacgac
aaagcctacgaccggcagctcgacagcggagacaacccgtacctcaagtacaaccacgccgacgcggagtttcaggagcgcctta
aagaagatacgtcttttgggggcaacctcggacgagcagtcttccaggcgaaaaagagggttcttgaacctctgggcctggttgag
gaacctgttaagacggctccgggaaaaaagaggccggtagagcactctcctgtggagccagactcctcctcgggaaccggaaagg
cgggccagcagcctgcaagaaaaagattgaattttggtcagactggagacgcagactcagtacctgacccccagcctctcggacag
ccaccagcagccccctctggtctgggaactaatacgatggctacaggcagtggcgcaccaatggcagacaataacgagggcgccg
acggagtgggtaattcctcgggaaattggcattgcgattccacatggatgggcgacagagtcatcaccaccagcacccgaacctgg
gccctgcccacctacaacaaccacctctacaaacaaatttccagccaatcaggagcctcgaacgacaatcactactttggctacagc
accccttgggggtattttgacttcaacagattccactgccacttttcaccacgtgactggcaaagactcatcaacaacaactggggat
tccgacccaagagactcaacttcaagctctttaacattcaagtcaaagaggtcacgcagaatgacggtacgacgacgattgccaat
aaccttaccagcacggttcaggtgtttactgactcggagtaccagctcccgtacgtcctcggctcggcgcatcaaggatgcctcccgc
cgttcccagcagacgtcttcatggtgccacagtatggatacctcaccctgaacaacgggagtcaggcagtaggacgctcttcattta
ctgcctggagtactttccttctcagatgctgcgtaccggaaacaactttaccttcagctacacttttgaggacgttcctttccacagcag
ctacgctcacagccagagtctggaccgtctcatgaatcctctcatcgaccagtacctgtattacttgagcagaacaaacactccaagt
ggaaccaccacgcagtcaaggcttcagttttctcaggccggagcgagtgacattcgggaccagtctaggaactggcttcctggaccc
tgttaccgccagcagcgagtatcaaagacatctgcggataacaacaacagtgaatactcgtggactggagctaccaagtaccacct
caatggcagagactctctggtgaatccgggcccggccatggcaagccacaaggacgatgaagaaaagtttttttcctcagagcggg
gttctcatctttgggaagcaaggctcagagaaaacaaatgtggacattgaaaaggtcatgattacagacgaagaggaaatcagga
caaccaatcccgtggctacggagcagtatggttctgtatctaccaacctccagagaggcaacagacaagcagctaccgcagatgtc
aacacacaaggcgttcttccaggcatggtctggcaggacagagatgtgtaccttcaggggcccatctgggcaaagattccacacac
ggacggacattttcacccctctcccctcatgggtggattcggacttaaacaccctcctccacagattctcatcaagaacaccccggta
ccAgcgaatccttcgaccaccttcagtgcggcaaagtttgcttccttcatcacacagtactccacgggacaggtcagcgtggagatc
gagtgggagctgcagaaggaaaacagcaaacgctggaatcccgaaattcagtacacttccaactacaacaagtctgttaatgtgg
actttactgtggacactaatggcgtgtattcagagcctcgccccattggcaccagatacctgactcgtaatctgTAACAATTGctt
gttaatcaataaaccgtttaattcgtttcagttgaactttggtctctgcgtatttctttcttatctagtttccatgctctagGATCCACT
AGTAACGGCCGCCAGTGTGCTGGAATTCGGCTTTGTAGTTAATGATTAACCCGCCATGCTACTTATCT
ACGTAGCCATGCTCTAGAGGTCCTGTATTAGAGGTCACGTGAGTGTTTTGCGACATTTTGCGACACC
ATGTGGTCACGCTGGGTATTTAAGCCCGAGTGAGCACGCAGGGTCTCCATTTTGAAGCGGGAGGTT
TGAACGCGCAGCCGCCAAGCCGAATTCTGCAGATCTAtcgATGTAGGATGTTGCCCCTCCTGACGCG
GTAGGAGAAGGGGAGGGTGCCCTGCATGTCTGCCGCTGCTCTTGCTCTTGCCGCTGCTGAGGAGGG
GGGCGCATCTGCCGCAGCACCGGATGCATCTGGGAAAAGCAAAAAGGGGCTCGTCCCTGTTTCCG
GAGGAATTTGCAAGCGGGGTCTTGCATGACGGGGAGGCAAACCCCCGTTCGCCGCAGTCCGGCCG
GCCCGAGACTCGAACCGGGGGTCCTGCGACTCAACCCTTGGAAAATAACCCTCCGGCTACAGGGAG
CGAGCCACTTAATGCTTTCGCTTTCCAGCCTAACCGCTTACGCCGCGCGCGGCCAGTGGCCAAAAAA
GCTAGCGCAGCAGCCGCCGCGCCTGGAAGGAAGCCAAAAGGAGCGCTCCCCCGTTGTCTGACGTCG
CACACCTGGGTTCGACACGCGGGCGGTAACCGCATGGATCACGGCGGACGGCCGGATCCGGGGTT
CGAACCCCGGTCGTCCGCCATGATACCCTTGCGAATTTATCCACCAGACCACGGAAGAGTGCCCGCT
TACAGGCTCTCCTTTTGCACGGTCTAGAGCGTCAACGACTGCGCACGCCTCACCGGCCAGAGCGTCC
CGACCATGGAGCACTTTTTGCCGCTGCGCAACATCTGGAACCGCGTCCGCGACTTTCCGCGCGCCTC
CACCACCGCCGCCGGCATCACCTGGATGTCCAGGTACATCTACGGATTACGTCGACGTTTAAACCAT
ATGATCAGCTCACTCAAAGGCGGTAATACGGTTATCCACAGAATCAGGGGATAACGCAGGAAAGAA
CATGTGAGCAAAAGGCCAGCAAAAGGCCAGGAACCGT

FIG. 14 (CONT.)

AAAAAGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTCGGGAA
GCGTGG
CGCTTTCTCATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGAACAGTATTTGG
TATCTGCGCTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAAT
CAATCTAAAGTATATATGAGTAAACTTGGTCTGACAGtcagaagaactcgtcaagaaggcgatagaaggcgatgc
gctgcgaatcgggagcggcgataccgtaaagcacgaggaagcggtcagcccattcgccgccaagctcttcagcaatatcacgggt
agccaacgctatgtcctgatagcggtccgccacacccagccggccacagtcgatgaatccagaaaagcggccattttccaccatga
tattcggcaagcaggcatcgccatgggtcacgacgagatcctcgccgtcgggcatgctcgccttgagcctggcgaacagttcggctg
gcgcgagcccctgatgctcttcgtccagatcatcctgatcgacaagaccggcttccatccgagtacgtgctcgctcgatgcgatgtttc
gcttggtggtcgaatgggcaggtagccggatcaagcgtatgcagccgccgcattgcatcagccatgatggatactttctcggcagga
gcaaggtgagatgacaggagatcctgccccggcacttcgcccaatagcagccagtcccttcccgcttcagtgacaacgtcgagTac
agctgcgcaaggaacgcccgtcgtggccagccacgatagccgcgctgcctcgtcttgcagttcattcagggcaccggacaggtcgg
tcttgacaaaaagaaccgggcgcccctgcgctgacagccggaacacggcggcatcagagcagccgattgtctgttgtgcccagtca
tagccgaatagcctctccacccaagcggccggagaacctgcgtgcaatccatcttgttcaatcatACTCTTCCTTTTTCAATA
TTATTGAAGCATTTATCAGGGTTATTGTCTCATGAGCGGATACATATTTGAATGTATTTAGAAAAATA
AACAAATAGGGGTTCCGCGCACATTTCCCCGAAAAGTGCCACCTAAATTGTAAGCGTTAATATTTTG
TTAAAATTCGCGTTAAATTTTTGTTAAATCAGCTCATTTTTTAACCAATAGGCCGAAATCGGCAAAAT
CCCTTATAAATCAAAAGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGCCCACTA
CGTGAACCATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGAAGGGAA
GAAAGCGAAAGGAGCGGGCGCTAGGGCGCTGGCAAGTGTAGCGGTCACGCTGCGCGTAACCACCA
CACCCGCCGCGCTTAATGCGCCGCTACAGGGCGCGATGGATCC

FIG. 14 (CONT.)

SEQ ID. NO.:11
Mini-pHelper- CMV-EGFP
GGCAGCTGCGCGCTCGCTCGCTCACTGAGGCCGCCCGGGCAAAGCCCGGGCGTCGGGCGACCTTTG
GTCGCCCGGCCTCAGTGAGCGAGCGAGCGCGCAGAGAGGGAGTGGCCAACTCCATCACTAGGGGT
TCCTGCGGCCGCACGCGTacattgattattgactagttattaatagtaatcaattacggggtcattagttcatagcccatatat
ggagttccgcgttacataacttacggtaaatggcccgcctggctgaccgcccaacgacccccgcccattgacgtcaataatgacgta
tgttcccatagtaacgccaatagggactttccattgacgtcaatgggtggagtatttacggtaaactgcccacttggcagtacatcaa
gtgtatcatatgccaagtacgccccctattgacgtcaatgacggtaaatggcccgcctggcattatgcccagtacatgaccttatggg
actttcctacttggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgggactttccaa
aatgtcgtaacaactccgccccattgacgcaaatgggcggtaggcgtgtacggtgggaggtctatataagctaGCGCCACCatg
gtgagcaagggcgaggagctgttcaccggggtggtgcccatcctggtcgagctggacggcgacgtaaacggccacaagttcagcg
tgtccggcgagggcgagggcgatgccacctacggcaagctgaccctgaagttcatctgcaccaccggcaagctgcccgtgccctgg
cccaccctcgtgaccaccctgacctacggcgtgcagtgcttcagccgctaccccgaccacatgaagcagcacgacttcttcaagtcc
gccatgcccgaaggctacgtccaggagcgcaccatcttcttcaaggacgacggcaactacaagacccgcgccgaggtgaagttcg
agggcgacaccctggtgaaccgcatcgagctgaagggcatcgacttcaaggaggacggcaacatcctggggcacaagctggagt
acaactacaacagccacaacgtctatatcatggccgacaagcagaagaacggcatcaaggtgaacttcaagatccgccacaacat
cgaggacggcagcgtgcagctcgccgaccactaccagcagaacacccccatcggcgacggccccgtgctgctgcccgacaaccac
tacctgagcacccagtccgccctgagcaaagaccccaacgagaagcgcgatcacatggtcctgctggagttcgtgaccgccgccgg
gatcactctcggcatggacgagctgtacaagtaaCGTACGGATATCAAGCTTATCGATAATCAACCTCTGGATTA
CAAAATTTGTGAAAGATTGACTGGTATTCTTAACTATGTTGCTCCTTTTACGCTATGTGGATACGCTG
CTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTT
GCTGACGCAACCCCCACTGGTTGGGGCATTGCCACCACCTGTCAGCTCCTTTCCGGGACTTTCGCTTT
CCCCCTCCCTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGCTCGCCTA
TGTTGCCACCTGGATTCTGCGCGGGACGTCCTTCTGCTACGTCCCTTCGGCCCTCAATCCAGCGGACC
TTCCTTCCCGCGGCCTGCTGCCGGCTCTGCGGCCTCTTCCGCGTCTTCGCCTTCGCCCTCAGACGAGT
CGGATCTCCCTTTGGGCCGCCTCCCCGCATCGATACCGAGCGCTGCTCGAGAGATCTACGGGTGGCA
TCCCTGTGACCCCTCCCCAGTGCCTCTCCTGGCCCTGGAAGTTGCCACTCCAGTGCCCACCAGCCTTG
TCCTAATAAAATTAAGTTGCATCATTTTGTCTGACTAGGTGTCCTTCTATAATATTATGGGGTGGAGG
GGGGTGGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTCAAGCGAT
TCTCCTGCCTCAGCCTCCCGAGTTGTTGGGATTCCAGGCATGCATGACCAGGCTCAGCTAATTTTTGT
TTTTTTGGTAGAGACGGGGTTTCACCATATTGGCCAGGCTGGTCTCCAACTCCTAATCTCAGGTGATC
TACCCACCTTGGCCTCCCAAATTGCTGGGATTACAGGCGTGAACCACTGCTCCCTTCCCTGTCCTTCT
GATTTTGTAGGTAACCACGTGCGGACCGAGCGGCCGCAGGAACCCCTAGTGATGGAGTTGGCCACT
CCCTCTCTGCGCGCTCGCTCGCTCACTGAGGCCGGGCGACCAAAGGTCGCCCGACGCCCGGGCTTTG
CCCGGGCGGCCTCAGTGAGCGAGCGAGCGCGCAGCTGCCAAACCATATGATCAGCTCACTCAAAGG
CGGTAATACGGTTATCCACAGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACCAG
GCGTTTCCCCCTGGAAGCTCCCTCGTGCGC

FIG. 14 (CONT.)

TCTCCTGTTCCGACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAA
TCTAAAGTATATATGAGTAAACTTGGTCTGACAGtcagaagaactcgtcaagaaggcgatagaaggcgatgcgctg
cgaatcgggagcggcgataccgtaaagcacgaggaagcggtcagcccattcgccgccaagctcttcagcaatatcacgggtagcc
aacgctatgtcctgatagcggtccgccacacccagccggccacagtcgatgaatccagaaaagcggccattttccaccatgatattc
ggcaagcaggcatcgccatgggtcacgacgagatcctcgccgtcgggcatgctcgccttgagcctggcgaacagttcggctggcgc
gagcccctgatgctcttcgtccagatcatcctgatcgacaagaccggcttccatccgagtacgtgctcgctcgatgcgatgtttcgctt
ggtggtcgaatgggcaggtagccggatcaagcgtatgcagccgccgcattgcatcagccatgatggatactttctcggcaggagca
aggtgagatgacaggagatcctgccccggcacttcgcccaatagcagccagtcccttcccgcttcagtgacaacgtcgagTacagc
tgcgcaaggaacgcccgtcgtggccagccacgatagccgcgctgcctcgtcttgcagttcattcagggcaccggacaggtcggtctt
gacaaaaagaaccgggcgcccctgcgctgacagccggaacacggcggcatcagagcagccgattgtctgttgtgcccagtcatag
ccgaatagcctctccacccaagcggccggagaacctgcgtgcaatccatcttgttcaatcatACTCTTCCTTTTTCAATATTA
TTGAAGCATTTATCAGGGTTATTGTCTCATGAGCGGATACATATTTGAATGTATTTAGAAAAATAAAC
AAATAGGGGTTCCGCGCACATTTCCCCGAAAAGTGCCACCTAAATTGTAAGCGTTAATATTTTGTTAA
AATTCGCGTTAAATTTTTGTTAAATCAGCTCATTTTTTAACCAATAGGCCGAAATCGGCAAAATCCCTT
ATAAATCAAAAGAATAGACCGAGATAGGGTTGAGTGTTGTTCCAGTTTGGAACAAGAGTCCACTATT
AAAGAACGTGGACTCCAACGTCAAAGGGCGAAAAACCGTCTATCAGGGCGATGGCCCACTACGTGA
ACCATCACCCTAATCAAGTTTTTTGGGGTCGAGGTGCCGTAAAGCACTAAATCGGAACCCTAAAGGG
AGCCCCCGATTTAGAGCTTGACGGGGAAAGCCGGCGAACGTGGCGAGAAAGGAAGGGAAGAAAG
CGAAAGGAGCGGGCGCTAGGGCGCTGGCAAGTGTAGCGGTCACGCTGCGCGTAACCACCACACCC
GCCGCGCTTAATGCGCCGCTACAGGGCGCGATGGATCCGGTACCCAACTCCATGCTTAACAGTCCCC
AGGTACAGCCCACCCTGCGTCGCAACCAGGAACAGCTCTACAGCTTCCTGGAGCGCCACTCGCCCTA
CTTCCGCAGCCACAGTGCGCAGATTAGGAGCGCCACTTCTTTTTGTCACTTGAAAAACATGTAAAAA
TAATGTACTAGGAGACACTTTCAATAAAGGCAAATGTTTTTATTTGTACACTCTCGGGTGATTATTTA
CCCCCCACCCTTGCCGTCTGCGCCGTTCAGAAGTCAAAAGGATTCTGTCTGGCGTCAGAGTGGGCCA
CGGGCAGAGACACATTCCGGTACTGATGCTTAGTGCTCCACTTGAACTCGGGCACCACCATGCGGG
GCAGCTCTGTGAAGTTCTCAGACCACAGGCTCCGCACCATCACGAGAGCGTTCAGCAGATCTGGGG
CGGAGATCTTGAAGTCGCAGTTGGGGCCTCCACCCTGAGCTCTGCTATTCCTGTACACGGGATTGCA
GCACTGGAACACGATCAGGGCGGGGTGGTGAACGGAGGCCAGCACGGACTTGTCGCTGATCAGAT
CGGCATCCAGATCTTCGGCGTTGCTCAGGGCAAAAGGGGTCAGTTTTGGCAGCTGCCTGCCCAGGA
AAGGGGCGTGGCCGGGCTTGGAGTTACATTCGCAGCGCAGGGGCATCAGGAGGTGGCCGTGGCCG
GTCTGGGCATTTGGATACAGGGCTTGCATGAAGGCCTTGATCTGCTTGAAGGCCACTTGCGCCTTGG
CTCCCTCGCTGAAGAACATTCCGCAGCTCTTGCCGCTAAACTGATTGGCAGGGCAGGCGGCGTCATG
CACGCAACATCTGGCGTCTGTGTTAGAAATCTGCACCACGTTCCTGCCCCACCTGTTCTTCACGATCT
TGGCCTTGCTGGACTGCTCCTTCAGGGCGCGCTGGCCGTTTTCGGAAGTCACATCCATCTCGATCAC
GTGCTCCTTGTTAATCATGATAGAGCCGTGCAGG

FIG. 14 (CONT.)

CATTTCAGCTCGCCCTCAATCTCGGCGCATCTGTGCAGCCACAGGGCGCAGCCGGTGGGCTCGTGGT
GCTTGTAAGTCACTTCGGCGAAAGATTGCAGGTAGGCCTGCAGAAACCTGCCCATCATGGTCACAAA
GGTCTTGTTTGATGTAAAGGTCAGCTGCAGCCCTCTATGCTCCTCATTCAGCCATGTCTTGCACACGG
CAGCCAGGGCCTCCACCTGGTCAGGCAGCAGTTTGAAATTAGCCTTCAGGTCGTTGTCCACGTGGTA
CTTGTCCATCAGGGCCCGGGCGGCCTCCATTCCCTTCTCCCAAGCGCTCACAATTGGCAGGGACAGT
GGATTAATCACTGTGCTCTCGCTCTCGGCCTCGGAGGATTCTTCCTTCTCCTCCTGTGTCCTCATGCCC
CTTGCCACAGGATCATCCTCGTTCAGCCTGCGCACGGTCCGTTTTCCCCCTTTGCCGTGCTTGATGAG
CACAGGTGGATTGCTGAATCCCACCATCTGCAGAGCGACGTCCTCGCGCTCTTCCTCTGAGTCCACG
ATCACTTCTGGGCTGGGTGGTCGTTCAGGTTTAGGGGAGGGCCTCTTCTTCTTTTTTTTGCTGGCAAT
GGCCAGGTCGGCGGTGGAAGTGGAGGGTCTTGGAGATGGTGTCCTAGGCACCAGAGCGTCCTGGG
AACTGTCTTCCTCGTCCTCGGACTCCAGGCGTCTCCGCAGTCTCTTTTTTGGGGGCGCGCGGGGAGG
CGGCGGCGACGGCGACGGGGACGACACGTCCTCCATGGTTGGTGGACGTCGCGCCGCACCGCGTC
CGCGCTCGGGGGTGGTTTCGCGCTGCTCCTCTTCCCGACTGGCCATTTCCTTCTCCCTGAGGACTACC
ACGCCCACGAGATTAGGTTCTACGAAGACCAATCCCGCCCGCCAAATGCGGAGCTTACCGCCTGCGT
CATTACCCAGGGCCACATCCTTGGCCAATTGCAAGCCATCAACAAAGCCCGCCAAGAGTTTCTGCTA
CGAAAGGGACGGGGGGTTTACCTGGACCCCCAGTCCGGCGAGGAGCTCAACCCAATCCCCCCGCCG
CCGCAGCCCTATCAGCAGCCGCGGGCCCTTGCTTCCCAGGATGGCACCCAAAAAGAAGCTGCAGCT
GCCGCCGCCGCCACCCACGGACGAGGAGGAATACTGGGACAGTCAGGCAGAGGAGGTTTTGGACG
AGGAGGAGGAGATGATGGAAGACTGGGACAGCCTAGACGAAGCTTCCGAGGCCGAAGAGGTGTC
AGACGAAACACCGTCACCCTCGGTCGCATTCCCCTCGCCGGCGCCCCAGAAATTGGCAACCGTTCCC
AGCATCGCTACAACCTCCGCTCCTCAGGCGCCGCCGGCACTGCCTGTTCGCCGACCCAACCGTAGAT
GGGACACCACTGGAACCAGGGCCGGTAAGTCTAAGCAGCCGCCGCCGTTAGCCCAAGAGCAACAA
CAGCGCCAAGGCTACCGCTCGTGGCGCGGGCACAAGAACGCCATAGTTGCTTGCTTGCAAGACTGT
GGGGGCAACATCTCCTTCGCCCGCCGCTTTCTTCTCTACCATCACGGCGTGGCCTTCCCCCGTAACAT
CCTGCATTACTACCGTCATCTCTACAGCCCCTACTGCACCGGCGGCAGCGGCAGCGGCAGCAACAGC
AGCGGTCACACAGAAGCAAAGGCGACCGGATAGCAAGACTCTGACAAAGCCCAAGAAATCCACAG
CGGCGGCAGCAGCAGGAGGAGGAGCGCTGCGTCTGGCGCCCAACGAACCCGTATCGACCCGCGAG
CTTAGAAATAGGATTTTTCCCACTCTGTATGCTATATTTCAACAAAGCAGGGGCCAAGAACAAGAGC
TGAAAATAAAAAACAGGTCTCTGCGCTCCCTCACCCGCAGCTGCCTGTATCACAAAAGCGAAGATCA
GCTTCGGCGCACGCTGGAAGACGCGGAGGCTCTCTTCAGCAAATACTGCGCGCTGACTCTTAAGGA
CTAGTTTCGCGCCCTTTCTCAAATTTAAGCGCGAAAACTACGTCATCTCCAGCGGCCACACCCGGCGC
CAGCACCTGTCGTCAGCGCCATTATGAGCAAGGAAATTCCCACGCCCTACATGTGGAGTTACCAGCC
ACAAATGGGACTTGCGGCTGGAGCTGCCCAAGACTACTCAACCCGAATAAACTACATGAGCGCGGG
ACCCCACATGATATCCCGGGTCAACGGAATCCGCGCCCACCGAAACCGAATTCTCCTCGAACAGGCG
GCTATTACCACCACACCTCGTAATAACCTTAATCCCCGTAGTTGGCCCGCTGCCCTGGTGTACCAGGA
AAGTCCCGCTCCCACCACTGTGGTACTTCCCAGAGACGCCCAGGCCGAAGTTCAGATGACTAACTCA
GGGGCGCAGCTTGCGGGCGGCTTTCGTCACAGGGTGCGGTCGCCCGGGCGTTTTAGGGCGGAGTA
ACTTGCATGTATTGGGAATTGTAGTTTTTTTAAAATGGGAAGTGACGTATCGTGGGAAAACGGAAGT
GAAGATTTGAGGAAGTTGTGGGTTTTTTGGCTTTCGTTTCTGGGCGTAGGTTCGCGTGCGGTTTTCT
GGGTGTTTTTTGTGGACTTTAACCGTTACGTCATTTTTTAGTCCTATATATACTCGCTCTGTACTTGGC
CCTTTTTACACTGTGACTGATTGAGCTGGTGCCGTGTCGAGTGGTGTTTTTTAATAGGTTTTTTTACTG
GTAAGGCTGACTGTTATGGCTGCCGCTGTGGAAGCGCTGTATGTTGTTCTGGAGCGGGAGGGTGCT
ATTTTGCCTAGGCGCCTGGATGCTTTGAGAGAGT

FIG. 14 (CONT.)

GGATATACTACAACTACTACACAGAGCGAGCTAAGCGACGAGACCGGAGACGCAGATCTGTTTGTC
ACGCCCGCACCTGGTTTTGCTTCAGGAAATATGACTACGTCCGGCGTTCCATTTGGCATGACACTAC
GACCAACACGATCTCGGTTGTCTCGGCGCACTCCGTACAGTAGGGATCGCCTACCTCCTTTTGAGAC
AGAGACCCGCGCTACCATACTGGAGGATCATCCGCTGCTGCCCGAATGTAACACTTTGACAATGCAC
AACGTGAGTTACGTGCGAGGTCTTCCCTGCAGTGTGGGATTTACGCTGATTCAGGAATGGGTTGTTC
CCTGGGATATGGTTCTGACGCGGGAGGAGCTTGTAATCCTGAGGAAGTGTATGCACGTGTGCCTGT
GTTGTGCCAACATTGATATCATGACGAGCATGATGATCCATGGTTACGAGTCCTGGGCTCTCCACTG
TCATTGTTCCAGTCCCGGTTCCCTGCAGTGCATAGCCGGCGGGCAGGTTTTGGCCAGCTGGTTTAGG
ATGGTGGTGGATGGCGCCATGTTTAATCAGAGGTTTATATGGTACCGGGAGGTGGTGAATTACAAC
ATGCCAAAAGAGGTAATGTTTATGTCCAGCGTGTTTATGAGGGGTCGCCACTTAATCTACCTGCGCT
TGTGGTATGATGGCCACGTGGGTTCTGTGGTCCCCGCCATGAGCTTTGGATACAGCGCCTTGCACTG
TGGGATTTTGAACAATATTGTGGTGCTGTGCTGCAGTTACTGTGCTGATTTAAGTGAGATCAGGGTG
CGCTGCTGTGCCCGGAGGACAAGGCGTCTCATGCTGCGGGCGGTGCGAATCATCGCTGAGGAGAC
CACTGCCATGTTGTATTCCTGCAGGACGGAGCGGCGGCGGCAGCAGTTTATTCGCGCGCTGCTGCA
GCACCACCGCCCTATCCTGATGCACGATTATGACTCTACCCCCATGTAGGCGTGGACTTCCCCTTCGC
CGCCCGTTGAGCAACCGCAAGTTGGACAGCAGCCTGTGGCTCAGCAGCTGGACAGCGACATGAACT
TAAGCGAGCTGCCCGGGGAGTTTATTAATATCACTGATGAGCGTTTGGCTCGACAGGAAACCGTGT
GGAATATAACACCTAAGAATATGTCTGTTACCCATGATATGATGCTTTTTAAGGCCAGCCGGGGAGA
AAGGACTGTGTACTCTGTGTGTTGGGAGGGAGGTGGCAGGTTGAATACTAGGGTTCTGTGAGTTTG
ATTAAGGTACGGTGATCAATATAAGCTATGTGGTGGTGGGGCTATACTACTGAATGAAAAATGACTT
GAAATTTTCTGCAATTGAAAAATAAACACGTTGAAACATAACATGCAACAGGTTCACGATTCTTTATT
CCTGGGCAATGTAGGAGAAGGTGTAAGAGTTGGTAGCAAAAGTTTCAGTGGTGTATTTTCCACTTTC
CCAGGACCATGTAAAAGACATAGAGTAAGTGCTTACCTCGCTAGTTTCTGTGGATTCACTAGAATCG
ATGTAGGATGTTGCCCCTCCTGACGCGGTAGGAGAAGGGGAGGGTGCCCTGCATGTCTGCCGCTGC
TCTTGCTCTTGCCGCTGCTGAGGAGGGGGGCGCATCTGCCGCAGCACCGGATGCATCTGGAAAAG
CAAAAAAGGGGCTCGTCCCTGTTTCCGGAGGAATTTGCAAGCGGGGTCTTGCATGACGGGGAGGC
AAACCCCCGTTCGCCGCAGTCCGGCCGGCCCGAGACTCGAACCGGGGGTCCTGCGACTCAACCCTT
GGAAAATAACCCTCCGGCTACAGGGAGCGAGCCACTTAATGCTTTCGCTTTCCAGCCTAACCGCTTA
CGCCGCGCGCGGCCAGTGGCCAAAAAAGCTAGCGCAGCAGCCGCCGCGCCTGGAAGGAAGCCAAA
AGGAGCGCTCCCCCGTTGTCTGACGTCGCACACCTGGGTTCGACACGCGGGCGGTAACCGCATGGA
TCACGGCGGACGGCCGGATCCGGGGTTCGAACCCCGGTCGTCCGCCATGATACCCTTGCGAATTTAT
CCACCAGACCACGGAAGAGTGCCCGCTTACAGGCTCTCCTTTTGCACGGTCTAGAGCGTCAACGACT
GCGCACGCCTCACCGGCCAGAGCGTCCCGACCATGGAGCACTTTTTGCCGCTGCGCAACATCTGGAA
CCGCGTCCGCGACTTTCCGCGCGCCTCCACCACCGCCGCCGGCATCACCTGGATGTCCAGGTACATC
TACGGATTACGTCGACGTTT

SEQ ID. NO.12
pAAVone-AAV2-CMV-EGFP
GGCAGCTGCGCGCTCGCTCGCTCACTGAGGCCGCCCGGGCAAAGCCCGGGCGTCGGGCGACCTTTG
GTCGCCCGGCCTCAGTGAGCGAGCGAGCGCGCAGAGAGGGAGTGGCCAACTCCATCACTAGGGGT
TCCTGCGGCCGCACGCGTacattgattattgactagttattaatagtaatcaattacggggtcattagttcatagcccatatat
ggagttccgcgttacataacttacggtaaatggcccgcctggctgaccgcccaacgacccccgcccattgacgtcaataatgacgta
tgttcccatagta

FIG. 14 (CONT.)

acgccaatagggactttccattgacgtcaatgggtggagtatttacggtaaactgcccacttggcagtacatcaagtgtatcatatgc
caagtacgccccctattgacgtcaatgacggtaaatggcccgcctggcattatgcccagtacatgaccttatgggactttcctacttg
gcagtacatctacgtattagtcatcgctattaccatggtgatgcggttttggcagtacatcaatgggcgtggatagcggtttgactcac
ggggatttccaagtctccaccccattgacgtcaatgggagtttgttttggcaccaaaatcaacgggactttccaaaatgtcgtaacaa
ctccgccccattgacgcaaatgggcggtaggcgtgtacggtgggaggtctatataagctaGCGCCACCatggtgagcaagggc
gaggagctgttcaccggggtggtgcccatcctggtcgagctggacggcgacgtaaacggccacaagttcagcgtgtccggcgaggg
cgagggcgatgccacctacggcaagctgaccctgaagttcatctgcaccaccggcaagctgcccgtgccctggcccaccctcgtga
ccaccctgacctacggcgtgcagtgcttcagccgctaccccgaccacatgaagcagcacgacttcttcaagtccgccatgcccgaag
gctacgtccaggagcgcaccatcttcttcaaggacgacggcaactacaagacccgcgccgaggtgaagttcgagggcgacaccct
ggtgaaccgcatcgagctgaagggcatcgacttcaaggaggacggcaacatcctggggcacaagctggagtacaactacaacag
ccacaacgtctatatcatggccgacaagcagaagaacggcatcaaggtgaacttcaagatccgccacaacatcgaggacggcagc
gtgcagctcgccgaccactaccagcagaacacccccatcggcgacggccccgtgctgctgcccgacaaccactacctgagcaccca
gtccgccctgagcaaagaccccaacgagaagcgcgatcacatggtcctgctggagttcgtgaccgccgccgggatcactctcggca
tggacgagctgtacaagtaaCGTACGGATATCAAGCTTATCGATAATCAACCTCTGGATTACAAAATTTGTG
AAAGATTGACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGACGCAAC
CCCCACTGGTTGGGGCATTGCCACCACCTGTCAGCTCCTTTCCGGGACTTTCGCTTTCCCCCTCCCTAT
TGCCACGGCGGAACTCATCGCCGCCTGCCTTGCCCGCTGCTGGACAGGGGCTCGGCTGTTGGGCAC
TGACAATTCCGTGGTGTTGTCGGGGAAATCATCGTCCTTTCCTTGGCTGCTCGCCTATGTTGCCACCT
GGATTCTGCGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGGATCTCCCT
TTGGGCCGCCTCCCCGCATCGATACCGAGCGCTGCTCGAGAGATCTACGGGTGGCATCCCTGTGACC
CCTCCCCAGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGTGGTAT
GGAGCAAGGGGCAAGTTGGGAAGACAACCTGTAGGGCCTGCGGGGTCTATTGGGAACCAAGCTGG
AGTGCAGTGGCACAATCTTGGCTCACTGCAATCTCCGCCTCCTGGGTTCAAGCGATTCTCCTGCCTCA
GCCTCCCGAGTTGTTGGGATTCCAGGCATGCATGACCAGGCTCAGCTAATTTTTGTTTTTTTGGTAGA
GACGGGGTTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTTCTGATTTTGTAGGT
AACCACGTGCGGACCGAGCGGCCGCAGGAACCCCTAGTGATGGAGTTGGCCACTCCCTCTCTGCGC
GCTCGCTCGCTCACTGAGGCCGGGCGACCAAAGGTCGCCCGACGCCCGGGCTTTGCCCGGGCGGCC
TCAGTGAGCGAGCGAGCGCGCAGCTGCCAAACCATATGATCAGCTCACTCAAAGGCGGTAATACGG
TTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCATCACAAA
AATCGACGCTCAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTACACTAGA
AGAACAGTATTTGGTATCTGCGCTCTGCT

FIG. 14 (CONT.)

GAAGCCAGTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAAAGTATA
TATGAGTAAACTTGGTCTGACAGtcagaagaactcgtcaagaaggcgatagaaggcgatgcgctgcgaatcgggagcg
gcgataccgtaaagcacgaggaagcggtcagcccattcgccgccaagctcttcagcaatatcacgggtagccaacgctatgtcctg
atagcggtccgccacacccagccggccacagtcgatgaatccagaaaagcggccattttccaccatgatattcggcaagcaggcat
cgccatgggtcacgacgagatcctcgccgtcgggcatgctcgccttgagcctggcgaacagttcggctggcgcgagcccctgatgct
cttcgtccagatcatcctgatcgacaagaccggcttccatccgagtacgtgctcgctcgatgcgatgtttcgcttggtggtcgaatggg
caggtagccggatcaagcgtatgcagccgccgcattgcatcagccatgatggatactttctcggcaggagcaaggtgagatgacag
gagatcctgccccggcacttcgcccaatagcagccagtcccttcccgcttcagtgacaacgtcgagTacagctgcgcaaggaacgc
ccgtcgtggccagccacgatagccgcgctgcctcgtcttgcagttcattcagggcaccggacaggtcggtcttgacaaaaagaaccg
ggcgcccctgcgctgacagccggaacacggcggcatcagagcagccgattgtctgttgtgcccagtcatagccgaatagcctctcc
acccaagcggccggagaacctgcgtgcaatccatcttgttcaatcatACTCTTCCTTTTTCAATATTATTGAAGCATTT
ATCAGGGTTATTGTCTCATGAGCGGATACATATTTGAATGTATTTAGAAAAATAAACAAATAGGGGT
TCCGCGCACATTTCCCCGAAAAGTGCCACCTAAATTGTAAGCGTTAATATTTTGTTAAAATTCGCGTT
AAATTTTTGTTAAATCAGCTCATTTTTTAACCAATAGGCCGAAATCGGCAAAATCCCTTATAAATCAA
AAGAATAGACCGAGATAGGGTTGAGTGTTGTTCCAGTTTGGAACAAGAGTCCACTATTAAAGAACG
TGGACTCCAACGTCAAAGGGCGAAAAACCGTCTATCAGGGCGATGGCCCACTACGTGAACCATCAC
CCTAATCAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCT
TAATGCGCCGCTACAGGGCGCGATGGATCCGGTACCCAACTCCATGCTTAACAGTCCCCAGGTACAG
CCCACCCTGCGTCGCAACCAGGAACAGCTCTACAGCTTCCTGGAGCGCCACTCGCCCTACTTCCGCA
GCCACAGTGCGCAGATTAGGAGCGCCACTTCTTTTTGTCACTTGAAAAACATGTAAAAATAATGTAC
TAGGAGACACTTTCAATAAAGGCAAATGTTTTTATTTGTACACTCTCGGGTGATTATTTACCCCCCAC
CCTTGCCGTCTGCGCCGTTCAGAAGTCAAAAGGATTCTGTCTGGCGTCAGAGTGGGCCACGGGCAG
AGACACATTCCGGTACTGATGCTTAGTGCTCCACTTGAACTCGGGCACCACCATGCGGGGCAGCTCT
GTGAAGTTCTCAGACCACAGGCTCCGCACCATCACGAGAGCGTTCAGCAGATCTGGGGCGGAGATC
TTGAAGTCGCAGTTGGGGCCTCCACCCTGAGCTCTGCTATTCCTGTACACGGGATTGCAGCACTGGA
ACACGATCAGGGCGGGGTGGTGAACGGAGGCCAGCACGGACTTGTCGCTGATCAGATCGGCATCC
AGATCTTCGGCGTTGCTCAGGGCAAAAGGGGTCAGTTTTGGCAGCTGCCTGCCCAGGAAAGGGGC
GTGGCCGGGCTTGGAGTTACATTCGCAGCGCAGGGGCATCAGGAGGTGGCCGTGGCCGGTCTGGG
CATTTGGATACAGGGCTTGCATGAAGGCCTTGATCTGCTTGAAGGCCACTTGCGCCTTGGCTCCCTC
GCTGAAGAACATTCCGCAGCTCTTGCCGCTAAACTGATTGGCAGGGCAGGCGGCGTCATGCACGCA
ACATCTGGCGTCTGTGTTAGAAATCTGCACCACGTTCCTGCCCCACCTGTTCTTCACGATCTTGGCCTT
GCTGGACTGCTCCTTCAGGGCGCGCTGGCCGTTTTCGGAAGTCACATCCATCTCGATCACGTGCTCCT
TGTTAATCATGATAGAGCCGTGCAGGCATTTCAGCTCGCCCTCAATCTCGGCGCATCTGTGCAGCCA
CAGGGCGCAGCCGGTGGGCTCGTGGTGCTTGTAAGTCACTTCGGCGAAAGATTGCAGGTAGGCCTG
CAGAAACCTGCCCATCATGGTCACAAAGGTCTTGTTTGATGTAAAGGTCAGCTGCAGCCCTCTATGC
TCCTCATTCAGCCATGTCTTGCACACGGCAGCCAGGGCCTCCACCTGGTCAGGCAGCAGTTTGAAAT
TAGCCTTCAGGTCGTTGTCCACGTGGTACTTGTCCATCAGGGCCCGGGCGGCCTCCATTCCCTTCTCC
CAAGCGCTCACAATTGGCAGGGACAGTGGATTAATCAC

FIG. 14 (CONT.)

TGTGCTCTCGCTCTCGGCCTCGGAGGATTCTTCCTTCTCCTCCTGTGTCCTCATGCCCCTTGCCACAGG
ATCATCCTCGTTCAGCCTGCGCACGGTCCGTTTTCCCCCTTTGCCGTGCTTGATGAGCACAGGTGGAT
TGCTGAATCCCACCATCTGCAGAGCGACGTCCTCGCGCTCTTCCTCTGAGTCCACGATCACTTCTGGG
CTGGGTGGTCGTTCAGGTTTAGGGGAGGGCCTCTTCTTCTTTTTTTTGCTGGCAATGGCCAGGTCGG
CGGTGGAAGTGGAGGGTCTTGGAGATGGTGTCCTAGGCACCAGAGCGTCCTGGGAACTGTCTTCCT
CGTCCTCGGACTCCAGGCGTCTCCGCAGTCTCTTTTTTGGGGGCGCGCGGGGAGGCGGCGGCGACG
GCGACGGGGACGACACGTCCTCCATGGTTGGTGGACGTCGCGCCGCACCGCGTCCGCGCTCGGGG
GTGGTTTCGCGCTGCTCCTCTTCCCGACTGGCCATTTCCTTCTCCCTGAGGACTACCACGCCCACGAG
ATTAGGTTCTACGAAGACCAATCCCGCCCGCCAAATGCGGAGCTTACCGCCTGCGTCATTACCCAGG
GCCACATCCTTGGCCAATTGCAAGCCATCAACAAAGCCCGCCAAGAGTTTCTGCTACGAAAGGGACG
GGGGGTTTACCTGGACCCCCAGTCCGGCGAGGAGCTCAACCCAATCCCCCCGCCGCCGCAGCCCTAT
CAGCAGCCGCGGGCCCTTGCTTCCCAGGATGGCACCCAAAAAGAAGCTGCAGCTGCCGCCGCCGCC
ACCCACGGACGAGGAGGAATACTGGGACAGTCAGGCAGAGGAGGTTTTGGACGAGGAGGAGGAG
ATGATGGAAGACTGGGACAGCCTAGACGAAGCTTCCGAGGCCGAAGAGGTGTCAGACGAAACACC
GTCACCCTCGGTCGCATTCCCCTCGCCGGCGCCCCAGAAATTGGCAACCGTTCCCAGCATCGCTACA
ACCTCCGCTCCTCAGGCGCCGCCGGCACTGCCTGTTCGCCGACCCAACCGTAGATGGGACACCACTG
GAACCAGGGCCGGTAAGTCTAAGCAGCCGCCGCCGTTAGCCCAAGAGCAACAACAGCGCCAAGGC
TACCGCTCGTGGCGCGGGCACAAGAACGCCATAGTTGCTTGCTTGCAAGACTGTGGGGGCAACATC
TCCTTCGCCCGCCGCTTTCTTCTCTACCATCACGGCGTGGCCTTCCCCCGTAACATCCTGCATTACTAC
CGTCATCTCTACAGCCCCTACTGCACCGGCGGCAGCGGCAGCGGCAGCAACAGCAGCGGTCACACA
GAAGCAAAGGCGACCGGATAGCAAGACTCTGACAAAGCCCAAGAAATCCACAGCGGCGGCAGCAG
CAGGAGGAGGAGCGCTGCGTCTGGCGCCCAACGAACCCGTATCGACCCGCGAGCTTAGAAATAGG
ATTTTTCCCACTCTGTATGCTATATTTCAACAAAGCAGGGGCCAAGAACAAGAGCTGAAAATAAAAA
ACAGGTCTCTGCGCTCCCTCACCCGCAGCTGCCTGTATCACAAAAGCGAAGATCAGCTTCGGCGCAC
GCTGGAAGACGCGGAGGCTCTCTTCAGCAAATACTGCGCGCTGACTCTTAAGGACTAGTTTCGCGCC
CTTTCTCAAATTTAAGCGCGAAAACTACGTCATCTCCAGCGGCCACACCCGGCGCCAGCACCTGTCG
TCAGCGCCATTATGAGCAAGGAAATTCCCACGCCCTACATGTGGAGTTACCAGCCACAAATGGGACT
TGCGGCTGGAGCTGCCCAAGACTACTCAACCCGAATAAACTACATGAGCGCGGGACCCCACATGAT
ATCCCGGGTCAACGGAATCCGCGCCCACCGAAACCGAATTCTCCTCGAACAGGCGGCTATTACCACC
ACACCTCGTAATAACCTTAATCCCCGTAGTTGGCCCGCTGCCCTGGTGTACCAGGAAAGTCCCGCTCC
CACCACTGTGGTACTTCCCAGAGACGCCCAGGCCGAAGTTCAGATGACTAACTCAGGGGCGCAGCT
TGCGGGCGGCTTTCGTCACAGGGTGCGGTCGCCCGGGCGTTTTAGGGCGGAGTAACTTGCATGTAT
TGGGAATTGTAGTTTTTTTAAAATGGGAAGTGACGTATCGTGGGAAAACGGAAGTGAAGATTTGAG
GAAGTTGTGGGTTTTTTGGCTTTCGTTTCTGGGCGTAGGTTCGCGTGCGGTTTTCTGGGTGTTTTTTG
TGGACTTTAACCGTTACGTCATTTTTTAGTCCTATATATACTCGCTCTGTACTTGGCCCTTTTTACACTG
TGACTGATTGAGCTGGTGCCGTGTCGAGTGGTGTTTTTTAATAGGTTTTTTTACTGGTAAGGCTGACT
GTTATGGCTGCCGCTGTGGAAGCGCTGTATGTTGTTCTGGAGCGGGAGGGTGCTATTTTGCCTAGG
CGCCTGGATGCTTTGAGAGAGTGGATATACTACAACTACTACACAGAGCGAGCTAAGCGACGAGAC
CGGAGACGCAGATCTGTTTGTCACGCCCGCACCTGGTTTTGCTTCAGGAAATATGACTACGTCCGGC
GTTCCATTTGGCATGACACTACGACCAACACGATCTCGGTTGTCTCGGCGCACTCCGTACAGTAGGG
ATCGCCTACCTCCTTTTGAGACAGAGACCCGCGCTACCATACTGGAGGATCATCCGCTGCTGCCCGA
ATGTAACACTTTGACAATGCACAACGTGAGTTACGTGCGAGGTCTTCCCTGCAGTGTGGGATTTACG
CTGATTCAGGAATGGGTTGTTCCCTGGGATATGGTT

FIG. 14 (CONT.)

CTGACGCGGGAGGAGCTTGTAATCCTGAGGAAGTGTATGCACGTGTGCCTGTGTTGTGCCAACATT
GATATCATGACGAGCATGATGATCCATGGTTACGAGTCCTGGGCTCTCCACTGTCATTGTTCCAGTCC
CGGTTCCCTGCAGTGCATAGCCGGCGGGCAGGTTTTGGCCAGCTGGTTTAGGATGGTGGTGGATGG
CGCCATGTTTAATCAGAGGTTTATATGGTACCGGGAGGTGGTGAATTACAACATGCCAAAAGAGGT
AATGTTTATGTCCAGCGTGTTTATGAGGGGTCGCCACTTAATCTACCTGCGCTTGTGGTATGATGGCC
ACGTGGGTTCTGTGGTCCCCGCCATGAGCTTTGGATACAGCGCCTTGCACTGTGGGATTTTGAACAA
TATTGTGGTGCTGTGCTGCAGTTACTGTGCTGATTTAAGTGAGATCAGGGTGCGCTGCTGTGCCCGG
AGGACAAGGCGTCTCATGCTGCGGGCGGTGCGAATCATCGCTGAGGAGACCACTGCCATGTTGTAT
TCCTGCAGGACGGAGCGGCGGCGGCAGCAGTTTATTCGCGCGCTGCTGCAGCACCACCGCCCTATC
CTGATGCACGATTATGACTCTACCCCCATGTAGGCGTGGACTTCCCCTTCGCCGCCCGTTGAGCAACC
GCAAGTTGGACAGCAGCCTGTGGCTCAGCAGCTGGACAGCGACATGAACTTAAGCGAGCTGCCCGG
GGAGTTTATTAATATCACTGATGAGCGTTTGGCTCGACAGGAAACCGTGTGGAATATAACACCTAAG
AATATGTCTGTTACCCATGATATGATGCTTTTTAAGGCCAGCCGGGGAGAAAGGACTGTGTACTCTG
TGTGTTGGGAGGGAGGTGGCAGGTTGAATACTAGGGTTCTGTGAGTTTGATTAAGGTACGGTGATC
AATATAAGCTATGTGGTGGTGGGGCTATACTACTGAATGAAAAATGACTTGAAATTTTCTGCAATTG
AAAAATAAACACGTTGAAACATAACATGCAACAGGTTCACGATTCTTTATTCCTGGGCAATGTAGGA
GAAGGTGTAAGAGTTGGTAGCAAAAGTTTCAGTGGTGTATTTTCCACTTTCCCAGGACCATGTAAAA
GACATAGAGTAAGTGCTTACCTCGCTAGTTTCTGTGGATTCACTAGAgcggccgcggtcctgtattagAGGT
CAACGTGAGTGTTTTGCGACATTTTGCGACACCATGTGGTCACGCtgaggtatatatggccgagtgagcgagc
aggatGCAACctccattttgAccgcgaaAtttgaacgagcagccgccatgCcggggttttacgagattgtgattaaggtccccag
cgaccttgacgAgcatctgcccggcatttctgacagctttgtgaactgggtggccgagaaggaatgggagttgccgccagattctga
catggatctgaatctgattgagcaggcacccctgaccgtggccgagaagctgcagcgcgactttctgacggaatggcgccgtgtga
gtaaggcAccggaggcccttttctttgtgcaatttgagaagggagagagctacttccacatgcacgtgctcgtggaaaccaccggg
gtgaaatccatggttttgggacgtttcctgagtcagattcgcgaaaaactgattcagagaatttaccgcgggatcgagccgactttgc
caaactggttcgcggtcacaaagaccagaaatggcgccggaggcgggaacaaggtggtggatgagtgctacatccccaattactt
gctccccaaaacccagcctgagctccagtgggcgtggactaatatggaacagtatttaagcgcctgtttgaatctcacggagcgtaa
acggttggtggcgcagcatctgacgcacgtgtcgcagacgcaggagcagaacaaagagaatcagaatcccaattctgatgcgccg
gtgatcagatcaaaaacttcagccaggtacatggagctggtcgggtggctcgtggacaaggggattacctcggagaagcagtggat
ccaggaggaccaggcctcatacatctccttcaatgcggcctccaactcgcggtcccaaatcaaggctgccttggacaatgcgggaa
agattatgagcctgactaaaaccgcccccgactacctggtgggccagcagcccgtggaggacatttccagcaatcggatttataaa
attttggaactaaacgggtacgatccccaatatgcggcttccgtctttctgggatgggccacgaaaaagttcggcaagaggaacacc
atctggctgtttgggcctgcaactaccgggaagaccaacatcgcggaggccatagcccacactgtgcccttctacgggtgcgtaaac
tggaccaatgagaactttcccttcaacgactgtgtcgacaagatggtgatctggtgggaggaggggaagatgaccgccaaggtcgt
ggagtcggccaaagccattctcggaggaagcaaggtgcgcgtggaccagaaatgcaagtcctcggcccagatagacccgactccc
gtgatcgtcacctccaacaccaacatgtgcgccgtgattgacgggaactcaacgaccttcgaacaccagcagccgttgcaagaccg
gatgttcaaatttgaactcacccgccgtctggatcatgactttgggaaggtcaccaagcaggaagtcaaagactttttccggtgggc
aaaggatcacgtggttgaggtggagcatgaattctacgtcaaaaagggtggagccaagaaaagacccgcccccagtgacgcaga
tataagtgagcccaaacgggtgcgcgagtcagttgcgcagccatcgacgtcagacgcggaagcttcgatcaactacgcagacagg
tacGTaaacaaatgttctcgtcacgtgggcatgaatctgatgctgtttccctgcagacaatgcgagagaatgaatcagaattcaaat
atctgcttcactcacggacagaaagactgtttagagtgctttcccgtgtcagaatctcaacccgtttctgtcgtcaaaaaggcgtatca
gaaactgtgctacattcatcatatcatgggaaaggtgccagacgcttgcactgcctgcgatctggtcaatgtggatttggatgactgc
atctttgaacaataaatgatttaaatcaggtatggctgccgatggttatcttccagattggctcgaggacactctctctgaaggaata
agacagtggtggaagctcaaacctggcccaccaccaccaaagcc

FIG. 14 (CONT.)

cgcagagcggcataaggacgacagcaggggtcttgtgcttcctgggtacaagtacctcggacccttcaacggactcgacaaggga
gagccggtcaacgaggcagacgccgcggccctcgagcacgacaaagcctacgaccggcagctcgacagcggagacaacccgtac
ctcaagtacaaccacgccgacgcggagtttcaggagcgccttaaagaagatacgtcttttgggggcaacctcggacgagcagtctt
ccaggcgaaaaagagggttcttgaacctctgggcctggttgaggaacctgttaagacggctccgggaaaaaagaggccggtagag
cactctcctgtggagccagactcctcctcgggaaccggaaaggcgggccagcagcctgcaagaaaaagattgaattttggtcagac
tggagacgcagactcagtacctgacccccagcctctcggacagccaccagcagccccctctggtctgggaactaatacgatggcta
caggcagtggcgcaccaatggcagacaataacgagggcgccgacggagtgggtaattcctcgggaaattggcattgcgattccac
atggatgggcgacagagtcatcaccaccagcacccgaacctgggccctgcccacctacaacaaccacctctacaaacaaatttcca
gccaatcaggagcctcgaacgacaatcactactttggctacagcaccccttgggggtattttgacttcaacagattccactgccactt
ttcaccacgtgactggcaaagactcatcaacaacaactggggattccgacccaagagactcaacttcaagctctttaacattcaagt
caaagaggtcacgcagaatgacggtacgacgacgattgccaataaccttaccagcacggttcaggtgtttactgactcggagtacc
agctcccgtacgtcctcggctcggcgcatcaaggatgcctcccgccgttcccagcagacgtcttcatggtgccacagtatggatacct
caccctgaacaacgggagtcaggcagtaggacgctcttcattttactgcctggagtactttccttctcagatgctgcgtaccggaaac
aactttaccttcagctacacttttgaggacgttcctttccacagcagctacgctcacagccagagtctggaccgtctcatgaatcctct
catcgaccagtacctgtattacttgagcagaacaaacactccaagtggaaccaccacgcagtcaaggcttcagttttctcaggccgg
agcgagtgacattcgggaccagtctaggaactggcttcctggaccctgttaccgccagcagcgagtatcaaagacatctgcggata
acaacaacagtgaatactcgtggactggagctaccaagtaccacctcaatggcagagactctctggtgaatccgggcccggccatg
gcaagccacaaggacgatgaagaaaagtttttttcctcagagcggggttctcatctttgggaagcaaggctcagagaaaacaaatgt
ggacattgaaaaggtcatgattacagacgaagaggaaatcaggacaaccaatcccgtggctacggagcagtatggttctgtatcta
ccaacctccagagaggcaacagacaagcagctaccgcagatgtcaacacacaaggcgttcttccaggcatggtctggcaggacag
agatgtgtaccttcaggggcccatctgggcaaagattccacacacggacggacattttcacccctctcccctcatgggtggattcgga
cttaaacaccctcctccacagattctcatcaagaacaccccggtaccAgcgaatccttcgaccaccttcagtgcggcaaagtttgctt
ccttcatcacacagtactccacgggacaggtcagcgtggagatcgagtgggagctgcagaaggaaaacagcaaacgctggaatcc
cgaaattcagtacacttccaactacaacaagtctgttaatgtggactttactgtggacactaatggcgtgtattcagagcctcgcccc
attggcaccagatacctgactcgtaatctgTAACAATTGcttgttaatcaataaaccgtttaattcgtttcagttgaactttggtctc
tgcgtatttctttcttatctagtttccatgctctagGATCCACTAGTAACGGCCGCCAGTGTGCTGGAATTCGGCTTT
GTAGTTAATGATTAACCCGCCATGCTACTTATCTACGTAGCCATGCTCTAGAGGTCCTGTATTAGAGG
TCACGTGAGTGTTTTGCGACATTTTGCGACACCATGTGGTCACGCTGGGTATTTAAGCCCGAGTGAG
CACGCAGGGTCTCCATTTTGAAGCGGGAGGTTTGAACGCGCAGCCGCCAAGCCGAATTCTGCAGAT
CTAtcgATGTAGGATGTTGCCCCTCCTGACGCGGTAGGAGAAGGGGAGGGTGCCCTGCATGTCTGCC
GCTGCTCTTGCTCTTGCCGCTGCTGAGGAGGGGGGCGCATCTGCCGCAGCACCGGATGCATCTGGG
AAAAGCAAAAAAGGGGCTCGTCCCTGTTTCCGGAGGAATTTGCAAGCGGGGTCTTGCATGACGGG
GAGGCAAACCCCCGTTCGCCGCAGTCCGGCCGGCCCGAGACTCGAACCGGGGGTCCTGCGACTCAA
CCCTTGGAAAATAACCCTCCGGCTACAGGGAGCGAGCCACTTAATGCTTTCGCTTTCCAGCCTAACC
GCTTACGCCGCGCGCGGCCAGTGGCCAAAAAAGCTAGCGCAGCAGCCGCCGCGCCTGGAAGGAAG
CCAAAAGGAGCGCTCCCCCGTTGTCTGACGTCGCACACCTGGGTTCGACACGCGGGCGGTAACCGC
ATGGATCACGGCGGACGGCCGGATCCGGGGTTCGAACCCCGGTCGTCCGCCATGATACCCTTGCGA
ATTTATCCACCAGACCACGGAAGAGTGCCCGCTTACAGGCTCTCCTTTTGCACGGTCTAGAGCGTCA
ACGACTGCGCACGCCTCACCGGCCAGAGCGTCCCGACCATGGAGCACTTTTTGCCGCTGCGCAACAT
CTGGAACCGCGTCCGCGACTTTCCGCGCGCCTCCACCACCGCCGCCGGCATCACCTGGATGTCCAGG
TACATCTACGGATTACGTCGACGTTT

FIG. 14 (CONT.)

SEQ ID. NO.:13
Mini-pHelper-Rep
TTTGGCTTCCTTCCAGGCGCGGCGGCTGCTGCGCTAGCTTTTTTGGCCACTGGCCGCGCGCGGCGTA
AGCGGTTAGGCTGGAAAGCGAAAGCATTAAGTGGCTCGCTCCCTGTAGCCGGAGGGTTATTTTCCA
AGGGTTGAGTCGCAGGACCCCCGGTTCGAGTCTCGGGCCGGCCGGACTGCGGCGAACGGGGGTTT
GCCTCCCCGTCATGCAAGACCCCGCTTGCAAATTCCTCCGGAAACAGGGACGAGCCCCTTTTTTGCTT
TTCCCAGATGCATCCGGTGCTGCGGCAGATGCGCCCCCCTCCTCAGCAGCGGCAAGAGCAAGAGCA
GCGGCAGACATGCAGGGCACCCTCCCCTTCTCCTACCGCGTCAGGAGGGGCAACATCCTACATCGAT
AGATCTGCAGAATTCGGCTTGGCGGCTGCGCGTTCAAACCTCCCGCTTCAAAATGGAGACCCTGCGT
GCTCACTCGGGCTTAAATACCCAGCGTGACCACATGGTGTCGCAAAATGTCGCAAAACACTCACGTG
ACCTCTAATACAGGACCTCTAGAGCATGGCTACaaatcatttattgttcaaagatgcagtcatccaaatccacattga
ccagatcgcaggcagtgcaagcgtctggcacctttcccatgatatgatgaatgtagcacagtttctgatacgcctttttgacgacaga
aacgggttgagattctgacacgggaaagcactctaaacagtctttctgtccgtgagtgaagcagatatttgaattctgattcattctct
cgcattgtctgcagggaaacagcatcagattcatgcccacgtgacgagaacatttgtttACgtacctgtctgcgtagttgatcgaag
cttccgcgtctgacgtcgatggctgcgcaactgactcgcgcacccgtttgggctcacttatatctgcgtcactgggggcgggtcttttct
tggctccacccttttgacgtagaattcatgctccacctcaaccacgtgatcctttgcccaccggaaaaagtctttgacttcctgcttgg
tgaccttcccaaagtcatgatccagacggcgggtgagttcaaatttgaacatccggtcttgcaacggctgctggtgttcgaaggtcgt
tgagttcccgtcaatcacggcgcacatgttggtgttggaggtgacgatcacgggagtcgggtctatctgggccgaggacttgcatttc
tggtccacgcgcaccttgcttcctccgagaatggctttggccgactccacgaccttggcggtcatcttcccctcctcccaccagatcac
catcttgtcgacacagtcgttgaagggaaagttctcattggtccagtttacgcacccgtagaagggcacagtgtgggctatggcctcc
gcgatgttggtcttcccggtagttgcaggcccaaacagccagatggtgttcctcttgccgaactttttcgtggcccatcccagaaaga
cggaagccgcatattggggatcgtacccgtttagttccaaaattttataaatccgattgctggaaatgtcctccacgggctgctggcc
caccaggtagtcgggggcggttttagtcaggctcataatctttcccgcattgtccaaggcagccttgatttgggaccgcgagttggag
gccgcattgaaggagatgtatgaggcctggtcctcctggatccactgcttctccgaggtaatccccttgtccacgagccacccgacca
gctccatgtacctggctgaagtttttgatctgatcaccggcgcatcagaattgggattctgattctctttgttctgctcctgcgtctgcga
cacgtgcgtcagatgctgcgccaccaaccgtttacgctccgtgagattcaaacaggcgcttaaatactgttccatattagtccacgcc
cactggagctcaggctgggttttggggagcaagtaattggggatgtagcactcatccaccaccttgttcccgcctccggcgccatttc
tggtctttgtgaccgcgaaccagtttggcaaagtcggctcgatcccgcggtaaattctctgaatcagtttttcgcgaatctgactcagg
aaacgtcccaaaaccatggatttcaccccggtggtttccacgagcacgtgcatgtggaagtagctctctcccttctcaaattgcacaa
agaaaagggcctccggTgccttactcacacggcgccattccgtcagaaagtcgcgctgcagcttctcggccacggtcaggggtgcc
tgctcaatcagattcagatccatgtcagaatctggcggcaactcccattccttctcggccacccagttcacaaagctgtcagaaatgc
cgggcagatgcTcgtcaaggtcgctggggaccttaatcacaatctcgtaaaaccccgGcAtggcggctgctcgttcaaaTttcgcg
gTcaaaatggagGTTGCatcctgctcgctcactcggccatatatacctcaGCGTGACCACATGGTGTCGCAAAATGT
CGCAAAACACTCACGTTGACCTctaatacaggaccgcggccgcTCTAGTGAATCCACAGAAACTAGCGAGG
TAAGCACTTACTCTATGTCTTTTACATGGTCCTGGGAAAGTGGAAAATACACCACTGAAACTTTTGCT
ACCAACTCTTACACCTTCTCCTACATTGCCCAGGAATAAAGAATCGTGAACCTGTTGCATGTTATGTT
TCAACGTGTTTATTTTTCAATTGCAGAAAATTTCAAGTCATTTTTCATTCAGTAGTATAGCCCCACCAC
CACATAGCTTATATTGATCACCGTACCTTAATCAAACTCACAGAACCCTAGTATTCAACCTGCCACCTC
CCTCCCAACACACAGAGTACACAGTCCTTTCTCCCCGGCTGGCCTTAAAAAGCATCATATCATGGGTA
ACAGACATATTCTTAGGTGTTATATTCCACACGGTTTCCTGTCGAGCCAAACGCTCATCAGTGATATT
AATAAACTCCCCGGGCAGCTCGCTTAAGTTCATGTCGCTGTCCAGCTGCTGAGCCACAGGCTGCTGT
CCAACTTGCGGTTGCTCAACGGGCGGCGAAGGGGAAGTCCACGCCTACATGGGGGTAGAGTCATA
ATCGTGCATCAGGATAGGGCGGTGGTG

FIG. 14 (CONT.)

CTGCAGCAGCGCGAATAAACTGCTGCCGCCGCTCCGTCCTGCAGGAATACAACATGGCAGT
GGTCTCCTCAGCGATGATTCGCACCGCCCGCAGCATGAGACGCCTTGTCCTCCGGGCACAGCAGCGC
ACCCTGATCTCACTTAAATCAGCACAGTAACTGCAGCACAGCACCACAATATTGTTCAAAATCCCACA
GTGCAAGGCGCTGTATCCAAAGCTCATGGCGGGGACCACAGAACCCACGTGGCCATCATACCACAA
GCGCAGGTAGATTAAGTGGCGACCCCTCATAAACACGCTGGACATAAACATTACCTCTTTTGGCATG
TTGTAATTCACCACCTCCCGGTACCATATAAACCTCTGATTAAACATGGCGCCATCCACCACCATCCTA
AACCAGCTGGCCAAAACCTGCCCGCCGGCTATGCACTGCAGGGAACCGGGACTGGAACAATGACAG
TGGAGAGCCCAGGACTCGTAACCATGGATCATCATGCTCGTCATGATATCAATGTTGGCACAACACA
GGCACACGTGCATACACTTCCTCAGGATTACAAGCTCCTCCCGCGTCAGAACCATATCCCAGGGAAC
AACCCATTCCTGAATCAGCGTAAATCCCACACTGCAGGGAAGACCTCGCACGTAACTCACGTTGTGC
ATTGTCAAAGTGTTACATTCGGGCAGCAGCGGATGATCCTCCAGTATGGTAGCGCGGGTCTCTGTCT
CAAAAGGAGGTAGGCGATCCCTACTGTACGGAGTGCGCCGAGACAACCGAGATCGTGTTGGTCGTA
GTGTCATGCCAAATGGAACGCCGGACGTAGTCATATTTCCTGAAGCAAAACCAGGTGCGGGCGTGA
CAAACAGATCTGCGTCTCCGGTCTCGTCGCTTAGCTCGCTCTGTGTAGTAGTTGTAGTATATCCACTC
TCTCAAAGCATCCAGGCGCCTAGGCAAAATAGCACCCTCCCGCTCCAGAACAACATACAGCGCTTCC
ACAGCGGCAGCCATAACAGTCAGCCTTACCAGTAAAAAAACCTATTAAAAAACACCACTCGACACGG
CACCAGCTCAATCAGTCACAGTGTAAAAAGGGCCAAGTACAGAGCGAGTATATATAGGACTAAAAA
ATGACGTAACGGTTAAAGTCCACAAAAAACACCCAGAAAACCGCACGCGAACCTACGCCCAGAAAC
GAAAGCCAAAAAACCCACAACTTCCTCAAATCTTCACTTCCGTTTTCCCACGATACGTCACTTCCCATT
TTAAAAAAACTACAATTCCCAATACATGCAAGTTACTCCGCCCTAAAACGCCCGGGCGACCGCACCC
TGTGACGAAAGCCGCCCGCAAGCTGCGCCCCTGAGTTAGTCATCTGAACTTCGGCCTGGGCGTCTCT
GGGAAGTACCACAGTGGTGGGAGCGGGACTTTCCTGGTACACCAGGGCAGCGGGCCAACTACGGG
GATTAAGGTTATTACGAGGTGTGGTGGTAATAGCCGCCTGTTCGAGGAGAATTCGGTTTCGGTGGG
CGCGGATTCCGTTGACCCGGGATATCATGTGGGGTCCCGCGCTCATGTAGTTTATTCGGGTTGAGTA
GTCTTGGGCAGCTCCAGCCGCAAGTCCCATTTGTGGCTGGTAACTCCACATGTAGGGCGTGGGAATT
TCCTTGCTCATAATGGCGCTGACGACAGGTGCTGGCGCCGGGTGTGGCCGCTGGAGATGACGTAGT
TTTCGCGCTTAAATTTGAGAAAGGGCGCGAAACTAGTCCTTAAGAGTCAGCGCGCAGTATTTGCTGA
AGAGAGCCTCCGCGTCTTCCAGCGTGCGCCGAAGCTGATCTTCGCTTTTGTGATACAGGCAGCTGCG
GGTGAGGGAGCGCAGAGACCTGTTTTTTATTTTCAGCTCTTGTTCTTGGCCCCTGCTTTGTTGAAATA
TAGCATACAGAGTGGGAAAAATCCTATTTCTAAGCTCGCGGGTCGATACGGGTTCGTTGGGCGCCA
GACGCAGCGCTCCTCCTCCTGCTGCTGCCGCCGCTGTGGATTTCTTGGGCTTTGTCAGAGTCTTGCTA
TCCGGTCGCCTTTGCTTCTGTGTGACCGCTGCTGTTGCTGCCGCTGCCGCTGCCGCCGGTGCAGTAG
GGGCTGTAGAGATGACGGTAGTAATGCAGGATGTTACGGGGGAAGGCCACGCCGTGATGGTAGAG
AAGAAAGCGGCGGGCGAAGGAGATGTTGCCCCCACAGTCTTGCAAGCAAGCAACTATGGCGTTCTT
GTGCCCGCGCCACGAGCGGTAGCCTTGGCGCTGTTGTTGCTCTTGGGCTAACGGCGGCGGCTGCTT
AGACTTACCGGCCCTGGTTCCAGTGGTGTCCCATCTACGGTTGGGTCGGCGAACAGGCAGTGCCGG
CGGCGCCTGAGGAGCGGAGGTTGTAGCGATGCTGGGAACGGTTGCCAATTTCTGGGGCGCCGGCG
AGGGGAATGCGACCGAGGGTGACGGTGTTTCGTCTGACACCTCTTCGGCCTCGGAAGCTTCGTCTA
GGCTGTCCCAGTCTTCCATCATCTCCTCCTCCTCGTCCAAAACCTCCTCTGCCTGACTGTCCCAGTATT
CCTCCTCGTCCGTGGGTGGCGGCGGCGGCAGCTGCAGCTTCTTTTTGGGTGCCATCCTGGGAAGCA
AGGGCCCGCGGCTGCTGATAGGGCTGCGGCGGCGGGGGGATTGGGTTGAGCTCCTCGCCGGACTG
GGGGTCCAGGTAAACCCCCCGTCCCTTTCGTAGCAGAAACTCTTGGCGGGCTTTGTTGATGGCTTGC
AATTGGCCAAGGATGTGGCCCTGGGTAATGACG

FIG. 14 (CONT.)

CAGGCGGTAAGCTCCGCATTTGGCGGGCGGGATTGGTCTTCGTAGAACCTAATCTCGTGGGCGTGG
TAGTCCTCAGGGAGAAGGAAATGGCCAGTCGGGAAGAGGAGCAGCGCGAAACCACCCCCGAGCGC
GGACGCGGTGCGGCGCGACGTCCACCAACCATGGAGGACGTGTCGTCCCCGTCGCCGTCGCCGCCG
CCTCCCCGCGCGCCCCCAAAAAAGAGACTGCGGAGACGCCTGGAGTCCGAGGACGAGGAAGACAG
TTCCCAGGACGCTCTGGTGCCTAGGACACCATCTCCAAGACCCTCCACTTCCACCGCCGACCTGGCCA
TTGCCAGCAAAAAAAAGAAGAAGAGGCCCTCCCCTAAACCTGAACGACCACCCAGCCCAGAAGTGA
TCGTGGACTCAGAGGAAGAGCGCGAGGACGTCGCTCTGCAGATGGTGGGATTCAGCAATCCACCTG
TGCTCATCAAGCACGGCAAAGGGGGAAAACGGACCGTGCGCAGGCTGAACGAGGATGATCCTGTG
GCAAGGGGCATGAGGACACAGGAGGAGAAGGAAGAATCCTCCGAGGCCGAGAGCGAGAGCACAG
TGATTAATCCACTGTCCCTGCCAATTGTGAGCGCTTGGGAGAAGGGAATGGAGGCCGCCCGGGCCC
TGATGGACAAGTACCACGTGGACAACGACCTGAAGGCTAATTTCAAACTGCTGCCTGACCAGGTGG
AGGCCCTGGCTGCCGTGTGCAAGACATGGCTGAATGAGGAGCATAGAGGGCTGCAGCTGACCTTTA
CATCAAACAAGACCTTTGTGACCATGATGGGCAGGTTTCTGCAGGCCTACCTGCAATCTTTCGCCGA
AGTGACTTACAAGCACCACGAGCCCACCGGCTGCGCCCTGTGGCTGCACAGATGCGCCGAGATTGA
GGGCGAGCTGAAATGCCTGCACGGCTCTATCATGATTAACAAGGAGCACGTGATCGAGATGGATGT
GACTTCCGAAAACGGCCAGCGCGCCCTGAAGGAGCAGTCCAGCAAGGCCAAGATCGTGAAGAACA
GGTGGGGCAGGAACGTGGTGCAGATTTCTAACACAGACGCCAGATGTTGCGTGCATGACGCCGCCT
GCCCTGCCAATCAGTTTAGCGGCAAGAGCTGCGGAATGTTCTTCAGCGAGGGAGCCAAGGCGCAAG
TGGCCTTCAAGCAGATCAAGGCCTTCATGCAAGCCCTGTATCCAAATGCCCAGACCGGCCACGGCCA
CCTCCTGATGCCCCTGCGCTGCGAATGTAACTCCAAGCCCGGCCACGCCCCTTTCCTGGGCAGGCAG
CTGCCAAAACTGACCCCTTTTGCCCTGAGCAACGCCGAAGATCTGGATGCCGATCTGATCAGCGACA
AGTCCGTGCTGGCCTCCGTTCACCACCCCGCCCTGATCGTGTTCCAGTGCTGCAATCCCGTGTACAGG
AATAGCAGAGCTCAGGGTGGAGGCCCCAACTGCGACTTCAAGATCTCCGCCCCAGATCTGCTGAAC
GCTCTCGTGATGGTGCGGAGCCTGTGGTCTGAGAACTTCACAGAGCTGCCCCGCATGGTGGTGCCC
GAGTTCAAGTGGAGCACTAAGCATCAGTACCGGAATGTGTCTCTGCCCGTGGCCCACTCTGACGCCA
GACAGAATCCTTTTGACTTCTGAACGGCGCAGACGGCAAGGGTGGGGGGTAAATAATCACCCGAGA
GTGTACAAATAAAAACATTTGCCTTTATTGAAAGTGTCTCCTAGTACATTATTTTTACATGTTTTTCAA
GTGACAAAAAGAAGTGGCGCTCCTAATCTGCGCACTGTGGCTGCGGAAGTAGGGCGAGTGGCGCT
CCAGGAAGCTGTAGAGCTGTTCCTGGTTGCGACGCAGGGTGGGCTGTACCTGGGGACTGTTAAGCA
TGGAGTTGGGTACCGGATCCATCGCGCCCTGTAGCGGCGCATTAAGCGCGGCGGGTGTGGTGGTTA
CGCGCAGCGTGACCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGGTTCCGATTTAGT
GCTTTACGGCACCTCGACCCCAAAAAACTTGATTAGGGTGATGGTTCACGTAGTGGGCCATCGCCCT
GATAGACGGTTTTTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCCGATTTCGGCCTAT
TGGTTAAAAAATGAGCTGATTTAACAAAAATTTAACGCGAATTTTAACAAAATATTAACGCTTACAAT
TTAGGTGGCACTTTTCGGGGAAATGTGCGCGGAACCCCTATTTGTTTATTTTTCTAAATACATTCAAA
TATGTATCCGCTCATGAGACAATAACCCTGATAAATGCTTCAATAATATTGAAAAAGGAAGAGTatga
ttgaacaagatggattgcacgcaggttctccggccgcttgggtggagaggctattcggctatgactgggcacaacagacaatcggct
gctctgatgccgccgtgttccggctgtcagcgcaggggcgcccggttctttttgtcaagaccgacctgtccggtgccctgaatgaact
gcaagacgaggcagcgcggctatcgtggctggccacgacgggcgttccttgcgcagctgtActcgacgttgtcactgaagcgggaa
gggactggctgctattgggcgaagtgccggggcaggatctcctgtcatctcaccttgctcctgccgagaaagtatccatcatggctga
tgcaatgcggcggctgcatacgcttgatccggctacc

FIG. 14 (CONT.)

tgcccattcgaccaccaagcgaaacatcgcatcgagcgagcacgtactcggatggaagccggtcttgtcgatcaggatgatctgga
cgaagagcatcaggggctcgcgccagccgaactgttcgccaggctcaaggcgagcatgcccgacggcgaggatctcgtcgtgacc
catggcgatgcctgcttgccgaatatcatggtggaaaatggccgcttttctggattcatcgactgtggccggctgggtgtggcggacc
gctatcaggacatagcgttggctacccgtgatattgctgaagagcttggcggcgaatgggctgaccgcttcctcgtgctttacggtat
cgccgctcccgattcgcagcgcatcgccttctatcgccttcttgacgagttcttctgaCTGTCAGACCAAGTTTACTCATAT
ATACTTTAGATTGATTTAAAACTTCATTTTTAATTTAAAAGGATCTAGGTGAAGATCCTTTTTGATAAT
CTCATGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGTAACTGGCTTCAGCA
GAGCGCAGATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGAACGGG
GGGTTCGTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGGCAGGG
TCGGAACAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGGCGGAGCCTATGGAA
AAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATCATATGGTTTAAA
CGTCGACGTAATCCGTAGATGTACCTGGACATCCAGGTGATGCCGGCGGCGGTGGTGGAGGCGCG
CGGAAAGTCGCGGACGCGGTTCCAGATGTTGCGCAGCGGCAAAAAGTGCTCCATGGTCGGGACGC
TCTGGCCGGTGAGGCGTGCGCAGTCGTTGACGCTCTAGACCGTGCAAAAGGAGAGCCTGTAAGCG
GGCACTCTTCCGTGGTCTGGTGGATAAATTCGCAAGGGTATCATGGCGGACGACCGGGGTTCGAAC
CCCGGATCCGGCCGTCCGCCGTGATCCATGCGGTTACCGCCCGCGTGTCGAACCCAGGTGTGCGAC
GTCAGACAACGGGGGAGCGCTCCT

SEQ ID. NO:14
Wild-type AAV2 P5 promoter (P5-AAV2)
GGTCCTGTATTAGAGGTCACGTGAGTGTTTTGCGACATTTTGCGACACCATGTGGTCACGCTGGGTA
TTTAAGCCCGAGTGAGCACGCAGGGTCTCCATTTTGAAGCGGGAGGTTTGAACGCGCAGCCGCC

SEQ ID. NO:15
Modified AAV2 P5 promoter (P5I)
GGTCCTGTATTAGAGGTCAACGTGAGTGTTTTGCGACATTTTGCGACACCATGTGGTCACGCTGAGG
TATATATGGCCGAGTGAGCGAGCAGGATGCAACCTCCATTTTGACCGCGAAATTTGAACGAGCAGC
CGCC

FIG. 14 (CONT.)

SEQ ID. NO:16

VA coding region of Ad2

GGGCACTCTTCCGTGGTCTGGTGGATAAATTCGCAAGGGTATCATGGCGGACGACCGGGGTTCGAA
CCCCGGATCCGGCCGTCCGCCGTGATCCATGCGGTTACCGCCCGCGTGTCGAACCCAGGTGTGCGA
CGTCAGACAACGGGGGAGCGCTCCTTTTGGCTTCCTTCCAGGCGCGGCGGCTGCTGCGCTAGCTTTT
TTGGCCACTGGCCGCGCGCGGCGTAAGCGGTTAGGCTGGAAAGCGAAAGCATTAAGTGGCTCGCTC
CCTGTAGCCGGAGGGTTATTTTCCAAGGGTTGAGTCGCAGGACCCCCGGTTCGAGTCTCGGGCCGG
CCGGACTGCGGCGAACGGGGGTTTGCCTCCCCGTCATGCAAGACCCCGCTTGCAAATTCCTCCGGAA
ACAGGGACGAGCCCCT

SEQ ID. NO:17

Modified E4 coding region of mini-pHelper

ATGACTACGTCCGGCGTTCCATTTGGCATGACACTACGACCAACACGATCTCGGTTGTCTCGGCGCA
CTCCGTACAGTAGGGATCGCCTACCTCCTTTTGAGACAGAGACCCGCGCTACCATACTGGAGGATCA
TCCGCTGCTGCCCGAATGTAACACTTTGACAATGCACAACGCGTGGACTTCCCCTTCGCCGCCCGTTG
AGCAACCGCAAGTTGGACAGCAGCCTGTGGCTCAGCAGCTGGACAGCGACATGAACTTAAGCGAGC
TGCCCGGGGAGTTTATTAATATCACTGATGAGCGTTTGGCTCGACAGGAAACCGTGTGGAATATAAC
ACCTAAGAATATGTCTGTTACCCATGATATGATGCTTTTTAAGGCCAGCCGGGGAGAAAGGACTGTG
TACTCTGTGTGTTGGGAGGGAGGTGGCAGGTTGAATACTAGGGTTCTGTGA

SEQ ID. NO:18

Modified E4 coding region of mini-pHelper1.0

ATGACTACGTCCGGCGTTCCATTTGGCATGACACTACGACCAACACGATCTCGGTTGTCTCGGCGCA
CTCCGTACAGTAGGGATCGCCTACCTCCTTTTGAGACAGAGACCCGCGCTACCATACTGGAGGATCA
TCCGCTGCTGCCCGAATGTAACACTTTGACAATGCACAACGTGAGTTACGTGCGAGGTCTTCCCTGC
AGTGTGGGATTTACGCTGATTCAGGAATGGGTTGTTCCCTGGGATATGGTTCTGACGCGGGAGGAG
CTTGTAATCCTGAGGAAGTGTATGCACGTGTGCCTGTGTTGTGCCAACATTGATATCATGACGAGCA
TGATGATCCATGGTTACGAGTCCTGGGCTCTCCACTGTCATTGTTCCAGTCCCGGTTCCCTGCAGTGC
ATAGCCGGCGGGCAGGTTTTGGCCAGCTGGTTTAGGATGGTGGTGGATGGCGCCATGTTTAATCAG
AGGTTTATATGGTACCGGGAGGTGGTGAATTACAACATGCCAAAAGAGGTAATGTTTATGTCCAGC
GTGTTTATGAGGGGTCGCCACTTAATCTACCTGCGCTTGTGGTATGATGGCCACGTGGGTTCTGTGG
TCCCCGCCATGAGCTTTGGATACAGCGCCTTGCACTGTGGGATTTTGAACAATATTGTGGTGCTGTG
CTGCAGTTACTGTGCTGATTTAAGTGAGATCAGGGTGCGCTGCTGTGCCCGGAGGACAAGGCGTCT
CATGCTGCGGGCGGTGCGAATCATCGCTGAGGAGACCACTGCCATGTTGTATTCCTGCAGGACGGA
GCGGCGGCGGCAGCAGTTTATTCGCGCGCTGCTGCAGCACCACCGCCCTATCCTGATGCACGATTAT
GACTCTACCCCCATGTAGGCGTGGACTTCCCCTTCGCCGCCCGTTGAGCAACCGCAAGTTGGACAGC
AGCCTGTGGCTCAGCAGCTGGACAGCGACATGAACTTAAGCGAGCTGCCCGGGGAGTTTATTAATA
TCACTGATGAGCGTTTGGCTCGACAGGAAACCGTGTGGAATATAACACCTAAGAATATGTCTGTTAC
CCATGATATGATGCTTTTTAAGGCCAGCCGGGGAGAAAGGACTGTGTACTCTGTGTGTTGGGAGGG
AGGTGGCAGGTTGAATACTAGGGTTCTGTGA

FIG. 14 (CONT.)

SEQ ID. NO:19
Ad2 E4 promoter + E2a promoter sequence
AACAGTCAGCCTTACCAGTAAAAAAACCTATTAAAAAACACCACTCGACACGGCACCAGCTCAATCA
GTCACAGTGTAAAAAGGGCCAAGTACAGAGCGAGTATATATAGGACTAAAAAATGACGTAACGGTT
AAAGTCCACAAAAAACACCCAGAAAACCGCACGCGAACCTACGCCCAGAAACGAAAGCCAAAAAAC
CCACAACTTCCTCAAATCTTCACTTCCGTTTTCCCACGATACGTCACTTCCCATTTTAAAAAAACTACA
ATTCCCAATACATGCAAGTTACTCCGCCCTAAAACGCCCGGGCGACCGCACCCTGTGACGAAAGCCG
CCCGCAAGCTGCGCCCCTGAGTTAGTCATCTGAACTTCGGCCTGGGCGTCTCTGGGAAGTACCACAG
TGGTGGGAGCGGGACTTTCCTGGTACACCAGGGCAGCGGGCCAACTACGGGGATTAAGGTTATTAC
GAGGTGTGGTGGTAATAGCCGCCTGTTCGAGGAGAATTCGGTTTCGGTGGGCGCGGATTCCGTTGA
CCCGGGATATCATGTGGGGTCCCGCGCTCATGTAGTTTATTCGGGTTGAGTAGTCTTGGGCAGCTCC
AGCCGCAAGTCCCATTTGTGGCTGGTAACTCCACATGTAGGGCGTGGGAATTTCCTTGCTCATAATG
GCGCTGACGACAGGTGCTGGCGCCGGGTGTGGCCGCTGGAGATGACGTAGTTTTCGCGCTTAAATT
TGAGAAAGGGCGCGAAACTAGTCCTTAAGAGTCAGCGCGCAGTATTTGCTGAAGAGAGCCTCCGCG
TCTTCCAGCGTGCGCCGAAGCTGATCTTCGCTTTT

SEQ ID. NO:20
AAV rep coding sequence
atgccggggttttacgagattgtgattaaggtccccagcgaccttgacgAgcatctgcccggcatttctgacagctttgtgaactggg
tggccgagaaggaatgggagttgccgccagattctgacatggatctgaatctgattgagcaggcacccctgaccgtggccgagaag
ctgcagcgcgactttctgacggaatggcgccgtgtgagtaaggcAccggaggcccttttctttgtgcaatttgagaagggagagagc
tacttccacatgcacgtgctcgtggaaaccaccggggtgaaatccatggttttgggacgtttcctgagtcagattcgcgaaaaactg
attcagagaatttaccgcgggatcgagccgactttgccaaactggttcgcggtcacaaagaccagaaatggcgccggaggcggga
acaaggtggtggatgagtgctacatccccaattacttgctccccaaaacccagcctgagctccagtgggcgtggactaatatggaac
agtatttaagcgcctgtttgaatctcacggagcgtaaacggttggtggcgcagcatctgacgcacgtgtcgcagacgcaggagcag
aacaaagagaatcagaatcccaattctgatgcgccggtgatcagatcaaaaacttcagccaggtacatggagctggtcgggtggct
cgtggacaaggggattacctcggagaagcagtggatccaggaggaccaggcctcatacatctccttcaatgcggcctccaactcgc
ggtcccaaatcaaggctgccttggacaatgcgggaaagattatgagcctgactaaaaccgcccccgactacctggtgggccagcag
cccgtggaggacatttccagcaatcggatttataaaattttggaactaaacgggtacgatccccaatatgcggcttccgtctttctgg
gatgggccacgaaaaagttcggcaagaggaacaccatctggctgtttgggcctgcaactaccgggaagaccaacatcgcggaggc
catagcccacactgtgcccttctacgggtgcgtaaactggaccaatgagaactttcccttcaacgactgtgtcgacaagatggtgatc
tggtgggaggaggggaagatgaccgccaaggtcgtggagtcggccaaagccattctcggaggaagcaaggtgcgcgtggaccag
aaatgcaagtcctcggcccagatagacccgactcccgtgatcgtcacctccaacaccaacatgtgcgccgtgattgacgggaactc
aacgaccttcgaacaccagcagccgttgcaagaccggatgttcaaatttgaactcacccgccgtctggatcatgactttgggaaggt
caccaagcaggaagtcaaagactttttccggtgggcaaaggatcacgtggttgaggtggagcatgaattctacgtcaaaaagggtg
gagccaagaaaagacccgcccccagtgacgcagatataagtgagcccaaacgggtgcgcgagtcagttgcgcagccatcgacgtc
agacgcggaagcttcgatcaactacgcagacaggtacGTaaacaaatgttctcgtcacgtgggcatgaatctgatgctgtttccctg
cagacaatgcgagagaatgaatcagaattcaaatatctgcttcactcacggacagaaagactgtttagagtgctttcccgtgtcaga
atctcaacccgtttctgtcgtcaaaaaggcgtatcagaaactgtgctacattcatcatatcatgggaaaggtgccagacgcttgcact
gcctgcgatctggtcaatgtggatttggatgactgcatctttgaacaa

FIG. 14 (CONT.)

SEQ ID. NO:21
AAV2cap coding sequence
atggctgccgatggttatcttccagattggctcgaggacactctctctgaaggaataagacagtggtggaagctcaaacctggcccacc
accaccaaagcccgcagagcggcataaggacgacagcaggggtcttgtgcttcctgggtacaagtacctcggacccttcaacggac
tcgacaagggagagccggtcaacgaggcagacgccgcggccctcgagcacgacaaagcctacgaccggcagctcgacagcgga
gacaacccgtacctcaagtacaaccacgccgacgcggagtttcaggagcgccttaaagaagatacgtcttttgggggcaacctcgga
cgagcagtcttccaggcgaaaaagagggttcttgaacctctgggcctggttgaggaacctgttaagacggctccgggaaaaaagagg
ccggtagagcactctcctgtggagccagactcctcctcgggaaccggaaaggcgggccagcagcctgcaagaaaaagattgaatttt
ggtcagactggagacgcagactcagtacctgacccccagcctctcggacagccaccagcagccccctctggtctgggaactaatac
gatggctacaggcagtggcgcaccaatggcagacaataacgagggcgccgacggagtgggtaattcctcgggaaattggcattgcg
attccacatggatgggcgacagagtcatcaccaccagcacccgaacctgggccctgcccacctacaacaaccacctctacaaacaaa
tttccagccaatcaggagcctcgaacgacaatcactactttggctacagcaccccttgggggtattttgacttcaacagattccactgcca
cttttcaccacgtgactggcaaagactcatcaacaacaactggggattccgacccaagagactcaacttcaagctctttaacattcaagt
caaagaggtcacgcagaatgacggtacgacgacgattgccaataaccttaccagcacggttcaggtgtttactgactcggagtaccag
ctcccgtacgtcctcggctcggcgcatcaaggatgcctcccgccgttcccagcagacgtcttcatggtgccacagtatggatacctcac
cctgaacaacgggagtcaggcagtaggacgctcttcattttactgcctggagtactttccttctcagatgctgcgtaccggaaacaacttt
accttcagctacacttttgaggacgttcctttccacagcagctacgctcacagccagagtctggaccgtctcatgaatcctctcatcgacc
agtacctgtattacttgagcagaacaaacactccaagtggaaccaccacgcagtcaaggcttcagttttctcaggccggagcgagtga
cattcgggaccagtctaggaactggcttcctggaccctgttaccgccagcagcgagtatcaaagacatctgcggataacaacaacagt
gaatactcgtggactggagctaccaagtaccacctcaatggcagagactctctggtgaatccgggcccggccatggcaagccacaa
ggacgatgaagaaaagtttttttcctcagagcggggttctcatctttgggaagcaaggctcagagaaaacaaatgtggacattgaaaag
gtcatgattacagacgaagaggaaatcaggacaaccaatcccgtggctacggagcagtatggttctgtatctaccaacctccagagag
gcaacagacaagcagctaccgcagatgtcaacacacaaggcgttcttccaggcatggtctggcaggacagagatgtgtaccttcagg
ggcccatctgggcaaagattccacacacggacggacattttcacccctctcccctcatgggtggattcggacttaaacaccctcctcca
cagattctcatcaagaacaccccggtaccAgcgaatccttcgaccaccttcagtgcggcaaagtttgcttccttcatcacacagtactcc
acgggacaggtcagcgtggagatcgagtgggagctgcagaaggaaaacagcaaacgctggaatcccgaaattcagtacacttcca
actacaacaagtctgttaatgtggactttactgtggacactaatggcgtgtattcagagcctcgccccattggcaccagatacctgactcg
taatctg

SEQ ID NO:22
Ad2 E4 promoter sequence
GACCCGGGATATCATGTGGGGTCCCGCGCTCATGTAGTTTATTCGGGTTGAGTAGTCTTGGGCAGCT
CCAGCCGCAAGTCCCATTTGTGGCTGGTAACTCCACATGTAGGGCGTGGGAATTTCCTTGCTCATAA
TGGCGCTGACGACAGGTGCTGGCGCCGGGTGTGGCCGCTGGAGATGACGTAGTTTTCGCGCTTAAA
TTTGAGAAAGGGCGCGAAACTAGTCCTTAAGAGTCAGCGCGCAGTATTTGCTGAAGAGAGCCTCCG
CGTCTTCCAGCGTGCGCCGAAGCTGATCTTCGCTTTT

SEQ ID NO:23
Ad2 E2a promoter sequence
GTTTTAGGGCGGAGTAACTTGCATGTATTGGGAATTGTAGTTTTTTTAAAATGGGAAGTGACGTATC
GTGGGAAAACGGAAGTGAAGATTTGAGGAAGTTGTGGGTTTTTTGGCTTTCGTTTCTGGGCGTAGG
TTCGCGTGCGGTTTTCTGGGTGTTTTTTGTGGACTTTAACCGTTACGTCATTTTTTAGTCCTATATATA
CTCGCTCTGTACTTGGCCCTTTTTACACTGTGACTGATTGAGCTGGTGCCGTGTCGAGTGGTGTTTTT
TAATAGGTTTTTTTACTGGTAAGGCTGACTGTT

COMPOSITIONS AND METHODS FOR RECOMBINANT PARVOVIRUS PRODUCTION

This application claims priority from U.S. Provisional App. No. 63/341,201, filed May 12, 2022, which is incorporated herein by reference.

FIELD

The present application relates generally to compositions and methods for producing recombinant viruses. More particularly, the application relates to compositions for production of recombinant parvoviruses, such as adeno-associated viruses (AAVs).

BACKGROUND

Recombinant viruses, such as recombinant adeno-associated viruses (rAAV) have been developed as vectors by replacing all viral genes with a therapeutic transgene expression cassette, while retaining the only cis elements, the ITRs, which are required for vector packaging and DNA replication. Early methods of rAAV production relied on a plasmid system comprising: 1) an AAV helper plasmid (generally encompassing AAV Rep and Cap coding regions, while lacking AAV ITRs so it cannot replicate or package itself) and 2) an ITR-containing plasmid (generally encompassing a selected transgene of interest bounded by AAV ITRs which provides for viral replication and packaging functions). Both the helper plasmid and the ITR-containing plasmid bearing the selected gene can be introduced into suitable cells for production by transient transfection. The transfected cell can then be infected with a helper virus, such as an adenovirus or herpes simplex virus, which transactivates the AAV promoters present on the helper plasmid that direct the transcription and translation of AAV Rep and Cap regions. Regarding the Ad helper virus, the E1a, E1b, E2a, E4, and VA RNA genes can supply the helper functions necessary for rAAV production.

Infection of helper virus into producer cells to generate rAAV was effective in producing rAAV. However, a consequence is that it can also produce Ad helper virus particles that can elicit immune responses from the host. In certain platforms, the viral helper genes necessary for AAV manufacturing can be stably transfected into the manufacturing cell line (e.g., HEK293 cells), thereby reducing the possibility of an anti-helper virus immune response by the host immune system coming from trace level of residual helper virus.

More recently, a triple-plasmid transfection method has been developed. This method uses an AAV serotype-specific Rep and Cap plasmid as well as the transgene-containing plasmid but eliminates the use of helper virus infection by supplying the essential helper viral genes on a third plasmid (i.e., the viral coding sequences were removed or reduced), thus lowering the potential anti-helper virus immune response by the host immune system. Supplying the viral helper genes on the third plasmid greatly decreased helper viral production in the transfected cells, providing only rAAV. Multiplasmid transient transfection of adherent HEK293 cells is a commonly used method for rAAV production.

In a multiplasmid system, it is important to maintain an appropriate plasmid size and plasmid ratio to maximize transfection efficiency and AAV production. There is a need in the art for a simplified and efficient plasmid-based system for producing rAAVs, which provides for improved transfection and lowered immunogenicity, while still retaining optimum expression of the transgene. The present application is predicated on the discovery of dispensable adenovirus regions in traditional helper plasmids to provide such benefits.

SUMMARY

One aspect of the present application relates to an expression construct for production of a recombinant parvovirus. The expression construct comprises: (1) a modified or unmodified adenovirus E4 coding region that encodes E4 open reading frame 6/7; (2) a modified or unmodified adenovirus E2a coding region that encodes an E2a protein; (3) an adenovirus VA RNA coding region that encodes adenovirus VAI and VAII RNA; (4) a parvovirus protein coding region that encodes parvovirus proteins necessary for the production of the recombinant parvovirus; (5) a recombinant parvovirus sequence comprising (a) an expression cassette comprising a nucleotide sequence encoding a transgene and a regulatory element operably linked to the nucleotide sequence, and (b) at least one ITR at one end of the expression cassette; and (6) one or more regulatory elements that allow expression of the E4 open reading frame 6/7, the E2a protein, the adenovirus VA RNA, and the parvovirus proteins necessary for the production of the recombinant parvovirus in a host cell.

Another aspect of the present application relates to a polynucleotide expression construct for production of recombinant parvoviruses. The expression construct comprises (a) a modified adenovirus E4 coding region encoding adenovirus E4orf6/7, wherein the modified adenovirus E4 coding region comprises (i) partial or complete deletion of E4orf6/7 intron 1, or (ii) a partial or complete deletion of E4orf6/7 intron 2, or both (i) and (ii); (b) a modified adenovirus E2a coding region encoding an adenovirus E2a protein, wherein the modified adenovirus E2a coding region comprises at least one deletion in E4orf6/7 intron 1 or E4orf6/7 intron 2; (c) a sequence encoding one or more adenovirus VA RNAs; and (d) one or more regulatory elements operably linked to (a), (b) and (c).

Another aspect of the present application relates to a method for producing a recombinant parvovirus particle using the expression construct of the present application. The method comprises the step of introducing the expression construct of the present application into a host cell, incubating the host cell harboring the expression construct for a desired period of time to produce recombinant parvovirus particles, and harvesting recombinant parvovirus particles after the incubation period.

BRIEF DESCRIPTION OF THE DRAWINGS

FIG. 13 shows that a modified P5 promoter (P5I) increase AAV yield compared to wild-type AAV2 P5 promoter.

FIG. 14 shows a list of nucleotide and amino acid sequences described in the instant application.

DETAILED DESCRIPTION

I. Definitions

Figure 1:
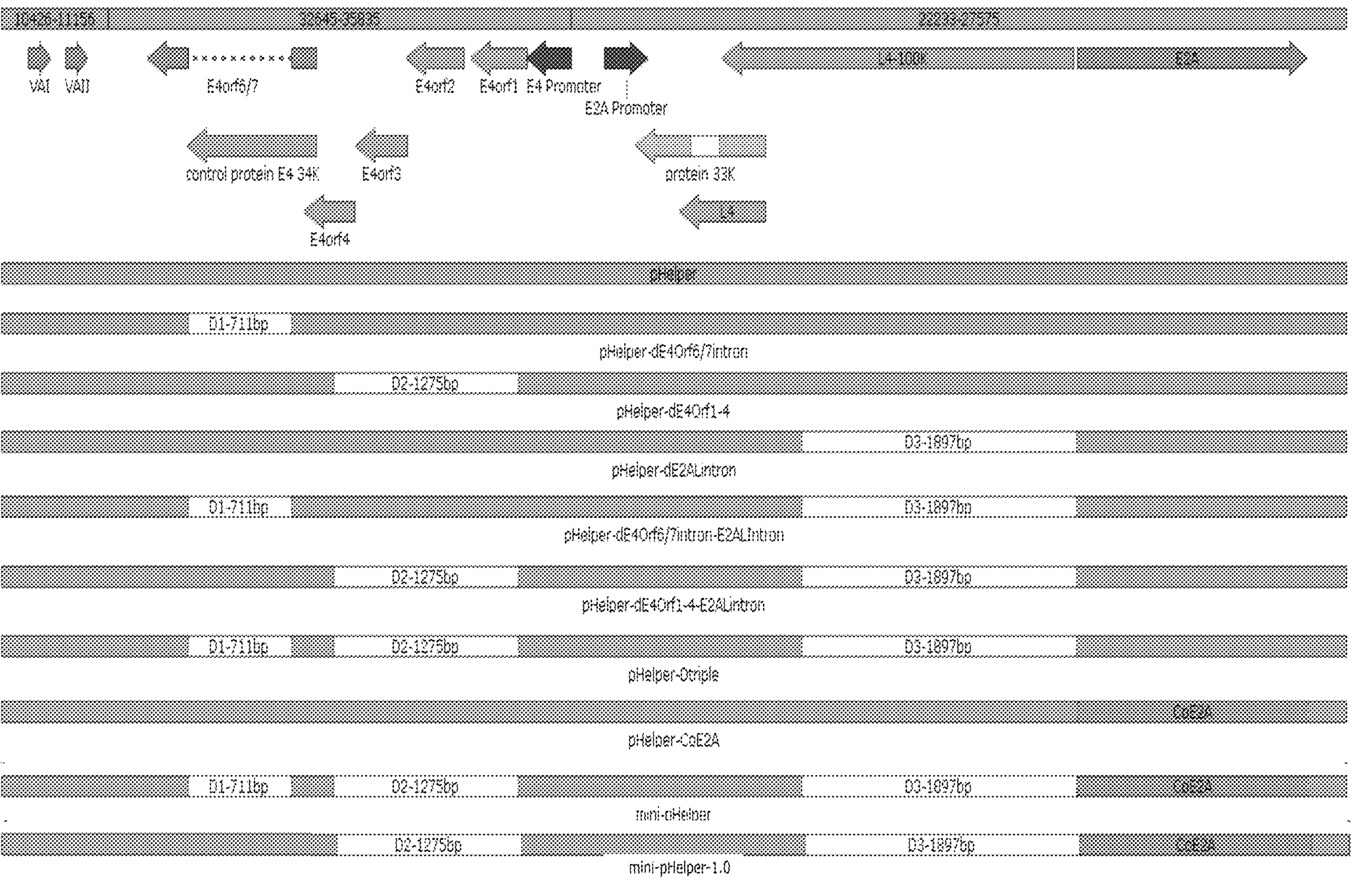
FIG. 1 shows a map depicting the arrangement of adenovirus (Ad2) coding regions relative to various deletions in a series of exemplary expression cassettes of the present application. CoE2A: codon optimized E2A coding sequence.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used herein, the term "polynucleotide" refers to polydeoxyribonucleotide, which may comprise unmodified DNA or modified DNA and may comprise both single- and double-stranded DNA.

As used herein, the term "heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector. As an example, "heterologous" when used in the context of nucleic acid sequences, such as coding sequences and control sequences, may refer to sequences that are not normally joined together, and/or are not normally associated with one another under ordinary circumstances found in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this application. Allelic variation or naturally occurring mutational events do not give rise to heterologous DNA, as used herein.

A "coding sequence," as used herein, refers to a nucleic acid sequence which "encodes" a particular protein or functional nucleotide, such as a siRNA. The nucleic acid sequence in a polynucleotide is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence is usually located 3' to the coding sequence.

A "coding region," as used herein, refers to a region in a genomic DNA where a coding sequence for a gene is located. The coding region of a gene may include both the exon and intron sequences of the gene, as well as the regulatory sequences (e.g., promoter and enhances) for the gene. For example, an adenovirus E4 coding region may include nucleotide sequence 32645-35835 of the Ad2 genome, and an adenovirus E2a coding region may include nucleotide sequence 22233-27575 of the Ad2 genome.

A "modified coding region," as used herein, refers to a coding region that have been modified by deletion, substitution and/or insertion of one or more nucleotides. For example, a modified adenovirus E4 coding region may include nucleotide sequence 32645-35835 of the Ad2 genome with a deletion of one or more nucleotides in E4orf6/7 intron 1 and/or intron 2, and a modified adenovirus E2a coding region may include nucleotide sequence 22233-27575 of the Ad2 genome with a deletion of one or more nucleotides in later-E2a intron 1 and/or intron 2.

The term "adenovirus E4 proteins" refers to proteins that are (1) produced by the adenovirus E4 region and (2) required for AAV production in host cell. Adenovirus E4 proteins may be encoded by different open reading frames in different adenoviruses. The term "adenovirus E4 proteins" as used herein, encompasses functional homologs and functional equivalents of adenovirus E4 proteins. Examples of the adenovirus E4 proteins include the protein encoded by E4 open reading frame 6/7 (E4orf6/7) of Ad2/5 and functional equivalents thereof.

The term "adenovirus E2a protein" refers to the protein encoded by the E2a region of an adenovirus genome. The adenovirus E2a protein is a DNA-binding protein that plays a role in the elongation phase of viral strand displacement replication by unwinding the template in an ATP-independent fashion. As used herein, the term "adenovirus E2a protein" encompasses functional homologs and functional equivalents of adenovirus E2a proteins.

As used herein, the term "adenovirus VA RNA" refers a type of non-coding RNA found in adenovirus that plays a role in regulating translation. VA RNAs include VAI and VAIL. As used herein, the term "adenovirus VA RNA" encompasses functional homologs and functional equivalents of adenovirus VA RNA.

The term "adenovirus VA RNA coding region" refers to a region encoding adenovirus VA RNAs. An exemplary VA coding region includes nucleotide sequence 10426-11156 (SEQ ID NO:16) of the Ad2 genome.

The terms "regulatory element," "regulatory sequence" and "regulatory region" are used with reference to promoters, enhancers, polyadenylation signals, transcription termination sequences, upstream regulatory domains, origins of replication, internal ribosome entry sites ("IRES"), and the like, which collectively provide for the replication, transcription, and translation of a coding sequence in a recipient cell. Not all of these regulatory sequences need always be present so long as the selected coding sequence is capable of being replicated, transcribed and translated in an appropriate host cell.

The terms "promoter" and "promoter region" are used herein with reference to a DNA regulatory sequence to which RNA polymerase binds, initiating transcription of a downstream (3' direction) coding sequence. Further, these terms should be broadly construed as additionally encompassing other regulatory elements, including enhancer regions, intron splice donors and acceptors, other 5' untranslated regions and the like. A promoter sequence may be homologous or heterologous to the desired gene sequence. A wide range of promoters are known and available in the art for the present application, including a wide range of viral and mammalian promoters. Cell type selective or tissue specific promoters can be utilized to target or enhance expression of gene sequences in specific cell populations relative to others. Suitable mammalian and viral promoters. A promoter may be constitutively active, conditionally active, or inducible, depending on the cell type.

The terms "enhancer" and "enhancer region" are used herein, denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. One example of an inducible enhancer is the metallothionein enhancer, which can be stimulated by glucocorticoids or heavy metals.

"Operably linked" refers to an arrangement of elements wherein the components so described are configured so as to perform their usual function. Thus, control sequences operably linked to a coding sequence are capable of effecting the expression of the coding sequence. Operably linking a heterologous sequence to a promoter, results in a chimeric gene. The control sequences need not be contiguous with the coding sequence, so long as they function to direct the expression thereof. Thus, for example, intervening untranslated yet transcribed sequences can be present between a promoter sequence and the coding sequence, and the promoter sequence can still be considered "operably linked" to the coding sequence.

For the purpose of describing the relative position of a nucleotide sequence in a particular nucleic acid molecule throughout the present application, such as when a particular nucleotide sequence is described as being situated "upstream", "downstream", "3'", or "5'" relative to another sequence, these modifiers should be construed as relating sequence portions in the "sense" or "coding" strand of a DNA molecule, as is conventional in the art.

The term "transgene" refers to a polynucleotide that is introduced into a cell and is capable of being transcribed into RNA and optionally, translated and/or expressed under appropriate conditions. The transgene confers a desired property to a cell into which it was introduced, or otherwise leads to a desired therapeutic or diagnostic outcome. In another aspect, it may be transcribed into a molecule that mediates RNA interference, such as a miRNA, an siRNA, an shRNA, or a guide RNA for CRISPR/Cas9 mediated targeting of the mutant allele.

The term "expression" encompasses the processes by which nucleic acids (e.g., DNA) are transcribed to produce RNAs, such as mRNAs that are processed and translated into polypeptides.

The term "gene product" (also referred to herein as "gene expression product" or "expression product") encompasses products resulting from expression of a gene, such as a mRNA transcribed from a gene and polypeptides arising from translation of the mRNA. It will be appreciated that certain gene products may undergo processing or modification, e.g., in a cell. For example, RNA transcripts may be spliced, polyadenylated, etc., prior to mRNA translation, and/or polypeptides may undergo co-translational or post-translational processing such as removal of secretion signal sequences, removal of organelle targeting sequences, or modifications such as phosphorylation, fatty acylation, etc. The term "gene product" encompasses such processed or modified forms. Genomic nucleotide sequences, cDNA sequences, mRNA sequences, and polypeptide sequences from a variety of species, including human, are known in the art and are available in publicly accessible databases such as those available at the National Center for Biotechnology Information (www.ncbi.nih.gov) or the Universal Protein Resource (www.uniprot.org). Databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest.

As used herein, the term "modified protein" refers to a protein that contains one or more modifications from the wide-type protein. Examples of modifications include, but are not limited to, substitutions, deletions and insertions of one or more amino acid residues, and post transcriptional modifications such glycosylation.

As used herein, the terms "transfection," "gene transfer", and "gene delivery" are used interchangeably herein with reference to methods or systems for inserting foreign nucleic acids into host cells. Gene transfer can result in transient expression of non-integrated transferred DNA, extrachromosomal replication, and expression of transferred replicons (e.g., episomes), or integration of transferred genetic material into the genomic DNA of host cells. Various techniques are known to those of ordinary skill in the art to introduce one or more exogenous nucleic acid molecules, into suitable host cells, including chemical, electrical, and viral-mediated transfection procedures.

The term "host cell" as used herein generally refers to a cell (e.g., bacterial cell, yeast cell, insect cell, mammalian cell) which serves as a recipient for exogenously introduced nucleic acids or has been transfected with an exogenous nucleic acid. It should be understood that the progeny of a single parental cell may not necessarily be completely identical in morphology or in genomic or total DNA complement to the original parent, due to natural, accidental, or deliberate mutation. A host cell can be a cell that has been engineered to express a desired gene product (e.g., stably transformed to express one or more exogenous gene products). such a cell that stably expresses adenovirus E1a and E1b proteins (E1-expressing cell).

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A nucleotide or amino acid residue in a first nucleic acid or protein "corresponds to" a residue in a second nucleic acid or protein if the two residues perform one or more corresponding functions and/or are located at corresponding positions in the first and second nucleic acids or proteins. Corresponding functions are typically the same, equivalent, or substantially equivalent functions, taking into account differences in the environments of the two nucleic acids or proteins as appropriate. Residues at corresponding positions typically align with each other when the sequences of the two nucleic acids or proteins are aligned to maximize identity (allowing the introduction of gaps) using a sequence alignment algorithm or computer program such as those referred to below (see "Identity") and/or are located at positions such that when the 3-dimensional structures of the proteins is superimposed the residues overlap or occupy structurally equivalent positions and/or form the same, equivalent, or substantially equivalent intramolecular and/or intermolecular contacts or bonds (e.g., hydrogen bonds). The structures may be experimentally determined, e.g., by X-ray crystallography or NMR or predicted, e.g., using structure prediction or molecular modeling software. An alignment may be over the entire length of one or more of the aligned nucleic acid or polypeptide sequences or over at least one protein domain (or nucleotide sequence encoding a protein domain).

The term "expression cassette" is used herein with reference to a polynucleotide containing a gene of interest in operable linkage to regulatory elements (also termed "regulatory sequences", "expression control elements", or "expression control sequences") mediating expression of a coding region therein in an mRNA transcript that can be translated into protein. The expression cassette may be contained or incorporated in a plasmid, virus vector, or may exist as a nucleic acid fragment.

An "expression vector" is a specialized vector that contains a gene or nucleic acid sequence with the necessary regulatory regions needed for expression in a host cell. Expression vectors include, for example, plasmids and viral vectors, such as adeno-associated virus (AAV) vectors, adenovirus vectors, lentivirus vectors, herpes virus vectors.

As used herein, the term "viral vector" refers to a recombinant polynucleotide vector comprising virally-derived nucleic acids containing sequences facilitating replication and expression of exogenously incorporated transgene sequences operatively linked to suitable control elements and one or more heterologous sequences (i.e., nucleic acid sequence not of viral origin).

The term "recombinant virus" is used herein with reference to a virus that has been genetically altered, e.g., by the addition or insertion of a heterologous nucleic acid construct into a virus particle.

The term "parvovirus" refers to a family of animal viruses that constitute the family Parvoviridae. They have linear, single-stranded DNA (ssDNA) genomes that typically contain two genes encoding for a replication initiator protein, called NS1, and the protein the viral capsid is made of. The coding portion of the genome is flanked by an inverted terminal repeat (ITR) at each end that form into hairpin loops that are important during replication. Parvovirus virions are small compared to most viruses, at 23-28 nanometers in diameter, and contain the genome enclosed in an icosahedral capsid that has a rugged surface. The parvovirus family contains three subfamilies and 126 species, including adeno-associated virus (AAV), bocavirus and protoparvovirus.

The term "parvovirus protein coding region" refers to the art-recognized region of a parvovirus genome which encodes non-structure proteins that are required to replicate the viral genome, such as NS1, and structure proteins for the viral capsid. The region need not include all of the wild-type genes but may be altered, e.g., by the insertion, deletion or substitution of nucleotides, so long as the non-structure proteins and structure proteins present provide for sufficient functions to allow production of the relevant recombinant parvovirus in a suitable host cell at a level of at least 25%, at least 40%, at least 50%, at least 60%, at least 70%, at least 80%, at least 90% or at least 95% of the level supported by a parvovirus protein coding region that encodes the corresponding wild-type non-structure and structure proteins.

The term "sequence encoding a recombinant parvovirus genome" refers to a nucleotide sequence that encodes sequences capable of producing a genome of a functional recombinant parvovirus in a suitable host cell. The sequence encoding a recombinant parvovirus genome typically comprises (1) an expression cassette comprising a sequence encoding a gene of interest (GOI), also referred to as a "transgene", and a regulatory sequence operably linked to the sequence encoding the GOI, and (2) an ITR that flank at least one end of the expression cassette. In some embodiments, the sequence encoding a recombinant parvovirus genome comprises an ITR at each end of the expression cassette.

The term "sequence encoding a recombinant AAV genome" refers to a nucleotide sequence that encodes sequences capable of producing a genome of a functional recombinant AAV in a suitable host cell. The sequence encoding a recombinant AAV genome typically comprises (1) an expression cassette comprising a sequence encoding a GOI, also referred to as a "transgene", and a regulatory sequence operably linked to the sequence encoding the GOI, and (2) an ITR that flank at least one end of the expression cassette. In some embodiments, the sequence encoding a recombinant AAV genome comprises an ITR at each end of the expression cassette.

The term "adeno-associated virus" (AAV) in the context of the present application includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, caprine AAV, porcine AAV, ovine AAV and any other AAV now known or later discovered serotypes and variants.

The terms "AAV cis construct" and "AAV vector" are used interchangeably herein with reference to a polynucleotide vector comprising one or more heterologous sequences (i.e., nucleic acid sequence not of AAV origin) that are flanked by at least one AAV ITR. Such AAV vectors can be replicated and packaged into infectious viral particles when present in a host cell that has been infected with a suitable helper virus (or that is expressing suitable helper functions) and that is expressing AAV Rep and Cap gene products (i.e. AAV Rep and Cap proteins). When an AAV vector is incorporated into a larger polynucleotide (e.g., in a chromosome or in another vector such as a plasmid used for cloning or transfection), then the AAV vector may be referred to as a "pro-vector" which can be "rescued" by replication and encapsidation in the presence of AAV packaging functions and suitable helper functions. An AAV vector can be in any of a number of forms, including, but not limited to, plasmids, linear artificial chromosomes, complexed with lipids, encapsulated within liposomes, and encapsidated in a viral particle, e.g., an AAV particle. An AAV vector can be packaged into an AAV virus capsid to generate a "recombinant adeno-associated viral particle (AAV particle)."

The "AAV cis construct" or "AAV vector" may be derived from any adeno-associated virus serotype, including without limitation, such as AAV-1, AAV-2, AAV-3, AAV-4, AAV-5, AAV-6, AAV-7, AAV-8, AAV-9, AAV-10 and AAV-11 and others described herein. AAV vectors can have one or more of the AAV wild-type genes deleted in whole or part, preferably the rep and/or Cap genes, but retain functional flanking ITR sequences. Functional ITR sequences are necessary for the rescue, replication, and packaging of the AAV virion. Thus, an AAV cis polynucleotide or AAV vector is defined herein to include at least those sequences required in cis for replication and packaging (e.g., functional ITRs) of the virus. The ITRs need not be the wild-type nucleotide sequences, and may be altered, e.g., by the insertion, deletion, or substitution of nucleotides, so long as the sequences provide for functional rescue, replication and packaging.

The term "AAV vector" also includes self-complementary adeno-associated virus (scAAV) vectors. A scAAV vector is a viral vector engineered from the naturally occurring AAV. scAAV is termed "self-complementary" because the coding region has been designed to form an intra-molecular double-stranded DNA template. A rate-limiting step during replication of the standard AAV genome involves the second-strand synthesis since the typical AAV genome is a single-stranded DNA template. However, this is not the case for scAAV genomes. Upon infection, rather than waiting for cell mediated synthesis of the second strand, the two complementary halves of scAAV will associate to form one double stranded DNA (dsDNA) unit that is ready for immediate replication and transcription.

The terms "recombinant AAV virion," "rAAV virion," and "rAAV virus particle" are used interchangeably herein with reference to an infectious, replication-defective virus particle composed of viral particle composed of at least one AAV capsid protein and an encapsidated rAAV vector genome comprising a heterologous nucleotide sequence of interest that is flanked on both sides by AAV ITRs. A rAAV virion is produced in a suitable host cell comprising an AAV vector, AAV helper functions, and accessory functions. A host cell containing these components is capable of encoding AAV polypeptides required for packaging the AAV vector (containing a recombinant nucleotide sequence of interest) into infectious recombinant virion particles for subsequent gene delivery.

The term "adeno-associated virus inverted terminal repeats" or "AAV ITRs" refers to the art-recognized regions found at each end of the AAV genome which function together in cis as origins of DNA replication and as packaging signals for the viral genome. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are well known in the art. As used herein, an "AAV ITR" need not have the wild-type nucleotide sequence depicted in the previously cited references, but may be altered, e.g., by the insertion, deletion, or substitution of nucleotides. Additionally, the AAV ITR may be derived from any of several AAV serotypes, including without limitation, AAV-1, AAV-2, AAV-3, AAV-4, AAV-5, AAV-6, AAV-7, AAV-8, AAV-9, AAV-10, AAV-11 etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

The term "Rep coding region" refers to the art-recognized region of a parvovirus that encodes a parvovirus Rep protein. The term also includes functional homologues thereof, such as the human herpesvirus 6 (HHV-6) rep gene which is also known to mediate AAV DNA replication and the rep genes in other parvoviruses such as bocavirus and protoparvovirus.

The term "AAV Rep coding region" refers to the art-recognized region of the AAV genome which encodes the replication proteins of the virus which are required to replicate the viral genome and to insert the viral genome into a host genome during latent infection. The Rep coding region, as used herein, can be derived from any viral serotype, such as the AAV serotypes described above.

The region need not include all of the wild-type genes but may be altered, e.g., by the insertion, deletion or substitution of nucleotides, so long as the altered rep genes present provide for sufficient integration functions when expressed in a suitable host cell. An altered Rep gene will be considered to encode a "functional variant" of a wild-type Rep protein, if the function variant supports rAAV production at a level at least 25%, at least 40%, at least 50%, at least 70%, at least 80%, at least 90% or at least 95% of the level supported by the wild type rep gene product.

The term "long forms of Rep" refers to the Rep 78 and Rep 68 gene products of the AAV Rep coding region, including functional homologues thereof. The long forms of Rep are normally expressed under the direction of the AAV p5 promoter.

The phrase "short forms of Rep" refers to the Rep 52 and Rep 40 gene products of the AAV Rep coding region, including functional homologues thereof. The short forms of Rep are expressed under the direction of the AAV p19 promoter.

The term "Cap coding region" refers to the art-recognized region of the parvoviruse genome which encodes the coat proteins of the virus which are required for packaging the viral genome.

The term "AAV Cap coding region" refers to the art-recognized region of the AAV genome which encodes the coat proteins of the virus (e.g., VP1, VP2 and VP3) which are required for packaging the viral genome. The AAV Cap coding region, as used herein, can be derived from any AAV serotype, as described above. The region need not include all of the wild-type Cap genes but may be altered, e.g., by the insertion, deletion or substitution of nucleotides, so long as the altered Cap genes provide for sufficient packaging functions when present in a host cell along with an AAV vector. An altered Cap gene will be considered to encode a "functional variant" of a wild-type Cap protein, if the function variant supports rAAV production at a level at least 25%, at least 40%, at least 50%, at least 70%, at least 80%, at least 90% or at least 95% of the level supported by the wild type Cap gene product.

The term "AAV helper functions" refers to AAV-derived coding sequences that can be expressed to provide AAV gene products that, in turn, function in trans for productive AAV replication. Thus, AAV helper functions include the Rep and Cap regions. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV trans construct" or "AAV helper construct" refers to a nucleic acid molecule that includes nucleotide sequences providing AAV functions deleted from an AAV vector which is to be used to produce a transducing vector for delivery of a nucleotide sequence of interest. AAV trans constructs are commonly used to provide transient expression of AAV Rep and/or Cap genes to complement missing AAV functions that are necessary for lytic AAV replication; however, trans constructs lack AAV ITRs and can neither replicate nor package themselves. AAV trans constructs can be in the form of a plasmid, mini-circle, phage, transposon, cosmid, virus, or virion. A number of AAV trans constructs have been described, such as the commonly used plasmids pAAV/Ad and pIM29+45 which encode both Rep and Cap expression products. See, e.g., Samulski et al. (1989) J. Virology 63, 3822-3828; McCarty et al. (1991) J. Virology 65, 2936-2945. A number of other vectors have been described which encode Rep and/or Cap expression products. See, e.g., U.S. Pat. No. 5,139,941.

The term "adenovirus" as used herein, has the same meaning as an adenovirus vector, and refers to a member of the family Adenoviridae. The Adenoviridae includes all animal adenoviruses of the genus Mastadenovirus. In particular, human adenoviruses include the A-F subgenera and the individual serotypes thereof. The A-F subgenera includes human adenovirus types 1, 2, 3, 4, 4a, 5, 6, 7, 8, 9, 10, 11 (Ad11A and Ad11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48 and 51.

The term "accessory functions" refers to non-AAV derived viral and/or cellular functions upon which AAV is dependent for its replication. Thus, the term embraces DNAs, RNAs and protein that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

Adenovirus-derived accessory functions have been widely studied, and a number of adenovirus genes involved in accessory functions have been identified and partially characterized. Specifically, early adenoviral E1A, E1B 55K, E2A, E4, and VA RNA gene regions are thought to participate in the accessory process.

A "functional homolog" or a "functional equivalent" of a given adenoviral nucleotide region includes similar regions derived from a heterologous adenovirus serotype, nucleotide regions derived from another virus or from a cellular source, and recombinantly produced or chemically synthesized polynucleotides which function in a manner similar to the reference nucleotide region to achieve a desired result. Thus, a functional homolog of an adenoviral VA RNA gene region or an adenoviral E2A gene region encompasses derivatives and analogues of such gene regions-including any single or multiple nucleotide base additions, substitutions and/or deletions occurring within the regions, so long as the homologue retains the ability to provide its inherent accessory function to support AAV virion production at levels detectable above background.

The term "percent identical" is used herein with reference to comparisons among nucleic acid or amino acid sequences. Nucleic acid and amino acid sequences are often compared using computer programs in e.g. the National Library of Medicine BLAST alignment program.

II. Compositions and Kits

One aspect of the present application relates to an expression construct for production of recombinant parvovirus, such as an rAAV. The expression construct of the present application encodes and is capable of expressing adenovirus proteins that provides accessory functions for production of recombinant parvovirus in a host cell.

In some embodiments, the expression construct of the present application is capable of providing adenovirus helper functions, such as adenovirus E4, E2, VA RNA and/or E1 functions, and can be used in a triple-plasmid system for recombinant parvovirus production.

In some embodiments, the expression construct of the present application comprises (1) sequences encoding adenovirus genes that provide adenovirus helper functions, and (2) a sequence encoding parvovirus non-structure and structure proteins, such as AAV Rep and Cap proteins, or a sequence encoding a recombinant parvovirus genome, and can be used in a dual-plasmid system for recombinant parvovirus production.

In some embodiments, the expression construct of the present application comprises (1) sequences encoding adenovirus genes that provide adenovirus helper functions, (2) a sequence encoding parvovirus non-structure and structure proteins, such as AAV Rep and Cap proteins, and (3) a sequence encoding a recombinant parvovirus genome, and can be used in a single-plasmid system for production of recombinant pravovirus. Table 1 shows some exemplary expression constructs for the production of rAAV.

TABLE 1

Exemplary expression constructs for AAV production.

| | E2A | E4orf6/7 | VA RNA | Rep | Cap | AAV-GOI | Size Limit |
|---|---|---|---|---|---|---|---|
| Mini-pHelper | Yes | Yes | Yes | No | No | No | 2-11 kb |
| Mini-pHelper-Rep-Cap | Yes | Yes | Yes | Yes | Yes | No | 6-15 kb |
| Mini-pHelper-GOI | Yes | Yes | Yes | Yes | Yes | Yes | 3-16 kb |
| pAAVone-AAVs-GOI (Mini-pHelper-Rep-Cap-GOI) | Yes | Yes | Yes | Yes | Yes | Yes | 7-20 kb |
| Mini-pHelper-Rep | Yes | Yes | Yes | Yes | No | No | 4-13 kb |

In some embodiments, the expression construct of the present application also encodes functional adenovirus E1a and/or E1b proteins. In some embodiments, the expression construct of the present application does not encode a functional adenovirus E1a and/or a E1b proteins.

Expression Constructs for Triple-Plasmid Parvovirus Production System

Figure 7:
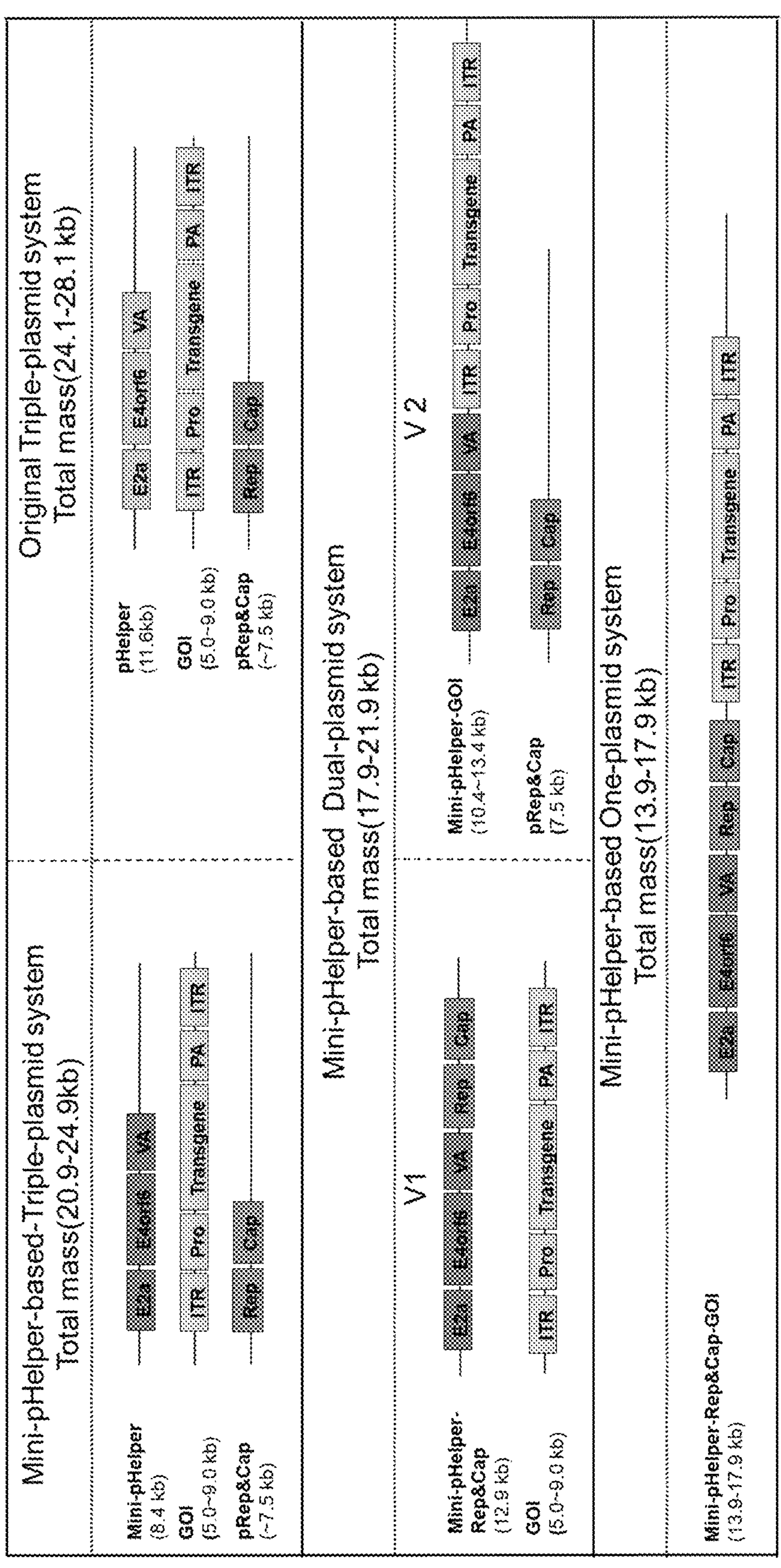
FIG. 7 is a composite of schematics showing mini-pHelper based triple-plasmid, dual-plasmid and single-plasmid virus production system.

In some embodiments, the expression construct of the preset application is designed to be used in a triple-plasmid parvovirus production system. FIG. 7 shows an exemplary construct for a triple-plasmid AAV production system. The expression construct comprises a modified adenovirus E4 coding region or a modified adenovirus E2a coding region and is capable of expressing one or more adenovirus E4 proteins, or an adenovirus E2a protein, that are required for AAV production in a host cell.

In some embodiments, the expression construct comprises both a modified adenovirus E4 coding region and a modified adenovirus E2a coding region, and is capable of expressing one or more adenovirus E4 proteins and an adenovirus E2a protein to provide the necessary adenovirus helper function for the production of recombinant parvovirus in a suitable host cell.

In some embodiments, the expression construct comprises a modified adenovirus E4 coding region, a modified adenovirus E2a coding region, and a sequence encoding one or more adenovirus-associated RNAs (VA RNAs), and is capable of expressing the encoded adenovirus proteins and RNAs to provide the necessary adenovirus helper function for the production of recombinant parvovirus in a suitable host cell. In some embodiments, the expression construct does not encode a functional adenovirus E1a and/or E1b protein, and the host cells provide the E1a and/or E1b helper function.

In some embodiments, the expression construct comprises a modified adenovirus E4 coding region, a modified adenovirus E2a coding region, a sequence encoding one or more adenovirus-associated RNAs (VA RNAs), an AAV Rep coding region, and is capable of expressing the encoded adenovirus proteins, VA RNAs and the AAV Rep protein for the production of recombinant AAV in a suitable host cell.

Modified Adenovirus E4 Coding Region

The modified adenovirus E4 coding region encodes a functional E4 protein capable of supporting a parvovirus replication in a host cell. In some embodiments, the functional E4 protein may only comprise amino acids encoded by adenovirus E4 open reading frames 6 and 7 (E4orfs6/7), as only the amino acids encoded by E4orfs6/7 are required for the activities necessary to support parvovirus replication. In some embodiments, the functional E4 protein comprises a polypeptide sequence encoded by all or a significant portion of E4orfs6/7 and does not comprise polypeptide sequence encoded by all or a portion of E4orfs 1-4 and E4 34K protein.

In some embodiments, the modified adenovirus E4 coding region comprises one or more deletions. In some embodiments, the modified adenovirus E4 coding region comprises a partial or complete deletion of E4orf6/7 intron 1.

In some embodiments, the modified adenovirus E4 coding region comprises a partial deletion of E4orf6/7 intron 1, wherein up to 10%, 20, 30%, 40%, 50%, 60%, 70%, 80%, 90% or 95% of the E4orf6/7 intron 1 sequence is deleted.

In some embodiments, the modified adenovirus E4 coding region comprises a partial or complete deletion of E4orf6/7 intron 2. In some embodiments, the modified adenovirus E4 coding region comprises a partial deletion of E4orf6/7 intron 2, wherein up to 10%, 20, 30%, 40%, 50%, 60%, 70%, 80%, 90% or 95% of the E4orf6/7 intron 2 sequence is deleted.

In some embodiments, the modified adenovirus E4 coding region comprises a partial or complete deletion of E4orf6/7 intron 1 and a partial or complete deletion of E4orf6/7 intron 2.

In some embodiments, the modified adenovirus E4 coding region has a total size of 400-500, 400-600, 400-800, 400-1000, 400-1200, 400-1500, 400-2000, 500-600, 500-800, 500-1000, 500-1200, 500-1500, or 500-2000 bp and encodes a functional E4 protein that is capable of providing the required E4 functions for parvovirus production in a non-E4 expressing host cell.

In some embodiments, the modified adenovirus E4 coding region comprises a sequence corresponding to nucleotide sequence 32645-35835 of the Ad2 genome with (a) a partial or complete deletion of E4orf6/7 intron 1, (b) a partial or complete deletion of E4orf6/7 intron 2, or both (a) and (b).

In some embodiments, the modified adenovirus E4 coding region comprises a sequence corresponding to nucleotide sequence 32645-35835 of the Ad2 genome with a deletion of the complete sequence of E4orf6/7 intron 2 (711 bp, SEQ ID NO:2) and a deletion of the complete sequence of E4orf6/7 intron 1 (1275 bp, SEQ ID NO:1). In some embodiments, the modified adenovirus E4orf6/7 coding region comprises a codon optimized nucleotide sequence (SEQ ID NO:7) encoding adenovirus E4orf6/7 protein (SEQ ID NO:8).

Modified Adenovirus E2a Coding Region

In some embodiments, the modified adenovirus E2a coding region comprises (a) a partial or complete deletion of early-E2a or later-E2a intron 1, (b) a partial or complete deletion of E2a intron 2, or both (a) and (b).

In some embodiments, the modified adenovirus E2a coding region comprises a partial deletion of later-E2a intron 1 and/or later-E2a intron 2, wherein up to 10%, 20, 30%, 40%, 50%, 60%, 70%, 80%, 90% or 95% of the later-E2a intron 1 and/or later-E2a intron 2 is deleted.

In some embodiments, the modified adenovirus E2a coding region has a total size of 1600-3500, 1600-3000, 1600-2500, 1600-2000, 1600-1800 or 1600-1700 bp and encodes a functional E2a protein that is capable of providing the required E2a functions for parvovirus production in a non-E2a expressing host cell.

In some embodiments, the modified adenovirus E2a coding region comprises a sequence corresponding to nucleotide sequence 22233-27575 of the Ad2 genome with (a) a partial or complete deletion of early-E2a or later-E2a intron 1, (b) a partial or complete deletion of E2a intron 2, or both (a) and (b). In some embodiments, the modified adenovirus E2a coding region comprises a sequence corresponding to nucleotide sequence 22233-27575 of the Ad2 genome with a 1897 bp deletion (SEQ ID NO:3) that encompasses the complete sequence of later-E2a intron 1 and later-E2a intron 2. In some embodiments, the modified adenovirus E2a coding region comprises a partial deletion of later-E2a intron 1 and/or later-E2a intron 2, wherein up to 10%, 20, 30%, 40%, 50%, 60%, 70%, 80%, 90% or 95% of the SEQ ID NO:3 is deleted.

In some embodiments, the modified adenovirus E2a coding region comprises (a) a partial or complete deletion of later a sequence encoding a codon optimized adenovirus E2a protein E2a intron 1, (b) a partial or complete deletion of later E2a intron 2, and (c) a codon modified nucleotide sequence encoding an adenovirus E2a protein.

Adenovirus VA RNA Coding Region

In some embodiments, the expression construct further comprises an adenovirus VA RNA coding region that encodes one or more adenovirus VA RNAs. In some embodiments, the expression construct comprises an adenovirus VA RNA coding region that encodes adenovirus VAI RNA and/or VAII RNA. In some embodiments, the VA RNA coding region encodes functional VA RNA I and/or VA RNAII that are capable of providing the required VA RNA functions for parvovirus production in a non-VA RNA expressing host cell. In some embodiments, the expression construct comprises SEQ ID NO:16.

As used herein and thereafter, a "functional" adenovirus E4 protein, adenovirus E2a protein or adenovirus VA RNA I or VA RNA II, is able to facilitate production of a recombinant parvovirus, such as bocavirus. It is within the abilities of the skilled person to determine whether a given VA RNA I and II, E2A protein or E4 protein is functional. In an embodiment, an adenovirus E4 protein, adenovirus E2a protein or adenovirus VA RNA I or VA RNA II will be considered to be"functional" if it supports parvovirus production at a level at least 25%, at least 40%, at least 50%, at least 70%, at least 80%, at least 90% or at least 95% of the level supported by the corresponding wild type protein or RNA in the same tri-plasmid, dual-plasmid or single-plasmid system.

Adenoviruses and their nucleic acid fragments for use in the compositions and methods of the present application include all human adenoviruses of the Adenoviridae family, which include members of the Mastadenovirus genera. To date, over fifty-one human serotypes of adenoviruses have been identified. The adenovirus may be of serogroups A, B, C, D, E, or F. The human adenovirus may be a serotype 1 (Ad 1), serotype 2 (Ad2), serotype 3 (Ad3), serotype 4 (Ad4), serotype 5 (Ad5), serotype 6 (Ad6), serotype 7 (Ad7), serotype 8 (Ad8), serotype 9 (Ad9), serotype 10 (Ad10), serotype 11 (Ad 11), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 19a (Ad19a), serotype 19p (Ad19p), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad33), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43 (Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), or combinations thereof, but are not limited to these examples. In certain embodiments, the adenovirus is serotype 5 (Ad5).

Regulatory Elements

In some embodiments, the expression construct of the present application comprises one or more regulatory elements that control expression of the encoded adenovirus proteins and/or RNAs. Exemplary promoters include, for example, viral promoters, mammalian promoters, composite promoters, cell type- or tissue-specific promoters, and inducible/repressible promoters.

Viral promoters include, for example, the SV40 early promoter, mouse mammary tumor virus LTR promoter; adenovirus major late promoter (Ad MLP); adenovirus E4 promoter, adenovirus e2a promoter, herpes simplex virus (HSV) promoter, cytomegalovirus (CMV) promoter, such as the CMV immediate early promoter region (CMV-IE), SFFV promoter, and Rous Sarcoma Virus (RSV) promoter.

Mammalian promoters include, for example, those for expressing EF1$\alpha$, ubiquitin (e.g., ubiquitin B or C), globin, actin, phosphoglycerate kinase (PGK), NSE (neuronal specific enolase), synapsin or NeuN, as well as composite promoters, such as the CAG promoter (combination of the CMV early enhancer element and chicken beta-actin promoter).

The promoters can be of human origin or from other species, including mice. In some embodiments a human promoter may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase I promoter, e.g., a promoter for transcription of ribosomal RNA (other than 5S rRNA) or a functional variant thereof may be used. In some embodiments, a promoter that ordinarily directs transcription by a eukaryotic RNA polymerase III (a "pol III promoter"), e.g., (a U6, H1, 7SK or tRNA promoter or a functional variant thereof) may be used.

In some embodiments, the modified adenovirus E4 coding region in the expression construct of the present application is operably linked to a regulatory element, such as a promoter, an enhancer or both. In some embodiments, the modified adenovirus E4 coding region is operably linked to an adenovirus E4 promoter. In some embodiments, the modified adenovirus E4 coding region is operably linked to an adenovirus E4 promoter comprising SEQ ID NO:22.

In some embodiments, the modified adenovirus E2a coding region in the expression construct of the present application is operably linked to a regulatory element, such as a promoter, an enhancer or both. In some embodiments, the modified adenovirus E2a coding region is operably linked to an adenovirus E2a promoter. In some embodiments, the modified adenovirus E2a coding region is operably linked to an adenovirus E2a promoter comprising SEQ ID NO:23.

Codon Optimized Coding Sequences

In some embodiments, the expression construct of the present application includes one or more polynucleotides encoding one or more codon optimized proteins for expression in e.g., human, mammalian or primate cells, such as HuH7, HEK293T or CHO cells. The polynucleotides encoding the proteins of the present application may be codon optimized to improve the activity, stability or expression in host cells without changing the encoded amino acid sequence. Codon optimization replaces codons present in a polynucleotide sequence with preferred codons encoding the same amino acid, for example, codons preferred for mammalian expression. Thus, the amino acid sequence is not altered during the process. Codon optimization can be performed using gene optimization software. The codon optimized nucleotide sequence is translated and aligned to the original protein sequence to ensure that no changes were made to the amino acid sequence. Methods of codon optimization are known in the art and are described, for example, in U.S. Application Publication No. 2008/0194511 and U.S. Pat. No. 6,114,148.

In some embodiments, the expression construct of the present application comprises (a) a modified adenovirus E4 coding region comprising a codon-modified E4 coding sequence or (b) a modified adenovirus E2a coding region comprising a codon-modified E2a coding sequence.

In some embodiments, the expression construct of the present application comprises (a) a modified adenovirus E4 coding region comprising a codon-modified E4 coding sequence and (b) a modified adenovirus E2a coding region comprising a codon-modified E2a coding sequence.

In some embodiments, the expression construct of the present application comprises a modified adenovirus E4 coding region comprising a codon modified nucleotide sequence (SEQ ID NO:7). In some embodiments, the expression construct of the present application comprises a modified adenovirus E2a coding region comprising a codon modified nucleotide sequence (SEQ ID NO:4).

Additional Elements

In some embodiments, the expression construct of the present application further comprises a sequence that encodes adenovirus E1a and E1b proteins.

In some embodiments, the expression construct further comprises one or more additional elements, such as plasmid replication origin sequences and selection markers. Examples of selection marks include, but are not limited to, ampicillin resistant genes, neomycine resistant genes and kanamycin resistant genes.

In some embodiments, the expression construct designed for triple-plasmid pravovirus production system has a size of less than 13 kb, 12 kb, 11 kb, 10 kb, 9 kb, 8 kb, 7 kb, 6, kb, 5 kb, 4 kb, 3 kb or 2 kb. In some embodiments, the expression construct has a size in the range of 2-11 kb, 2-4 kb, 2-6 kb, 2-8 kb, 2-10 kb, 4-6 kb, 4-8 kb, 4-10 kb, 4-11 kb, 6-8 kb, 6-10 kb, 6-11 kb, 8-10 kb, 8-11 kb or 10-11 kb.

In some embodiments, the expression construct designed for triple-plasmid pravovirus production system comprises a modified adenovirus E4 coding region, a modified adenovirus E2a coding region, a sequence encoding one or more adenovirus-associated RNAs (VA RNAs), a sequence encoding an AAV Rep protein, and has a size of less than 13 kb, 12 kb, 11 kb, 10 kb, 9 kb, 8 kb, 7 kb, 6, kb, 5 kb, or 4 kb. In some embodiments, the expression construct has a size in the range of 4-13 kb, 4-11 kb, 4-9 kb, 4-7 kb, 7-13 kb, 7-11 kb, 7-9 kb, 9-13 kb, 9-11 kb, or 11-13 kb.

Preferred Embodiments of Expression Constructs for Triple-Plasmid Parvovirus Production System In some embodiments, the expression construct is a plasmid for triple-plasmid AAV production. The plasmid comprises a modified adenovirus E4 coding region comprising SEQ ID NO:17 or SEQ ID NO:18, a modified adenovirus E2a coding region comprising SEQ ID NO:4, a sequence that encodes adenovirus VAI RNA coding region comprising SEQ ID NO:16, and a regulatory region comprising SEQ ID NO:19, wherein the plasmid has a size in the range of 6-7 kb, 6-8 kb, 6-9 kb, 7-8 kb, 7-9 kb and 8-9 kb. In some embodiments, the plasmid has a size of 7-9 kb.

Expression Constructs for Dual-Plasmid Parvovirus Production System

In some embodiments, the expression construct of the preset application is designed to be used in a dual-plasmid parvovirus production system. FIG. 7 shows two exemplary dual-plasmid systems for AAV production.

Constructs Encoding Adenovirus Proteins and Parvovirus Proteins

In some embodiments, the expression constructs for the dual-plasmid parvovirus production comprise, in addition to one or more of the elements described in the expression constructs for triple-plasmid parvovirus production system, a parvovirus protein coding region. In some embodiments, the parvovirus coding region comprises a sequence encompassing an AAV Rep coding region and a sequence encompassing an AAV Cap coding region.

In some embodiments, the expression construct for dual-plasmid parvovirus production is constructed for AAV production and comprises (1) a modified adenovirus E4 coding region that encodes E4orf6/7, (2) a modified adenovirus E2a coding region that encodes an E2a protein, (3) an adenovirus VA RNA coding region, (4) an AAV Rep coding region, (5) an AAV Cap coding region, and (6) one or more regulatory elements that allow expression of the E4orf6/7; the E2a protein, the adenovirus VA RNAs, the AAV Rep protein, and the AAV Cap protein in a host cell. As shown in FIG. 7, such an expression construct may be used in combination with another expression vector encoding a recombinant AAV genome (e.g., a transgene expression cassette flanked by at least one ITR at one side) for production of the recombinant AAV in a host cell. In some embodiments, the AAV Rep coding region is operably linked to one or more regulatory elements, such as an AAV P5 promoter or AAV P5I promoter. In some embodiments, the AAV Rep coding region is operably linked to one or more regulatory elements, such as an AAV P19 promoter. In some embodiments, the regulatory element comprises a P5I promoter (SEQ ID NO:15). In some embodiments, the expression construct for dual-plasmid AAV production further comprises a sequence that encodes adenovirus E1a and/or E1b proteins. In some embodiments, the expression construct for dual-plasmid AAV production does not comprise a sequence that encodes adenovirus E1a or E1b protein. In some embodiments, the expression construct has a size of less than 15 kb, 14 kb, 13 kb, 12 kb, 11 kb, 10 kb, 9 kb, 8 kb, or 7 kb. In some embodiments, the expression construct has a size in the range of 6-15 kb, 6-13 kb, 6-11 kb, 6-9 kb, 9-15 kb, 9-13 kb, 9-11 kb, 11-15 kb, 11-13 kb or 13-15 kb.

Construct Encoding Adenovirus Proteins and Recombinant Parvovirus Genome

In some embodiments, the expression construct for dual-plasmid parvovirus production system comprises (1) a modified adenovirus E4 coding region that encodes E4 open reading frame 6/7, (2) a modified adenovirus E2a coding region that encodes an E2a protein, (3) a sequence that encodes an adenovirus VA RNA, (4) a sequence encoding a recombinant parvovirus genome (e.g., a transgene expression cassette flanked by at least one ITR on one side), and (5) one or more regulatory elements that allow expression of the E4 open reading frame 6/7; the E2a protein, and the adenovirus VA RNA in a host cell.

In some embodiments, the expression construct designed for dual-plasmid AAV production system comprise (1) a modified adenovirus E4 coding region that encodes E4 open reading frame 6/7, (2) a modified adenovirus E2a coding region that encodes an E2a protein, (3) a sequence that encodes an adenovirus VA RNA, (4) a sequence encoding a recombinant AAV genome (e.g., a transgene expression cassette flanked by two ITRs), (5) one or more regulatory elements that allow expression of the E4 open reading frame 6/7; the E2a protein, and the adenovirus VA RNA in a host cell. As shown in FIG. 7, such an expression construct may be used in combination with another expression vector encoding the AAV Rep and Cap proteins for production of the recombinant AAV in a host cell. In some embodiments, the expression construct for dual-plasmid AAV production further comprises a sequence that encodes adenovirus E1a and E1b proteins. In some embodiments, the expression construct has a size of less than 16 kb, 15 kb, 14 kb, 13 kb, 12 kb, 11 kb, 10 kb, 9 kb, 8 kb, 7 kb, 6 kb, 5 kb, or 4 kb. In some embodiments, the expression construct has a size in the range of 3-16 kb, 3-14 kb, 3-12 kb, 3-10 kb, 3-8 kb, 3-6 kb, 6-16 kb, 6-14 kb, 6-12 kb, 6-10 kb, 6-8 kb, 8-16 kb, 8-14 kb, 8-12 kb, 8-10 kb, 10-16 kb, 10-14 kb, 10-12 kb, 12-16 kb, 12-14 kb, or 14-16 kb.

Preferred Embodiments of Expression Constructs for Dual-Plasmid AAV Production System In some embodiments, the expression construct for dual-plasmid parvovirus production system is a plasmid for AAV production. The plasmid comprises a modified adenovirus E4 coding region comprising SEQ ID NO:17 or SEQ ID NO:18, a modified adenovirus E2a coding region comprising SEQ ID NO:4, a sequence that encodes adenovirus VAI RNA coding region comprising SEQ ID NO:16, a regulatory region comprising SEQ ID NO:19, a sequence that comprise SEQ ID NO:20 and encodes an AAV Rep protein, and a sequence that comprising SEQ ID NO:21 and encodes an AAV Cap protein, wherein the plasmid has a size in the range of 12-14 kb.

In some embodiments, the expression construct for dual-plasmid parvovirus production system is a plasmid for AAV production. The plasmid comprises a modified adenovirus E4 coding region comprising SEQ ID NO:17 or SEQ ID NO:18, a modified adenovirus E2a coding region comprising SEQ ID NO:4, a sequence that encodes adenovirus VAI RNA coding region comprising SEQ ID NO:16, a regulatory region comprising SEQ ID NO:19, a sequence that encodes a recombinant AAV genome, wherein the recombinant AAV genome comprises transgene expression cassette comprising a transgene of interest operably linked to one or more regulatory elements, and two AAV ITRs flanking the transgene expression cassette, wherein the plasmid has a size in the range of 10-14 kb.

Expression Construct for One-Plasmid Parvovirus Production System

In some embodiments, the expression construct of the preset application is designed to be used in a single-plasmid parvovirus production system. The expression construct contains any or all of the foregoing modified adenovirus coding regions, a parvovirus protein coding region, as well as sequences encoding a recombinant parvovirus genome that comprises an expression cassette having a GOI operably liked to a regulatory element, and at least one ITR at one end of the expression cassette. The expression construct allows for production of a recombinant parvovirus by transfecting a host cell with a single plasmid. In some embodiments, the expression construct does not provide adenovirus E1a and E1b function and needs to be used for parvovirus production in host cells that provide endogenous expression of adenovirus E1a and E1b proteins. In some embodiments, the expression construct also provides adenovirus E1a and E1b function and can be used for parvovirus production in host cells that do not provide endogenous expression of adenovirus E1a and E1b proteins.

FIG. 7 provides an exemplary embodiment for an expression construct for a single-plasmid AAV production system. In some embodiments the expression construct comprises (1) a modified adenovirus E4 coding region that encodes E4 open reading frame 6/7, (2) a modified adenovirus E2a coding region that encodes an E2a protein, (3) an adenovirus VA RNA coding region, (4) an AAV Rep coding region, (5) an AAV Cap coding region, (6) a sequence encoding a recombinant AAV genome, comprising an expression cassette having a nucleotide sequence encoding a transgene and a regulatory element operably linked to the nucleotide sequence, and at least one ITR at one end of the expression cassette, and (7) one or more regulatory elements that allow expression of the E4 open reading frame 6/7; the E2a protein, the adenovirus VA RNA, the AAV Rep protein, and the AAV Cap protein in a host cell. In some embodiments, the expression cassette in the recombinant AAV genome is flanked by an AAV ITR on each end.

In some embodiments, the expression construct of the preset application comprises (1) a modified adenovirus E4 coding region that encodes E4 open reading frame 6/7, (2) a modified adenovirus E2a coding region that encodes an E2a protein, (3) an adenovirus VA RNA coding region, (4) a parvovirus protein coding region, (5) a recombinant parvovirus cloning region, and (6) one or more regulatory elements that allow expression of the E4 open reading frame 6/7; the E2a protein, the adenovirus VA RNA, and parvovirus proteins in a host cell.

In some embodiments, the recombinant parvovirus cloning region comprises a cloning site for insertion of a recombinant parvovirus sequence comprising (1) an expression cassette comprising a gene of interest (GOI) operably linked to a regulatory element and (2) at least one ITR at one side of the expression cassette. In some embodiments, the recombinant parvovirus sequence comprises two ITRs, one at each end of the expression cassette.

In some embodiments, a recombinant parvovirus cloning region comprises (1) a cloning site for insertion of a sequence comprising an expression cassette comprising a GOI operably linked to a regulatory element, and (2) at least one ITR at one side of the cloning site. In some embodiments, the recombinant parvovirus sequence comprises two ITRs, one at each side of the cloning site.

In some embodiments, a recombinant parvovirus cloning region comprises (1) an expression cassette comprising a cloning site for insertion of a GOI and a regulatory element in the proximity of the cloning site and is capable of being operably linked to the GOI when the GOI is inserted at the cloning site, and (2) at least one ITR at one side of the expression cassette. In some embodiments, the recombinant parvovirus sequence comprises two ITRs, one at each side of the expression cassette.

In some embodiments, the modified adenovirus E4 coding region encodes E4orf6/7 with a partial or complete deletion of E4orf6/7 intron 1 In some embodiments, the modified adenovirus E4 coding region encodes E4orf6/7 with a partial or complete deletion of E4orf6/7 intron 2. In some embodiments, the modified adenovirus E4 coding region encodes E4orf6/7 with a partial or complete deletion of both E4orf6/7 intron 1 and E4orf6/7 intron 2.

In some embodiments, the modified adenovirus E4 coding region has a total size of 400-500, 400-600, 400-800, 400-1000, 400-1200, 400-1500, 400-2000, 500-600, 500-800, 500-1000, 500-1200, 500-1500, or 500-2000 bp and encodes a functional E4 protein that is capable of providing the required E4 functions for parvovirus production in a non-E4 expressing host cell.

In some embodiments, the modified adenovirus E4 coding region comprises a sequence corresponding to nucleotide sequence 32645-35835 of the Ad2 genome with (a) a partial or complete deletion of E4orf6/7 intron 1, (b) a partial or complete deletion of E4orf6/7 intron 2, or both (a) and (b).

In some embodiments, the modified adenovirus E4 coding region comprises a sequence corresponding to nucleotide sequence 32645-35835 of the Ad2 genome with a deletion of the complete sequence of E4orf6/7 intron 2 (711 bp, SEQ ID NO:2) and a deletion of the complete sequence of E4orf6/7 intron 1 (1275 bp, SEQ ID NO:1).

In some embodiments, the modified adenovirus E4 coding region comprises a partial deletion of E4orf6/7 intron 1, wherein up to 10%, 20, 30%, 40%, 50%, 60%, 70%, 80%, 90% or 95% of SEQ ID NO:1 is deleted, and/or a partial deletion of E4orf6/7 intron 2, wherein up to 10%, 20, 30%, 40%, 50%, 60%, 70%, 80%, 90% or 95% of SEQ ID NO:2 is deleted.

In some embodiments, the modified adenovirus E4orf6/7 coding region comprises a codon optimized nucleotide sequence (SEQ ID NO:7) encoding adenovirus E4orf6/7 protein (SEQ ID NO:8).

In some embodiments, the modified adenovirus E4 coding region encodes Ad2 E4orf6/7. In some embodiments, the modified adenovirus E4 coding region comprises SEQ ID NO:17. In some embodiments, the modified adenovirus E4 coding region comprises SEQ ID NO:18.

In some embodiments, the modified adenovirus E2a coding region contains a codon-modified, or un-modified sequence encoding adenovirus E2a protein with a partial or complete deletion of early E2a intron 1.

In some embodiments, the modified adenovirus E2a coding region contains a codon-modified, or un-modified, sequence encoding adenovirus E2a protein with a partial or complete deletion of late E2a intron 1.

In some embodiments, the modified adenovirus E2a coding region contains a codon-modified, or un-modified, sequence encoding adenovirus E2a protein with a partial or complete deletion of E2a intron 2.

In some embodiments, the modified adenovirus E2a coding region contains a codon-modified, or un-modified sequence encoding adenovirus E2a protein with a partial or complete deletion of early E2a intron 1 and a partial or complete deletion of E2a intron 2.

In some embodiments, the modified adenovirus E2a coding region contains a codon-modified, or un-modified sequence encoding adenovirus E2a protein with a partial or complete deletion of late E2a intron 1 and a partial or complete deletion of E2a intron 2.

In some embodiments, the modified adenovirus E2a coding region comprises a partial deletion of later-E2a intron 1 and/or later-E2a intron 2, wherein up to 10%, 20, 30%, 40%, 50%, 60%, 70%, 80%, 90% or 95% of the later-E2a intron 1 and/or later-E2a intron 2 is deleted.

In some embodiments, the modified adenovirus E2a coding region has a total size of 1600-3500, 1600-3000, 1600-2500, 1600-2000, 1600-1800 or 1600-1700 bp and encodes a functional E2a protein that is capable of providing the required E2a functions for parvovirus production in a non-E2a expressing host cell.

In some embodiments, the modified adenovirus E2a coding region comprises a sequence corresponding to nucleotide sequence 22233-27575 of the Ad2 genome with (a) a partial or complete deletion of early-E2a or later-E2a intron 1, (b) a partial or complete deletion of E2a intron 2, or both (a) and (b). In some embodiments, the modified adenovirus E2a coding region comprises a sequence corresponding to nucleotide sequence 22233-27575 of the Ad2 genome with a 1897 bp deletion (SEQ ID NO:3) that encompasses the complete sequence of later-E2a intron 1 and later-E2a intron 2. In some embodiments, the modified adenovirus E2a coding region comprises a partial deletion of later-E2a intron 1 and/or later-E2a intron 2, wherein up to 10%, 20, 30%, 40%, 50%, 60%, 70%, 80%, 90% or 95% of the SEQ ID NO:3 is deleted.

In some embodiments, the modified adenovirus E2a coding region comprises (a) a partial or complete deletion of later a sequence encoding a codon optimized adenovirus E2a protein E2a intron 1, (b) a partial or complete deletion of later E2a intron 2, and (c) a codon modified nucleotide sequence encoding an adenovirus E2a protein.

In some embodiments, the modified adenovirus E2a coding region comprises SEQ ID NO:4.

In some embodiments, the adenovirus VA RNA coding region comprises sequences encoding adenovirus VA1, adenovirus VAII or both. In some embodiments, the adenovirus VA RNA coding region comprises sequences encoding Ad2 VA1, Ad2 VAII or both. In some embodiments, the adenovirus VA RNA coding region comprises SEQ ID NO:16.

In some embodiments, the AAV Rep coding region comprises SEQ ID NO:20.

In some embodiments, the AAV Cap coding region comprises SEQ ID NO:21.

In some embodiments, the one or more regulatory elements comprise an adenovirus E4 promoter operably linked to the modified adenovirus E4 coding region, an adenovirus E2a promoter operably linked to the modified adenovirus E2a coding region, and a modified AAV P5 promoter operably linked to the sequences that encode AAV Rep and Cap proteins. In some embodiments, the adenovirus E4 promoter comprises SEQ ID NO:22. In some embodiments, the adenovirus E2a promoter comprises SEQ ID NO:23. In some embodiments, the modified AAV P5 promoter comprises SEQ ID NO:16.

In some embodiments, the expression construct further comprises a nucleotide sequence encoding an adenovirus E1a protein and/or a nucleotide sequence encoding an adenovirus E1b protein.

In some embodiments, the expression construct designed for single-plasmid parvovirus production system has a size of less than 20 kb, 19 kb, 18 kb, 16 kb, 15 kb, 14 kb, 13 kb, 12 kb, 11 kb, 10 kb, 9 kb, 8 kb, or 7 kb.

In some embodiments the expression construct designed for single-plasmid parvovirus production system has a size in the range of 7-25 kb, 7-20 kb, 7-18 kb, 7-16 kb, 7-14 kb, 7-12 kb, 7-10 kb, 10-25 kb, 10-20 kb, 10-18 kb, 10-16 kb, 10-14 kb, 10-12 kb, 12-25 kb, 12-20 kb, 12-18 kb, 12-16 kb, 12-14 kb, 14-25 kb, 14-20 kb, 14-18 kb, 14-16 kb, 16-25 kb, 16-20 kb, 16-18 kb, 18-25 kb, 18-20 kb, or 20-25 kb.

In some embodiments, the expression construct is a plasmid having a total size of 10-15 kb, 10-20 kb, 10-25 kb, 15-20 kb, 15-25 kb or 20-25 kb.

Preferred Embodiments of Expression Constructs for One-Plasmid AAV Production System In some embodiments, the expression construct is a plasmid for one-plasmid AAV production and comprises a modified adenovirus E4 coding region comprising SEQ ID NO:17 or SEQ ID NO:18, a modified adenovirus E2a coding region comprising SEQ ID NO:4, a sequence that encodes adenovirus VAI RNA coding region comprising SEQ ID NO:16, a regulatory region comprising SEQ ID NO:19, an AAV Rep coding region comprising SEQ ID NO:20, an AAV Cap coding region comprising SEQ ID NO:21, and a sequence encoding a recombinant AAV genome, wherein the expression construct has a size in the range of 7-19 kb.

In another embodiment, the present application provides one or more cells, each containing one or more of the expression constructs described herein. In another embodiment, the present application provides one or more cell lines, each stably transformed with one or more of the expression construct described herein.

In another aspect, the present application provides a kit for producing recombinant AAV particles. In one embodiment, the kit comprises a plasmid comprising the expression construct of the present application.

In a particular embodiment, the kit further comprises instructions for use, e.g., instructions for use in a method described herein. In some embodiments, the kit further comprises one or more tubes or other types of containers for cell lysate (e.g., Eppendorf tubes) and/or one or more tubes or other types of containers for waste generated.

III. Methods for Producing Recombinant Parvovirus

Another aspect of the present application relates to methods for producing a recombinant parvovirus particle using the expression constructs of the present application. The method comprises the step of introducing the expression construct of the present application into a host cell that provides the necessary helper function for the parvovirus production, incubating the host cell harboring the expression cassette for a desired period of time to product recombinant parvovirus particles, and harvesting recombinant parvovirus particles after the incubation period. In some embodiments, the parvovirus is AAV.

In some embodiments, the method comprises the step of (1) introducing into a host cell (A) the expression construct of the triple-plasmid parvovirus production system, (B) a parvovirus trans construct that is capable of expressing parvovirus proteins necessary for the production of recombinant parvovirus, and (C) a parvovirus cis construct containing a sequence encoding the recombinant parvovirus genome, (2) incubating the host cell harboring the three constructs for a desired period of time to produce recombinant parvovirus particles, and (3) harvesting recombinant parvovirus particles after the incubation period. In some embodiments, constructs A, B and C are cotransfected into the host cell at a A:B:C molar ratio of 1-10:1-10:1-10. In some embodiments, constructs A, B and C are cotransfected into the host cell at a A:B:C molar ratio of 1:1:1. This method is often referred to as triple-transfection method. In some embodiments, the parvovirus is AAV and the trans construct comprises an AAV Rep coding region and an AAV Cap coding region.

In some embodiments, the method comprises the step of (1) introducing into a host cell (A) an expression construct (construct A) of the dual-plasmid parvovirus production system that contains a modified adenovirus E4 coding region that encodes E4orf6/7, a modified adenovirus E2a coding region that encodes an E2a protein, an adenovirus VA RNA coding region, a parvovirus protein coding region, and one or more regulatory elements that allow expression of the adenovirus E4orf6/7, E2a, VA RNA and the parvovirus proteins, and (B) an expression construct (construct B) comprising a sequence encoding a recombinant parvovirus genome (2) incubating the host cell harboring the constructs for a desired period of time to produce recombinant parvovirus particles, and (3) harvesting the recombinant parvovirus particles after the incubation period. In some embodiment, the recombinant parvovirus is a rAAV. In some embodiments, constructs A and B are cotransfected into the host cell at a A:B molar ratio in the range of 1:10 to 10:1. In some embodiments, constructs A and B are cotransfected into the host cell at a A:B molar ratio of 1:1, 1:2, 1:3, 2:1 or 3:1.

In some embodiments, the method comprises the step of (1) introducing into a host cell (A) an expression construct (construct A) of the dual-plasmid parvovirus production system that contains a modified adenovirus E4 coding region that encodes E4orf6/7, a modified adenovirus E2a coding region that encodes an E2a protein, an adenovirus VA RNA coding region, a sequence encoding a recombinant parvovirus genome, and one or more regulatory elements that allow expression of the adenovirus E4orf6/7, E2a, VA RNA, and (B) an expression construct (construct B) comprising parvovirus protein coding region (2) incubating the host cell harboring the constructs for a desired period of time to produce recombinant parvovirus particles, and (3) harvesting the recombinant parvovirus particles after the incubation period. In some embodiments, the recombinant parvovirus is a rAAV. In some embodiments, constructs A and B are cotransfected into the host cell at a A:B molar ratio in the range of 1:10 to 10:1. In some embodiments, constructs A and B are cotransfected into the host cell at a A:B molar ratio of 1:1, 1:2, 1:3, 2:1 or 3:1.

In some embodiments, the method comprises the step of (1) introducing into a host cell the expression construct of the single-plasmid parvovirus production system, (2) incubating the host cell harboring the expression cassette for a desired period of time to product recombinant parvovirus particles, and (3) harvesting recombinant parvovirus particles after the incubation period. In some embodiments, the expression construct is a plasmid for production of recombinant AAV. In some embodiments, the plasmid does not encode for adenovirus E1a and E1b proteins and the host cell expresses adenovirus E1a and E1b proteins endogenously.

A host cell for producing parvovirus particles can contain the expression construct of the present application in the form of e.g., episomal plasmids. The expression construct of the present application may also be stably integrated into the host cell genome. Further, the host cell can constitute an expression system for producing adenovirus proteins, such as E1a and E1b, that are required for parvovirus production. Examples of host cells include, but are not limited to, microorganisms, yeast cells, insect cells and animal cells. In some embodiments, the host cell is a mammalian host cell, such as human HuH7 and HEK293 cells, Chinese hamster ovary cells ("CHO"), and baby hamster kidney ("BHK") cells. Mammalian cells suitable for carrying out the present application include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, HuH7, HEK293 and NS-1 cells. The term "host cell" includes the progeny of the original cell which has been transfected. It is understood that the progeny of a single parental cell may not necessarily be completely identical in morphology or in genomic or total DNA complement as the original parent, due to natural, accidental, or deliberate mutation. A "mammalian host cell" is a cell originally derived from a mammal or is a progeny cell thereof.

In one embodiment, the host cell expresses Ad E1a and E1b protein. In certain preferred embodiments, the host cell is an HEK-293 cell that expresses adenovirus E1a and E1b.

In some embodiments, the expression construct of the present application and other expression constructs (if any) are transfected into HEK293 cells (available from ATCC®) via $CaPO_4$-mediated transfection, lipids or polymeric molecules such as Polyethylenimine (PEI). The HEK293 cells are then incubated for at least 60 hours to allow for recombinant parvovirus particle production.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

IV. Kits

Another aspect of the present application relates to a kit for producing a recombinant parvovirus. In some embodiments, the kit comprises an expression construct of the present application and an instruction on how to use the expression construct.

In some embodiments, the expression construct comprises (1) a modified adenovirus E4 coding region that encodes E4 open reading frame 6/7, (2) a modified adenovirus E2a coding region that encodes an E2a protein, (3) an adenovirus VA RNA coding region, (4) a parvovirus protein coding region, (5) a recombinant parvovirus cloning region, and (6) one or more regulatory elements that allow expression of the E4 open reading frame 6/7; the E2a protein, the adenovirus VA RNA, and parvovirus proteins in a host cell. In some embodiments, the recombinant parvovirus cloning region comprises a cloning site for insertion of a recombinant parvovirus sequence comprising (1) an expression cassette comprising a gene of interest (GOI) operably linked to a regulatory element and (2) at least one ITR at one side of the expression cassette. In some embodiments, the recombinant parvovirus sequence comprises two ITRs, one at each end of the expression cassette. In some embodiments, a recombinant parvovirus cloning region comprises (1) a cloning site for insertion of a sequence comprising an expression cassette comprising a GOI operably linked to a regulatory element, and (2) at least one ITR at one side of the cloning site. In some embodiments, the recombinant parvovirus sequence comprises two ITRs, one at each side of the cloning site. bIn some embodiments, a recombinant parvovirus cloning region comprises (1) an expression cassette comprising a cloning site for insertion of a GOI and a regulatory element in the proximity of the cloning site and is capable of being operably linked to the GOI when the GOI is inserted at the cloning site, and (2) at least one ITR at one side of the expression cassette. In some embodiments, the recombinant parvovirus sequence comprises two ITRs, one at each side of the expression cassette.

In some embodiments, the expression construct comprises (1) a modified adenovirus E4 coding region that encodes E4 open reading frame 6/7, (2) a modified adenovirus E2a coding region that encodes an E2a protein, (3) an adenovirus VA RNA coding region, (4) an AAV Rep coding region, (5) an AAV Cap coding region, (6) a sequence encoding a recombinant AAV genome, comprising an expression cassette having a nucleotide sequence encoding a transgene and a regulatory element operably linked to the nucleotide sequence, and at least one ITR at one end of the expression cassette, and (7) one or more regulatory elements that allow expression of the E4 open reading frame 6/7; the E2a protein, the adenovirus VA RNA, the AAV Rep protein, and the AAV Cap protein in a host cell. In some embodiments, the expression cassette in the recombinant AAV genome is flanked by an AAV ITR on each end.

In some embodiments, the kit further comprises a reagent for transfection of the expression construct.

EXAMPLES

Example 1: Construction of AAV Helper Constructs

To examine the dispensability of Ad sequences for packaging AAV vectors, a series of Ad-based deletion mutants were constructed in order to reduce the size of plasmids and increase helper functions for producing recombinant AAV virus particles. FIG. 1 depicts a series of expression cassettes with regard to their arrangement of adenovirus (Ad2) coding regions and surrounding deletions relative to Ad2 nucleotide sequence coordinates.

Figure 2:
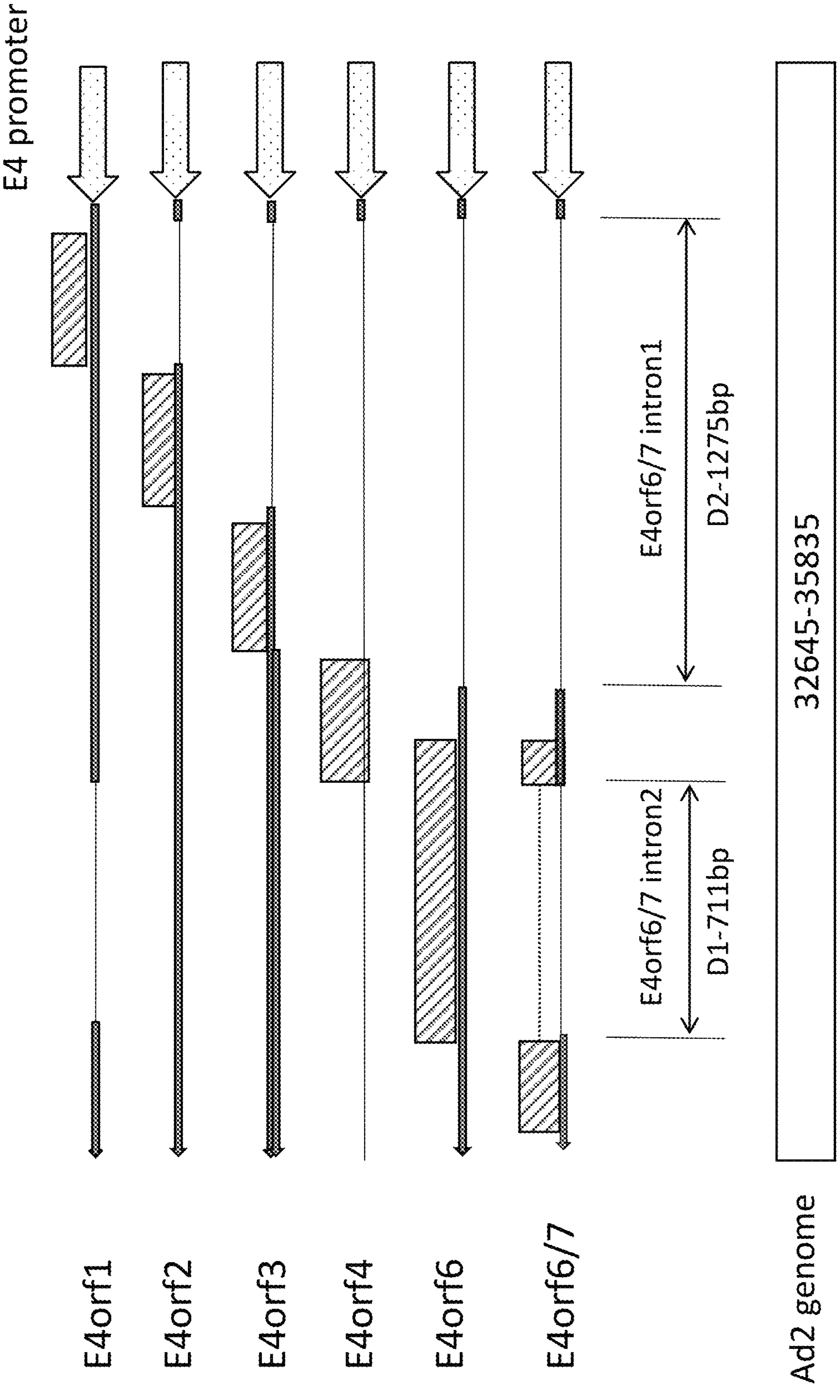
FIG. 2 shows an expanded map depicting an Ad2 E4 coding region, the arrangement of Ad E4orfs in the coding region, and the deletions depicted in FIG. 1.

FIG. 2 shows an expanded map depicting the arrangement of Ad E4orfs and the surrounding deletions depicted in FIG. 1 relative to the Ad2 genomic sequences.

Figure 3:
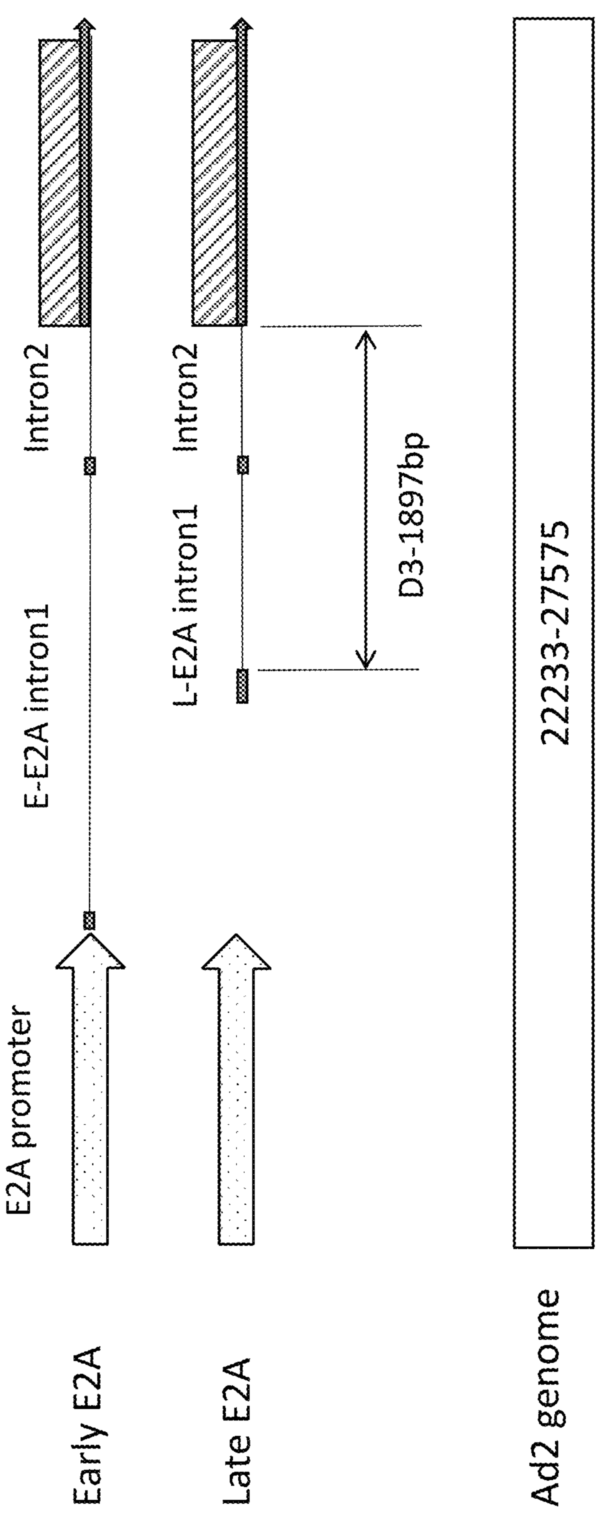
FIG. 3 shows an expanded map depicting an Ad2 E2a coding region, the Ad2 E2A promoter and Ad2 mRNAs expressed at early and late times in infection, and deletions depicted in FIG.

FIG. 3 shows an expanded map depicting the Ad2 E2a promoter and Ad2 mRNAs expressed at early and late times in infection, including the surrounding deletions depicted in FIG. 1 relative to the Ad genomic sequences.

Figure 4:
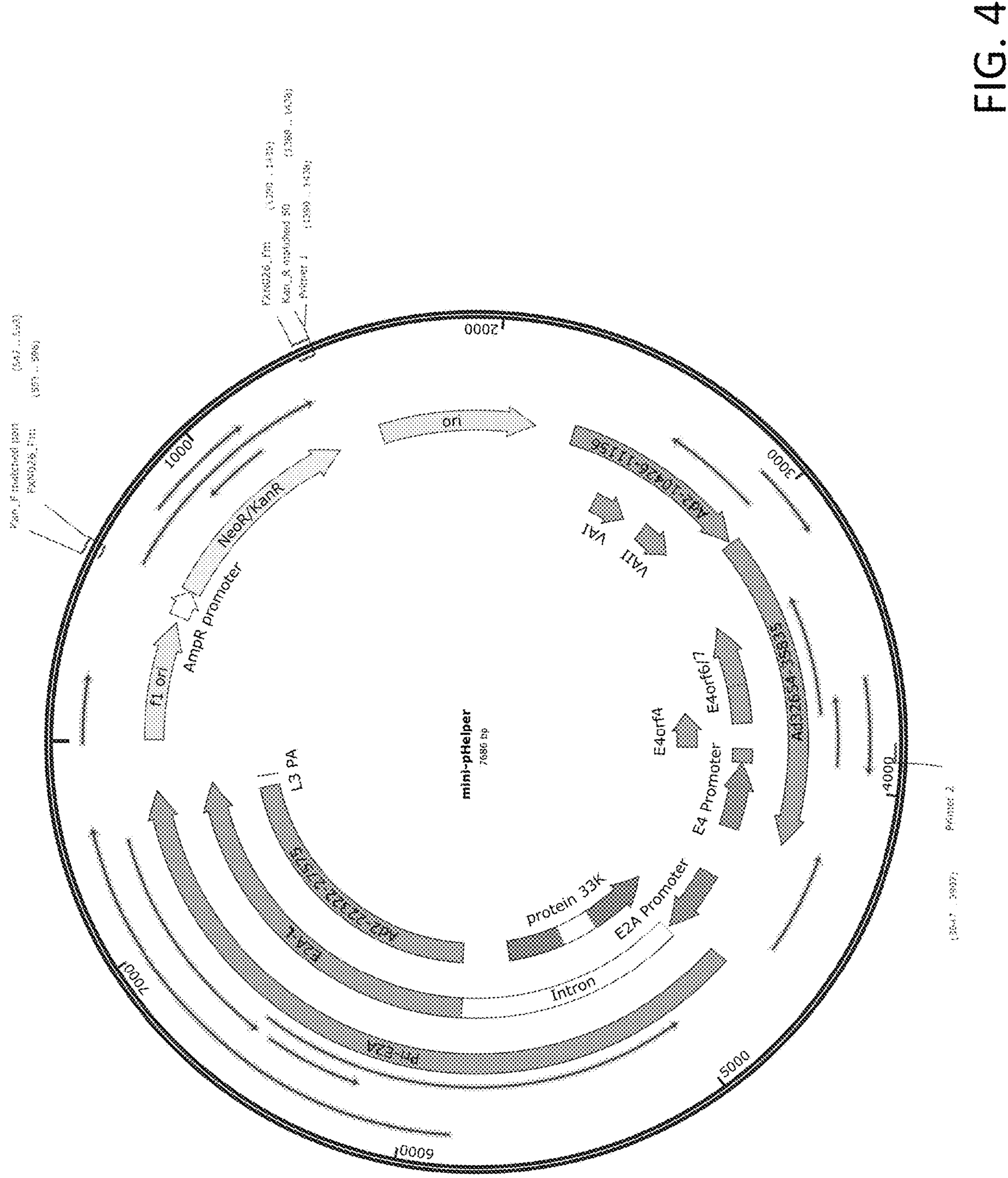
FIG. 4 shows a plasmid construct, mini-pHelper, that contains the corresponding arrangement of Ad helper genes shown in FIG. 1.

FIG. 4 shows an exemplary helper plasmid, mini-pHelper plasmid (SEQ ID NO:6) that contains an embodiment of the expression cassette of the present application. The plasmid contains the mini-pHelper Ad helper gene arrangement shown in FIG. 1. The mini-pHelper backbone plasmid includes a codon-optimized Ad E2a coding region sequence (SEQ ID NO:4) encoding the wild-type Ad E2a amino acid sequence set forth in SEQ ID NO:5.

Figure 5:
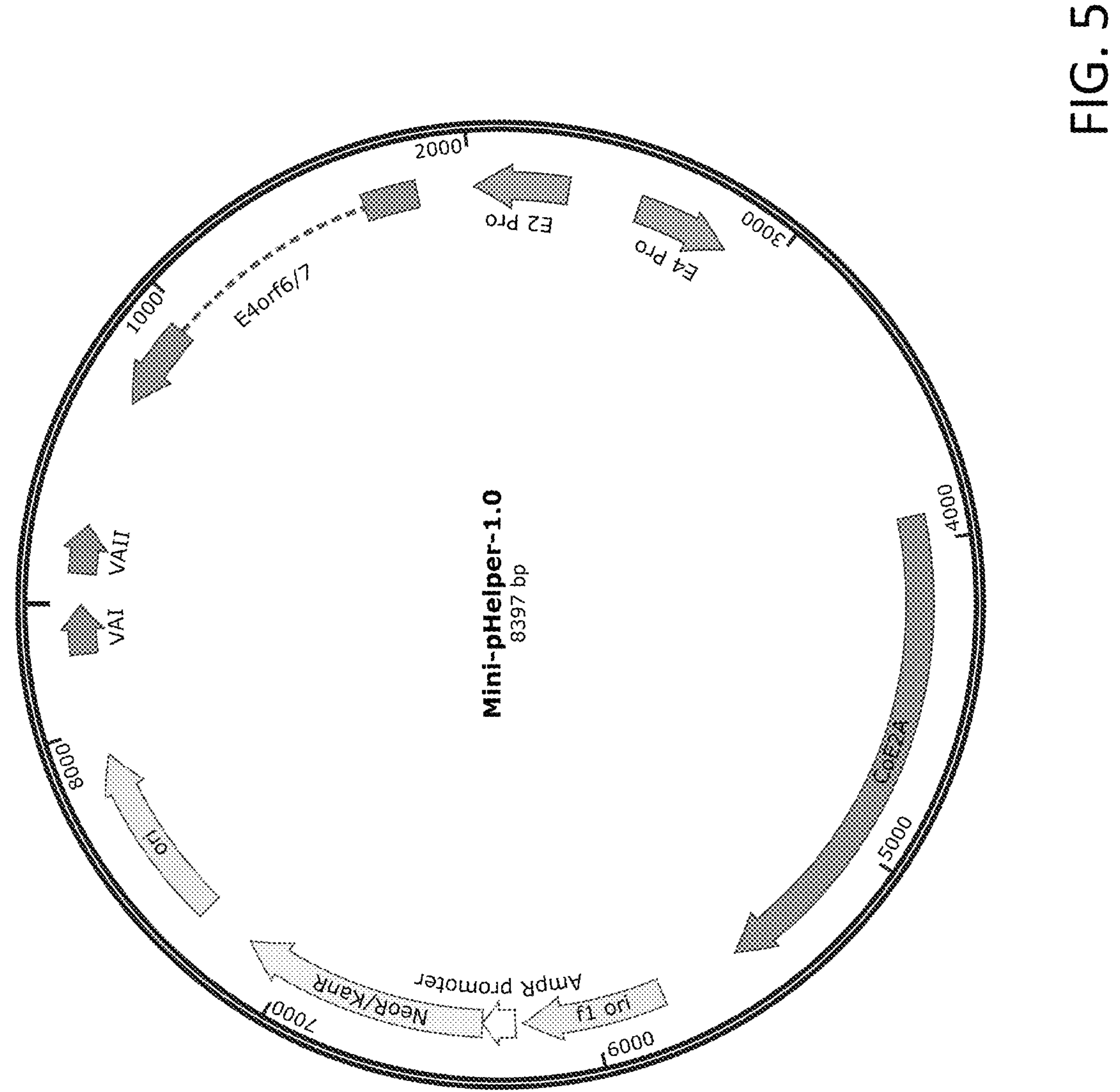
FIG. 5 shows a plasmid construct, mini-pHelper-1.0, that contains the corresponding arrangement of Ad helper genes shown in FIG. 1.

FIG. 5 shows another exemplary helper plasmid, mini-pHelper-1.0 plasmid (SEQ ID NO:10) that contains another embodiment of the expression cassette of the present application. The plasmid contains the mini-pHelper Ad helper gene arrangement shown in FIG. 1.

Example 2: Identification of Adenovirus Regions Dispensable for AAV Production

Figure 6:
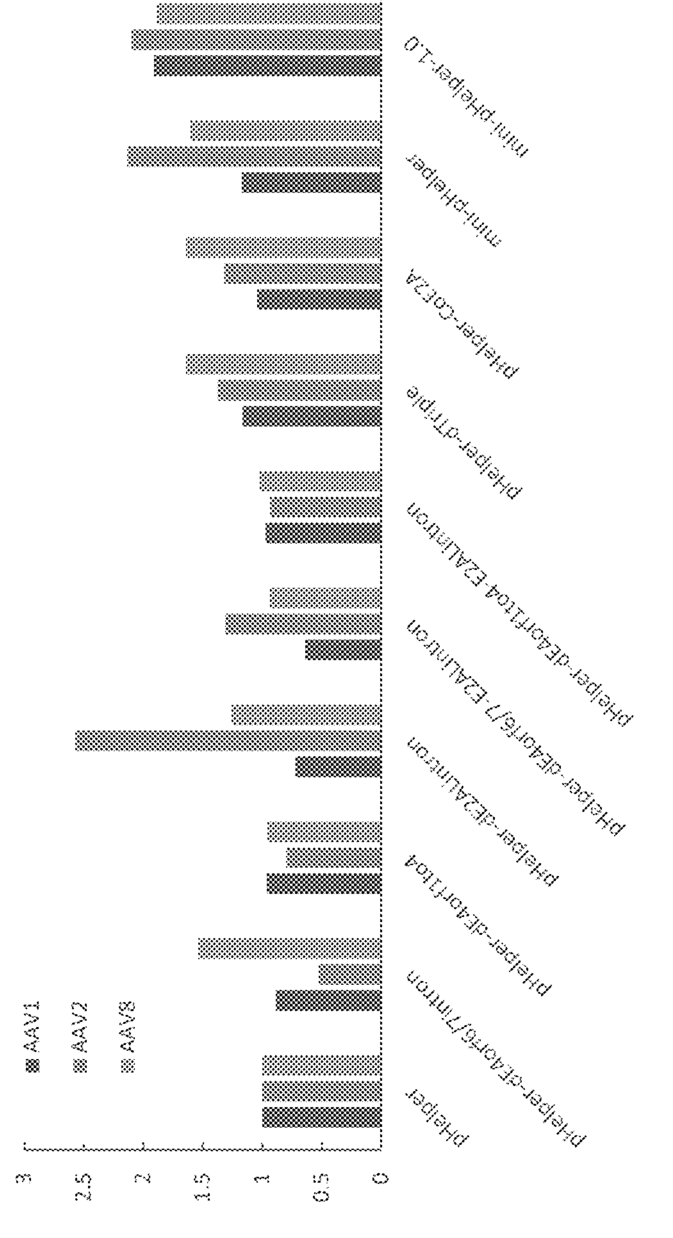
FIG. 6 shows the effects of various deletions and combination of deletions in FIG. 1 on the ability of the expression cassette to sufficiently provide helper functions for AAV packaging.

FIG. 6 shows the effects of the deletions or combinations of deletions in FIG. 1 on the ability of the expression cassette to sufficiently provide helper functions for adeno-associated virus (AAV) packaging. The production titers of rAAV were obtained using a triple plasmid transfection system: an ITR containing plasmid (such as pAAV-CAG-EGFP), an AAV helper plasmid (such as pRep2-AAV1, pRep2-AAV2 or pRep2-AAV9), and an Ad helper plasmid Ad with an Ad helper gene arrangement shown in FIG. 1 (such as pHelper, pHelper-dE4Orf6/7intron, mini-pHelper1.0 etc.) that provided the required adenoviral functions. All the AAV vectors were produced in HEK 293T cells. The Y-axis showed the fold increase of using different novel pHelpers compared with the original pHelper.

Example 3: Construction of Mini-Helper Plasmids for AAV Library Production

FIG. 7 shows schematics comparing the original triple-plasmid transfection system with the mini-pHelper based-production system. Green-Ad genes, blue-AAV genes, pink transgene elements. In the original triple-plasmid system, the total mass of three plasmids (pHelper, pRep&Cap, GOI) is between 24.1-28.1 kb. In the mini-phelper plasmid system, the total mass of three plasmids was reduced to 20.9-24.9 kb. There are two different versions of dual-plasmid system (V1, the AAV genes (Rep and Cap) were inserted into mini-pHelper; V2, the transgene elements were inserted into mini-pHelper. The total mass of V1 and/or V2 is 17.9-21.9 kb. In the one plasmid system, both the AAV genes and the transgene elements were inserted into mini-pHelper. The total mass of the plasmid is 13.9-17.9 kb.

Construction of mini-pHelper-AAV2 (SEQ ID NO:10): Mini-pHelper1.0 plasmid was digested with ClaI. AAV helper genes (Rep and Cap) were PCR amplified and assembled into ClaI site.

Construction of mini-pHelper-CMV-EGFP (SEQ ID NO:11): Mini-pHelper1.0 plasmid (SEQ ID NO:9) was digested with PmeI and used as backbone. The insert ITR-CMV-EGFP-ITR cassette was digested from pAAV-CMV-EGFP with SbfI. The backbone and insert were ligated with T4 DNA ligase.

Construction of pAAVone-AAV2-CMV-EGFP (SEQ ID NO:12): Mini-pHelper-AAV2 plasmid was digested with PmeI and used as backbone. The insert ITR-CMV-EGFP-ITR cassette was digested from pAAV-CMV-EGFP with Sbf1. The backbone and insert were ligated with T4 DNA ligase.

Figure 8:
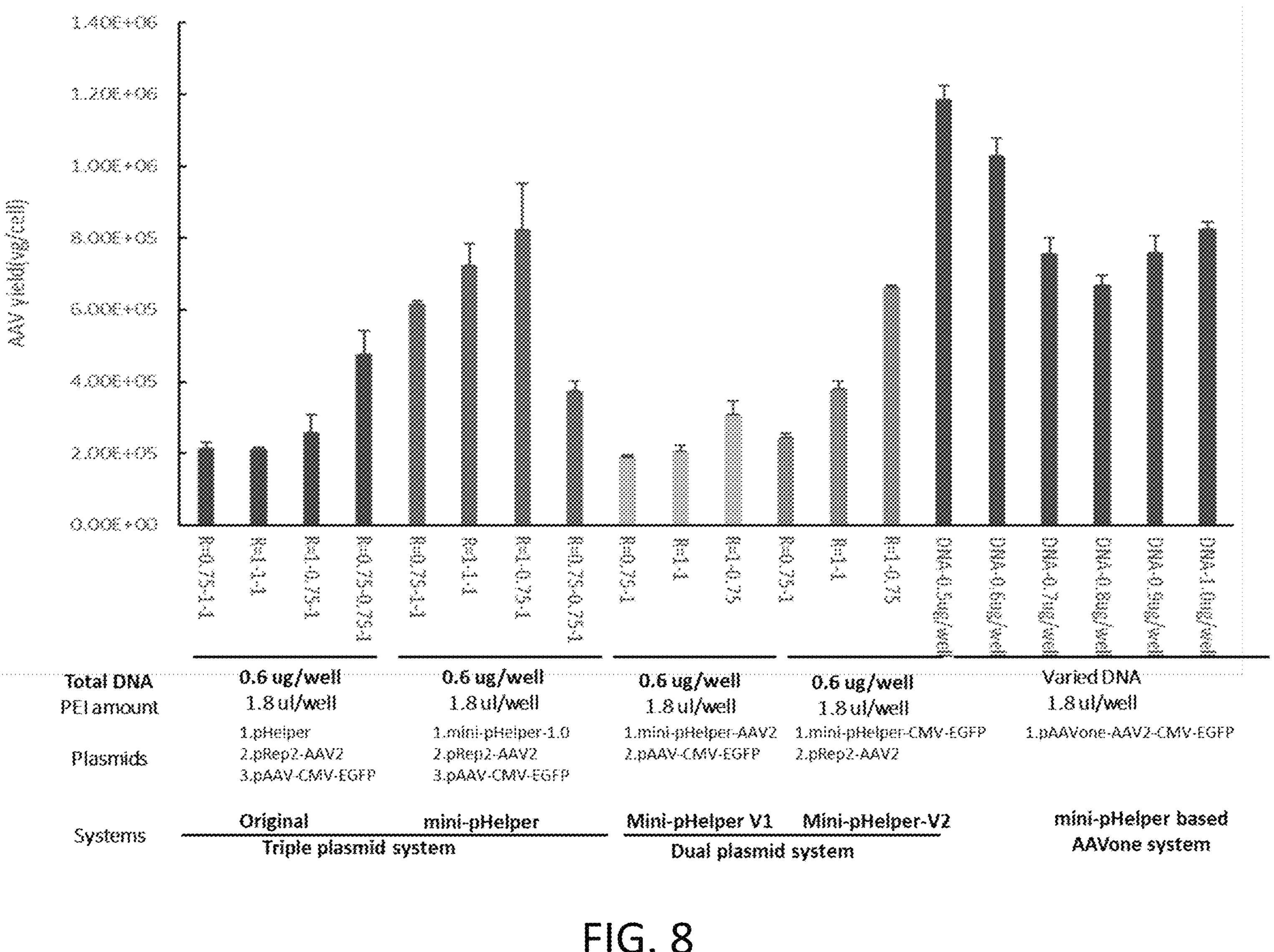
FIG. 8 shows the package efficiency of mini-helper based AAV production system in adherent HEK 293T cells.

FIG. 8 shows the package efficiency of mini-helper based AAV production system in adherent HEK 293 T cells. The production titers of rAAV were obtained in HEK 293T cells at 72 h post transfection. In the triple plasmid transfection systems, 4 different molecular ratios of three plasmids (pHelper or mini-phelper-1.0):pRep2-AAV2:pAAV-CMV-EGFP) with total DNA mass of 0.6 ug/well were transfected into HEK 293T cells used fixed amount of polyethylenimine (PEI) (1.8 ul/well). For the dual plasmid system, 3 different molecular ratios were evaluated. In the one plasmid system, different amounts of plasmids were transfected with fixed amount of PEI.

Figure 9:
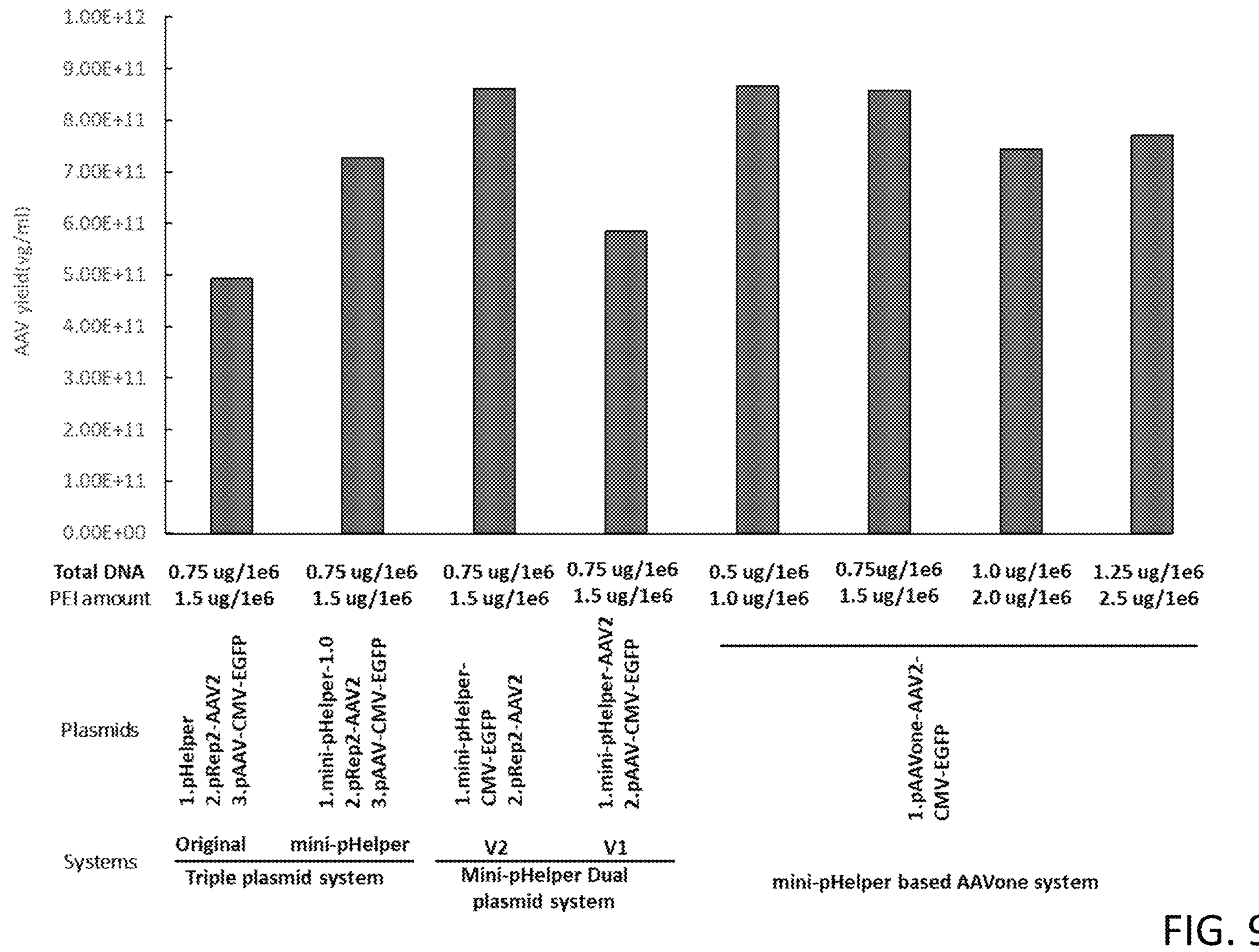
FIG. 9 shows the package efficiency of mini-helper based AAV production systems in suspension cultured HEK 293T cells.

FIG. 9 shows the package efficiency of mini-helper based AAV production system in suspension cultured HEK 293T cells. The production titers of rAAV were obtained at 72 h post transfection. In the triple plasmid transfection system, the ratio of three plasmid is 1:1:1 and the total DNA is 0.75 ug/$10^6$ cells, In the dual plasmid transfection systems, the ratio of two plasmids is 1:1 and the total DNA is 0.75 ug/$10^6$ cells. In the one plasmid system, different amounts of plasmids were transfected with fixed PEI:DNA ratio of 2.

Figure 10:
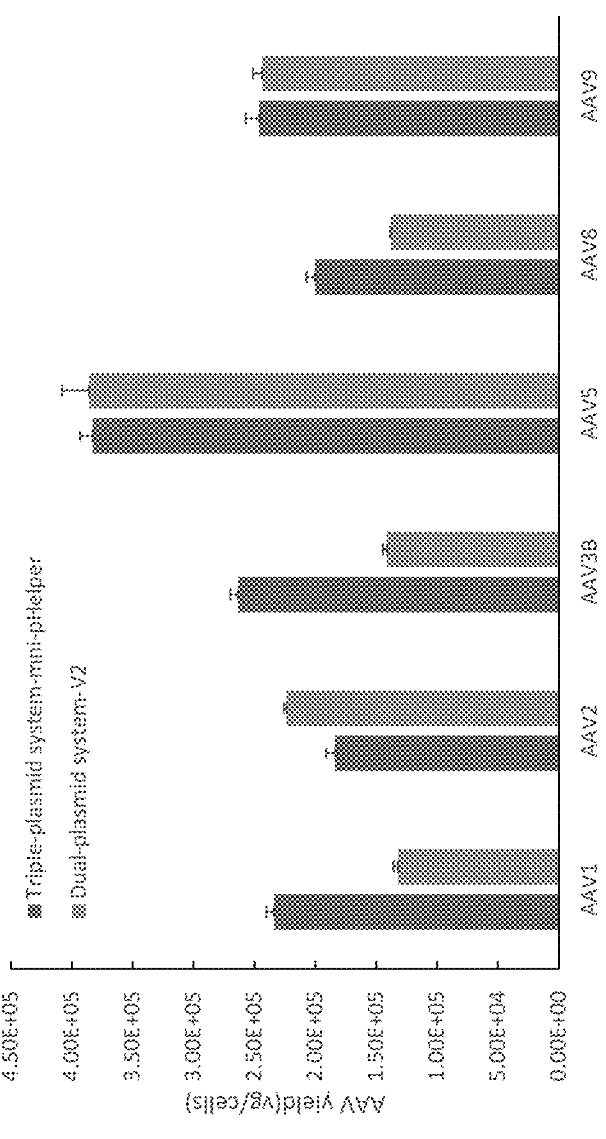
FIG. 10 shows the package efficiency of mini-helper based dual-plasmid V2 system for different AAV serotypes.

FIG. 10 shows the package efficiency of mini-helper based dual-plasmid V2 system for different AAV serotypes. In the dual-plasmid V2 system, the transgene elements were inserted into mini-pHelper. AAV production system in suspension cultured HEK 293T cells. The production titers of rAAV were obtained at 72 h post transfection. In the triple plasmid transfection system, the molecular ratio of three plasmids is 1:1:1 and the total DNA is total DNA mass of 0.6 ug/well. In the dual plasmid transfection systems, the molecular ratio of two plasmids is 1:1 and the total DNA is total DNA mass of 0.6 ug/well.

Example 4: Use of Mini Helper for Aav Library Production

Figure 11:
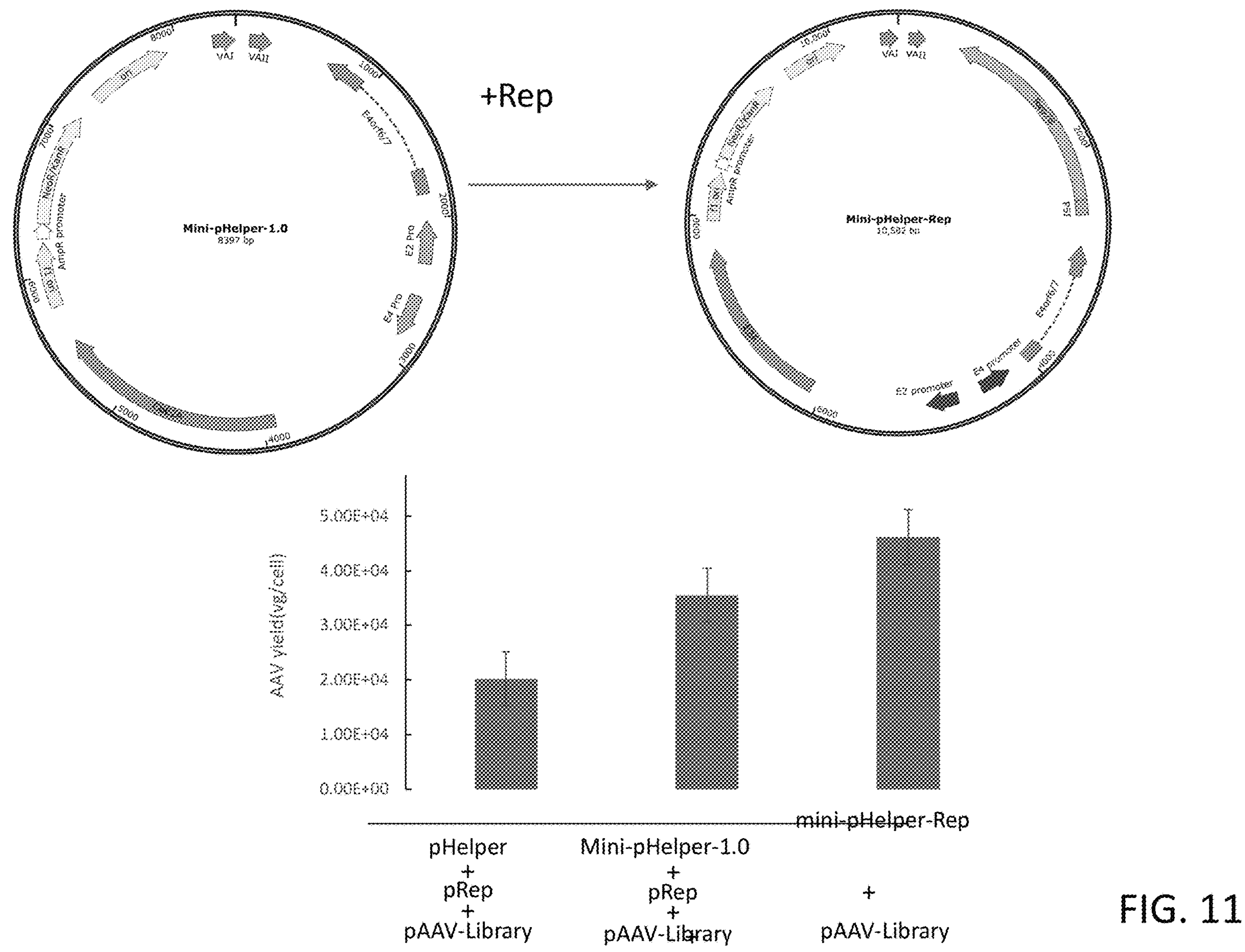
FIG. 11 shows the use of mini-helper for AAV library production.

FIG. 11 shows the use of mini-helper for AAV library production. The production titers of rAAV were obtained in HEK 293T cells at 72 h post transfection. The pAAV-Library plasmid was used as 200 copies/cell. pHelper and pRep, mini-pHelper-1.0 and mini-pHelper-Rep (SEQ ID NO:13) were used as $10^5$ copies/cell. The PEI was used as 1.5 ug/well. Mini-pHelper-Rep: Mini-pHelper-AAV2 plasmid was digested with SwaI and SnaBI to remove the Cap gene.

Figure 12:
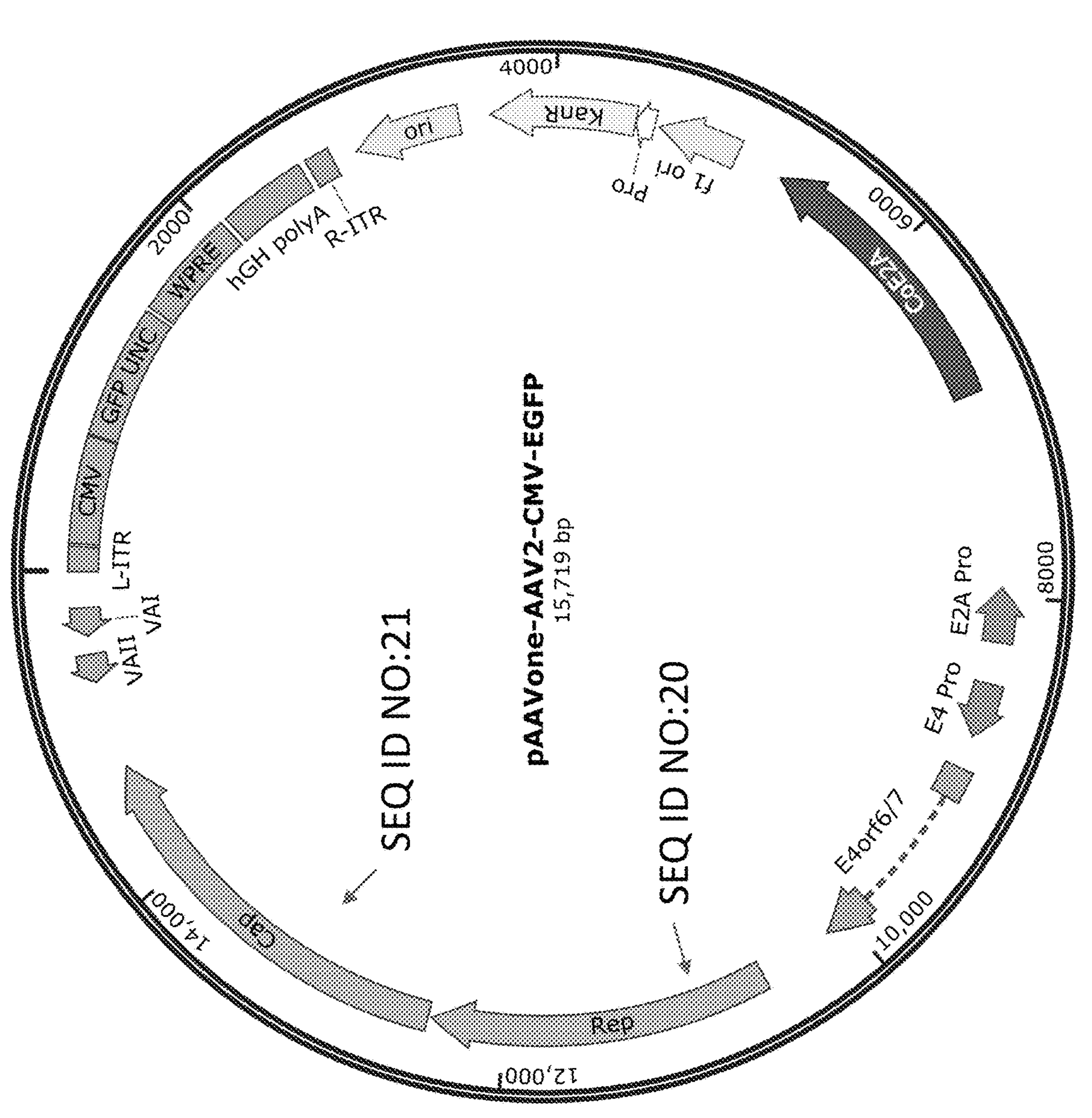
FIG. 12 shows an exemplary plasmid construct, pAAVone-AAV2-CMV-EGFP, for single-plasmid AAV production system.

FIG. 12 shows an exemplary helper plasmid pAAVone-AAV2-CMV-EGFP (SEQ ID NO:12) that contains another embodiment of the expression cassette of the present application. The plasmid contains the mini-pHelper Ad helper gene arrangement shown in FIG. 1, AAV Rep and Cap genes, and the sequence of a recombinant AAV genome (ITR-CMV-EGFP-PolyA-ITR)

FIG. 13 shows the sequences of a wild-type AAV2 P5 promoter P5 (P5-AAV2, SEQ ID NO:14) and a modified AAV P5 promoter P5 (P5I, SEQ ID NO:15) and their effect on package efficiency of AAV one system. The total DNA is total DNA mass of 0.6 ug/well. The production titers of rAAV were obtained at 72 h post transfection FIG. 14 is a list of sequences described in the present application.

Herein, incorporated by reference is the sequence listing filed with the USPTO as 2037-004 US.xml, which was created on Feb. 27, 2023, and the size is 109,567 bytes.

The above description is for the purpose of teaching a person of ordinary skill in the art how to practice the present application. It is not intended to detail all those obvious modifications and variations of it which will become apparent to the skilled worker upon reading the description. It is intended, however, that all such obvious modifications and variations be included within the scope of the present application, which is defined by the following claims. Any patents or patent publications described herein are expressly incorporated by reference in their entirety. The claims are intended to cover the claimed components and steps in any sequence effective to meet the objectives there intended, unless the context specifically indicates the contrary.

What is claimed is:

1. A single polynucleotide expression construct for production of a recombinant parvovirus, the expression construct comprising:

(1) a modified adenovirus E4 coding region that encodes E4 open reading frame 6/7;

(2) a modified adenovirus E2a coding region that encodes an E2a protein;

(3) an adenovirus VA RNA coding region that encodes adenovirus VAI RNA and VAII RNA;

(4) a parvovirus protein coding region that encodes parvovirus proteins necessary for the production of the recombinant parvovirus;

(5) a recombinant parvovirus sequence comprising (i) an expression cassette comprising a nucleotide sequence encoding a transgene and a regulatory element operably linked to the nucleotide sequence, and (ii) at least one ITR at one end of the expression cassette; and (6) one or more regulatory elements that allow expression of the E4 open reading frame 6/7, the E2a protein, the adenovirus VAI RNA and VAII RNA, and the parvovirus proteins necessary for the production of the recombinant parvovirus in a host cell, wherein the single polynucleotide expression construct has a size of 7-25 kb.

2. The expression construct of claim 1, wherein the modified adenovirus E4 coding region comprises (i) partial or complete deletion of E4orf6/7 intron 1, or (ii) a partial or complete deletion of E4orf6/7 intron 2, or both (i) and (ii).

3. The expression construct of claim 2, wherein the modified adenovirus E4 coding region comprises a sequence corresponding to nucleotide sequence 32645-35835 of the Ad2 genome with a partial or complete deletion E4orf6/7 intron 2, wherein the E4orf6/7 intron 2 has the sequence of SEQ ID NO:2, and a partial or complete deletion of E4orf6/7 intron 1, wherein the E4orf6/7 intron 1 has the sequence of SEQ ID NO:1.

4. The expression construct of claim 1, wherein the modified adenovirus E2a coding region comprises (i) a partial or complete deletion of early-E2a or later-E2a intron 1, (ii) a partial or complete deletion of E2a intron 2, or both (i) and (ii).

5. The expression construct of claim 1, wherein the modified adenovirus E2a coding region comprises a sequence corresponding to nucleotide sequence 22233-27575 of the Ad2 genome with (i) a partial or complete deletion of early-E2a or later-E2a intron 1, (ii) a partial or complete deletion of E2a intron 2, or both (i) and (ii).

6. The expression construct of claim 1, wherein the recombinant parvovirus is rAAV and wherein the parvovirus protein coding region comprises an AAV Rep coding region encoding a AAV Rep protein and an AAV Cap coding region encoding an AAV Cap protein.

7. The expression construct of claim 6, wherein the AAV Rep coding region comprises an AAV Rep coding sequence operably linked to an AAV P5I promoter.

8. The expression construct of claim 1, comprising:

(1) SEQ ID NO: 17 or SEQ ID NO:18;

(2) SEQ ID NO: 4;

(3) SEQ ID NO: 16;

(4) SEQ ID NO: 19;

(5) SEQ ID NO:20; and (6) SEQ ID NO:21.

9. The expression construct of claim 1, having a size of less than 20 kilobases.

10. A method of producing recombinant parvovirus, comprising the steps of:

introducing the expression construct of claim 1 into a host cell;

incubating the host cell harboring the expression construct for a desired period of time to produce recombinant parvovirus particles; and harvesting the recombinant parvovirus particles after the incubation period.

11. A single polynucleotide expression construct for production of recombinant parvovirus, the expression construct comprising:

(a) a modified adenovirus E4 coding region encoding adenovirus E4orf6/7, wherein the modified adenovirus E4 coding region comprises (i) partial or complete deletion of E4orf6/7 intron 1, or (ii) a partial or complete deletion of E4orf6/7 intron 2, or both (i) and (ii);

(b) a modified adenovirus E2a coding region encoding an adenovirus E2a protein, wherein the modified adenovirus E2a coding region comprises at least one deletion in early-E2a intron 1, or later-E2a intron 1, or E2a intron 2;

(c) a sequence encoding one or more adenovirus VA RNAs; and (d) one or more regulatory elements operably linked to (a), (b) and (c), wherein the single polynucleotide expression construct has a size of 2-11 kb.

12. The expression construct of claim 11, wherein the modified adenovirus E4 coding region comprises a sequence corresponding to nucleotide sequence 32645-35835 of the Ad2 genome with a partial or complete deletion E4orf6/7 intron 2 wherein the E4orf6/7 intron 2 has the sequence of SEQ ID NO:2, and a partial or complete deletion of E4orf6/7 intron 1, wherein the E4orf6/7 intron 1 has the sequence of SEQ ID NO:1.

13. The expression construct of claim 11, wherein the modified adenovirus E2a coding region comprises a sequence corresponding to nucleotide sequence 22233-27575 of the Ad2 genome with a 1897 bp deletion of SEQ ID NO: 3 that encompasses the complete sequence of later-E2a intron 1 and E2a intron 2.

14. The expression construct of claim 11, comprising (1) SEQ ID NO:17 or SEQ ID NO:18; (2) SEQ ID NO:4; (3) SEQ ID NO:16; and (4) SEQ ID NO:19.

15. The expression construct of claim 11, wherein the expression construct further comprises an AAV Rep coding region and an AAV Cap coding region.

16. The expression construct of claim 15, comprising SEQ ID NO:20 and SEQ ID NO: 21.

17. The expression construct of claim 11, wherein the expression construct further comprises a recombinant AAV genome comprising:

an expression cassette comprising a sequence encoding a gene of interest and a regulatory element operably linked to the sequence encoding a gene of interest; and two AAV ITRs flanking the expression cassette.

18. A method for producing recombinant AAV, comprising the step of:

introducing the expression construct of claim 11, an AAV trans plasmid encoding an AAV Rep protein and an AAV Cap protein, and an AAV cis plasmid encoding a recombinant AAV genome into a host cell;

incubating the host cell harboring the expression construct of claim 11, the AAV trans plasmid and the AAV cis plasmid for a desired period of time to produce recombinant AAV particles; and harvesting the recombinant AAV particles after the incubation period.

19. A method for producing recombinant AAV, comprising the step of:

introducing the expression construct of claim 15 and an AAV cis plasmid encoding a recombinant AAV genome into a host cell;

Incubating the host cell harboring the expression construct and the AAV cis plasmid for a desired period of time to produce recombinant AAV particles; and harvesting the recombinant AAV particles after the incubation period.

20. A method for producing recombinant AAV, comprising the step of:

introducing the expression construct of claim 17 and an AAV trans plasmid encoding an AAV Rep protein and an AAV Cap protein into a host cell;

incubating the host cell harboring the expression construct and the AAV trans plasmid for a desired period of time to produce recombinant AAV particles; and harvesting the recombinant AAV particles after the incubation period.

* * * * *

SEQUENCE LISTING

```
Sequence total quantity: 23
SEQ ID NO: 1            moltype = DNA  length = 1275
FEATURE                 Location/Qualifiers
misc_feature            1..1275
                        note = Synthetic: D2-1275 bp Ad2 sequence
source                  1..1275
                        mol_type = other DNA
                        organism = synthetic construct
SEQUENCE: 1
ccctggcttc gggttctatg taaactcctt catgcgccgc tgccctgata acatccacca  60
ccgcagaata agccacaccc agccaaccta cacattcgtt ctgcgagtca cacacgggag  120
gagcgggaag agctggaaga accatgtttt ttttttttta ttccaaaaga ttatccaaaa  180
cctcaaaatg aagatctatt aagtgaacgc gctcccctcc ggtggcgtgg tcaaactcta  240
cagccaaaga acagataatg gcatttgtaa gatgttgcac aatggcttcc aaaaggcaaa  300
ctgccctcac gtccaagtgg acgtaaaggc taaacccttc agggtgaatc tcctctataa  360
acattccagc accttcaacc atgcccaaat aattttcatc tcgccacctt atcaatatgt  420
ctctaagcaa atcccgaata ttaagtccgg ccattgtaaa aatctgctcc agagcgccct  480
ccaccttcag cctcaagcag cgaatcatga ttgcaaaaat tcaggttcct cacagacctg  540
tataagattc aaaagcggaa cattaacaaa aataccgcga tcccgtaggt cccttcgcag  600
ggccagctga acataatcgt gcaggtctgc acggaccagc gcggccactt ccccgccagg  660
aaccatgaca aaagaaccca cactgattat gacacgcata ctcggagcta tgctaaccag  720
cgtagcccct atgtaagctt gttgcatggg cggcgatata aaatgcaagg tgctgctcaa  780
aaaatcaggc aaagcctcgc gcaaaaaagc aagcacatcg tagtcatgct catgcagata  840
aaggcaggta agttccggaa ccaccacaga aaaagacacc atttttctct caaacatgtc  900
tgcgggttcc tgcattaaac acaaaataaa ataacaaaaa aaaaaacatt taaacattag  960
aagcctgtct tacaacagga aaaacaaccc ttataagcat aagacggact acggccatgc  1020
cggcgtgacc gtaaaaaaac tggtcaccgt gattaaaaag caccaccgac agttcctcgg  1080
tcatgtccgg agtcataatg taagactcgg taaacacatc aggttggtta acatcggtca  1140
gtgctaaaaa gcgaccgaaa tagcccgggg gaatacatac ccgcaggcgt agagacaaca  1200
ttacagcccc cataggaggt ataacaaaat taataggaga gaaaaacaca taaacacctg  1260
aaaaaccctc ctgcc                                                   1275

SEQ ID NO: 2            moltype = DNA  length = 711
FEATURE                 Location/Qualifiers
misc_feature            1..711
                        note = Synthetic: D1-711 bp Ad2 sequence
source                  1..711
                        mol_type = other DNA
                        organism = synthetic construct
SEQUENCE: 2
ctacatgggg gtagagtcat aatcgtgcat caggataggg cggtggtgct gcagcagcgc  60
gcgaataaac tgctgccgcc gccgctccgt cctgcaggaa tacaacatgg cagtggtctc  120
ctcagcgatg attcgcaccg cccgcagcat gagacgcctt gtcctccggg cacagcagcg  180
caccctgatc tcacttaaat cagcacagta actgcagcac agcaccacaa tattgttcaa  240
aatcccacag tgcaaggcgc tgtatccaaa gctcatggcg gggaccacag aacccacgtg  300
gccatcatac cacaagcgca ggtagattaa gtggcgaccc ctcataaaca cgctggacat  360
aaacattacc tcttttggca tgttgtaatt caccacctcc cggtaccata taaacctctg  420
attaaacatg gcgccatcca ccaccatcct aaaccagctg gccaaaacct gcccgccggc  480
tatgcactgc agggaaccgg gactggaaca atgacagtgg agagcccagg actcgtaacc  540
atggatcatc atgctcgtca tgatatcaat gttggcacaa cacaggcaca cgtgcataca  600
cttcctcagg attacaagct cctcccgcgt cagaaccata tcccagggaa caacccattc  660
ctgaatcagc gtaaatccca cactgcaggg aagacctcgc acgtaactca c           711

SEQ ID NO: 3            moltype = DNA  length = 1194
FEATURE                 Location/Qualifiers
misc_feature            1..1194
                        note = Synthetic: D3-1897 bp Ad2 sequence
source                  1..1194
                        mol_type = other DNA
                        organism = synthetic construct
SEQUENCE: 3
tacaaatttg cgaaggtaag ccgacgtcca cagccccgga gtgagtttca accccggagc  60
cgcggacttt tcgtcaggcg agggaccctg cagctcaaag gtaccgataa tttgactttc  120
gctaagcagt tgcgaattgc agaccaggga gcggtgcggg gtgcataggt tgcagcgaca  180
gtgacactcc agtaggccgt caccgctcac gtcttccatg atgtcggagt ggtaggcaag  240
gtagttggct agctgcagaa ggtagcagtg accccaaagc ggcggagggc attcacggta  300
cttaatgggc acaaagtcgc taggaagcgc acagcaggtg gcgggcagaa ttcctgaacg  360
ctctaggata aagttcctaa agttttgcaa catgctttga ctggtgaagt ctggcagacc  420
ctgttgcagg gttttaagca ggcgttcggg gaagataatg tccgccaggt gcgcggccac  480
ggagcgctcg ttgaaggccg tccataggtc cttcaagttt tgctttagca gcttctgcag  540
ctcctttagg ttgcgctcct ccaggcattg ctgccacacg cccatggccg tttgccaggt  600
gtagcacaga aataagtaaa cgcagtcgcg gacgtagtcg cggcgcgcct cgcccttgag  660
cgtggaatga agcacgtttt gcccgaggcg gttttcgtgc aaaattccaa ggtaggagac  720
caggttgcag agctccacgt tggaaatttt gcaggcctgg cgcacgtagc cctggcgaaa  780
ggtgtagtgc aacgtttcct ctagcttgcg ctgcatctcc gggtcagcaa agaaccgctg  840
```

```
catgcactca agctccacgg taacaagcac tgcggccatc attagcttgc gtcgctcctc  900
caagtcggca ggctcgcgcg tctcaagcca gcgcgccagc tgctcatcgc caactgcggg  960
taggccctcc tcggtttgtt cttgcaagtt tgcatccctc tccaggggtc gtgcacggcg  1020
cacgatcagc tcgctcatga ctgtgctcat aaccttgggg ggtaggttaa gtgccgggta  1080
ggcaaagtgg gtgacctcga tgctgcgttt cagcacggct aggcgcgcgt tgtcaccctc  1140
aagttccacc agcactccac agtgactttc attttcgctg ttttcttgtt gcag        1194

SEQ ID NO: 4            moltype = DNA  length = 1590
FEATURE                 Location/Qualifiers
misc_feature            1..1590
                        note = Synthetic: Codon optimized Ad2 E2a coding sequence
source                  1..1590
                        mol_type = other DNA
                        organism = synthetic construct
SEQUENCE: 4
atggccagtc gggaagagga gcagcgcgaa accacccccg agcgcggacg cggtgcggcg  60
cgacgtccac caaccatgga ggacgtgtcg tccccgtcgc cgtcgccgcc gcctccccgc  120
gcgcccccaa aaaagagact gcggagacgc ctggagtccg aggacgagga agacagttcc  180
caggacgctc tggtgcctag gacaccatct ccaagaccct ccacttccac cgccgacctg  240
gccattgcca gcaaaaaaaa gaagaagagg ccctccccta aacctgaacg accacccagc  300
ccagaagtga tcgtggactc agaggaagag cgcgaggacg tcgctctgca gatggtggga  360
ttcagcaatc cacctgtgct catcaagcac ggcaaagggg gaaaacggac cgtgcgcagg  420
ctgaacgagg atgatcctgt ggcaagggggc atgaggacac aggaggagaa ggaagaatcc  480
tccgaggccg agagcgagag cacagtgatt aatccactgt ccctgccaat tgtgagcgct  540
tgggagaagg gaatggaggc cgcccgggcc ctgatggaca agtaccacgt ggacaacgac  600
ctgaaggcta atttcaaact gctgcctgac caggtggagg ccctggctgc cgtgtgcaag  660
acatggctga atgaggagca tagagggctg cagctgacct ttacatcaaa caagaccttt  720
gtgaccatga tgggcaggtt tctgcaggcc tacctgcaat ctttcgccga agtgacttac  780
aagcaccacg agcccaccgg ctgcgccctg tggctgcaca gatgcgccga gattgagggc  840
gagctgaaat gcctgcacgg ctctatcatg attaacaagg agcacgtgat cgagatggat  900
gtgacttccg aaaacggcca gcgcgccctg aaggagcagt ccagcaaggc caagatcgtg  960
aagaacaggt ggggcaggaa cgtggtgcag atttctaaca cagacgccag atgttgcgtg  1020
catgacgccg cctgccctgc caatcagttt agcggcaaga gctgcggaat gttcttcagc  1080
gagggagcca aggcgcaagt ggccttcaag cagatcaagg ccttcatgca agccctgtat  1140
ccaaatgccc agaccggcca cggccacctc ctgatgcccc tgcgctgcga atgtaactcc  1200
aagcccggcc acgccccttt cctgggcagg cagctgccaa aactgacccc ttttgccctg  1260
agcaacgccg aagatctgga tgccgatctg atcagcgaca agtccgtgct ggcctccgtt  1320
caccaccccg ccctgatcgt gttccagtgc tgcaatcccg tgtacaggaa tagcagagct  1380
cagggtggag gccccaactg cgacttcaag atctccgccc cagatctgct gaacgctctc  1440
gtgatggtgc ggagcctgtg gtctgagaac ttcacagagc tgccccgcat ggtggtgccc  1500
gagttcaagt ggagcactaa gcatcagtac cggaatgtgt ctctgcccgt ggcccactct  1560
gacgccagac agaatccttt tgacttctga                                   1590

SEQ ID NO: 5            moltype = AA  length = 529
FEATURE                 Location/Qualifiers
REGION                  1..529
                        note = Synthetic: Wild-type Ad2 E2a amino acid sequence
source                  1..529
                        mol_type = protein
                        organism = synthetic construct
SEQUENCE: 5
MASREEEQRE TTPERGRGAA RRPPTMEDVS SPSPSPPPPR APPKKRLRRR LESEDEEDSS  60
QDALVPRTPS PRPSTSTADL AIASKKKKKR PSPKPERPPS PEVIVDSEEE REDVALQMVG  120
FSNPPVLIKH GKGGKRTVRR LNEDDPVARG MRTQEEKEES SEAESESTVI NPLSLPIVSA  180
WEKGMEAARA LMDKYHVDND LKANFKLLPD QVEALAAVCK TWLNEEHRGL QLTFTSNKTF  240
VTMMGRFLQA YLQSFAEVTY KHHEPTGCAL WLHRCAEIEG ELKCLHGSIM INKEHVIEMD  300
VTSENGQRAL KEQSSKAKIV KNRWGRNVVQ ISNTDARCCV HDAACPANQF SGKSCGMFFS  360
EGAKAQVAFK QIKAFMQALY PNAQTGHGHL LMPLRCECNS KPGHAPFLGR QLPKLTPFAL  420
SNAEDLDADL ISDKSVLASV HHPALIVFQC CNPVYRNSRA QGGGPNCDFK ISAPDLLNAL  480
VMVRSLWSEN FTELPRMVVP EFKWSTKHQY RNVSLPVAHS DARQNPFDF              529

SEQ ID NO: 6            moltype = DNA  length = 7686
FEATURE                 Location/Qualifiers
misc_feature            1..7686
                        note = Synthetic: mini-pHelper plasmid sequence
source                  1..7686
                        mol_type = other DNA
                        organism = synthetic construct
SEQUENCE: 6
ggatccatcg cgccctgtag cggcgcatta agcgcggcgg gtgtggtggt tacgcgcagc  60
gtgaccgcta cacttgccag cgccctagcg cccgctcctt tcgctttctt cccttccttt  120
ctcgccacgt tcgccggctt tccccgtcaa gctctaaatc gggggctccc tttagggttc  180
cgatttagtg ctttacggca cctcgacccc aaaaaacttg attagggtga tggttcacgt  240
agtgggccat cgccctgata gacggttttt cgccctttga cgttggagtc cacgttcttt  300
aatagtggac tcttgttcca aactggaaca acactcaacc ctatctcggt ctattctttt  360
gatttataag ggattttgcc gatttcggcc tattggttaa aaaatgagct gatttaacaa  420
aaatttaacg cgaattttaa caaaatatta acgcttacaa tttaggtggc acttttcggg  480
gaaatgtgcg cggaacccct atttgtttat ttttctaaat acattcaaat atgtatccgc  540
tcatgagaca ataaccctga taaatgcttc aataatattg aaaaaggaag agtatgattg  600
```

aacaagatgg attgcacgca ggttctccgg ccgcttgggt ggagaggcta ttcggctatg 660
actgggcaca acagacaatc ggctgctctg atgccgccgt gttccggctg tcagcgcagg 720
ggcgcccggt tctttttgtc aagaccgacc tgtccggtgc cctgaatgaa ctgcaagacg 780
aggcagcgcg gctatcgtgg ctggccacga cgggcgttcc ttgcgcagct gtactcgacg 840
ttgtcactga agcgggaagg gactggctgc tattgggcga agtgccgggg caggatctcc 900
tgtcatctca ccttgctcct gccgagaaag tatccatcat ggctgatgca atgcggcggc 960
tgcatacgct tgatccggct acctgcccat tcgaccacca agcgaaacat cgcatcgagc 1020
gagcacgtac tcggatggaa gccggtcttg tcgatcagga tgatctggac gaagagcatc 1080
aggggctcgc gccagccgaa ctgttcgcca ggctcaaggc gagcatgccc gacggcgagg 1140
atctcgtcgt gacccatggc gatgcctgct tgccgaatat catggtggaa aatggccgct 1200
tttctggatt catcgactgt ggccggctgg gtgtggcgga ccgctatcag gacatagcgt 1260
tggctacccg tgatattgct gaagagcttg gcggcgaatg ggctgaccgc ttcctcgtgc 1320
tttacggtat cgccgctccc gattcgcagc gcatcgcctt ctatcgcctt cttgacgagt 1380
tcttctgact gtcagaccaa gtttactcat atatacttta gattgattta aaacttcatt 1440
tttaatttaa aaggatctag gtgaagatcc tttttgataa tctcatgacc aaaatccctt 1500
aacgtgagtt ttcgttccac tgagcgtcag accccgtaga aaagatcaaa ggatcttctt 1560
gagatccttt ttttctgcgc gtaatctgct gcttgcaaac aaaaaaacca ccgctaccag 1620
cggtggtttg tttgccggat caagagctac caactctttt tccgaaggta actggcttca 1680
gcagagcgca gataccaaat actgttcttc tagtgtagcc gtagttaggc caccacttca 1740
agaactctgt agcaccgcct acatacctcg ctctgctaat cctgttacca gtggctgctg 1800
ccagtggcga taagtcgtgt cttaccgggt tggactcaag acgatagtta ccggataagg 1860
cgcagcggtc gggctgaacg gggggttcgt gcacacagcc cagcttggag cgaacgacct 1920
acaccgaact gagataccta cagcgtgagc tatgagaaag cgccacgctt cccgaaggga 1980
gaaaggcgga caggtatccg gtaagcggca gggtcggaac aggagagcgc acgagggagc 2040
ttccaggggg aaacgcctgg tatctttata gtcctgtcgg gtttcgccac ctctgacttg 2100
agcgtcgatt tttgtgatgc tcgtcagggg ggcggagcct atggaaaaac gccagcaacg 2160
cggccttttt acggttcctg gccttttgct ggccttttgc tcacatgttc tttcctgcgt 2220
tatcccctga ttctgtggat aaccgtatta ccgcctttga gtgagctgat catatggttt 2280
aaacgtcgac gtaatccgta gatgtacctg gacatccagg tgatgccggc ggcggtggtg 2340
gaggcgcgcg gaaagtcgcg gacgcggttc cagatgttgc gcagcggcaa aaagtgctcc 2400
atggtcggga cgctctggcc ggtgaggcgt gcgcagtcgt tgacgctcta gaccgtgcaa 2460
aaggagagcc tgtaagcggg cactcttccg tggtctggtg gataaattcg caagggtatc 2520
atggcggacg accggggttc gaaccccgga tccggccgtc cgccgtgatc catgcggtta 2580
ccgcccgcgt gtcgaaccca ggtgtgcgac gtcagacaac gggggagcgc tccttttggc 2640
ttccttccag gcgcggcggc tgctgcgcta gcttttttgg ccactggccg cgcgcggcgt 2700
aagcggttag gctggaaagc gaaagcatta agtggctcgc tccctgtagc cggagggtta 2760
ttttccaagg gttgagtcgc aggacccccg gttcgagtct cgggccggcc ggactgcggc 2820
gaacgggggt ttgcctcccc gtcatgcaag accccgcttg caaattcctc cggaaacagg 2880
gacgagcccc tttttttgctt ttcccagatg catccggtgc tgcggcagat gcgccccct 2940
cctcagcagc ggcaagagca agagcagcgg cagacatgca gggcaccctc cccttctcct 3000
accgcgtcag gaggggcaac atcctacatc gattctagtg aatccacaga aactagcgag 3060
gtaagcactt actctatgtc ttttacatgg tcctgggaaa gtggaaaata caccactgaa 3120
acttttgcta ccaactctta caccttctcc tacattgccc aggaataaag aatcgtgaac 3180
ctgttgcatg ttatgtttca acgtgtttat ttttcaattg cagaaaattt caagtcattt 3240
ttcattcagt agtatagccc caccaccaca tagcttatat tgatcaccgt accttaatca 3300
aactcacaga accctagtat tcaacctgcc acctccctcc caacacacag agtacacagt 3360
cctttctccc cggctggcct taaaaagcat catatcatgg gtaacagaca tattcttagg 3420
tgttatattc cacacggttt cctgtcgagc caaacgctca tcagtgatat taataaactc 3480
cccgggcagc tcgcttaagt tcatgtcgct gtccagctgc tgagccacag gctgctgtcc 3540
aacttgcggt tgctcaacgg gcggcgaagg ggaagtccac gcgttgtgca ttgtcaaagt 3600
gttacattcg ggcagcagcg gatgatcctc cagtatggta gcgcgggtct ctgtctcaaa 3660
aggaggtagg cgatccctac tgtacggagt gcgccgagac aaccgagatc gtgttggtcg 3720
tagtgtcatg ccaaatggaa cgccggacgt agtcatattt cctgaagcaa aaccaggtgc 3780
gggcgtgaca aacagatctg cgtctccggt ctggtcgctt agctcgctct gtgtagtagt 3840
tgtagtatat ccactctctc aaagcatcca ggcgcctagg caaaatagca ccctcccgct 3900
ccagaacaac atacagcgct tccacagcgg cagccataac agtcagcctt accagtaaaa 3960
aaacctatta aaaaacacca ctcgacacgg caccagctca atcagtcaca gtgtaaaaag 4020
ggccaagtac agagcgagta tatataggac taaaaaatga cgtaacggtt aaagtccaca 4080
aaaaacaccc agaaaaccgc acgcgaacct acgcccagaa acgaaagcca aaaaacccac 4140
aacttcctca aatcttcact tccgttttcc cacgatacgt cacttcccat tttaaaaaaa 4200
ctacaattcc caatacatgc aagttactcc gccctaaaac gcccgggcga ccgcaccctg 4260
tgacgaaagc cgcccgcaag ctgcgcccct gagttagtca tctgaacttc ggcctgggcg 4320
tctctgggaa gtaccacagt ggtgggagcg ggactttcct ggtacaccag ggcagcgggc 4380
caactacggg gattaaggtt attacgaggt gtggtggtaa tagccgcctg ttcgaggaga 4440
attcggtttc ggtgggcgcg gattccgttg acccgggata tcatgtgggg tcccgcgctc 4500
atgtagttta ttcgggttga gtagtcttgg gcagctccag ccgcaagtcc catttgtggc 4560
tggtaactcc acatgtaggg cgtgggaatt tccttgctca taatggcgct gacgacaggt 4620
gctggcgccg ggtgtggccg ctggagatga cgtagttttc gcgcttaaat ttgagaaagg 4680
gcgcgaaact agtccttaag agtcagcgcg cagtatttgc tgaagagagc ctccgcgtct 4740
tccagcgtgc gccgaagctg atcttcgctt ttgtgataca ggcagctgcg ggtgagggag 4800
cgcagagacc tgttttttat tttcagctct tgttcttggc cctgctttg ttgaaatata 4860
gcatacagag tgggaaaaat cctatttcta agctcgcggg tcgatacggg ttcgttgggc 4920
gccagacgca gcgctcctcc tcctgctgct gccgccgctg tggatttctt gggctttgtc 4980
agagtcttgc tatccggtcg cctttgcttc tgtgtgaccg ctgctgttgc tgccgctgcc 5040
gctgccgccg gtgcagtagg ggctgtagag atgacggtag taatgcagga tgttacgggg 5100
gaaggccacg ccgtgatggt agagaagaaa gcggcgggcg aaggagatgt tgccccccaca 5160
gtcttgcaag caagcaacta tggcgttctt gtgcccgcgc cacgagcggt agccttggcg 5220
ctgttgttgc tcttgggcta acggcggcgg ctgcttagac ttaccggccc tggttccagt 5280
ggtgtcccat ctacggttgg gtcggcgaac aggcagtgcc ggcggcgcct gaggagcgga 5340

-continued

```
ggttgtagcg atgctgggaa cggttgccaa tttctggggc gccggcgagg ggaatgcgac  5400
cgagggtgac ggtgtttcgt ctgacacctc ttcggcctcg gaagcttcgt ctaggctgtc  5460
ccagtcttcc atcatctcct cctcctcgtc caaaacctcc tctgcctgac tgtcccagta  5520
ttcctcctcg tccgtgggtg gcggcggcgg cagctgcagc ttctttttgg gtgccatcct  5580
gggaagcaag ggcccgcggc tgctgatagg gctgcggcgg cggggggatt gggttgagct  5640
cctcgccgga ctgggggtcc aggtaaaccc cccgtccctt tcgtagcaga aactcttggc  5700
gggctttgtt gatggcttgc aattggccaa ggatgtggcc ctgggtaatg acgcaggcgg  5760
taagctccgc atttggcggg cgggattggt cttcgtagaa cctaatctcg tgggcgtggt  5820
agtcctcagg gagaaggaaa tggccagtcg ggaagaggag cagcgcgaaa ccacccccga  5880
gcgcggacgc ggtgcggcgc gacgtccacc aaccatggag gacgtgtcgt ccccgtcgcc  5940
gtcgccgccg cctccccgcg cgcccccaaa aaagagactg cggagacgcc tggagtccga  6000
ggacgaggaa gacagttccc aggacgctct ggtgcctagg acaccatctc caagaccctc  6060
cacttccacc gccgacctgg ccattgccag caaaaaaaag aagaagaggc cctcccctaa  6120
acctgaacga ccacccagcc cagaagtgat cgtggactca gaggaagagc gcgaggacgt  6180
cgctctgcag atggtgggat tcagcaatcc acctgtgctc atcaagcacg gcaaaggggg  6240
aaaacggacc gtgcgcaggc tgaacgagga tgatcctgtg gcaaggggca tgaggacaca  6300
ggaggagaag gaagaatcct ccgaggccga gagcgagagc acagtgatta atccactgtc  6360
cctgccaatt gtgagcgctt gggagaaggg aatggaggcc gcccgggccc tgatggacaa  6420
gtaccacgtg gacaacgacc tgaaggctaa tttcaaactg ctgcctgacc aggtggaggc  6480
cctggctgcc gtgtgcaaga catggctgaa tgaggagcat agagggctgc agctgacctt  6540
tacatcaaac aagacctttg tgaccatgat gggcaggttt ctgcaggcct acctgcaatc  6600
tttcgccgaa gtgacttaca agcaccacga gcccaccggc tgcgccctgt ggctgcacag  6660
atgcgccgag attgagggcg agctgaaatg cctgcacggc tctatcatga ttaacaagga  6720
gcacgtgatc gagatggatg tgacttccga aaacggccag cgcgccctga aggagcagtc  6780
cagcaaggcc aagatcgtga agaacaggtg gggcaggaac gtggtgcaga tttctaacac  6840
agacgccaga tgttgcgtgc atgacgccgc ctgccctgcc aatcagttta gcggcaagag  6900
ctgcggaatg ttcttcagcg agggagccaa ggcgcaagtg gccttcaagc agatcaaggc  6960
cttcatgcaa gccctgtatc caaatgccca gaccggccac ggccacctcc tgatgcccct  7020
gcgctgcgaa tgtaactcca agcccggcca cgcccctttc ctgggcaggc agctgccaaa  7080
actgacccct tttgccctga gcaacgccga agatctggat gccgatctga tcagcgacaa  7140
gtccgtgctg gcctccgttc accaccccgc cctgatcgtg ttccagtgct gcaatcccgt  7200
gtacaggaat agcagagctc agggtggagg ccccaactgc gacttcaaga tctccgcccc  7260
agatctgctg aacgctctcg tgatggtgcg gagcctgtgg tctgagaact tcacagagct  7320
gccccgcatg gtggtgcccg agttcaagtg gagcactaag catcagtacc ggaatgtgtc  7380
tctgcccgtg gcccactctg acgccagaca gaatcctttt gacttctgaa cggcgcagac  7440
ggcaagggtg gggggtaaat aatcacccga gagtgtacaa ataaaaacat ttgcctttat  7500
tgaaagtgtc tcctagtaca ttatttttac atgtttttca agtgacaaaa agaagtggcg  7560
ctcctaatct gcgcactgtg gctgcggaag tagggcgagt ggcgctccag gaagctgtag  7620
agctgttcct ggttgcgacg cagggtgggc tgtacctggg gactgttaag catggagttg  7680
ggtacc                                                             7686
```

```
SEQ ID NO: 7            moltype = DNA  length = 453
FEATURE                 Location/Qualifiers
misc_feature            1..453
                        note = Synthetic: Codon optimized Ad2 E4orf6/7 coding
                         sequence
source                  1..453
                        mol_type = other DNA
                        organism = synthetic construct
SEQUENCE: 7
atgaccacaa gcggcgtgcc ctttggcatg accctgaggc caaccaggag caggctgtcc  60
agacgcacac catacagcag ggaccggctg cctcctttcg agacagagac cagagccact  120
atcctcgagg atcatcctct gctgcctgag tgcaatacac tgaccatgca caatgcctgg  180
acctcccctt cccccccgt ggaacagcca caggtgggac agcagcctgt ggcccagcag  240
ctggacagcg acatgaacct gagcgaactg cccggcgagt tcatcaatat caccgacgag  300
agactggcca gacaggagac cgtgtggaat atcaccccca aaaatatgag cgtgacccac  360
gacatgatgc tgttcaaagc cagccggggc gagagaaccg tgtacagcgt gtgctgggag  420
ggcggcggaa gactgaatac tagggtgctg tga                                453
```

```
SEQ ID NO: 8            moltype = AA  length = 150
FEATURE                 Location/Qualifiers
REGION                  1..150
                        note = Synthetic: Wild-type Ad2 E4orf6/7 amino acid sequence
source                  1..150
                        mol_type = protein
                        organism = synthetic construct
SEQUENCE: 8
MTTSGVPFGM TLRPTRSRLS RRTPYSRDRL PPFETETRAT ILEDHPLLPE CNTLTMHNAW  60
TSPSPPVEQP QVGQQPVAQQ LDSDMNLSEL PGEFINITDE RLARQETVWN ITPKNMSVTH  120
DMMLFKASRG ERTVYSVCWE GGGRLNTRVL                                   150
```

```
SEQ ID NO: 9            moltype = DNA  length = 7674
FEATURE                 Location/Qualifiers
misc_feature            1..7674
                        note = Synthetic: Mini pHelper 1.0
source                  1..7674
                        mol_type = other DNA
                        organism = synthetic construct
SEQUENCE: 9
```

-continued

```
tttggcttcc ttccaggcgc ggcggctgct gcgctagctt ttttggccac tggccgcgcg   60
cggcgtaagc ggttaggctg gaaagcgaaa gcattaagtg gctcgctccc tgtagccgga  120
gggttatttt ccaagggttg agtcgcagga cccccggttc gagtctcggg ccggccggac  180
tgcggcgaac gggggtttgc ctccccgtca tgcaagaccc cgcttgcaaa ttcctccgga  240
aacagggacg agcccctttt ttgcttttcc cagatgcatc cggtgctgcg gcagatgcgc  300
ccccctcctc agcagcggca agagcaagag cagcggcaga catgcagggc accctcccct  360
tctcctaccg cgtcaggagg ggcaacatcc tacatcgatt ctagtgaatc cacagaaact  420
agcgaggtaa gcacttactc tatgtctttt acatggtcct gggaaagtgg aaaatacacc  480
actgaaactt ttgctaccaa ctcttacacc ttctcctaca ttgcccagga ataaagaatc  540
gtgaacctgt tgcatgttat gtttcaacgt gtttattttt caattgcaga aaatttcaag  600
tcatttttca ttcagtagta tagccccacc accacatagc ttatattgat caccgtacct  660
taatcaaact cacagaaccc tagtattcaa cctgccacct ccctcccaac acacagagta  720
cacagtcctt tctccccggc tggccttaaa aagcatcata tcatgggtaa cagacatatt  780
cttaggtgtt atattccaca cggtttcctg tcgagccaaa cgctcatcag tgatattaat  840
aaactccccg ggcagctcgc ttaagttcat gtcgctgtcc agctgctgag ccacaggctg  900
ctgtccaact tgcggttgct caacgggcgg cgaaggggaa gtccacgcct acatgggggt  960
agagtcataa tcgtgcatca ggatagggcg gtggtgctgc agcagcgcgc gaataaactg 1020
ctgccgccgc cgctccgtcc tgcaggaata caacatggca gtggtctcct cagcgatgat 1080
tcgcaccgcc cgcagcatga gacgccttgt cctccgggca cagcagcgca ccctgatctc 1140
acttaaatca gcacagtaac tgcagcacag caccacaata ttgttcaaaa tcccacagtg 1200
caaggcgctg tatccaaagc tcatggcggg gaccacagaa cccacgtggc catcatacca 1260
caagcgcagg tagattaagt ggcgacccct cataaacacg ctggacataa acattacctc 1320
ttttggcatg ttgtaattca ccacctcccg gtaccatata aacctctgat taaacatggc 1380
gccatccacc accatcctaa accagctggc caaaacctgc ccgccggcta tgcactgcag 1440
ggaaccggga ctggaacaat gacagtggag agcccaggac tcgtaaccat ggatcatcat 1500
gctcgtcatg atatcaatgt tggcacaaca caggcacacg tgcatacact tcctcaggat 1560
tacaagctcc tcccgcgtca gaaccatatc ccagggaaca acccattcct gaatcagcgt 1620
aaatcccaca ctgcagggaa gacctcgcac gtaactcacg ttgtgcattg tcaaagtgtt 1680
acattcgggc agcagcggat gatcctccag tatggtagcg cgggtctctg tctcaaaagg 1740
aggtaggcga tccctactgt acggagtgcg ccgagacaac cgagatcgtg ttggtcgtag 1800
tgtcatgcca aatggaacgc cggacgtagt catatttcct gaagcaaaac caggtgcggg 1860
cgtgacaaac agatctgcgt ctccggtctc gtcgcttagc tcgctctgtg tagtagttgt 1920
agtatatcca ctctctcaaa gcatccaggc gcctaggcaa aatagcaccc tcccgctcca 1980
gaacaacata cagcgcttcc acagcggcag ccataacagt cagccttacc agtaaaaaaa 2040
cctattaaaa aacaccactc gacacggcac cagctcaatc agtcacagtg taaaaagggc 2100
caagtacaga gcgagtatat ataggactaa aaaatgacgt aacggttaaa gtccacaaaa 2160
aacacccaga aaaccgcacg cgaacctacg cccagaaacg aaagccaaaa aacccacaac 2220
ttcctcaaat cttcacttcc gttttcccac gatacgtcac ttcccatttt aaaaaaacta 2280
caattcccaa tacatgcaag ttactccgcc ctaaaacgcc cgggcgaccg caccctgtga 2340
cgaaagccgc ccgcaagctg cgcccctgag ttagtcatct gaacttcggc ctgggcgtct 2400
ctgggaagta ccacagtggt gggagcggga ctttcctggt acaccagggc agcgggccaa 2460
ctacggggat taaggttatt acgaggtgtg gtggtaatag ccgcctgttc gaggagaatt 2520
cggtttcggt gggcgcggat tccgttgacc cgggatatca tgtggggtcc cgcgctcatg 2580
tagtttattc gggttgagta gtcttgggca gctccagccg caagtcccat ttgtggctgg 2640
taactccaca tgtagggcgt gggaatttcc ttgctcataa tggcgctgac gacaggtgct 2700
ggcgccgggt gtggccgctg gagatgacgt agttttcgcg cttaaatttg agaaagggcg 2760
cgaaactagt ccttaagagt cagcgcgcag tatttgctga agagagcctc cgcgtcttcc 2820
agcgtgcgcc gaagctgatc ttcgcttttg tgatacaggc agctgcgggt gagggagcgc 2880
agagacctgt tttttatttt cagctcttgt tcttggcccc tgctttgttg aaatatagca 2940
tacagagtgg gaaaaatcct atttctaagc tcgcgggtcg atacgggttc gttgggcgcc 3000
agacgcagcg ctcctcctcc tgctgctgcc gccgctgtgg atttcttggg ctttgtcaga 3060
gtcttgctat ccggtcgcct ttgcttctgt gtgaccgctg ctgttgctgc cgctgccgct 3120
gccgccggtg cagtaggggc tgtagagatg acggtagtaa tgcaggatgt tacgggggaa 3180
ggccacgccg tgatggtaga gaagaaagcg gcgggcgaag gagatgttgc cccacagtc  3240
ttgcaagcaa gcaactatgg cgttcttgtg cccgcgccac gagcggtagc cttggcgctg 3300
ttgttgctct tgggctaacg gcggcggctg cttagactta ccggccctgg ttccagtggt 3360
gtcccatcta cggttgggtc ggcgaacagg cagtgccggc ggcgcctgag gagcggaggt 3420
tgtagcgatg ctgggaacgg ttgccaattt ctggggcgcc ggcgagggga atgcgaccga 3480
gggtgacggt gtttcgtctg acacctcttc ggcctcggaa gcttcgtcta ggctgtccca 3540
gtcttccatc atctcctcct cctcgtccaa aacctcctct gcctgactgt cccagtattc 3600
ctcctcgtcc gtgggtggcg gcggcggcag ctgcagcttc tttttgggtg ccatcctggg 3660
aagcaagggc ccgcggctgc tgatagggct gcggcggcgg ggggattggg ttgagctcct 3720
cgccggactg gggggtccagg taaacccccc gtccctttcg tagcagaaac tcttggcggg 3780
ctttgttgat ggcttgcaat tggccaagga tgtggccctg ggtaatgacg caggcggtaa 3840
gctccgcatt tggcgggcgg gattggtctt cgtagaacct aatctcgtgg gcgtggtagt 3900
cctcagggag aaggaaatgg ccagtcggga agaggagcag cgcgaaacca cccccgagcg 3960
cggacgcggt gcggcgcgac gtccaccaac catggaggac gtgtcgtccc cgtcgccgtc 4020
gccgccgcct ccccgcgcgc ccccaaaaaa gagactgcgg agacgcctgg agtccgagga 4080
cgaggaagac agttcccagg acgctctggt gcctaggaca ccatctccaa gaccctccac 4140
ttccaccgcc gacctggcca ttgccagcaa aaaaaagaag aagaggccct cccctaaacc 4200
tgaacgacca cccagcccag aagtgatcgt ggactcagag gaagagcgcg aggacgtcgc 4260
tctgcagatg gtgggattca gcaatccacc tgtgctcatc aagcacggca aaggggggaaa 4320
acggaccgtg cgcaggctga acgaggatga tcctgtggca aggggcatga ggacacagga 4380
ggagaaggaa gaatcctccg aggccgagag cgagagcaca gtgattaatc cactgtccct 4440
gccaattgtg agcgcttggg agaagggaat ggaggccgcc cgggccctga tggacaagta 4500
ccacgtggac aacgacctga aggctaattt caaactgctg cctgaccagg tggaggccct 4560
ggctgccgtg tgcaagacat ggctgaatga ggagcataga gggctgcagc tgacctttac 4620
atcaaacaag acctttgtga ccatgatggg caggtttctg caggcctacc tgcaatcttt 4680
cgccgaagtg acttacaagc accacgagcc caccggctgc gccctgtggc tgcacagatg 4740
```

```
cgccgagatt gagggcgagc tgaaatgcct gcacggctct atcatgatta acaaggagca  4800
cgtgatcgag atggatgtga cttccgaaaa cggccagcgc gccctgaagg agcagtccag  4860
caaggccaag atcgtgaaga acaggtgggg caggaacgtg gtgcagattt ctaacacaga  4920
cgccagatgt tgcgtgcatg acgccgcctg ccctgccaat cagtttagcg gcaagagctg  4980
cggaatgttc ttcagcgagg gagccaaggc gcaagtggcc ttcaagcaga tcaaggcctt  5040
catgcaagcc ctgtatccaa atgcccagac cggccacggc cacctcctga tgcccctgcg  5100
ctgcgaatgt aactccaagc ccggccacgc ccctttcctg ggcaggcagc tgccaaaact  5160
gacccctttt gccctgagca acgccgaaga tctggatgcc gatctgatca gcgacaagtc  5220
cgtgctggcc tccgttcacc accccgccct gatcgtgttc cagtgctgca atcccgtgta  5280
caggaatagc agagctcagg gtggaggccc caactgcgac ttcaagatct ccgccccaga  5340
tctgctgaac gctctcgtga tggtgcggag cctgtggtct gagaacttca cagagctgcc  5400
ccgcatggtg gtgcccgagt tcaagtggag cactaagcat cagtaccgga atgtgtctct  5460
gcccgtggcc cactctgacg ccagacagaa tccttttgac ttctgaacgg cgcagacggc  5520
aagggtgggg ggtaaataat cacccgagag tgtacaaata aaaacatttg cctttattga  5580
aagtgtctcc tagtacatta tttttacatg tttttcaagt gacaaaaaga agtggcgctc  5640
ctaatctgcg cactgtggct gcggaagtag ggcgagtggc gctccaggaa gctgtagagc  5700
tgttcctggt tgcgacgcag ggtgggctgt acctggggac tgttaagcat ggagttgggt  5760
accggatcca tcgcgccctg tagcggcgca ttaagcgcgg cgggtgtggt ggttacgcgc  5820
agcgtgaccg ctacacttgc cagcgcccta gcgcccgctc ctttcgcttt cttcccttcc  5880
tttctcgcca cgttcgccgg ctttccccgt caagctctaa atcgggggct ccctttaggg  5940
ttccgattta gtgctttacg gcacctcgac cccaaaaaac ttgattaggg tgatggttca  6000
cgtagtgggc catcgccctg atagacggtt tttcgccctt tgacgttgga gtccacgttc  6060
tttaatagtg gactcttgtt ccaaactgga acaacactca accctatctc ggtctattct  6120
tttgatttat aagggatttt gccgatttcg gcctattggt taaaaaatga gctgatttaa  6180
caaaaattta acgcgaattt taacaaaata ttaacgctta caatttaggt ggcacttttc  6240
ggggaaatgt gcgcggaacc cctatttgtt tatttttcta aatacattca aatatgtatc  6300
cgctcatgag acaataaccc tgataaatgc ttcaataata ttgaaaaagg aagagtatga  6360
ttgacggtat cgccgctccc gattcgcagc gcatcgcctt ctatcgcctt cttgacgagt  6420
tcttctgact gtcagaccaa gtttactcat atatacttta gattgattta aaacttcatt  6480
tttaatttaa aaggatctag gtgaagatcc tttttgataa tctcatgacc aaaatccctt  6540
aacgtgagtt ttcgttccac tgagcgtcag accccgtaga aaagatcaaa ggatcttctt  6600
gagatccttt ttttctgcgc gtaatctgct gcttgcaaac aaaaaaacca ccgctaccag  6660
cggtggtttg tttgccggat caagagctac caactctttt tccgaaggta actggcttca  6720
gcagagcgca gataccaaat actgttcttc tagtgtagcc gtagttaggc caccacttca  6780
agaactctgt agcaccgcct acatacctcg ctctgctaat cctgttacca gtggctgctg  6840
ccagtggcga taagtcgtgt cttaccgggt tggactcaag acgatagtta ccggataagg  6900
cgcagcggtc gggctgaacg gggggttcgt gcacacagcc cagcttggag cgaacgacct  6960
acaccgaact gagataccta cagcgtgagc tatgagaaag cgccacgctt cccgaaggga  7020
gaaaggcgga caggtatccg gtaagcggca gggtcggaac aggagagcgc acgagggagc  7080
ttccaggggg aaacgcctgg tatctttata gtcctgtcgg gtttcgccac ctctgacttg  7140
agcgtcgatt tttgtgatgc tcgtcagggg ggcggagcct atggaaaaac gccagcaacg  7200
cggccttttt acggttcctg gccttttgct ggccttttgc tcacatgttc tttcctgcgt  7260
tatcccctga ttctgtggat aaccgtatta ccgcctttga gtgagctgat catatggttt  7320
aaacgtcgac gtaatccgta gatgtacctg gacatccagg tgatgccggc ggcggtggtg  7380
gaggcgcgcg gaaagtcgcg gacgcggttc cagatgttgc gcagcggcaa aaagtgctcc  7440
atggtcggga cgctctggcc ggtgaggcgt gcgcagtcgt tgacgctcta gaccgtgcaa  7500
aaggagagcc tgtaagcggg cactcttccg tggtctggtg gataaattcg caagggtatc  7560
atggcggacg accggggttc gaaccccgga tccggccgtc cgccgtgatc catgcggtta  7620
ccgcccgcgt gtcgaaccca ggtgtgcgac gtcagacaac gggggagcgc tcct        7674
```

```
SEQ ID NO: 10          moltype = DNA  length = 12968
FEATURE                Location/Qualifiers
misc_feature           1..12968
                       note = Synthetic: Mini-pHelper-AAV2
source                 1..12968
                       mol_type = other DNA
                       organism = synthetic construct
SEQUENCE: 10
ggtacccaac tccatgctta acagtcccca ggtacagccc accctgcgtc gcaaccagga  60
acagctctac agcttcctgg agcgccactc gccctacttc cgcagccaca gtgcgcagat  120
taggagcgcc acttcttttt gtcacttgaa aaacatgtaa aaataatgta ctaggagaca  180
ctttcaataa aggcaaatgt ttttatttgt acactctcgg gtgattattt accccccacc  240
cttgccgtct gcgccgttca gaagtcaaaa ggattctgtc tggcgtcaga gtgggccacg  300
ggcagagaca cattccggta ctgatgctta gtgctccact tgaactcggg caccaccatg  360
cggggcagct cttgtgaagtt ctcagaccac aggctccgca ccatcacgag agcgttcagc  420
agatctgggg cggagatctt gaagtcgcag ttggggcctc caccctgagc tctgctattc  480
ctgtacacgg gattgcagca ctggaacacg atcagggcgg ggtggtgaac ggaggccagc  540
acggacttgt cgctgatcag atcggcatcc agatcttcgg cgttgctcag ggcaaaaggg  600
gtcagttttg gcagctgcct gcccaggaaa ggggcgtggc cgggcttgga gttacattcg  660
cagcgcaggg gcatcaggag gtggccgtgg ccggtctggg catttggata cagggcttgc  720
atgaaggcct tgatctgctt gaaggccact tgcgccttgg ctccctcgct gaagaacatt  780
ccgcagctct tgccgctaaa ctgattggca gggcaggcgg cgtcatgcac gcaacatctg  840
gcgtctgtgt tagaaatctg caccacgttc ctgccccacc tgttcttcac gatcttggcc  900
ttgctggact gctccttcag ggcgcgctgg ccgttttcgg aagtcacatc catctcgatc  960
acgtgctcct tgttaatcat gatagagccg tgcaggcatt tcagctcgcc ctcaatctcg  1020
gcgcatctgt gcagccacag ggcgcagccg gtgggctcgt ggtgcttgta agtcacttcg  1080
gcgaaagatt gcaggtaggc ctgcagaaac ctgcccatca tggtcacaaa ggtcttgttt  1140
gatgtaaagg tcagctgcag ccctctatgc tcctcattca gccatgtctt gcacacggca  1200
gccagggcct ccacctggtc aggcagcagt ttgaaattag ccttcaggtc gttgtccacg  1260
```

-continued

```
tggtacttgt ccatcagggc ccgggcggcc tccattccct tctcccaagc gctcacaatt  1320
ggcagggaca gtggattaat cactgtgctc tcgctctcgg cctcggagga ttcttccttc  1380
tcctcctgtg tcctcatgcc ccttgccaca ggatcatcct cgttcagcct gcgcacggtc  1440
cgttttcccc ctttgccgtg cttgatgagc acaggtggat tgctgaatcc caccatctgc  1500
agagcgacgt cctcgcgctc ttcctctgag tccacgatca cttctgggct gggtggtcgt  1560
tcaggtttag gggagggcct cttcttcttt tttttgctgg caatggccag gtcggcggtg  1620
gaagtggagg gtcttggaga tggtgtccta ggcaccagag cgtcctggga actgtcttcc  1680
tcgtcctcgg actccaggcg tctccgcagt ctctttttttg ggggcgcgcg gggaggcggc  1740
ggcgacggcg acggggacga cacgtcctcc atggttggtg gacgtcgcgc cgcaccgcgt  1800
ccgcgctcgg gggtggtttc gcgctgctcc tcttcccgac tggccatttc cttctccctg  1860
aggactacca cgcccacgag attaggttct acgaagacca atcccgcccg ccaaatgcgg  1920
agcttaccgc ctgcgtcatt acccagggcc acatccttgg ccaattgcaa gccatcaaca  1980
aagcccgcca agagtttctg ctacgaaagg gacggggggt ttacctggac ccccagtccg  2040
gcgaggagct caacccaatc cccccgccgc cgcagcccta tcagcagccg cgggcccttg  2100
cttcccagga tggcacccaa aaagaagctg cagctgccgc cgccgccacc cacggacgag  2160
gaggaatact gggacagtca ggcagaggag gttttggacg aggaggagga gatgatggaa  2220
gactgggaca gcctagacga agcttccgag gccgaagagg tgtcagacga aacaccgtca  2280
ccctcggtcg cattcccctc gccggcgccc cagaaattgg caaccgttcc cagcatcgct  2340
acaacctccg ctcctcaggc gccgccggca ctgcctgttc gccgacccaa ccgtagatgg  2400
gacaccactg gaaccagggc cggtaagtct aagcagccgc cgccgttagc ccaagagcaa  2460
caacagcgcc aaggctaccg ctcgtggcgc gggcacaaga acgccatagt tgcttgcttg  2520
caagactgtg gggggcaacat ctccttcgcc cgccgctttc ttctctacca tcacggcgtg  2580
gccttccccc gtaacatcct gcattactac cgtcatctct acagccccta ctgcaccggc  2640
ggcagcggca gcggcagcaa cagcagcggt cacacagaag caaaggcgac cggatagcaa  2700
gactctgaca aagcccaaga aatccacagc ggcggcagca gcaggaggag gagcgctgcg  2760
tctggcgccc aacgaacccg tatcgacccg cgagcttaga aataggattt ttcccactct  2820
gtatgctata tttcaacaaa gcaggggcca agaacaagag ctgaaaataa aaaacaggtc  2880
tctgcgctcc ctcacccgca gctgcctgta tcacaaaagc gaagatcagc ttcggcgcac  2940
gctggaagac gcggaggctc tcttcagcaa atactgcgcg ctgactctta aggactagtt  3000
tcgcgccctt tctcaaattt aagcgcgaaa actacgtcat ctccagcggc cacacccggc  3060
gccagcacct gtcgtcagcg ccattatgag caaggaaatt cccacgccct acatgtggag  3120
ttaccagcca caaatgggac ttgcggctgg agctgcccaa gactactcaa cccgaataaa  3180
ctacatgagc gcgggacccc acatgatatc ccgggtcaac ggaatccgcg cccaccgaaa  3240
ccgaattctc ctcgaacagg cggctattac caccacacct cgtaataacc ttaatccccg  3300
tagttggccc gctgccctgg tgtaccagga aagtcccgct cccaccactg tggtacttcc  3360
cagagacgcc caggccgaag ttcagatgac taactcaggg gcgcagcttg cgggcggctt  3420
tcgtcacagg gtgcggtcgc ccgggcgttt tagggcggag taacttgcat gtattgggaa  3480
ttgtagtttt tttaaaatgg gaagtgacgt atcgtgggaa aacggaagtg aagatttgag  3540
gaagttgtgg gttttttggc tttcgtttct gggcgtaggt tcgcgtgcgg ttttctgggt  3600
gttttttgtg gactttaacc gttacgtcat tttttagtcc tatatatact cgctctgtac  3660
ttggcccttt ttacactgtg actgattgag ctggtgccgt gtcgagtggt gttttttaat  3720
aggttttttt actggtaagg ctgactgtta tggctgccgc tgtggaagcg ctgtatgttg  3780
ttctggagcg ggagggtgct attttgccta ggcgcctgga tgctttgaga gagtggatat  3840
actacaacta ctacacagag cgagctaagc gacgagaccg gagacgcaga tctgtttgtc  3900
acgcccgcac ctggttttgc ttcaggaaat atgactacgt ccggcgttcc atttggcatg  3960
acactacgac caacacgatc tcggttgtct cggcgcactc cgtacagtag ggatcgccta  4020
cctccttttg agacagagac ccgcgctacc atactggagg atcatccgct gctgcccgaa  4080
tgtaacactt tgacaatgca caacgtgagt tacgtgcgag gtcttccctg cagtgtggga  4140
tttacgctga ttcaggaatg ggttgttccc tgggatatgg ttctgacgcg ggaggagctt  4200
gtaatcctga ggaagtgtat gcacgtgtgc ctgtgttgtg ccaacattga tatcatgacg  4260
agcatgatga tccatggtta cgagtcctgg gctctccact gtcattgttc cagtcccggt  4320
tccctgcagt gcatagccgg cgggcaggtt ttggccagct ggtttaggat ggtggtggat  4380
ggcgccatgt ttaatcagag gtttatatgg taccgggagg tggtgaatta caacatgcca  4440
aaagaggtaa tgtttatgtc cagcgtgttt atgaggggtc gccacttaat ctacctgcgc  4500
ttgtggtatg atggccacgt gggttctgtg gtccccgcca tgagctttgg atacagcgcc  4560
ttgcactgtg ggattttgaa caatattgtg gtgctgtgct gcagttactg tgctgattta  4620
agtgagatca gggtgcgctg ctgtgcccgg aggacaaggc gtctcatgct gcgggcggtg  4680
cgaatcatcg ctgaggagac cactgccatg ttgtattcct gcaggacgga gcggcggcgg  4740
cagcagttta ttcgcgcgct gctgcagcac caccgcccta tcctgatgca cgattatgac  4800
tctaccccca tgtaggcgtg gacttcccct tcgccgcccg ttgagcaacc gcaagttgga  4860
cagcagcctg tggctcagca gctggacagc gacatgaact taagcgagct gcccggggag  4920
tttattaata tcactgatga gcgtttggct cgacaggaaa ccgtgtggaa tataacacct  4980
aagaatatgt ctgttaccca tgatatgatg ctttttaagg ccagccgggg agaaaggact  5040
gtgtactctg tgtgttggga gggaggtggc aggttgaata ctagggttct gtgagtttga  5100
ttaaggtacg gtgatcaata taagctatgt ggtggtgggg ctatactact gaatgaaaaa  5160
tgacttgaaa ttttctgcaa ttgaaaaata aacacgttga aacataacat gcaacaggtt  5220
cacgattctt tattcctggg caatgtagga gaaggtgtaa gagttggtag caaaagtttc  5280
agtggtgtat ttttccactt tcccaggacca tgtaaaagac atagagtaag tgcttacctc  5340
gctagtttct gtggattcac tagagcggcc gcggtcctgt attagaggtc aacgtgagtg  5400
ttttgcgaca ttttgcgaca ccatgtggtc acgctgaggt atatatggcc gagtgagcga  5460
gcaggatgca acctccattt tgaccgcgaa atttgaacga gcagccgcca tgccggggtt  5520
ttacgagatt gtgattaagg tccccagcga ccttgacgag catctgcccg gcatttctga  5580
cagctttgtg aactgggtgg ccgagaagga atgggagttg ccgccagatt ctgacatgga  5640
tctgaatctg attgagcagg cacccctgac cgtggccgag aagctgcagc gcgactttct  5700
gacggaatgg cgccgtgtga gtaaggcacc ggaggccctt ttctttgtgc aatttgagaa  5760
gggagagagc tacttccaca tgcacgtgct cgtggaaacc accggggtga aatccatggt  5820
tttgggacgt ttcctgagtc agattcgcga aaaactgatt cagagaattt accgcgggat  5880
cgagccgact ttgccaaact ggttcgcggt cacaaagacc agaaatggcg ccggaggcgg  5940
gaacaaggtg gtggatgagt gctacatccc caattacttg ctccccaaaa cccagcctga  6000
```

-continued

```
gctccagtgg gcgtggacta atatggaaca gtatttaagc gcctgtttga atctcacgga  6060
gcgtaaacgg ttggtggcgc agcatctgac gcacgtgtcg cagacgcagg agcagaacaa  6120
agagaatcag aatcccaatt ctgatgcgcc ggtgatcaga tcaaaaactt cagccaggta  6180
catggagctg gtcgggtggc tcgtggacaa ggggattacc tcggagaagc agtggatcca  6240
ggaggaccag gcctcataca tctccttcaa tgcggcctcc aactcgcggt cccaaatcaa  6300
ggctgccttg gacaatgcgg gaaagattat gagcctgact aaaaccgccc ccgactacct  6360
ggtgggccag cagcccgtgg aggacatttc cagcaatcgg atttataaaa ttttggaact  6420
aaacgggtac gatccccaat atgcggcttc cgtctttctg ggatgggcca cgaaaaagtt  6480
cggcaagagg aacaccatct ggctgtttgg gcctgcaact accgggaaga ccaacatcgc  6540
ggaggccata gcccacactg tgccettcta cgggtgcgta aactggacca atgagaactt  6600
tcccttcaac gactgtgtcg acaagatggt gatctggtgg gaggagggga agatgaccgc  6660
caaggtcgtg gagtcggcca aagccattct cggaggaagc aaggtgcgcg tggaccagaa  6720
atgcaagtcc tcggcccaga tagacccgac tcccgtgatc gtcacctcca acaccaacat  6780
gtgcgccgtg attgacggga actcaacgac cttcgaacac cagcagccgt tgcaagaccg  6840
gatgttcaaa tttgaactca cccgccgtct ggatcatgac tttgggaagg tcaccaagca  6900
ggaagtcaaa gactttttcc ggtgggcaaa ggatcacgtg gttgaggtgg agcatgaatt  6960
ctacgtcaaa aagggtggag ccaagaaaag acccgccccc agtgacgcag atataagtga  7020
gcccaaacgg gtgcgcgagt cagttgcgca gccatcgacg tcagacgcgg aagcttcgat  7080
caactacgca gacaggtacg taaacaaatg ttctcgtcac gtgggcatga atctgatgct  7140
gtttccctgc agacaatgcg agagaatgaa tcagaattca aatatctgct tcactcacgg  7200
acagaaagac tgtttagagt gctttcccgt gtcagaatct caacccgttt ctgtcgtcaa  7260
aaaggcgtat cagaaactgt gctacattca tcatatcatg ggaaaggtgc cagacgcttg  7320
cactgcctgc gatctggtca atgtggattt ggatgactgc atctttgaac aataaatgat  7380
ttaaatcagg tatggctgcc gatggttatc ttccagattg gctcgaggac actctctctg  7440
aaggaataag acagtggtgg aagctcaaac ctggcccacc accaccaaag cccgcagagc  7500
ggcataagga cgacagcagg ggtcttgtgc ttcctgggta caagtacctc ggacccttca  7560
acggactcga caagggagag ccggtcaacg aggcagacgc cgcggccctc gagcacgaca  7620
aagcctacga ccggcagctc gacagcggag acaacccgta cctcaagtac aaccacgccg  7680
acgcggagtt tcaggagcgc cttaaagaag atacgtcttt tgggggcaac ctcggacgag  7740
cagtcttcca ggcgaaaaag agggttcttg aacctctggg cctggttgag gaacctgtta  7800
agacggctcc gggaaaaaag aggccggtag agcactctcc tgtggagcca gactcctcct  7860
cgggaaccgg aaaggcgggc cagcagcctg caagaaaaag attgaatttt ggtcagactg  7920
gagacgcaga ctcagtacct gacccccagc ctctcggaca gccaccagca gccccctctg  7980
gtctgggaac taatacgatg gctacaggca gtggcgcacc aatggcagac aataacgagg  8040
gcgccgacgg agtgggtaat tcctcgggaa attggcattg cgattccaca tggatgggcg  8100
acagagtcat caccaccagc acccgaacct gggccctgcc cacctacaac aaccacctct  8160
acaaacaaat ttccagccaa tcaggagcct cgaacgacaa tcactacttt ggctacagca  8220
ccccttgggg gtattttgac ttcaacagat tccactgcca cttttcacca cgtgactggc  8280
aaagactcat caacaacaac tggggattcc gacccaagag actcaacttc aagctcttta  8340
acattcaagt caaagaggtc acgcagaatg acggtacgac gacgattgcc aataacctta  8400
ccagcacggt tcaggtgttt actgactcgg agtaccagct cccgtacgtc ctcggctcgg  8460
cgcatcaagg atgcctcccg ccgttcccag cagacgtctt catggtgcca cagtatggat  8520
acctcaccct gaacaacggg agtcaggcag taggacgctc ttcattttac tgcctggagt  8580
actttccttc tcagatgctg cgtaccggaa acaactttac cttcagctac acttttgagg  8640
acgttccttt ccacagcagc tacgctcaca gccagagtct ggaccgtctc atgaatcctc  8700
tcatcgacca gtacctgtat tacttgagca gaacaaacac tccaagtgga accaccacgc  8760
agtcaaggct tcagttttct caggccggag cgagtgacat tcgggaccag tctaggaact  8820
ggcttcctgg accctgttac cgccagcagc gagtatcaaa gacatctgcg gataacaaca  8880
acagtgaata ctcgtggact ggagctacca agtaccacct caatggcaga gactctctgg  8940
tgaatccggg cccggccatg gcaagccaca aggacgatga agaaaagttt tttcctcaga  9000
gcggggttct catctttggg aagcaaggct cagagaaaac aaatgtggac attgaaaagg  9060
tcatgattac agacgaagag gaaatcagga caaccaatcc cgtggctacg gagcagtatg  9120
gttctgtatc taccaacctc cagagaggca acagacaagc agctaccgca gatgtcaaca  9180
cacaaggcgt tcttccaggc atggtctggc aggacagaga tgtgtacctt caggggccca  9240
tctgggcaaa gattccacac acggacggac attttcaccc ctctcccctc atgggtggat  9300
tcggacttaa acaccctcct ccacagattc tcatcaagaa caccccggta ccagcgaatc  9360
cttcgaccac cttcagtgcg gcaaagtttg cttccttcat cacacagtac tccacgggac  9420
aggtcagcgt ggagatcgag tgggagctgc agaaggaaaa cagcaaacgc tggaatcccg  9480
aaattcagta cacttccaac tacaacaagt ctgttaatgt ggactttact gtggacacta  9540
atggcgtgta ttcagagcct cgccccattg gcaccagata cctgactcgt aatctgtaac  9600
aattgcttgt taatcaataa accgtttaat tcgtttcagt tgaactttgg tctctgcgta  9660
tttctttctt atctagtttc catgctctag gatccactag taacggccgc cagtgtgctg  9720
gaattcggct ttgtagttaa tgattaaccc gccatgctac ttatctacgt agccatgctc  9780
tagaggtcct gtattagagg tcacgtgagt gttttgcgac attttgcgac accatgtggt  9840
cacgctgggt atttaagccc gagtgagcac gcagggtctc cattttgaag cgggaggttt  9900
gaacgcgcag ccgccaagcc gaattctgca gatctatcga tgtaggatgt tgcccctcct  9960
gacgcggtag gagaagggga gggtgccctg catgtctgcc gctgctcttg ctcttgccgc  10020
tgctgaggag gggggcgcat ctgccgcagc accggatgca tctgggaaaa gcaaaaaagg  10080
ggctcgtccc tgtttccgga ggaatttgca agcggggtct tgcatgacgg ggaggcaaac  10140
ccccgttcgc cgcagtccgg ccggcccgag actcgaaccg ggggtcctgc gactcaaccc  10200
ttggaaaata accctccggc tacagggagc gagccactta atgctttcgc tttccagcct  10260
aaccgcttac gccgcgcgcg gccagtggcc aaaaaagcta gcgcagcagc cgccgcgcct  10320
ggaaggaagc caaaaggagc gctcccccgt tgtctgacgt cgcacacctg ggttcgacac  10380
gcgggcggta accgcatgga tcacggcgga cggccggatc cggggttcga accccggtcg  10440
tccgccatga taccettgcg aatttatcca ccagaccacg gaagagtgcc cgcttacagg  10500
ctctcctttt gcacggtcta gagcgtcaac gactgcgcac gcctcaccgg ccagagcgtc  10560
ccgaccatgg agcacttttt gccgctgcgc aacatctgga accgcgtccg cgactttccg  10620
cgcgcctcca ccaccgccgc cggcatcacc tggatgtcca ggtacatcta cggattacgt  10680
cgacgtttaa accatatgat cagctcactc aaaggcggta atacggttat ccacagaatc  10740
```

```
aggggataac gcaggaaaga acatgtgagc aaaaggccag caaaaggcca ggaaccgtaa  10800
aaaggccgcg ttgctggcgt ttttccatag gctccgcccc cctgacgagc atcacaaaaa  10860
tcgacgctca agtcagaggt ggcgaaaccc gacaggacta taaagatacc aggcgtttcc  10920
ccctggaagc tccctcgtgc gctctcctgt tccgaccctg ccgcttaccg gatacctgtc  10980
cgcctttctc ccttcgggaa gcgtggcgct ttctcatagc tcacgctgta ggtatctcag  11040
ttcggtgtag gtcgttcgct ccaagctggg ctgtgtgcac gaaccccccg ttcagcccga  11100
ccgctgcgcc ttatccggta actatcgtct tgagtccaac ccggtaagac acgacttatc  11160
gccactggca gcagccactg gtaacaggat tagcagagcg aggtatgtag gcggtgctac  11220
agagttcttg aagtggtggc ctaactacgg ctacactaga agaacagtat ttggtatctg  11280
cgctctgctg aagccagtta ccttcggaaa aagagttggt agctcttgat ccggcaaaca  11340
aaccaccgct ggtagcggtg gtttttttgt ttgcaagcag cagattacgc gcagaaaaaa  11400
aggatctcaa gaagatcctt tgatcttttc tacggggtct gacgctcagt ggaacgaaaa  11460
ctcacgttaa gggattttgg tcatgagatt atcaaaaagg atcttcacct agatcctttt  11520
aaattaaaaa tgaagtttta aatcaatcta aagtatatat gagtaaactt ggtctgacag  11580
tcagaagaac tcgtcaagaa ggcgatagaa ggcgatgcgc tgcgaatcgg gagcggcgat  11640
accgtaaagc acgaggaagc ggtcagccca ttcgccgcca agctcttcag caatatcacg  11700
ggtagccaac gctatgtcct gatagcggtc cgccacaccc agccggccac agtcgatgaa  11760
tccagaaaag cggccatttt ccaccatgat attcggcaag caggcatcgc catgggtcac  11820
gacgagatcc tcgccgtcgg gcatgctcgc cttgagcctg gcgaacagtt cggctggcgc  11880
gagcccctga tgctcttcgt ccagatcatc ctgatcgaca agaccggctt ccatccgagt  11940
acgtgctcgc tcgatgcgat gtttcgcttg gtggtcgaat gggcaggtag ccggatcaag  12000
cgtatgcagc cgccgcattg catcagccat gatggatact ttctcggcag gagcaaggtg  12060
agatgacagg agatcctgcc ccggcacttc gcccaatagc agccagtccc ttcccgcttc  12120
agtgacaacg tcgagtacag ctgcgcaagg aacgcccgtc gtggccagcc acgatagccg  12180
cgctgcctcg tcttgcagtt cattcagggc accggacagg tcggtcttga caaaaagaac  12240
cgggcgcccc tgcgctgaca gccggaacac ggcggcatca gagcagccga ttgtctgttg  12300
tgcccagtca tagccgaata gcctctccac ccaagcggcc ggagaacctg cgtgcaatcc  12360
atcttgttca atcatactct tcctttttca atattattga agcatttatc agggttattg  12420
tctcatgagc ggatacatat ttgaatgtat ttagaaaaat aaacaaatag gggttccgcg  12480
cacatttccc cgaaaagtgc cacctaaatt gtaagcgtta atattttgtt aaaattcgcg  12540
ttaaattttt gttaaatcag ctcatttttt aaccaatagg ccgaaatcgg caaaatccct  12600
tataaatcaa aagaatagac cgagataggg ttgagtgttg ttccagtttg gaacaagagt  12660
ccactattaa agaacgtgga ctccaacgtc aaagggcgaa aaaccgtcta tcagggcgat  12720
ggcccactac gtgaaccatc accctaatca agttttttgg ggtcgaggtg ccgtaaagca  12780
ctaaatcgga accctaaagg gagcccccga tttagagctt gacggggaaa gccggcgaac  12840
gtggcgagaa aggaagggaa gaaagcgaaa ggagcgggcg ctagggcgct ggcaagtgta  12900
gcggtcacgc tgcgcgtaac caccacaccc gccgcgctta atgcgccgct acagggcgcg  12960
atggatcc                                                          12968
```

```
SEQ ID NO: 11          moltype = DNA  length = 11148
FEATURE                Location/Qualifiers
misc_feature           1..11148
                       note = Synthetic: Mini-pHelper- CMV-EGFP
source                 1..11148
                       mol_type = other DNA
                       organism = synthetic construct
SEQUENCE: 11
ggcagctgcg cgctcgctcg ctcactgagg ccgcccgggc aaagcccggg cgtcgggcga  60
cctttggtcg cccggcctca gtgagcgagc gagcgcgcag agagggagtg gccaactcca  120
tcactagggg ttcctgcggc cgcacgcgta cattgattat tgactagtta ttaatagtaa  180
tcaattacgg ggtcattagt tcatagccca tatatggagt tccgcgttac ataacttacg  240
gtaaatggcc cgcctggctg accgcccaac gacccccgcc cattgacgtc aataatgacg  300
tatgttccca tagtaacgcc aatagggact ttccattgac gtcaatgggt ggagtattta  360
cggtaaactg cccacttggc agtacatcaa gtgtatcata tgccaagtac gccccctatt  420
gacgtcaatg acggtaaatg gcccgcctgg cattatgccc agtacatgac cttatgggac  480
tttcctactt ggcagtacat ctacgtatta gtcatcgcta ttaccatggt gatgcggttt  540
tggcagtaca tcaatgggcg tggatagcgg tttgactcac ggggatttcc aagtctccac  600
cccattgacg tcaatgggag tttgttttgg caccaaaatc aacgggactt tccaaaatgt  660
cgtaacaact ccgccccatt gacgcaaatg ggcggtaggc gtgtacggtg ggaggtctat  720
ataagctagc gccaccatgg tgagcaaggg cgaggagctg ttcaccgggg tggtgcccat  780
cctggtcgag ctggacggcg acgtaaacgg ccacaagttc agcgtgtccg gcgagggcga  840
gggcgatgcc acctacggca agctgaccct gaagttcatc tgcaccaccg gcaagctgcc  900
cgtgccctgg cccaccctcg tgaccaccct gacctacggc gtgcagtgct tcagccgcta  960
ccccgaccac atgaagcagc acgacttctt caagtccgcc atgcccgaag gctacgtcca  1020
ggagcgcacc atcttcttca aggacgacgg caactacaag acccgcgccg aggtgaagtt  1080
cgagggcgac accctggtga accgcatcga gctgaagggc atcgacttca aggaggacgg  1140
caacatcctg gggcacaagc tggagtacaa ctacaacagc cacaacgtct atatcatggc  1200
cgacaagcag aagaacggca tcaaggtgaa cttcaagatc cgccacaaca tcgaggacgg  1260
cagcgtgcag ctcgccgacc actaccagca gaacaccccc atcggcgacg gccccgtgct  1320
gctgcccgac aaccactacc tgagcaccca gtccgccctg agcaaagacc ccaacgagaa  1380
gcgcgatcac atggtcctgc tggagttcgt gaccgccgcc gggatcactc tcggcatgga  1440
cgagctgtac aagtaacgta cggatatcaa gcttatcgat aatcaacctc tggattacaa  1500
aatttgtgaa agattgactg gtattcttaa ctatgttgct ccttttacgc tatgtggata  1560
cgctgcttta atgcctttgt atcatgctat tgcttcccgt atggctttca ttttctcctc  1620
cttgtataaa tcctggttgc tgtctcttta tgaggagttg tggcccgttg tcaggcaacg  1680
tggcgtggtg tgcactgtgt ttgctgacgc aacccccact ggttggggca ttgccaccac  1740
ctgtcagctc ctttccggga ctttcgcttt ccccctccct attgccacgg cggaactcat  1800
cgccgcctgc cttgcccgct gctggacagg ggctcggctg ttgggcactg acaattccgt  1860
ggtgttgtcg ggaaatcatc gtcctttcc ttggctgctc gcctatgttg ccacctggat  1920
```

-continued

```
tctgcgcggg acgtccttct gctacgtccc ttcggccctc aatccagcgg accttccttc  1980
ccgcggcctg ctgccggctc tgcggcctct tccgcgtctt cgccttcgcc ctcagacgag  2040
tcggatctcc ctttgggccg cctccccgca tcgataccga gcgctgctcg agagatctac  2100
gggtggcatc cctgtgaccc ctccccagtg cctctcctgg ccctggaagt tgccactcca  2160
gtgcccacca gccttgtcct aataaaatta agttgcatca ttttgtctga ctaggtgtcc  2220
ttctataata ttatggggtg gaggggggtg gtatggagca aggggcaagt tgggaagaca  2280
acctgtaggg cctgcggggt ctattgggaa ccaagctgga gtgcagtggc acaatcttgg  2340
ctcactgcaa tctccgcctc ctgggttcaa gcgattctcc tgcctcagcc tcccgagttg  2400
ttgggattcc aggcatgcat gaccaggctc agctaatttt tgtttttttg gtagagacgg  2460
ggtttcacca tattggccag gctggtctcc aactcctaat ctcaggtgat ctacccacct  2520
tggcctccca aattgctggg attacaggcg tgaaccactg ctcccttccc tgtccttctg  2580
attttgtagg taaccacgtg cggaccgagc ggccgcagga acccctagtg atggagttgg  2640
ccactccctc tctgcgcgct cgctcgctca ctgaggccgg gcgaccaaag gtcgcccgac  2700
gcccgggctt tgcccgggcg gcctcagtga gcgagcgagc gcgcagctgc caaaccatat  2760
gatcagctca ctcaaaggcg gtaatacggt tatccacaga atcaggggat aacgcaggaa  2820
agaacatgtg agcaaaaggc cagcaaaagg ccaggaaccg taaaaaggcc gcgttgctgg  2880
cgtttttcca taggctccgc ccccctgacg agcatcacaa aaatcgacgc tcaagtcaga  2940
ggtggcgaaa cccgacagga ctataaagat accaggcgtt tccccctgga agctccctcg  3000
tgcgctctcc tgttccgacc ctgccgctta ccggatacct gtccgccttt ctcccttcgg  3060
gaagcgtggc gctttctcat agctcacgct gtaggtatct cagttcggtg taggtcgttc  3120
gctccaagct gggctgtgtg cacgaacccc ccgttcagcc cgaccgctgc gccttatccg  3180
gtaactatcg tcttgagtcc aacccggtaa gacacgactt atcgccactg gcagcagcca  3240
ctggtaacag gattagcaga gcgaggtatg taggcggtgc tacagagttc ttgaagtggt  3300
ggcctaacta cggctacact agaagaacag tatttggtat ctgcgctctg ctgaagccag  3360
ttaccttcgg aaaaagagtt ggtagctctt gatccggcaa acaaaccacc gctggtagcg  3420
gtggtttttt tgtttgcaag cagcagatta cgcgcagaaa aaaaggatct caagaagatc  3480
ctttgatctt ttctacgggg tctgacgctc agtggaacga aaactcacgt taagggattt  3540
tggtcatgag attatcaaaa aggatcttca cctagatcct tttaaattaa aaatgaagtt  3600
ttaaatcaat ctaaagtata tatgagtaaa cttggtctga cagtcagaag aactcgtcaa  3660
gaaggcgata gaaggcgatg cgctgcgaat cgggagcggc gataccgtaa agcacgagga  3720
agcggtcagc ccattcgccg ccaagctctt cagcaatatc acgggtagcc aacgctatgt  3780
cctgatagcg gtccgccaca cccagccggc cacagtcgat gaatccagaa aagcggccat  3840
tttccaccat gatattcggc aagcaggcat cgccatgggt cacgacgaga tcctcgccgt  3900
cgggcatgct cgccttgagc ctggcgaaca gttcggctgg cgcgagcccc tgatgctctt  3960
cgtccagatc atcctgatcg acaagaccgg cttccatccg agtacgtgct cgctcgatgc  4020
gatgtttcgc ttggtggtcg aatgggcagg tagccggatc aagcgtatgc agccgccgca  4080
ttgcatcagc catgatggat actttctcgg caggagcaag gtgagatgac aggagatcct  4140
gccccggcac ttcgcccaat agcagccagt cccttcccgc ttcagtgaca acgtcgagta  4200
cagctgcgca aggaacgccc gtcgtggcca gccacgatag ccgcgctgcc tcgtcttgca  4260
gttcattcag ggcaccggac aggtcggtct tgacaaaaag aaccgggcgc ccctgcgctg  4320
acagccggaa cacggcggca tcagagcagc cgattgtctg ttgtgcccag tcatagccga  4380
atagcctctc cacccaagcg gccggagaac ctgcgtgcaa tccatcttgt tcaatcatac  4440
tcttcctttt tcaatattat tgaagcattt atcagggtta ttgtctcatg agcggataca  4500
tatttgaatg tatttagaaa aataaacaaa taggggttcc gcgcacattt ccccgaaaag  4560
tgccacctaa attgtaagcg ttaatatttt gttaaaattc gcgttaaatt tttgttaaat  4620
cagctcattt tttaaccaat aggccgaaat cggcaaaatc ccttataaat caaaagaata  4680
gaccgagata gggttgagtg ttgttccagt ttggaacaag agtccactat taaagaacgt  4740
ggactccaac gtcaaagggc gaaaaaccgt ctatcagggc gatggcccac tacgtgaacc  4800
atcaccctaa tcaagttttt tggggtcgag gtgccgtaaa gcactaaatc ggaaccctaa  4860
agggagcccc cgatttagag cttgacgggg aaagccggcg aacgtggcga gaaaggaagg  4920
gaagaaagcg aaaggagcgg gcgctagggc gctggcaagt gtagcggtca cgctgcgcgt  4980
aaccaccaca cccgccgcgc ttaatgcgcc gctacagggc gcgatggatc cggtacccaa  5040
ctccatgctt aacagtcccc aggtacagcc caccctgcgt cgcaaccagg aacagctcta  5100
cagcttcctg gagcgccact cgccctactt ccgcagccac agtgcgcaga ttaggagcgc  5160
cacttctttt tgtcacttga aaaacatgta aaaataatgt actaggagac actttcaata  5220
aaggcaaatg tttttatttg tacactctcg ggtgattatt taccccccac ccttgccgtc  5280
tgcgccgttc agaagtcaaa aggattctgt ctggcgtcag agtgggccac gggcagagac  5340
acattccggt actgatgctt agtgctccac ttgaactcgg gcaccaccat gcggggcagc  5400
tctgtgaagt tctcagacca caggctccgc accatcacga gagcgttcag cagatctggg  5460
gcggagatct tgaagtcgca gttggggcct ccaccctgag ctctgctatt cctgtacacg  5520
ggattgcagc actggaacac gatcagggcg gggtggtgaa cggaggccag cacggacttg  5580
tcgctgatca gatcggcatc cagatcttcg gcgttgctca gggcaaaagg ggtcagtttt  5640
ggcagctgcc tgcccaggaa aggggcgtgg ccgggcttgg agttacattc gcagcgcagg  5700
ggcatcagga ggtggccgtg gccggtctgg gcatttggat acagggcttg catgaaggcc  5760
ttgatctgct tgaaggccac ttgcgccttg gctccctcgc tgaagaacat tccgcagctc  5820
ttgccgctaa actgattggc agggcaggcg gcgtcatgca cgcaacatct ggcgtctgtg  5880
ttagaaatct gcaccacgtt cctgccccac ctgttcttca cgatcttggc cttgctggac  5940
tgctccttca gggcgcgctg gccgttttcg gaagtcacat ccatctcgat cacgtgctcc  6000
ttgttaatca tgatagagcc gtgcaggcat ttcagctcgc cctcaatctc ggcgcatctg  6060
tgcagccaca gggcgcagcc ggtgggctcg tggtgcttgt aagtcacttc ggcgaaagat  6120
tgcaggtagg cctgcagaaa cctgcccatc atggtcacaa aggtcttgtt tgatgtaaag  6180
gtcagctgca gccctctatg ctcctcattc agccatgtct tgcacacggc agccagggcc  6240
tccacctggt caggcagcag tttgaaatta gccttcaggt cgttgtccac gtggtacttg  6300
tccatcaggg cccgggcggc ctccattccc ttctcccaag cgctcacaat tggcagggac  6360
agtggattaa tcactgtgct ctcgctctcg gcctcggagg attcttcctt ctcctcctgt  6420
gtcctcatgc cccttgccac aggatcatcc tcgttcagcc tgcgcacggt ccgttttccc  6480
cctttgccgt gcttgatgag cacaggtgga ttgctgaatc ccaccatctg cagagcgacg  6540
tcctcgcgct cttcctctga gtccacgatc acttctgggc tgggtggtcg ttcaggttta  6600
ggggagggcc tcttcttctt ttttttgctg gcaatggcca ggtcggcggt ggaagtggag  6660
```

```
ggtcttggag atggtgtcct aggcaccaga gcgtcctggg aactgtcttc ctcgtcctcg  6720
gactccaggc gtctccgcag tctctttttt gggggcgcgc ggggaggcgg cggcgacggc  6780
gacggggacg acacgtcctc catggttggt ggacgtcgcg ccgcaccgcg tccgcgctcg  6840
ggggtggttt cgcgctgctc ctcttcccga ctggccattt ccttctccct gaggactacc  6900
acgcccacga gattaggttc tacgaagacc aatcccgccc gccaaatgcg gagcttaccg  6960
cctgcgtcat tacccagggc cacatccttg gccaattgca agccatcaac aaagcccgcc  7020
aagagtttct gctacgaaag ggacgggggg tttacctgga cccccagtcc ggcgaggagc  7080
tcaacccaat ccccccgccg ccgcagccct atcagcagcc gcgggccctt gcttcccagg  7140
atggcaccca aaaagaagct gcagctgccg ccgccgccac ccacggacga ggaggaatac  7200
tgggacagtc aggcagagga ggttttggac gaggaggagg agatgatgga agactgggac  7260
agcctagacg aagcttccga ggccgaagag gtgtcagacg aaacaccgtc accctcggtc  7320
gcattcccct cgccggcgcc ccagaaattg gcaaccgttc ccagcatcgc tacaacctcc  7380
gctcctcagg cgccgccggc actgcctgtt cgccgaccca accgtagatg ggacaccact  7440
ggaaccaggg ccggtaagtc taagcagccg ccgccgttag cccaagagca acaacagcgc  7500
caaggctacc gctcgtggcg cgggcacaag aacgccatag ttgcttgctt gcaagactgt  7560
gggggcaaca tctccttcgc ccgccgcttt cttctctacc atcacggcgt ggccttcccc  7620
cgtaacatcc tgcattacta ccgtcatctc tacagcccct actgcaccgg cggcagcggc  7680
agcggcagca acagcagcgg tcacacagaa gcaaaggcga ccggatagca agactctgac  7740
aaagcccaag aaatccacag cggcggcagc agcaggagga ggagcgctgc gtctggcgcc  7800
caacgaaccc gtatcgaccc gcgagcttag aaataggatt tttcccactc tgtatgctat  7860
atttcaacaa agcaggggcc aagaacaaga gctgaaaata aaaaacaggt ctctgcgctc  7920
cctcacccgc agctgcctgt atcacaaaag cgaagatcag cttcggcgca cgctggaaga  7980
cgcggaggct ctcttcagca aatactgcgc gctgactctt aaggactagt ttcgcgccct  8040
ttctcaaatt taagcgcgaa aactacgtca tctccagcgg ccacacccgg cgccagcacc  8100
tgtcgtcagc gccattatga gcaaggaaat tcccacgccc tacatgtgga gttaccagcc  8160
acaaatggga cttgcggctg gagctgccca agactactca acccgaataa actacatgag  8220
cgcgggaccc cacatgatat cccgggtcaa cggaatccgc gcccaccgaa accgaattct  8280
cctcgaacag gcggctatta ccaccacacc tcgtaataac cttaatcccc gtagttggcc  8340
cgctgccctg gtgtaccagg aaagtcccgc tcccaccact gtggtacttc ccagagacgc  8400
ccaggccgaa gttcagatga ctaactcagg ggcgcagctt gcgggcggct ttcgtcacag  8460
ggtgcggtcg cccgggcgtt ttagggcgga gtaacttgca tgtattggga attgtagttt  8520
ttttaaaatg ggaagtgacg tatcgtggga aaacggaagt gaagatttga ggaagttgtg  8580
ggtttttggc tttcgtttc tgggcgtagg ttcgcgtgcg gttttctggg tgttttttgt  8640
ggactttaac cgttacgtca tttttagtc ctatatatac tcgctctgta cttggccctt  8700
tttacactgt gactgattga gctggtgccg tgtcgagtgg tgtttttaa taggtttttt  8760
tactggtaag gctgactgtt atggctgccg ctgtggaagc gctgtatgtt gttctggagc  8820
gggagggtgc tattttgcct aggcgcctgg atgctttgag agagtggata tactacaact  8880
actacacaga gcgagctaag cgacgagacc ggagacgcag atctgtttgt cacgcccgca  8940
cctggttttg cttcaggaaa tatgactacg tccggcgttc catttggcat gacactacga  9000
ccaacacgat ctcggttgtc tcggcgcact ccgtacagta gggatcgcct acctcctttt  9060
gagacagaga cccgcgctac catactggag gatcatccgc tgctgcccga atgtaacact  9120
ttgacaatgc acaacgtgag ttacgtgcga ggtcttccct gcagtgtggg atttacgctg  9180
attcaggaat gggttgttcc ctgggatatg gttctgacgc gggaggagct tgtaatcctg  9240
aggaagtgta tgcacgtgtg cctgtgttgt gccaacattg atatcatgac gagcatgatg  9300
atccatggtt acgagtcctg ggctctccac tgtcattgtt ccagtcccgg ttccctgcag  9360
tgcatagccg gcgggcaggt tttggccagc tggtttagga tggtggtgga tggcgccatg  9420
tttaatcaga ggtttatatg gtaccgggag gtggtgaatt acaacatgcc aaaagaggta  9480
atgtttatgt ccagcgtgtt tatgaggggt cgccacttaa tctacctgcg cttgtggtat  9540
gatggccacg tgggttctgt ggtccccgcc atgagctttg gatacagcgc cttgcactgt  9600
gggattttga acaatattgt ggtgctgtgc tgcagttact gtgctgattt aagtgagatc  9660
agggtgcgct gctgtgcccg gaggacaagg cgtctcatgc tgcgggcggt gcgaatcatc  9720
gctgaggaga ccactgccat gttgtattcc tgcaggacgg agcggcggcg gcagcagttt  9780
attcgcgcgc tgctgcagca ccaccgccct atcctgatgc acgattatga ctctaccccc  9840
atgtaggcgt ggacttcccc ttcgccgccc gttgagcaac cgcaagttgg acagcagcct  9900
gtggctcagc agctggacag cgacatgaac ttaagcgagc tgcccgggga gtttattaat  9960
atcactgatg agcgtttggc tcgacaggaa accgtgtgga atataacacc taagaatatg  10020
tctgttaccc atgatatgat gctttttaag gccagccggg gagaaaggac tgtgtactct  10080
gtgtgttggg agggaggtgg caggttgaat actagggttc tgtgagtttg attaaggtac  10140
ggtgatcaat ataagctatg tggtggtggg gctatactac tgaatgaaaa atgacttgaa  10200
attttctgca attgaaaaat aaacacgttg aaacataaca tgcaacaggt tcacgattct  10260
ttattcctgg gcaatgtagg agaaggtgta agagttggta gcaaaagttt cagtggtgta  10320
ttttccactt tcccaggacc atgtaaaaga catagagtaa gtgcttacct cgctagtttc  10380
tgtggattca ctagaatcga tgtaggatgt tgcccctcct gacgcggtag gagaagggga  10440
gggtgccctg catgtctgcc gctgctcttg ctcttgccgc tgctgaggag gggggcgcat  10500
ctgccgcagc accggatgca tctgggaaaa gcaaaaaagg ggctcgtccc tgtttccgga  10560
ggaatttgca agcggggtct tgcatgacgg ggaggcaaac ccccgttcgc cgcagtccgg  10620
ccggcccgag actcgaaccg ggggtcctgc gactcaaccc ttggaaaata accctccggc  10680
tacagggagc gagccactta atgctttcgc tttccagcct aaccgcttac gccgcgcgcg  10740
gccagtggcc aaaaaagcta gcgcagcagc cgccgcgcct ggaaggaagc caaaaggagc  10800
gctccccccgt tgtctgacgt cgcacacctg ggttcgacac gcgggcggta accgcatgga  10860
tcacggcgga cggccggatc cggggttcga accccggtcg tccgccatga tacccttgcg  10920
aatttatcca ccagaccacg gaagagtgcc cgcttacagg ctctcctttt gcacggtcta  10980
gagcgtcaac gactgcgcac gcctcaccgg ccagagcgtc ccgaccatgg agcacttttt  11040
gccgctgcgc aacatctgga accgcgtccg cgactttccg cgcgcctcca ccaccgccgc  11100
cggcatcacc tggatgtcca ggtacatcta cggattacgt cgacgttt             11148
```

```
SEQ ID NO: 12          moltype = DNA  length = 15719
FEATURE                Location/Qualifiers
misc_feature           1..15719
```

-continued

```
                        note = Synthetic: pAAVone-AAV2-CMV-EGFP
source                  1..15719
                        mol_type = other DNA
                        organism = synthetic construct
SEQUENCE: 12
ggcagctgcg cgctcgctcg ctcactgagg ccgcccgggc aaagcccggg cgtcgggcga  60
cctttggtcg cccggcctca gtgagcgagc gagcgcgcag agagggagtg gccaactcca  120
tcactagggg ttcctgcggc cgcacgcgta cattgattat tgactagtta ttaatagtaa  180
tcaattacgg ggtcattagt tcatagccca tatatggagt tccgcgttac ataacttacg  240
gtaaatggcc cgcctggctg accgcccaac gacccccgcc cattgacgtc aataatgacg  300
tatgttccca tagtaacgcc aatagggact ttccattgac gtcaatgggt ggagtattta  360
cggtaaactg cccacttggc agtacatcaa gtgtatcata tgccaagtac gccccctatt  420
gacgtcaatg acggtaaatg gcccgcctgg cattatgccc agtacatgac cttatgggac  480
tttcctactt ggcagtacat ctacgtatta gtcatcgcta ttaccatggt gatgcggttt  540
tggcagtaca tcaatgggcg tggatagcgg tttgactcac ggggatttcc aagtctccac  600
cccattgacg tcaatgggag tttgttttgg caccaaaatc aacgggactt tccaaaatgt  660
cgtaacaact ccgccccatt gacgcaaatg ggcggtaggc gtgtacggtg ggaggtctat  720
ataagctagc gccaccatgg tgagcaaggg cgaggagctg ttcaccgggg tggtgcccat  780
cctggtcgag ctggacggcg acgtaaacgg ccacaagttc agcgtgtccg gcgagggcga  840
gggcgatgcc acctacggca agctgaccct gaagttcatc tgcaccaccg gcaagctgcc  900
cgtgccctgg cccaccctcg tgaccaccct gacctacggc gtgcagtgct tcagccgcta  960
ccccgaccac atgaagcagc acgacttctt caagtccgcc atgcccgaag gctacgtcca  1020
ggagcgcacc atcttcttca aggacgacgg caactacaag acccgcgccg aggtgaagtt  1080
cgagggcgac accctggtga accgcatcga gctgaagggc atcgacttca aggaggacgg  1140
caacatcctg gggcacaagc tggagtacaa ctacaacagc cacaacgtct atatcatggc  1200
cgacaagcag aagaacggca tcaaggtgaa cttcaagatc cgccacaaca tcgaggacgg  1260
cagcgtgcag ctcgccgacc actaccagca gaacaccccc atcggcgacg gccccgtgct  1320
gctgcccgac aaccactacc tgagcaccca gtccgccctg agcaaagacc ccaacgagaa  1380
gcgcgatcac atggtcctgc tggagttcgt gaccgccgcc gggatcactc tcggcatgga  1440
cgagctgtac aagtaacgta cggatatcaa gcttatcgat aatcaacctc tggattacaa  1500
aatttgtgaa agattgactg gtattcttaa ctatgttgct ccttttacgc tatgtggata  1560
cgctgcttta atgcctttgt atcatgctat tgcttcccgt atggctttca ttttctcctc  1620
cttgtataaa tcctggttgc tgtctcttta tgaggagttg tggcccgttg tcaggcaacg  1680
tggcgtggtg tgcactgtgt ttgctgacgc aacccccact ggttggggca ttgccaccac  1740
ctgtcagctc ctttccggga ctttcgcttt ccccctccct attgccacgg cggaactcat  1800
cgccgcctgc cttgcccgct gctggacagg ggctcggctg ttgggcactg acaattccgt  1860
ggtgttgtcg gggaaatcat cgtcctttcc ttggctgctc gcctatgttg ccacctggat  1920
tctgcgcggg acgtccttct gctacgtccc ttcggccctc aatccagcgg accttccttc  1980
ccgcggcctg ctgccggctc tgcggcctct tccgcgtctt cgccttcgcc ctcagacgag  2040
tcggatctcc ctttgggccg cctccccgca tcgataccga gcgctgctcg agagatctac  2100
gggtggcatc cctgtgaccc ctccccagtg cctctcctgg ccctggaagt tgccactcca  2160
gtgcccacca gccttgtcct aataaaatta agttgcatca ttttgtctga ctaggtgtcc  2220
ttctataata ttatggggtg gaggggggtg gtatggagca aggggcaagt tgggaagaca  2280
acctgtaggg cctgcggggt ctattgggaa ccaagctgga gtgcagtggc acaatcttgg  2340
ctcactgcaa tctccgcctc ctgggttcaa gcgattctcc tgcctcagcc tcccgagttg  2400
ttgggattcc aggcatgcat gaccaggctc agctaatttt tgttttttttg gtagagacgg  2460
ggtttcacca tattggccag gctggtctcc aactcctaat ctcaggtgat ctacccacct  2520
tggcctccca aattgctggg attacaggcg tgaaccactg ctcccttccc tgtccttctg  2580
attttgtagg taaccacgtg cggaccgagc ggccgcagga acccctagtg atggagttgg  2640
ccactccctc tctgcgcgct cgctcgctca ctgaggccgg gcgaccaaag gtcgcccgac  2700
gcccgggctt tgcccgggcg gcctcagtga gcgagcgagc gcgcagctgc caaaccatat  2760
gatcagctca ctcaaaggcg gtaatacggt tatccacaga atcaggggat aacgcaggaa  2820
agaacatgtg agcaaaaggc cagcaaaagg ccaggaaccg taaaaaggcc gcgttgctgg  2880
cgtttttcca taggctccgc ccccctgacg agcatcacaa aaatcgacgc tcaagtcaga  2940
ggtggcgaaa cccgacagga ctataaagat accaggcgtt tccccctgga agctccctcg  3000
tgcgctctcc tgttccgacc ctgccgctta ccggatacct gtccgccttt ctcccttcgg  3060
gaagcgtggc gctttctcat agctcacgct gtaggtatct cagttcggtg taggtcgttc  3120
gctccaagct gggctgtgtg cacgaacccc ccgttcagcc cgaccgctgc gccttatccg  3180
gtaactatcg tcttgagtcc aacccggtaa gacacgactt atcgccactg gcagcagcca  3240
ctggtaacag gattagcaga gcgaggtatg taggcggtgc tacagagttc ttgaagtggt  3300
ggcctaacta cggctacact agaagaacag tatttggtat ctgcgctctg ctgaagccag  3360
ttaccttcgg aaaaagagtt ggtagctctt gatccggcaa acaaaccacc gctggtagcg  3420
gtggtttttt tgtttgcaag cagcagatta cgcgcagaaa aaaaggatct caagaagatc  3480
ctttgatctt ttctacgggg tctgacgctc agtggaacga aaactcacgt taagggattt  3540
tggtcatgag attatcaaaa aggatcttca cctagatcct tttaaattaa aaatgaagtt  3600
ttaaatcaat ctaaagtata tatgagtaaa cttggtctga cagtcagaag aactcgtcaa  3660
gaaggcgata gaaggcgatg cgctgcgaat cgggagcggc gataccgtaa agcacgagga  3720
agcggtcagc ccattcgccg ccaagctctt cagcaatatc acgggtagcc aacgctatgt  3780
cctgatagcg gtccgccaca cccagccggc cacagtcgat gaatccagaa aagcggccat  3840
tttccaccat gatattcggc aagcaggcat cgccatgggt cacgacgaga tcctcgccgt  3900
cgggcatgct cgccttgagc ctggcgaaca gttcggctgg cgcgagcccc tgatgctctt  3960
cgtccagatc atcctgatcg acaagaccgg cttccatccg agtacgtgct cgctcgatgc  4020
gatgtttcgc ttggtggtcg aatgggcagg tagccggatc aagcgtatgc agccgccgca  4080
ttgcatcagc catgatggat actttctcgg caggagcaag gtgagatgac aggagatcct  4140
gccccggcac ttcgcccaat agcagccagt cccttcccgc ttcagtgaca acgtcgagta  4200
cagctgcgca aggaacgccc gtcgtggcca gccacgatag ccgcgctgcc tcgtcttgca  4260
gttcattcag ggcaccggac aggtcggtct tgacaaaaag aaccgggcgc cctgcgctg  4320
acagccggaa cacggcggca tcagagcagc cgattgtctg ttgtgcccag tcatagccga  4380
atagcctctc cacccaagcg gccggagaac ctgcgtgcaa tccatcttgt tcaatcatac  4440
```

-continued

```
tcttcctttt tcaatattat tgaagcattt atcagggtta ttgtctcatg agcggataca  4500
tatttgaatg tatttagaaa aataaacaaa taggggttcc gcgcacattt ccccgaaaag  4560
tgccacctaa attgtaagcg ttaatatttt gttaaaattc gcgttaaatt tttgttaaat  4620
cagctcattt tttaaccaat aggccgaaat cggcaaaatc ccttataaat caaaagaata  4680
gaccgagata gggttgagtg ttgttccagt ttggaacaag agtccactat taaagaacgt  4740
ggactccaac gtcaaagggc gaaaaaccgt ctatcagggc gatggcccac tacgtgaacc  4800
atcaccctaa tcaagttttt tggggtcgag gtgccgtaaa gcactaaatc ggaaccctaa  4860
agggagcccc cgatttagag cttgacgggg aaagccggcg aacgtggcga gaaaggaagg  4920
gaagaaagcg aaaggagcgg gcgctagggc gctggcaagt gtagcggtca cgctgcgcgt  4980
aaccaccaca cccgccgcgc ttaatgcgcc gctacagggc gcgatggatc cggtacccaa  5040
ctccatgctt aacagtcccc aggtacagcc caccctgcgt cgcaaccagg aacagctcta  5100
cagcttcctg gagcgccact cgccctactt ccgcagccac agtgcgcaga ttaggagcgc  5160
cacttctttt tgtcacttga aaaacatgta aaaataatgt actaggagac actttcaata  5220
aaggcaaatg tttttatttg tacactctcg ggtgattatt tacccccac ccttgccgtc  5280
tgcgccgttc agaagtcaaa aggattctgt ctggcgtcag agtgggccac gggcagagac  5340
acattccggt actgatgctt agtgctccac ttgaactcgg gcaccaccat gcgggggcagc  5400
tctgtgaagt tctcagacca caggctccgc accatcacga gagcgttcag cagatctggg  5460
gcggagatct tgaagtcgca gttggggcct ccaccctgag ctctgctatt cctgtacacg  5520
ggattgcagc actggaacac gatcagggcg gggtggtgaa cggaggccag cacggacttg  5580
tcgctgatca gatcggcatc cagatcttcg gcgttgctca gggcaaaagg ggtcagtttt  5640
ggcagctgcc tgcccaggaa aggggcgtgg ccgggcttgg agttacattc gcagcgcagg  5700
ggcatcagga ggtggccgtg gccggtctgg gcatttggat acagggcttg catgaaggcc  5760
ttgatctgct tgaaggccac ttgcgccttg gctccctcgc tgaagaacat tccgcagctc  5820
ttgccgctaa actgattggc agggcaggcg gcgtcatgca cgcaacatct ggcgtctgtg  5880
ttagaaatct gcaccacgtt cctgccccac ctgttcttca cgatcttggc cttgctggac  5940
tgctccttca gggcgcgctg gccgttttcg gaagtcacat ccatctcgat cacgtgctcc  6000
ttgttaatca tgatagagcc gtgcaggcat ttcagctcgc cctcaatctc ggcgcatctg  6060
tgcagccaca gggcgcagcc ggtgggctcg tggtgcttgt aagtcacttc ggcgaaagat  6120
tgcaggtagg cctgcagaaa cctgcccatc atggtcacaa aggtcttgtt tgatgtaaag  6180
gtcagctgca gccctctatg ctcctcattc agccatgtct tgcacacggc agccagggcc  6240
tccacctggt caggcagcag tttgaaatta gccttcaggt cgttgtccac gtggtacttg  6300
tccatcaggg cccgggcggc ctccattccc ttctcccaag cgctcacaat tggcagggac  6360
agtggattaa tcactgtgct ctcgctctcg gcctcggagg attcttcctt ctcctcctgt  6420
gtcctcatgc cccttgccac aggatcatcc tcgttcagcc tgcgcacggt ccgttttccc  6480
cctttgccgt gcttgatgag cacaggtgga ttgctgaatc ccaccatctg cagagcgacg  6540
tcctcgcgct cttcctctga gtccacgatc acttctgggc tgggtggtcg ttcaggttta  6600
ggggagggcc tcttcttctt tttttgctg gcaatggcca ggtcggcggt ggaagtggag  6660
ggtcttggag atggtgtcct aggcaccaga gcgtcctggg aactgtcttc ctcgtcctcg  6720
gactccaggc gtctccgcag tctctttttt gggggcgcgc ggggaggcgg cggcgacggc  6780
gacggggacg acacgtcctc catggttggt ggacgtcgcg ccgcaccgcg tccgcgctcg  6840
ggggtggttt cgcgctgctc ctcttcccga ctggccattt ccttctccct gaggactacc  6900
acgcccacga gattaggttc tacgaagacc aatcccgccc gccaaatgcg gagcttaccg  6960
cctgcgtcat tacccagggc cacatccttg gccaattgca agccatcaac aaagcccgcc  7020
aagagtttct gctacgaaag ggacgggggg tttacctgga cccccagtcc ggcgaggagc  7080
tcaacccaat cccccgccg ccgcagccct atcagcagcc gcgggccctt gcttcccagg  7140
atggcaccca aaaagaagct gcagctgccg ccgccgccac ccacggacga ggaggaatac  7200
tgggacagtc aggcagagga ggttttggac gaggaggagg agatgatgga agactgggac  7260
agcctagacg aagcttccga ggccgaagag gtgtcagacg aaacaccgtc accctcggtc  7320
gcattcccct cgccggcgcc ccagaaattg gcaaccgttc ccagcatcgc tacaacctcc  7380
gctcctcagg cgccgccggc actgcctgtt cgccgaccca accgtagatg ggacaccact  7440
ggaaccaggg ccggtaagtc taagcagccg ccgccgttag cccaagagca acaacagcgc  7500
caaggctacc gctcgtggcg cgggcacaag aacgccatag ttgcttgctt gcaagactgt  7560
gggggcaaca tctccttcgc ccgccgcttt cttctctacc atcacggcgt ggccttcccc  7620
cgtaacatcc tgcattacta ccgtcatctc tacagcccct actgcaccgg cggcagcggc  7680
agcggcagca acagcagcgg tcacacagaa gcaaaggcga ccggatagca agactctgac  7740
aaagcccaag aaatccacag cggcggcagc agcaggagga ggagcgctgc gtctggcgcc  7800
caacgaaccc gtatcgaccc gcgagcttag aaataggatt tttcccactc tgtatgctat  7860
atttcaacaa agcaggggcc aagaacaaga gctgaaaata aaaaacaggt ctctgcgctc  7920
cctcacccgc agctgcctgt atcacaaaag cgaagatcag cttcggcgca cgctggaaga  7980
cgcggaggct ctcttcagca aatactgcgc gctgactctt aaggactagt ttcgcgccct  8040
ttctcaaatt taagcgcgaa aactacgtca tctccagcgg ccacacccgg cgccagcacc  8100
tgtcgtcagc gccattatga gcaaggaaat tcccacgccc tacatgtgga gttaccagcc  8160
acaaatggga cttgcggctg gagctgccca agactactca acccgaataa actacatgag  8220
cgcgggaccc cacatgatat cccgggtcaa cggaatccgc gcccaccgaa accgaattct  8280
cctcgaacag gcggctatta ccaccacacc tcgtaataac cttaatcccc gtagttggcc  8340
cgctgccctg gtgtaccagg aaagtcccgc tcccaccact gtggtacttc ccagagacgc  8400
ccaggccgaa gttcagatga ctaactcagg ggcgcagctt gcgggcggct ttcgtcacag  8460
ggtgcggtcg cccgggcgtt ttagggcgga gtaacttgca tgtattggga attgtagttt  8520
ttttaaaatg ggaagtgacg tatcgtggga aaacggaagt gaagatttga ggaagttgtg  8580
ggtttttttgg ctttcgtttc tgggcgtagg ttcgcgtgcg gttttctggg tgttttttgt  8640
ggactttaac cgttacgtca tttttagtc ctatatatac tcgctctgta cttggccctt  8700
tttacactgt gactgattga gctggtgccg tgtcgagtgg tgtttttaa taggtttttt  8760
tactggtaag gctgactgtt atggctgccg ctgtggaagc gctgtatgtt gttctggagc  8820
gggagggtgc tattttgcct aggcgcctgg atgctttgag agagtggata tactacaact  8880
actacacaga gcgagctaag cgacgagacc ggagacgcag atctgtttgt cacgcccgca  8940
cctggttttg cttcaggaaa tatgactacg tccggcgttc catttggcat gacactacga  9000
ccaacacgat ctcggttgtc tcggcgcact ccgtacagta gggatcgcct acctcctttt  9060
gagacagaga cccgcgctac catactggag gatcatccgc tgctgcccga atgtaacact  9120
ttgacaatgc acaacgtgag ttacgtgcga ggtcttccct gcagtgtggg atttacgctg  9180
```

-continued

```
attcaggaat gggttgttcc ctgggatatg gttctgacgc gggaggagct tgtaatcctg  9240
aggaagtgta tgcacgtgtg cctgtgttgt gccaacattg atatcatgac gagcatgatg  9300
atccatggtt acgagtcctg ggctctccac tgtcattgtt ccagtcccgg ttccctgcag  9360
tgcatagccg gcgggcaggt tttggccagc tggtttagga tggtggtgga tggcgccatg  9420
tttaatcaga ggtttatatg gtaccgggag gtggtgaatt acaacatgcc aaaagaggta  9480
atgtttatgt ccagcgtgtt tatgaggggt cgccacttaa tctacctgcg cttgtggtat  9540
gatggccacg tgggttctgt ggtccccgcc atgagctttg gatacagcgc cttgcactgt  9600
gggatttga acaatattgt ggtgctgtgc tgcagttact gtgctgattt aagtgagatc  9660
agggtgcgct gctgtgcccg gaggacaagg cgtctcatgc tgcgggcggt gcgaatcatc  9720
gctgaggaga ccactgccat gttgtattcc tgcaggacgg agcggcggcg gcagcagttt  9780
attcgcgcgc tgctgcagca ccaccgccct atcctgatgc acgattatga ctctaccccc  9840
atgtaggcgt ggacttcccc ttcgccgccc gttgagcaac cgcaagttgg acagcagcct  9900
gtggctcagc agctggacag cgacatgaac ttaagcgagc tgcccgggga gtttattaat  9960
atcactgatg agcgtttggc tcgacaggaa accgtgtgga atataacacc taagaatatg  10020
tctgttaccc atgatatgat gctttttaag gccagccggg gagaaaggac tgtgtactct  10080
gtgtgttggg agggaggtgg caggttgaat actagggttc tgtgagtttg attaaggtac  10140
ggtgatcaat ataagctatg tggtggtggg gctatactac tgaatgaaaa atgacttgaa  10200
attttctgca attgaaaaat aaacacgttg aaacataaca tgcaacaggt tcacgattct  10260
ttattcctgg gcaatgtagg agaaggtgta agagttggta gcaaaagttt cagtggtgta  10320
ttttccactt tcccaggacc atgtaaaaga catagagtaa gtgcttacct cgctagtttc  10380
tgtggattca ctagagcggc cgcggtcctg tattagaggt caacgtgagt gttttgcgac  10440
attttgcgac accatgtggt cacgctgagg tatatatggc cgagtgagcg agcaggatgc  10500
aacctccatt ttgaccgcga aatttgaacg agcagccgcc atgccggggt tttacgagat  10560
tgtgattaag gtccccagcg accttgacga gcatctgccc ggcatttctg acagctttgt  10620
gaactgggtg gccgagaagg aatgggagtt gccgccagat tctgacatgg atctgaatct  10680
gattgagcag gcacccctga ccgtggccga gaagctgcag cgcgactttc tgacggaatg  10740
gcgccgtgtg agtaaggcac cggaggccct tttctttgtg caatttgaga agggagagag  10800
ctacttccac atgcacgtgc tcgtggaaac caccggggtg aaatccatgg ttttgggacg  10860
tttcctgagt cagattcgcg aaaaactgat tcagagaatt taccgcggga tcgagccgac  10920
tttgccaaac tggttcgcgg tcacaaagac cagaaatggc gccggaggcg ggaacaaggt  10980
ggtggatgag tgctacatcc ccaattactt gctccccaaa acccagcctg agctccagtg  11040
ggcgtggact aatatggaac agtatttaag cgcctgtttg aatctcacgg agcgtaaacg  11100
gttggtggcg cagcatctga cgcacgtgtc gcagacgcag gagcagaaca aagagaatca  11160
gaatcccaat tctgatgcgc cggtgatcag atcaaaaact tcagccaggt acatggagct  11220
ggtcgggtgg ctcgtggaca aggggattac ctcggagaag cagtggatcc aggaggacca  11280
ggcctcatac atctccttca atgcggcctc caactcgcgg tcccaaatca aggctgcctt  11340
ggacaatgcg ggaaagatta tgagcctgac taaaaccgcc cccgactacc tggtgggcca  11400
gcagcccgtg gaggacattt ccagcaatcg gatttataaa attttggaac taaacgggta  11460
cgatccccaa tatgcggctt ccgtctttct gggatgggcc acgaaaaagt tcggcaagag  11520
gaacaccatc tggctgtttg ggcctgcaac taccgggaag accaacatcg cggaggccat  11580
agcccacact gtgcccttct acgggtgcgt aaactggacc aatgagaact ttcccttcaa  11640
cgactgtgtc gacaagatgg tgatctggtg ggaggagggg aagatgaccg ccaaggtcgt  11700
ggagtcggcc aaagccattc tcggaggaag caaggtgcgc gtggaccaga aatgcaagtc  11760
ctcggcccag atagacccga ctcccgtgat cgtcacctcc aacaccaaca tgtgcgccgt  11820
gattgacggg aactcaacga ccttcgaaca ccagcagccg ttgcaagacc ggatgttcaa  11880
atttgaactc acccgccgtc tggatcatga ctttgggaag gtcaccaagc aggaagtcaa  11940
agacttttc cggtgggcaa aggatcacgt ggttgaggtg gagcatgaat tctacgtcaa  12000
aaagggtgga gccaagaaaa gacccgcccc cagtgacgca gatataagtg agcccaaacg  12060
ggtgcgcgag tcagttgcgc agccatcgac gtcagacgcg gaagcttcga tcaactacgc  12120
agacaggtac gtaaacaaat gttctcgtca cgtgggcatg aatctgatgc tgtttccctg  12180
cagacaatgc gagagaatga atcagaattc aaatatctgc ttcactcacg gacagaaaga  12240
ctgtttagag tgctttcccg tgtcagaatc tcaacccgtt tctgtcgtca aaaaggcgta  12300
tcagaaactg tgctacattc atcatatcat gggaaaggtg ccagacgctt gcactgcctg  12360
cgatctggtc aatgtggatt tggatgactg catctttgaa caataaatga tttaaatcag  12420
gtatggctgc cgatggttat cttccagatt ggctcgagga cactctctct gaaggaataa  12480
gacagtggtg gaagctcaaa cctggcccac caccaccaaa gcccgcagag cggcataagg  12540
acgacagcag gggtcttgtg cttcctgggt acaagtacct cggacccttc aacggactcg  12600
acaagggaga gccggtcaac gaggcagacg ccgcggccct cgagcacgac aaagcctacg  12660
accggcagct cgacagcgga gacaacccgt acctcaagta caaccacgcc gacgcggagt  12720
ttcaggagcg ccttaaagaa gatacgtctt ttgggggcaa cctcggacga gcagtcttcc  12780
aggcgaaaaa gagggttctt gaacctctgg gcctggttga ggaacctgtt aagacggctc  12840
cgggaaaaaa gaggccggta gagcactctc ctgtggagcc agactcctcc tcgggaaccg  12900
gaaaggcggg ccagcagcct gcaagaaaaa gattgaattt tggtcagact ggagacgcag  12960
actcagtacc tgacccccag cctctcggac agccaccagc agccccctct ggtctgggaa  13020
ctaatacgat ggctacaggc agtggcgcac caatggcaga caataacgag ggcgccgacg  13080
gagtgggtaa ttcctcggga aattggcatt gcgattccac atggatgggc gacagagtca  13140
tcaccaccag cacccgaacc tgggccctgc ccacctacaa caaccacctc tacaaacaaa  13200
tttccagcca atcaggagcc tcgaacgaca atcactactt tggctacagc accccttggg  13260
ggtattttga cttcaacaga ttccactgcc acttttcacc acgtgactgg caaagactca  13320
tcaacaacaa ctggggattc cgacccaaga gactcaactt caagctcttt aacattcaag  13380
tcaaagaggt cacgcagaat gacggtacga cgacgattgc caataacctt accagcacgg  13440
ttcaggtgtt tactgactcg gagtaccagc tcccgtacgt cctcggctcg gcgcatcaag  13500
gatgcctccc gccgttccca gcagacgtct tcatggtgcc acagtatgga tacctcaccc  13560
tgaacaacgg gagtcaggca gtaggacgct cttcatttta ctgcctggag tactttcctt  13620
ctcagatgct gcgtaccgga aacaacttta ccttcagcta cacttttgag gacgttcctt  13680
tccacagcag ctacgctcac agccagagtc tggaccgtct catgaatcct ctcatcgacc  13740
agtacctgta ttacttgagc agaacaaaca ctccaagtgg aaccaccacg cagtcaaggc  13800
ttcagttttc tcaggccgga gcgagtgaca ttcgggacca gtctaggaac tggcttcctg  13860
gaccctgtta ccgccagcag cgagtatcaa agacatctgc ggataacaac aacagtgaat  13920
```

```
actcgtggac tggagctacc aagtaccacc tcaatggcag agactctctg gtgaatccgg  13980
gcccggccat ggcaagccac aaggacgatg aagaaaagtt ttttcctcag agcggggttc  14040
tcatctttgg gaagcaaggc tcagagaaaa caaatgtgga cattgaaaag gtcatgatta  14100
cagacgaaga ggaaatcagg acaaccaatc ccgtggctac ggagcagtat ggttctgtat  14160
ctaccaacct ccagagaggc aacagacaag cagctaccgc agatgtcaac acacaaggcg  14220
ttcttccagg catggtctgg caggacagag atgtgtacct tcaggggccc atctgggcaa  14280
agattccaca cacggacgga cattttcacc cctctcccct catgggtgga ttcggactta  14340
aacaccctcc tccacagatt ctcatcaaga acaccccggt accagcgaat ccttcgacca  14400
ccttcagtgc ggcaaagttt gcttccttca tcacacagta ctccacggga caggtcagcg  14460
tggagatcga gtgggagctg cagaaggaaa acagcaaacg ctggaatccc gaaattcagt  14520
acacttccaa ctacaacaag tctgttaatg tggactttac tgtggacact aatggcgtgt  14580
attcagagcc tcgccccatt ggcaccagat acctgactcg taatctgtaa caattgcttg  14640
ttaatcaata aaccgtttaa ttcgtttcag ttgaactttg gtctctgcgt atttctttct  14700
tatctagttt ccatgctcta ggatccacta gtaacggccg ccagtgtgct ggaattcggc  14760
tttgtagtta atgattaacc cgccatgcta cttatctacg tagccatgct ctagaggtcc  14820
tgtattagag gtcacgtgag tgttttgcga catttgcga caccatgtgg tcacgctggg  14880
tatttaagcc cgagtgagca cgcagggtct ccattttgaa gcgggaggtt tgaacgcgca  14940
gccgccaagc cgaattctgc agatctatcg atgtaggatg ttgcccctcc tgacgcggta  15000
ggagaagggg agggtgccct gcatgtctgc cgctgctctt gctcttgccg ctgctgagga  15060
ggggggcgca tctgccgcag caccggatgc atctgggaaa agcaaaaaag ggctcgtcc   15120
ctgtttccgg aggaatttgc aagcggggtc ttgcatgacg gggaggcaaa cccccgttcg  15180
ccgcagtccg gccggcccga gactcgaacc gggggtcctg cgactcaacc cttggaaaat  15240
aaccctccgg ctacagggag cgagccactt aatgctttcg ctttccagcc taaccgctta  15300
cgccgcgcgc ggccagtggc caaaaaagct agcgcagcag ccgccgcgcc tggaaggaag  15360
ccaaaaggag cgctcccccg ttgtctgacg tcgcacacct gggttcgaca cgcgggcggt  15420
aaccgcatgg atcacggcgg acggccggat ccggggttcg aaccccggtc gtccgccatg  15480
ataccttgc gaatttatcc accagaccac ggaagagtgc ccgcttacag gctctccttt  15540
tgcacggtct agagcgtcaa cgactgcgca cgcctcaccg gccagagcgt cccgaccatg  15600
gagcactttt tgccgctgcg caacatctgg aaccgcgtcc gcgactttcc gcgcgcctcc  15660
accaccgccg ccggcatcac ctggatgtcc aggtacatct acggattacg tcgacgttt   15719
```

```
SEQ ID NO: 13          moltype = DNA  length = 10582
FEATURE                Location/Qualifiers
misc_feature           1..10582
                       note = Synthetic: Mini-pHelper-Rep
source                 1..10582
                       mol_type = other DNA
                       organism = synthetic construct
SEQUENCE: 13
tttggcttcc ttccaggcgc ggcggctgct gcgctagctt ttttggccac tggccgcgcg  60
cggcgtaagc ggttaggctg gaaagcgaaa gcattaagtg gctcgctccc tgtagccgga  120
gggttatttt ccaagggttg agtcgcagga cccccggttc gagtctcggg ccggccggac  180
tgcggcgaac gggggtttgc ctccccgtca tgcaagaccc cgcttgcaaa ttcctccgga  240
aacagggacg agcccctttt ttgcttttcc cagatgcatc cggtgctgcg gcagatgcgc  300
ccccctcctc agcagcggca agagcaagag cagcggcaga catgcagggc accctcccct  360
tctcctaccg cgtcaggagg ggcaacatcc tacatcgata gatctgcaga attcggcttg  420
gcggctgcgc gttcaaacct cccgcttcaa aatggagacc ctgcgtgctc actcgggctt  480
aaatacccag cgtgaccaca tggtgtcgca aaatgtcgca aaacactcac gtgacctcta  540
atacaggacc tctagagcat ggctacaaat catttattgt tcaaagatgc agtcatccaa  600
atccacattg accagatcgc aggcagtgca agcgtctggc acctttccca tgatatgatg  660
aatgtagcac agtttctgat acgccttttt gacgacagaa acgggttgag attctgacac  720
gggaaagcac tctaaacagt ctttctgtcc gtgagtgaag cagatatttg aattctgatt  780
cattctctcg cattgtctgc agggaaacag catcagattc atgcccacgt gacgagaaca  840
tttgtttacg tacctgtctg cgtagttgat cgaagcttcc gcgtctgacg tcgatggctg  900
cgcaactgac tcgcgcaccc gtttgggctc acttatatct gcgtcactgg gggcgggtct  960
tttcttggct ccaccctttt tgacgtagaa ttcatgctcc acctcaacca cgtgatcctt  1020
tgcccaccgg aaaaagtctt tgacttcctg cttggtgacc ttcccaaagt catgatccag  1080
acggcgggtg agttcaaatt tgaacatccg gtcttgcaac ggctgctggt gttcgaaggt  1140
cgttgagttc ccgtcaatca cggcgcacat gttggtgttg gaggtgacga tcacgggagt  1200
cgggtctatc tgggccgagg acttgcattt ctggtccacg cgcaccttgc ttcctccgag  1260
aatggctttg gccgactcca cgaccttggc ggtcatcttc ccctcctccc accagatcac  1320
catcttgtcg acacagtcgt tgaagggaaa gttctcattg gtccagttta cgcacccgta  1380
gaagggcaca gtgtgggcta tggcctccgc gatgttggtc ttcccggtag ttgcaggccc  1440
aaacagccag atggtgttcc tcttgccgaa ctttttcgtg gcccatccca gaaagacgga  1500
agccgcatat tggggatcgt acccgtttag ttccaaaatt ttataaatcc gattgctgga  1560
aatgtcctcc acgggctgct ggcccaccag gtagtcgggg gcggttttag tcaggctcat  1620
aatctttccc gcattgtcca aggcagcctt gatttgggac cgcgagttgg aggccgcatt  1680
gaaggagatg tatgaggcct ggtcctcctg gatccactgc ttctccgagg taatcccctt  1740
gtccacgagc cacccgacca gctccatgta cctggctgaa gtttttgatc tgatcaccgg  1800
cgcatcagaa ttgggattct gattctcttt gttctgctcc tgcgtctgcg acacgtgcgt  1860
cagatgctgc gccaccaacc gtttacgctc cgtgagattc aaacaggcgc ttaaatactg  1920
ttccatatta gtccacgccc actggagctc aggctgggtt ttggggagca agtaattggg  1980
gatgtagcac tcatccacca ccttgttccc gcctccggcg ccatttctgg tctttgtgac  2040
cgcgaaccag tttggcaaag tcggctcgat cccgcggtaa attctctgaa tcagtttttc  2100
gcgaatctga ctcaggaaac gtcccaaaac catggatttc accccggtgg tttccacgag  2160
cacgtgcatg tggaagtagc tctctccctt ctcaaattgc acaaagaaaa gggcctccgg  2220
tgccttactc acacggcgcc attccgtcag aaagtcgcgc tgcagcttct cggccacggt  2280
caggggtgcc tgctcaatca gattcagatc catgtcagaa tctggcggca actcccattc  2340
cttctcggcc acccagttca caaagctgtc agaaatgccg ggcagatgct cgtcaaggtc  2400
```

```
gctggggacc ttaatcacaa tctcgtaaaa ccccggcatg gcggctgctc gttcaaattt  2460
cgcggtcaaa atggaggttg catcctgctc gctcactcgg ccatatatac ctcagcgtga  2520
ccacatggtg tcgcaaaatg tcgcaaaaca ctcacgttga cctctaatac aggaccgcgg  2580
ccgctctagt gaatccacag aaactagcga ggtaagcact tactctatgt cttttacatg  2640
gtcctgggaa agtggaaaat acaccactga aacttttgct accaactctt acaccttctc  2700
ctacattgcc caggaataaa gaatcgtgaa cctgttgcat gttatgtttc aacgtgttta  2760
tttttcaatt gcagaaaatt tcaagtcatt tttcattcag tagtatagcc ccaccaccac  2820
atagcttata ttgatcaccg taccttaatc aaactcacag aaccctagta ttcaacctgc  2880
cacctccctc ccaacacaca gagtacacag tcctttctcc ccggctggcc ttaaaaagca  2940
tcatatcatg ggtaacagac atattcttag gtgttatatt ccacacggtt tcctgtcgag  3000
ccaaacgctc atcagtgata ttaataaact ccccgggcag ctcgcttaag ttcatgtcgc  3060
tgtccagctg ctgagccaca ggctgctgtc caacttgcgg ttgctcaacg ggcggcgaag  3120
gggaagtcca cgcctacatg gggtagagt cataatcgtg catcaggata gggcggtggt  3180
gctgcagcag cgcgcgaata aactgctgcc gccgccgctc cgtcctgcag gaatacaaca  3240
tggcagtggt ctcctcagcg atgattcgca ccgcccgcag catgagacgc cttgtcctcc  3300
gggcacagca gcgcaccctg atctcactta aatcagcaca gtaactgcag cacagcacca  3360
caatattgtt caaaatccca cagtgcaagg cgctgtatcc aaagctcatg gcggggacca  3420
cagaacccac gtggccatca taccacaagc gcaggtagat taagtggcga cccctcataa  3480
acacgctgga cataaacatt acctcttttg gcatgttgta attcaccacc tcccggtacc  3540
atataaacct ctgattaaac atggcgccat ccaccaccat cctaaaccag ctggccaaaa  3600
cctgcccgcc ggctatgcac tgcagggaac cgggactgga acaatgacag tggagagccc  3660
aggactcgta accatggatc atcatgctcg tcatgatatc aatgttggca caacacaggc  3720
acacgtgcat acacttcctc aggattacaa gctcctcccg cgtcagaacc atatcccagg  3780
gaacaaccca ttcctgaatc agcgtaaatc ccacactgca gggaagacct cgcacgtaac  3840
tcacgttgtg cattgtcaaa gtgttacatt cgggcagcag cggatgatcc tccagtatgg  3900
tagcgcgggt ctctgtctca aaaggaggta ggcgatccct actgtacgga gtgcgccgag  3960
acaaccgaga tcgtgttggt cgtagtgtca tgccaaatgg aacgccggac gtagtcatat  4020
ttcctgaagc aaaaccaggt gcgggcgtga caaacagatc tgcgtctccg gtctcgtcgc  4080
ttagctcgct ctgtgtagta gttgtagtat atccactctc tcaaagcatc caggcgccta  4140
ggcaaaatag caccctcccg ctccagaaca acatacagcg cttccacagc ggcagccata  4200
acagtcagcc ttaccagtaa aaaaacctat taaaaaacac cactcgacac ggcaccagct  4260
caatcagtca cagtgtaaaa agggccaagt acagagcgag tatatatagg actaaaaaat  4320
gacgtaacgg ttaaagtcca caaaaaacac ccagaaaacc gcacgcgaac ctacgcccag  4380
aaacgaaagc caaaaaaccc acaacttcct caaatcttca cttccgtttt cccacgatac  4440
gtcacttccc attttaaaaa aactacaatt cccaatacat gcaagttact ccgccctaaa  4500
acgcccgggc gaccgcaccc tgtgacgaaa gccgcccgca agctgcgccc ctgagttagt  4560
catctgaact tcggcctggg cgtctctggg aagtaccaca gtggtgggag cgggactttc  4620
ctggtacacc agggcagcgg gccaactacg gggattaagg ttattacgag gtgtggtggt  4680
aatagccgcc tgttcgagga gaattcggtt tcggtgggcg cggattccgt tgacccggga  4740
tatcatgtgg ggtcccgcgc tcatgtagtt tattcgggtt gagtagtctt gggcagctcc  4800
agccgcaagt cccatttgtg gctggtaact ccacatgtag ggcgtgggaa tttccttgct  4860
cataatggcg ctgacgacag gtgctggcgc cgggtgtggc cgctggagat gacgtagttt  4920
tcgcgcttaa atttgagaaa gggcgcgaaa ctagtcctta agagtcagcg cgcagtattt  4980
gctgaagaga gcctccgcgt cttccagcgt gcgccgaagc tgatcttcgc ttttgtgata  5040
caggcagctg cgggtgaggg agcgcagaga cctgtttttt attttcagct cttgttcttg  5100
gcccctgctt tgttgaaata tagcatacag agtgggaaaa atcctatttc taagctcgcg  5160
ggtcgatacg ggttcgttgg gcgccagacg cagcgctcct cctcctgctg ctgccgccgc  5220
tgtggatttc ttgggctttg tcagagtctt gctatccggt cgcctttgct tctgtgtgac  5280
cgctgctgtt gctgccgctg ccgctgccgc cggtgcagta ggggctgtag agatgacggt  5340
agtaatgcag gatgttacgg gggaaggcca cgccgtgatg gtagagaaga aagcggcggg  5400
cgaaggagat gttgcccccca cagtcttgca agcaagcaac tatggcgttc ttgtgcccgc  5460
gccacgagcg gtagccttgg cgctgttgtt gctcttgggc taacggcggc ggctgcttag  5520
acttaccggc cctggttcca gtggtgtccc atctacggtt gggtcggcga acaggcagtg  5580
ccggcggcgc ctgaggagcg gaggttgtag cgatgctggg aacggttgcc aatttctggg  5640
gcgccggcga ggggaatgcg accgagggtg acggtgtttc gtctgacacc tcttcggcct  5700
cggaagcttc gtctaggctg tcccagtctt ccatcatctc ctcctcctcg tccaaaacct  5760
cctctgcctg actgtcccag tattcctcct cgtccgtggg tggcggcggc ggcagctgca  5820
gcttcttttt gggtgccatc ctgggaagca agggcccgcg gctgctgata gggctgcggc  5880
ggcgggggga ttgggttgag ctcctcgccg gactgggggt ccaggtaaac cccccgtccc  5940
tttcgtagca gaaactcttg gcgggctttg ttgatggctt gcaattggcc aaggatgtgg  6000
ccctgggtaa tgacgcaggc ggtaagctcc gcatttggcg ggcgggattg gtcttcgtag  6060
aacctaatct cgtgggcgtg gtagtcctca gggagaagga aatggccagt cgggaagagg  6120
agcagcgcga aaccaccccc gagcgcggac gcggtgcggc gcgacgtcca ccaaccatgg  6180
aggacgtgtc gtccccgtcg ccgtcgccgc cgcctccccg cgcgccccca aaaaagagac  6240
tgcggagacg cctggagtcc gaggacgagg aagacagttc ccaggacgct ctggtgccta  6300
ggacaccatc tccaagaccc tccacttcca ccgccgacct ggccattgcc agcaaaaaaa  6360
agaagaagag gccctcccct aaacctgaac gaccacccag cccagaagtg atcgtggact  6420
cagaggaaga gcgcgaggac gtcgctctgc agatggtggg attcagcaat ccacctgtgc  6480
tcatcaagca cggcaaaggg ggaaaacgga ccgtgcgcag gctgaacgag gatgatcctg  6540
tggcaagggg catgaggaca caggaggaga aggaagaatc ctccgaggcc gagagcgaga  6600
gcacagtgat taatccactg tccctgccaa ttgtgagcgc ttgggagaag ggaatggagg  6660
ccgcccgggc cctgatggac aagtaccacg tggacaacga cctgaaggct aatttcaaac  6720
tgctgcctga ccaggtggag gccctggctg ccgtgtgcaa gacatggctg aatgaggagc  6780
atagagggct gcagctgacc tttacatcaa acaagacctt tgtgaccatg atgggcaggt  6840
ttctgcaggc ctacctgcaa tctttcgccg aagtgactta caagcaccac gagcccaccg  6900
gctgcgccct gtggctgcac agatgcgccg agattgaggg cgagctgaaa tgcctgcacg  6960
gctctatcat gattaacaag gagcacgtga tcgagatgga tgtgacttcc gaaaacggcc  7020
agcgcgccct gaaggagcag tccagcaagg ccaagatcgt gaagaacagg tggggcagga  7080
acgtggtgca gatttctaac acagacgcca gatgttgcgt gcatgacgcc gcctgccctg  7140
```

```
ccaatcagtt tagcggcaag agctgcggaa tgttcttcag cgagggagcc aaggcgcaag  7200
tggccttcaa gcagatcaag gccttcatgc aagccctgta tccaaatgcc cagaccggcc  7260
acggccacct cctgatgccc ctgcgctgcg aatgtaactc caagcccggc cacgcccctt  7320
tcctgggcag gcagctgcca aaactgaccc cttttgccct gagcaacgcc gaagatctgg  7380
atgccgatct gatcagcgac aagtccgtgc tggcctccgt tcaccacccc gccctgatcg  7440
tgttccagtg ctgcaatccc gtgtacagga atagcagagc tcagggtgga ggccccaact  7500
gcgacttcaa gatctccgcc ccagatctgc tgaacgctct cgtgatggtg cggagcctgt  7560
ggtctgagaa cttcacagag ctgccccgca tggtggtgcc cgagttcaag tggagcacta  7620
agcatcagta ccggaatgtg tctctgcccg tggcccactc tgacgccaga cagaatcctt  7680
ttgacttctg aacggcgcag acggcaaggg tggggggtaa ataatcaccc gagagtgtac  7740
aaataaaaac atttgccttt attgaaagtg tctcctagta cattattttt acatgttttt  7800
caagtgacaa aaagaagtgg cgctcctaat ctgcgcactg tggctgcgga agtagggcga  7860
gtggcgctcc aggaagctgt agagctgttc ctggttgcga cgcagggtgg gctgtacctg  7920
gggactgtta agcatggagt tggtaccgg atccatcgcg ccctgtagcg gcgcattaag  7980
cgcggcgggt gtggtggtta cgcgcagcgt gaccgctaca cttgccagcg ccctagcgcc  8040
cgctcctttc gctttcttcc cttcctttct cgccacgttc gccggctttc cccgtcaagc  8100
tctaaatcgg gggctccctt tagggttccg atttagtgct ttacggcacc tcgaccccaa  8160
aaaacttgat tagggtgatg gttcacgtag tgggccatcg ccctgataga cggtttttcg  8220
ccctttgacg ttggagtcca cgttctttaa tagtggactc ttgttccaaa ctggaacaac  8280
actcaaccct atctcggtct attcttttga tttataaggg attttgccga tttcggccta  8340
ttggttaaaa aatgagctga tttaacaaaa atttaacgcg aattttaaca aaatattaac  8400
gcttacaatt taggtggcac ttttcgggga aatgtgcgcg gaacccctat ttgtttattt  8460
ttctaaatac attcaaatat gtatccgctc atgagacaat aaccctgata aatgcttcaa  8520
taatattgaa aaaggaagag tatgattgaa caagatggat tgcacgcagg ttctccggcc  8580
gcttgggtgg agaggctatt cggctatgac tgggcacaac agacaatcgg ctgctctgat  8640
gccgccgtgt tccggctgtc agcgcagggg cgcccggttc tttttgtcaa gaccgacctg  8700
tccggtgccc tgaatgaact gcaagacgag gcagcgcggc tatcgtggct ggccacgacg  8760
ggcgttcctt gcgcagctgt actcgacgtt gtcactgaag cgggaaggga ctggctgcta  8820
ttgggcgaag tgccggggca ggatctcctg tcatctcacc ttgctcctgc cgagaaagta  8880
tccatcatgg ctgatgcaat gcggcggctg catacgcttg atccggctac ctgcccattc  8940
gaccaccaag cgaaacatcg catcgagcga gcacgtactc ggatggaagc cggtcttgtc  9000
gatcaggatg atctggacga agagcatcag gggctcgcgc cagccgaact gttcgccagg  9060
ctcaaggcga gcatgcccga cggcgaggat ctcgtcgtga cccatggcga tgcctgcttg  9120
ccgaatatca tggtggaaaa tggccgcttt tctggattca tcgactgtgg ccggctgggt  9180
gtggcggacc gctatcagga catagcgttg gctacccgtg atattgctga agagcttggc  9240
ggcgaatggg ctgaccgctt cctcgtgctt tacggtatcg ccgctcccga ttcgcagcgc  9300
atcgccttct atcgccttct tgacgagttc ttctgactgt cagaccaagt ttactcatat  9360
atactttaga ttgatttaaa acttcatttt taatttaaaa ggatctaggt gaagatcctt  9420
tttgataatc tcatgaccaa aatcccttaa cgtgagtttt cgttccactg agcgtcagac  9480
cccgtagaaa agatcaaagg atcttcttga gatccttttt ttctgcgcgt aatctgctgc  9540
ttgcaaacaa aaaaaccacc gctaccagcg gtggtttgtt tgccggatca agagctacca  9600
actctttttc cgaaggtaac tggcttcagc agagcgcaga taccaaatac tgttcttcta  9660
gtgtagccgt agttaggcca ccacttcaag aactctgtag caccgcctac atacctcgct  9720
ctgctaatcc tgttaccagt ggctgctgcc agtggcgata agtcgtgtct taccgggttg  9780
gactcaagac gatagttacc ggataaggcg cagcggtcgg gctgaacggg gggttcgtgc  9840
acacagccca gcttggagcg aacgacctac accgaactga gatacctaca gcgtgagcta  9900
tgagaaagcg ccacgcttcc cgaagggaga aaggcggaca ggtatccggt aagcggcagg  9960
gtcggaacag gagagcgcac gagggagctt ccagggggaa acgcctggta tctttatagt  10020
cctgtcgggt ttcgccacct ctgacttgag cgtcgatttt tgtgatgctc gtcagggggg  10080
cggagcctat ggaaaaacgc cagcaacgcg gcctttttac ggttcctggc cttttgctgg  10140
ccttttgctc acatgttctt tcctgcgtta tcccctgatt ctgtggataa ccgtattacc  10200
gcctttgagt gagctgatca tatggtttaa acgtcgacgt aatccgtaga tgtacctgga  10260
catccaggtg atgccggcgg cggtggtgga ggcgcgcgga aagtcgcgga cgcggttcca  10320
gatgttgcgc agcggcaaaa agtgctccat ggtcgggacg ctctggccgg tgaggcgtgc  10380
gcagtcgttg acgctctaga ccgtgcaaaa ggagagcctg taagcgggca ctcttccgtg  10440
gtctggtgga taaattcgca agggtatcat ggcggacgac cggggttcga accccggatc  10500
cggccgtccg ccgtgatcca tgcggttacc gcccgcgtgt cgaacccagg tgtgcgacgt  10560
cagacaacgg gggagcgctc ct                                          10582
```

```
SEQ ID NO: 14          moltype = DNA  length = 131
FEATURE                Location/Qualifiers
misc_feature           1..131
                       note = Synthetic: Wild-type AAV2 P5 promoter (P5-AAV2)
source                 1..131
                       mol_type = other DNA
                       organism = synthetic construct
SEQUENCE: 14
ggtcctgtat tagaggtcac gtgagtgttt tgcgacattt tgcgacacca tgtggtcacg  60
ctgggtattt aagcccgagt gagcacgcag ggtctccatt ttgaagcggg aggtttgaac  120
gcgcagccgc c                                                      131
```

```
SEQ ID NO: 15          moltype = DNA  length = 137
FEATURE                Location/Qualifiers
misc_feature           1..137
                       note = Synthetic: Modified AAV2 P5 promoter (P5I)
source                 1..137
                       mol_type = other DNA
                       organism = synthetic construct
SEQUENCE: 15
```

```
ggtcctgtat tagaggtcaa cgtgagtgtt ttgcgacatt ttgcgacacc atgtggtcac  60
gctgaggtat atatggccga gtgagcgagc aggatgcaac ctccattttg accgcgaaat  120
ttgaacgagc agccgcc                                                 137

SEQ ID NO: 16          moltype = DNA  length = 414
FEATURE                Location/Qualifiers
misc_feature           1..414
                       note = Synthetic: VA coding region of Ad2
source                 1..414
                       mol_type = other DNA
                       organism = synthetic construct
SEQUENCE: 16
gggcactctt ccgtggtctg gtggataaat tcgcaagggt atcatggcgg acgaccgggg  60
ttcgaacccc ggatccggcc gtccgccgtg atccatgcgg ttaccgcccg cgtgtcgaac  120
ccaggtgtgc gacgtcagac aacgggggag cgctcctttt ggcttccttc caggcgcggc  180
ggctgctgcg ctagcttttt tggccactgg ccgcgcgcgg cgtaagcggt taggctggaa  240
agcgaaagca ttaagtggct cgctccctgt agccggaggg ttattttcca agggttgagt  300
cgcaggaccc ccggttcgag tctcgggccg gccggactgc ggcgaacggg ggtttgcctc  360
cccgtcatgc aagaccccgc ttgcaaattc ctccggaaac agggacgagc ccct        414

SEQ ID NO: 17          moltype = DNA  length = 453
FEATURE                Location/Qualifiers
misc_feature           1..453
                       note = Synthetic: Modified E4 coding region of mini-pHelper
source                 1..453
                       mol_type = other DNA
                       organism = synthetic construct
SEQUENCE: 17
atgactacgt ccggcgttcc atttggcatg acactacgac caacacgatc tcggttgtct  60
cggcgcactc cgtacagtag ggatcgccta cctccttttg agacagagac ccgcgctacc  120
atactggagg atcatccgct gctgcccgaa tgtaacactt tgacaatgca caacgcgtgg  180
acttcccctt cgccgcccgt tgagcaaccg caagttggac agcagcctgt ggctcagcag  240
ctggacagcg acatgaactt aagcgagctg cccggggagt ttattaatat cactgatgag  300
cgtttggctc gacaggaaac cgtgtggaat ataacaccta agaatatgtc tgttacccat  360
gatatgatgc tttttaaggc cagccgggga gaaaggactg tgtactctgt gtgttgggag  420
ggaggtggca ggttgaatac tagggttctg tga                               453

SEQ ID NO: 18          moltype = DNA  length = 1164
FEATURE                Location/Qualifiers
misc_feature           1..1164
                       note = Synthetic: Modified E4 coding region of
                        mini-pHelper1.0
source                 1..1164
                       mol_type = other DNA
                       organism = synthetic construct
SEQUENCE: 18
atgactacgt ccggcgttcc atttggcatg acactacgac caacacgatc tcggttgtct  60
cggcgcactc cgtacagtag ggatcgccta cctccttttg agacagagac ccgcgctacc  120
atactggagg atcatccgct gctgcccgaa tgtaacactt tgacaatgca caacgtgagt  180
tacgtgcgag gtcttccctg cagtgtggga tttacgctga ttcaggaatg ggttgttccc  240
tgggatatgg ttctgacgcg ggaggagctt gtaatcctga ggaagtgtat gcacgtgtgc  300
ctgtgttgtg ccaacattga tatcatgacg agcatgatga tccatggtta cgagtcctgg  360
gctctccact gtcattgttc cagtcccggt tccctgcagt gcatagccgg cgggcaggtt  420
ttggccagct ggtttaggat ggtggtggat ggcgccatgt ttaatcagag gtttatatgg  480
taccgggagg tggtgaatta caacatgcca aaagaggtaa tgtttatgtc cagcgtgttt  540
atgaggggtc gccacttaat ctacctgcgc ttgtggtatg atggccacgt gggttctgtg  600
gtccccgcca tgagctttgg atacagcgcc ttgcactgtg ggattttgaa caatattgtg  660
gtgctgtgct gcagttactg tgctgattta agtgagatca gggtgcgctg ctgtgcccgg  720
aggacaaggc gtctcatgct gcgggcggtg cgaatcatcg ctgaggagac cactgccatg  780
ttgtattcct gcaggacgga gcggcggcgg cagcagttta ttcgcgcgct gctgcagcac  840
caccgcccta tcctgatgca cgattatgac tctaccccca tgtaggcgtg gacttcccct  900
tcgccgcccg ttgagcaacc gcaagttgga cagcagcctg tggctcagca gctggacagc  960
gacatgaact taagcgagct gcccggggag tttattaata tcactgatga gcgtttggct  1020
cgacaggaaa ccgtgtggaa tataacacct aagaatatgt ctgttaccca tgatatgatg  1080
ctttttaagg ccagccgggg agaaaggact gtgtactctg tgtgttggga gggaggtggc  1140
aggttgaata ctagggttct gtga                                         1164

SEQ ID NO: 19          moltype = DNA  length = 835
FEATURE                Location/Qualifiers
misc_feature           1..835
                       note = Synthetic: Ad2 E4 promoter + E2a promoter sequence
source                 1..835
                       mol_type = other DNA
                       organism = synthetic construct
SEQUENCE: 19
aacagtcagc cttaccagta aaaaaaccta ttaaaaaaca ccactcgaca cggcaccagc  60
tcaatcagtc acagtgtaaa aagggccaag tacagagcga gtatatatag gactaaaaaa  120
tgacgtaacg gttaaagtcc acaaaaaaca cccagaaaac cgcacgcgaa cctacgccca  180
gaaacgaaag ccaaaaaacc cacaacttcc tcaaatcttc acttccgttt tcccacgata  240
```

```
cgtcacttcc cattttaaaa aaactacaat tcccaataca tgcaagttac tccgccctaa  300
aacgcccggg cgaccgcacc ctgtgacgaa agccgcccgc aagctgcgcc cctgagttag  360
tcatctgaac ttcggcctgg gcgtctctgg gaagtaccac agtggtggga gcgggacttt  420
cctggtacac cagggcagcg ggccaactac ggggattaag gttattacga ggtgtggtgg  480
taatagccgc ctgttcgagg agaattcggt ttcggtgggc gcggattccg ttgacccggg  540
atatcatgtg gggtcccgcg ctcatgtagt ttattcgggt tgagtagtct tgggcagctc  600
cagccgcaag tcccatttgt ggctggtaac tccacatgta gggcgtggga atttccttgc  660
tcataatggc gctgacgaca ggtgctggcg ccgggtgtgg ccgctggaga tgacgtagtt  720
ttcgcgctta aatttgagaa agggcgcgaa actagtcctt aagagtcagc gcgcagtatt  780
tgctgaagag agcctccgcg tcttccagcg tgcgccgaag ctgatcttcg ctttt       835

SEQ ID NO: 20          moltype = DNA  length = 1863
FEATURE                Location/Qualifiers
misc_feature           1..1863
                       note = Synthetic: AAV rep coding sequence
source                 1..1863
                       mol_type = other DNA
                       organism = synthetic construct
SEQUENCE: 20
atgccggggt tttacgagat tgtgattaag gtccccagcg accttgacga gcatctgccc  60
ggcatttctg acagctttgt gaactgggtg gccgagaagg aatgggagtt gccgccagat  120
tctgacatgg atctgaatct gattgagcag gcacccctga ccgtggccga gaagctgcag  180
cgcgactttc tgacggaatg gcgccgtgtg agtaaggcac cggaggccct tttctttgtg  240
caatttgaga agggagagag ctacttccac atgcacgtgc tcgtggaaac caccggggtg  300
aaatccatgg ttttgggacg tttcctgagt cagattcgcg aaaaactgat tcagagaatt  360
taccgcggga tcgagccgac tttgccaaac tggttcgcgg tcacaaagac cagaaatggc  420
gccggaggcg ggaacaaggt ggtggatgag tgctacatcc ccaattactt gctccccaaa  480
acccagcctg agctccagtg ggcgtggact aatatggaac agtatttaag cgcctgtttg  540
aatctcacgg agcgtaaacg gttggtggcg cagcatctga cgcacgtgtc gcagacgcag  600
gagcagaaca aagagaatca gaatcccaat tctgatgcgc cggtgatcag atcaaaaact  660
tcagccaggt acatggagct ggtcgggtgg ctcgtggaca aggggattac ctcggagaag  720
cagtggatcc aggaggacca ggcctcatac atctccttca atgcggcctc caactcgcgg  780
tcccaaatca aggctgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatccccaa tatgcggctt ccgtctttct gggatgggcc  960
acgaaaaagt tcggcaagag gaacaccatc tggctgtttg ggcctgcaac taccgggaag  1020
accaacatcg cggaggccat agcccacact gtgcccttct acgggtgcgt aaactggacc  1080
aatgagaact ttcccttcaa cgactgtgtc gacaagatgg tgatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac gtaaacaaat gttctcgtca cgtgggcatg  1620
aatctgatgc tgtttccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caa                                                                1863

SEQ ID NO: 21          moltype = DNA  length = 2205
FEATURE                Location/Qualifiers
misc_feature           1..2205
                       note = Synthetic: AAV2cap coding sequence
source                 1..2205
                       mol_type = other DNA
                       organism = synthetic construct
SEQUENCE: 21
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
```

-continued

```
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccggtac cagcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga aattcagtac  2100
acttccaact acaacaagtc tgttaatgtg gactttactg tggacactaa tggcgtgtat  2160
tcagagcctc gccccattgg caccagatac ctgactcgta atctg                   2205

SEQ ID NO: 22          moltype = DNA  length = 303
FEATURE                Location/Qualifiers
misc_feature           1..303
                       note = Synthetic: Ad2 E4 promoter sequence
source                 1..303
                       mol_type = other DNA
                       organism = synthetic construct
SEQUENCE: 22
gacccgggat atcatgtggg gtcccgcgct catgtagttt attcgggttg agtagtcttg  60
ggcagctcca gccgcaagtc ccatttgtgg ctggtaactc cacatgtagg gcgtgggaat  120
ttccttgctc ataatggcgc tgacgacagg tgctggcgcc gggtgtggcc gctggagatg  180
acgtagtttt cgcgcttaaa tttgagaaag ggcgcgaaac tagtccttaa gagtcagcgc  240
gcagtatttg ctgaagagag cctccgcgtc ttccagcgtg cgccgaagct gatcttcgct  300
ttt                                                                303

SEQ ID NO: 23          moltype = DNA  length = 303
FEATURE                Location/Qualifiers
misc_feature           1..303
                       note = Synthetic: Ad2 E2a promoter sequence
source                 1..303
                       mol_type = other DNA
                       organism = synthetic construct
SEQUENCE: 23
gttttagggc ggagtaactt gcatgtattg ggaattgtag ttttttttaaa atgggaagtg  60
acgtatcgtg ggaaaacgga agtgaagatt tgaggaagtt gtgggttttt tggctttcgt  120
ttctgggcgt aggttcgcgt gcggttttct gggtgttttt tgtggacttt aaccgttacg  180
tcatttttta gtcctatata tactcgctct gtacttggcc ctttttacac tgtgactgat  240
tgagctggtg ccgtgtcgag tggtgttttt taataggttt ttttactggt aaggctgact  300
gtt                                                                303
```